United States Patent [19]
Garman et al.

[11] Patent Number: 5,968,526
[45] Date of Patent: Oct. 19, 1999

[54] T CELL EPITOPES OF THE MAJOR ALLERGENS FROM DERMATOPHAGOIDES (HOUSE DUST MITE)

[75] Inventors: Richard D. Garman, Arlington; Julia L. Greenstein, West Newton; Mei-chang Kuo, Winchester; Bruce L. Rogers, Belmont; Henry M. Franzén, Watertown; Xian Chen, North Chelmsford; Sean Evans, Acton, all of Mass.; Ze'ev Shaked, Berkeley, Calif.

[73] Assignee: Immulogic Pharamaceutical Corporation, Waltham, Mass.

[21] Appl. No.: 08/478,572

[22] Filed: Jun. 7, 1995

Related U.S. Application Data

[60] Division of application No. 08/445,307, May 19, 1995, which is a continuation-in-part of application No. 08/227,772, Apr. 14, 1994, abandoned, which is a continuation-in-part of application No. PCT/US95/04481, Apr. 12, 1995.

[51] Int. Cl.$^6$ .......................... A61K 39/35; A61K 39/395; G01N 33/53; G01N 33/573
[52] U.S. Cl. .................................. 424/275.1; 424/184.1; 424/185.1; 424/171.1; 435/7.1; 435/7.4; 435/7.92; 435/69.3; 514/2; 514/12
[58] Field of Search .............................. 424/184.1, 171.1, 424/185.1, 200.1, 275.1; 435/7.92, 69.3, 7.1, 7.4; 530/350, 300; 514/12, 2

[56] References Cited

FOREIGN PATENT DOCUMENTS

| A-50598/90 | 2/1991 | Australia. |
|---|---|---|
| A-71277/91 | 9/1991 | Australia. |
| 0510848 | 7/1990 | European Pat. Off.. |
| 0445971 | 2/1991 | European Pat. Off.. |
| WO88/10297 | 12/1988 | WIPO. |
| WO91/06571 | 5/1991 | WIPO. |
| WO92/04445 | 3/1992 | WIPO. |

OTHER PUBLICATIONS

Lind et al., The Journal of Immunology, vol. 140, 4256–4262, No. 12, Jun. 15, 1988.
Chapman, et al., *The Journal of Immunology*, 1988, vol. 140(3): 812–818.
Chua, et al., *J. Exp. Med.*, 1988, vol. 167(1): 175–182.
Chua, et al., *Int. Arch. Allergy Appl. Immunol.*, 1990, vol. 91:124–129.
Chua, et al., *Int. Arch. Allergy Appl. Immunol.*, 1990, vol. 91: 118–123.
Chua, et al., *Clinical and Exp. Allergy*, 1991, vol. 21: 161–166.
Dilworth, et al., *Clinical and Exp. Allergy*, 1991, vol. 21: 25–32.
Ford, et al., *Clinical and Exp. Allergy*, 1989, vol. 20: 27–31.
Greene, et al., *The Journal of Immunol.*, 1991, vol. 147: 3766–3733.
Gurka, et al., *J. Allergy Clin. Immunol.*, 1989, vol. 83(5): 945–954.
Heymann, et al., *The Journal of Immunol.*, 1986, vol. 9: 2841–2847.
Jenkins, et al., *Journal of Exp. Medicine*, 1987, vol.165: 302–319.
Krillis, et al., *J. Allergy Clin. Immunol.*, 1984, vol. 74: 142–146.
Lamb, et al., *Clinical and Exp. Allergy*, 1989, vol. 19: 389–393.
Lamb, et al., *Journal of Immunol. Methods*, 1988, vol. 110: 1–10.
Lerner, et al., *Nature*, 1982, vol. 299: 592–596.
Margalit, et al., *The Journal of Immunol.*, 1987, vol. 138: 2213–2229.
O'Hehir, et al., *Int. Arch. Allergy Appl. Immunol.*, 1989, vol. 88: 170–172.
O'Hehir, et al., *Annu. Rev. Immunol.*, 1991, vol. 9: 67–95.
Rosenwasser, et al., Post Graduate Education Course Syllabus, AAAI Meeting, Mar. 5, 1991.
Schad, et al., *Immunology*, 1991, vol. 3: 217–224.
Stewart, et al., *Int. Archs. Allergy Appl. Immunol.*, 1987, vol. 83: 44–51.
Stewart, et al., *Int. Archs. Allergy Appl. Immunol.*, 1987, vol. 83: 384–359.
Stewart, et al., Proceedings of the DPC First Int'l Symposium on Allergy and Molecular Biology, Apr. 11–12, 1988, Laguna Niguel California.
Stewart, et al., *J. Allergy Immunol.*, 1986, vol. 4: 71 (Abstract).
Stewart, et al., Workshop XIVth Congress Europe Acad. Allergy and Clinical Immunol., Berlin, Germany, 1989.
Thomas, et al., *Int. Archs. Allergy Appl. Immunol.*, 1988, vol. 85: 127–129.
Thomas, et al., Mite Allergy A World–Wide problem, Bad Dreuznach, Sep. 1–2, 1987.
Thomas, et al., Epiotpes of Allergies, Proc. of Workshop XIVth Congress Europe Acad. Allergy and Clinical Immunol. Berlin, Germany, Sep. 1989.
Tovey, et al., *J. Exp. Med.*, 1991, vol. 170: 1457–1462.
Trudinger, et al., *Clinical and Exp. Allergy*, 1991, vol. 21: 33–37.
van't Hoff, et al., *Molecular Immunology*, 1991, vol. 28(11): 1225–1232.
Yssel, et al., Trinity College, Oxford, United Kingdom, Sep. 22–26, 1990.
Yssel, et al., *The Journal of Immunol.*, 1992, vol. 148(3): 738–745.
Yuuki, et al., *Arerugi*, 1990, vol. 39(6): 557–561 (Abstract).

*Primary Examiner*—Laurie Scheiner
*Attorney, Agent, or Firm*—Lanive & Cockfield, LLP

[57] ABSTRACT

The present invention provides isolated peptides of the major protein allergens of the genus Dermatophagoides. Peptides within the scope of the invention comprises at least one T cell epitope, or preferably at least two T cell epitopes of a protein allergen selected from the allergens Der p I, Der p II, Der f I, or Der f II. The invention also pertains to modified peptides having similar or enhanced therapeutic properties as the corresponding, naturally-occurring allergen or portion thereof, but having reduced side effects. The invention further provides nucleic acid sequences coding for peptides of the invention. Methods of treatment or of diagnosis of sensitivity to house dust mites in an individual and therapeutic compositions comprising one or more peptides of the invention are also provided.

13 Claims, 58 Drawing Sheets

Der fI adaptor

```
                T  S  A  C  R  I  N  S  V  N
5'-AATTTACCTCTGCTTGCCGTATCAACTCTGTTAACGCGGAATTCA-3' Hind III
φEcoR I 3'-ATGGAGACGAACGGCATAGTTGAGACAATTGCGCCTTAAGTTCGA-5'
                                          Hpa I    EcoR I
```

Der pI adaptor

```
                T  N  A  C  S
5'-AATTTACCAACGCCCTGCAGGCGAAGAATTCA-3' Hind III
φEcoR I 3'-ATGGTTGCGGGACGTCCGCTTCTTAAGTTCGA-5'
                       Pst I    EcoR I
```

Fig. 2a

5' Der fII/pII primer
5'-GGGAATTCGATCAAGTCGATGTCAAA-3'

3' fII/pII primer
5'-GGCTGCAGTTATATTTAATCGCGGATTTT-3'

Der fII mutagenesis primer
5'-AATTGAAAT[T]CAAAGCCA-3'

Fig. 2b

| Peptide Name | Sequence |
|---|---|
| DPI-1(1-20) | TNACSING*NAPAEIDLRQMR |
| DPI-2(13-39) | EIDLRQMRTVTPIRMQGGCGSCWAFSG |
| DPI-3(21-49) | TVTPIRMQGGCGSCWAFSGVAATESAYLA |
| DPI-4(40-60) | VAATESAYLAHRNQSLDLAEQ |
| DPI-11.1(50-71) | HRNQSLDLAEQELVDCASQHGC |
| DPI-12.1(61-81) | ELVDCASQHGCHGDTIPRGIE |
| DPI-5(73-100) | GDTIPRGIEYIQHNGVVQESYYRYVARE |
| DPI-5.1(81-100) | EYIQHNGVVQESYYRYVARE |
| DPI-13(85-109) | HNGVVQESYYRYVAREQSCRRPNAQ |
| DPI-14(101-119) | QSCRRPNAQRFGISNYCQI |
| DPI-15(110-131) | RFGISNYCQIYPPNANKIREAL |
| DPI-6.1(120-143) | YPPNANKIREALAQTHSAIAVIIG |
| DPI-7.1(132-157) | AQTHSAIAVIIGIKDLDAFRHYDGRT |
| DPI-8(144-169) | IKDLDAFRHYDGRTIIQRDNGYQPNY |
| DPI-9(158-180) | IIQRDNGYQPNYHAVNIVGYSNA |
| DPI-16(170-191) | HAVNIVGYSNAQGVDYWIVRNS |
| DPI-10(181-204) | QGVDYWIVRNSWDTNWGDNGYGYF |
| DPI-17(197-222) | GDNGYGYFAANIDLMMIEEYPYVVIL |
| DPI-21.1(1-28) | TNACSING*NAPAEIDLRQMRTVTPIRMQ |
| DPI-21.2(5-28) | SING*NAPAEIDLRQMRTVTPIRMQ |
| DPI-22.1(36-64) | AFSGVAATESAYLAHRNQSLDLAEQELVD |
| DPI-22.2(40-64) | VAATESAYLAHRNQSLDLAEQELVD |
| DPI-22.3(36-60) | AFSGVAATESAYLAHRNQSLDLAEQ |
| DPI-22.4(40-68) | VAATESAYLAHRNQSLDLAEQELVDCASQ |
| DPI-23.1(81-109) | EYIQHNGVVQESYYRYVAREQSCRRPNAQ |
| DPI-23.2(74-102) | DTIPRGIEYIQHNGVVQESYYRYVAREQS |
| DPI-25.1(118-146) | QIYPPNANKIREALAQTHSAIAVIIGIKD |

Fig. 3

```
DPI-25.2(118-139)    QIYPPNANKIREALAQTHSAIA
DPI-26.1(141-166)    IIGIKDLDAFRHYDGRTIIQRDNGYQ
DPI-27.1(161-185)    RDNGYQPNYHAVNIVGYSNAQGVDY
DPI-28.1(173-201)    NIVGYSNAQGVDYWIVRNSWDTNWGDNGY
DPI-28.2(173-195)    NIVGYSNAQGVDYWIVRNSWDTN
DPII-1(1-20)         DQVDVKDCANHEIKKVLVPG
DPII-2(11-35)        HEIKKVLVPGCHGSEPCIIHRGKPF
DPII-3.1(22-50)      HGSEPCIIHRGKPFQLEAVFEANQNTKTA
DPII-4(36-60)        QLEAVFEANQNTKTAKIEIKASIDG
DPII-5(51-77)        KIEIKASIDGLEVDVPGIDPNACHYMK
DPII-6(61-86)        LEVDVPGIDPNACHYMKCPLVKGQQY
DPII-7(78-104)       CPLVKGQQYDIKYTWNVPKIAPKSENV
DPII-8(87-112)       DIKYTWNVPKIAPKSENVVTVKVMG
DPII-9(105-129)      VVTVKVMGDDGVLACAIATHAKIRD
DPII-20(1-26)        DQVDVKDCANHEIKKVLVPGCHGSEP
DPII-20.1(1-26)E8    DQVDVKDEANHEIKKVLVPGCHGSEP
DPII-20.2(1-26)S8    DQVDVKDSANHEIKKVLVPGCHGSEP
DPII-20.3(1-26)E21   DQVDVKDCANHEIKKVLVPGEHGSEP
DPII-20.4(1-26)S21   DQVDVKDCANHEIKKVLVPGSHGSEP
DPII-20.5(1-26)E8E21 DQVDVKDEANHEIKKVLVPGEHGSEP
DPII-20.6(1-26)S8S21 DQVDVKDSANHEIKKVLVPGSHGSEP
```

Fig. 3 cont.

```
DPII-1.1(1-20)E8              DQVDVKDEANHEIKKVLVPG
DPII-1.2(1-20)S8              DQVDVKDSANHEIKKVLVPG
DPII-2.1(11-26)               HEIKKVLVPGCHGSEP
DPII-2.2(11-26)E21            HEIKKVLVPGEHGSEP
DPII-2.3(11-26)S21            HEIKKVLVPGSHGSEP
DPII-21(33-60)                KPFQLEAVFEANQNTKTAKIEIKASIDG
DPII-22(36-63)                QLEAVFEANQNTKTAKIEIKASIDGLEV
DPII-26(41-67)                FEANQNTKTAKIEIKASIDGLEVDVPG
DPII-26.1(45-67)              QNTKTAKIEIKASIDGLEVDVPG
DPII-23(79-104)               PLVKGQQYDIKYTWNVPKIAPKSENV
DPII-23.1(79-104)Y92          PLVKGQQYDIKYTYNVPKIAPKSENV
DPII-24(100-112)              KSENVVTVKVMG
DPII-25(107-129)              TVKVMGDDGVLACAIATHAKIRD
DPII-25.1(107-129)E119        TVKVMGDDGVLAEAIATHAKIRD
DPII-25.2(107-129)L111S119    TVKVLGDDGVLASAIATHAKIRD
```

Fig. 3 cont.

| Peptide Name | Sequence |
|---|---|
| DFI-1(1-20) | TSACRINSVNVPSELDLRSLR |
| DFI-2.1(13-39) | ELDLRSLRTVTPIRMQGGCGSCWAFSG |
| DFI-3(21-49) | TVTPIRMQGGCGSCWAFSGVAATESAYLA |
| DFI-4(40-60) | VAATESAYLAYRNTSLDLSEQ |
| DFI-11(50-71) | YRNTSLDLSEQELVDCASQHGC |
| DFI-12(61-81) | ELVDCASQHGCHGDTIPRGIE |
| DFI-5(73-100) | GDTIPRGIEYIQQNGVVEERSYPYVARE |
| DFI-13(85-109) | QNGVVEERSYPYVAREQRCRRPNSQ |
| DFI-14(101-119) | QRCRRPNSQHYGISNYCQI |
| DFI-15(110-131) | HYGISNYCQIYPPDVKQIREAL |
| DFI-6(120-143) | YPPDVKQIREALTQTHTAIAVIIG |
| DFI-7(132-157) | TQTHTAIAVIIGIKDLRAFRHYDGRT |
| DFI-8.1(144-169) | IKDLRAFQHYDGRTIIQHDNGYQPNY |
| DFI-8(154-168) | DGRTIIQHDNGYQPN |
| DFI-9(158-180) | IIQHDNGYQPNYHAVNIVGYGST |
| DFI-16(170-191) | HAVNIVGYGSTQGDDYWIVRNS |
| DFI-10(181-204) | QGDDYWIVRNSWDTTWGDSGYGYF |
| DFI-17(197-222) | GDSGYGYFQAGNNLMMIEQYPYVVIM |
| DFI-21.1(1-28) | TSACRINSVNVPSELDLRSLRTVTPIRMQ |
| DFI-21.2(5-28) | RINSVNVPSELDLRSLRTVTPIRMQ |
| DFI-22.1(36-64) | AFSGVAATESAYLAYRNTSLDLSEQELVD |
| DFI-22.2(40-64) | VAATESAYLAYRNTSLDLSEQELVD |
| DFI-22.4(40-68) | VAATESAYLAYRNTSLDLSEQELVDCASQ |
| DFI-23.1(81-109) | EYIQQNGVVEERSYPYVAREQRCRRPNSQ |
| DFI-23.2(74-102) | DTIPRGIEYIQQNGVVEERSYPYVAREQR |
| DFI-25.1(118-146) | QIYPPDVKQIREALTQTHTAIAVIIGIKD |
| DFI-25.2(118-139) | QIYPPDVKQIREALTQTHTAIA |
| DFI-26.1(141-166) | IIGIKDLRAFQHYDGRTIIQHDNGYQ |

Fig. 4

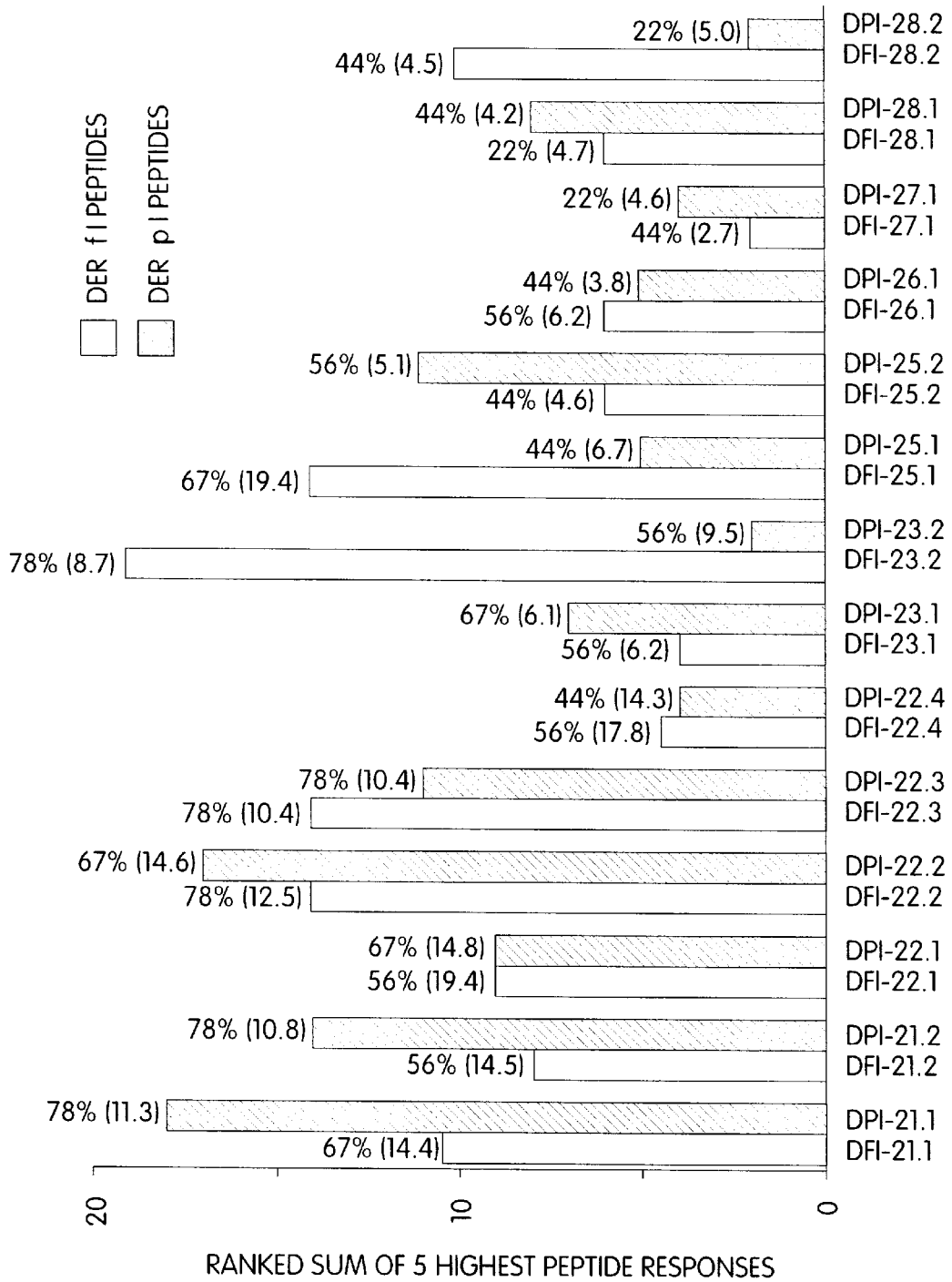

|  |  | 10 | 20 | 30 | 40 | 50 | 60 |
|---|---|---|---|---|---|---|---|
|  |  | TNACSINGNA | PAEIDLRQMR | TVTPIRMQGG | CGSCWAFSGV | AATESAYLAH | RNQSLDLAEQ |
| Der p I | (a) | ---------- | ---------- | ---------- | ---------- | ---------- | ---------- |
| Der p I | (b) | ---------- | ---------- | ---------- | ---------- | ------Y--- | ---------- |
| Der p I | (c) | ---------- | ---------- | ---------- | ---------- | ------Y--- | ---------- |
| Der p I | (d) | ---------- | ---------- | ---------- | ---------- | ---------- | ---------- |

|  |  | 70 | 80 | 90 | 100 | 110 | 120 |
|---|---|---|---|---|---|---|---|
|  |  | ELVDCASQHG | CHGDTIPRGI | EYIQHNGVVQ | ESYYRYVARE | QSCRRPNAQR | FGISNYCQIY |
| Der p I | (a) | ---------- | ---------- | ---------- | ---------- | ---------- | ---------- |
| Der p I | (b) | ---V------ | ---------- | K--------- | ---------- | ---------- | ---------- |
| Der p I | (c) | ---V------ | ---------- | ---------- | ---------- | ---------- | ---------- |
| Der p I | (d) | ---------- | ---------- | ---------- | ---------- | ---------- | ---------- |

|  |  | 130 | 140 | 150 | 160 | 170 | 180 |
|---|---|---|---|---|---|---|---|
|  |  | PPNANKIREA | LAQTHSAIAV | IIGIKDLDAF | RHYDGRTIIQ | RDNGYQPNYH | AVNIVGYSNA |
| Der p I | (a) | ---------- | ---------- | ---------- | ---------- | ---------- | ---------- |
| Der p I | (b) | ---------- | ---------- | ---------- | ---------- | ---------- | ---------- |
| Der p I | (c) | ---------- | ---------- | ---------- | ---------- | ---------- | ---------- |
| Der p I | (d) | ---------- | ----T----- | ---------- | ---------- | ---------- | ---------- |
| Der p I | (e) | ---------- | ---------- | ---------- | ---------- | ---------- | ---------- |

|  |  | 190 | 200 | 210 | 220 |  |  |
|---|---|---|---|---|---|---|---|
|  |  | QGVDYWIVRN | SWDTNWGDNG | YGYFAANIDL | MMIEEYPYVV | IL |  |
| Der p I | (a) | ---------- | ---------- | ---------- | ---------- | -- |  |
| Der p I | (b) | ---------- | ---------- | ---------- | ---Q------ | -- |  |
| Der p I | (c) | ---------- | ---------- | ---------- | ---------- | -- |  |
| Der p I | (d) | ---------- | ---------- | ---------- | ---------- | -- |  |
| Der p I | (e) | ---------- | ---------- | ---------- | ---------- | -- |  |

Fig. 22

```
                       10        20        30        40        50
Der p II (c) DQVDVKDCANHEIKKVLVPGCHGSEPCIIHRGKPFQLEAVFEANQNTKTAK
         (1) ................H....L.P.....E.........Q...V.E....T....
         (2) ................H....L.P.....E.........Q...V.E....S....
Der f II     ...........N......M.D....D..........T...L.D....T....

60        70        80        90       100
Der p II (c) IEIKASIDGLEVDVPGIDPNACHYMKCPLVKGQQYDIKYTWNVPKIAPKSE
         (1) .......I..........P....YM............I...........
         (2) .......I..........P....YM............I...........
Der f II     .......L..........T....FM....V.......A...........
                                                   I 110       120
Der p II (c) NVVVTVKVMGDDGVLACAIATHAKIRD
         (1) .......VM.DD.......A....I..
         (2) .......VM.ND.......A....L..
Der f II     .......LV.DN.......A....I..
                      I            G
```

Fig. 23

```
                  10         20         30         40         50         60
pFL1      DQVDVKDCANNEIKKVMVPGCHGSEPCIIHRGKPFTLEALFDANQNTKTAKIEIKASLDGLE
pFL2      ..........N.................................................
MT 3      ..........N...............................I.I..............
MT 5 (1-92) .......S.................................I..T..............
MT18 (1-84) ..........N...............................I.I..............
MT16 (1-70) ..........N...............................I.I..............
                                                  T.I 70         80         90        100        110        120        130
pFL1      IDVPGIDTNACHFVKCPLVKGQQYDIKYTWNVPKIAPKSENVVVTVKLIGDNGVLACAIATHAKIRD
pFL2      .............M...........A.......................V...............
MT 3      .............M...........A.......................V...............
MT 5      .............M............I.......................................
MT18      .............M.....................................................
```

Fig. 24

```
3'-ATTATTGGCATCAAAGATTTAGACGCATTCCGTCATTATGATGGCCGAACAATCATTCAA
    I  I  G  I  K  D  L  D  A  F  R  H  Y  D  G  R  T  I  I  Q

CGCGATAATGGTTACCAAACTGTTAAAGTTCTGGGTGATGATGGTGTTTTGGCCTCTGCT
 R  D  N  G  Y  Q  T  V  K  V  L  G  D  D  G  V  L  A  S  A

ATTGCTACTCATGCTAAAATCCGCGATGTTGCCGCAACTGAATCAGCTTATTTGGCCTAC
 I  A  T  H  A  K  I  R  D  V  A  A  T  E  S  A  Y  L  A  Y

CGTAACACGTCTTTGGATCTTTCTGAACAGGAACTCGTCGATCAATTGGAAGCCGTTTTC
 R  N  T  S  L  D  L  S  E  Q  E  L  V  D  Q  L  E  A  V  F

GAAGCCAACCAAAACACAAAAACCGCTAAAATTGAAATCAAAGCCTCAATCGATGGTTTA
 E  A  N  Q  N  T  K  T  A  K  I  E  I  K  A  S  I  D  G  L
```

Fig. 25

```
         310                320              330                340              350              360
          |                  |                |                  |                |                |
GAAGTTGAATACATCCAACATAATGGTGTCGTCCAAGAAAGCTACTATCGATACGTTGCA

E   V   E   Y   I   Q   H   N   G   V   V   Q   E   S   Y   Y   R   Y   V   A 370                380              390                400              410              420
          |                  |                |                  |                |                |
CGAGAACAATCATGCCGACGACCAAATGCACAAGATCAAGTCGATGTCAAAGATTCTGCC

R   E   Q   S   C   R   R   P   N   A   Q   D   Q   V   D   V   K   D   S   A 430                440              450                460              470              480
          |                  |                |                  |                |                |
AATCATGAAATCAAAAAAGTTTTGGTACCAGGATCGCATGGTTCAGAACCAAGTATCAAT

N   H   E   I   K   K   V   L   V   P   G   S   H   G   S   E   P   S   I   N 490                500              510                520              530              540
          |                  |                |                  |                |                |
GGAAATGCTCCAGCTGAAATCGATTTGCGACAAATGCGAACTGTCACTCCCATTCGTATG

G   N   A   P   A   E   I   D   L   R   Q   M   R   T   V   T   P   I   R   M

CAATAATGA-3'

```
5'-ACTGTTAAAGTTCTGGGTGATGATGGTGTTTTGGCCCTCTGCTATTGCTACTCATGCTAAA   60
    T  V  K  V  L  G  D  D  G  V  L  A  S  A  I  A  T  H  A  K

ATCCGCGATGTTGCCGCAACTGAATCAGCTTATTTGGCCTACCGTAACACGTCTTTGGAT    120
    I  R  D  V  A  A  T  E  S  A  Y  L  A  Y  R  N  T  S  L  D

CTTTCTGAACAGGAACTCGTTGACGAATACATCCAACATAATGGTGTCGTCCAAGAAAGC    180
    L  S  E  Q  E  L  V  D  E  Y  I  Q  H  N  G  V  V  Q  E  S

TACTATCGATACGTTGCACGAGAACAATCATGCCGACGACCAAATGCACAACAATTGGAA    240
    Y  Y  R  Y  V  A  R  E  Q  S  C  R  R  P  N  A  Q  Q  L  E

GCCGTTTTCGAAGCCAACCAAAACACAAAAACGGCTAAATTGAAATCAAAGCCTCAATC    300
    A  V  F  E  A  N  Q  N  T  K  T  A  K  I  E  I  K  A  S  I

Fig. 26
```

```
       310—        320—        330—        340—        350—        360—
GATGGTTTAGAAGTTATTATTGGCATCAAAGATTTAGACGCATTCCGTCATTATGATGGC
 D  G  L  E  V  I  I  G  I  K  D  L  D  A  F  R  H  Y  D  G

370—        380—        390—        400—        410—        420—
CGAACAATCATTCAACGCGATAATGGTTACCAAAGTATCAATGGAAATGCTCCAGCTGAA
 R  T  I  I  Q  R  D  N  G  Y  Q  S  I  N  G  N  A  P  A  E

430—        440—        450—        460—        470—        480—
ATCGATTTGCGACAAATGCGAACTGTCACTCCCATTCGTATGCAAGATCAAGTCGATGTC
 I  D  L  R  Q  M  R  T  V  T  P  I  R  M  Q  D  Q  V  D  V

490—        500—        510—        520—        530—        540—
AAAGATTCTGCCAATCATGAAATCAAAAAAGTTTTGGTACCAGGATCGCATGGTTCAGAA
 K  D  S  A  N  H  E  I  K  K  V  L  V  P  G  S  H  G  S  E

CCATAATGA-5'
 P  -  -
```

Fig. 26 cont.

5'-ACTGTTAAAGTTTTGGGTGATGATGGTGTTTTGGCCTCAGCTATTGCTACTCATGCTAAA

T V K V L G D D D G V L A S A I A T H A K

ATCCGCGATAGTATCAATGGAAATGCTCCAGCTGAAATCGATTTGCGACAAATGCGAACT

I R D S I N G N A P A E I D L R Q M R T

GTCACTCCCATTCGTATGCAAGAATACATTCAACATAATGGTGTCGTCCAAGAAAGCTAC

V T P I R M Q E Y I Q H N G V V Q E S Y

TATCGATACGTTGCACGAGAACAATCATGCCGACGACCAAATGCACAAATTATTGGCATC

Y R Y V A R E Q S C R R P N A Q I I G I

AAAGATTTAGACGCATTCCGTCATTATGATGGCCGAACAATCATTCAACGCGATAATGGT

```
           310        320        330        340        350        360
            |          |          |          |          |          |
         TACCAACAATTGGAAGCCGTTTTCGAAGCCAACCAAAACACAAAAACGGCTAAAATTGAA
          Y  Q  Q  L  E  A  V  F  E  A  N  Q  N  T  K  T  A  K  I  E 370        380        390        400        410        420
            |          |          |          |          |          |
         ATCAAAGCCTCAATCGATGGTGTTTAGAAGTTGATCAAGTCGATGTCAAAGATTCAGCCAAT
          I  K  A  S  I  D  G  L  E  V  D  Q  V  D  V  K  D  S  A  N 430        440        450        460        470        480
            |          |          |          |          |          |
         CATGAAATCAAAAAAGTTTTGGTACCAGGATCACACATGGTTCAGAACCAGTTGCCGCAACT
          H  E  I  K  K  V  L  V  P  G  S  H  G  S  E  P  V  A  A  T 490        500        510        520        530        540
            |          |          |          |          |          |
         GAATCAGCTTATTTGGCCTACCGTAACACGTCTTTTGGATCTTTCTGAACAGGAACTCGTC
          E  S  A  Y  L  A  Y  R  N  T  S  L  D  L  S  E  Q  E  L  V

GATTAGTAG-5'
          D  -  -
```

Fig. 27 cont.

DP I-23.1    EYIQHNGVVQESYYRYVAREQSCRRPNAQ
DP I-23.1.1  KKEYIQHNGVVQESYYRYVAREQSCRRPNAQ
DP I-23.1.2   KEYIQHNGVVQESYYRYVAREQSCRRPNAQ
DP I-23.1.3    EYIQHNGVVQESYYRYVAREQSSRRPNAQ
DP I-23.1.4    EYIQHNGVVQESYYRYVAREQSERRPNAQ

DP II-22      QLEAVFEANQNTKTAKIEIKASIDGLEV
DP II-22.1  KKQLEAVFEANQNTKTAKIEIKASIDGLEV
DP II-22.2   KQLEAVFEANQNTKTAKIEIKASIDGLEVK

Fig. 28

| | |
|---|---|
| DPI-21.7 | KSINGNAPAEIDLRQLRTVTPIRLQ |
| DPI-23.10 | KKEYIQHNGVVQESYYRYVAREQSCRRPNAQ |
| DPI-23.13 | KKEYIQHNGVVQESYYRYVAREQSSRRPNAQ |
| DPI-23.14 | KKEYIQHNGVVQESYYRYVAREQSERRPNAQ |
| DPI-23.11 | DKEYIQHNGVVQESYYRYVAREQSSRRPNAQR |
| DPI-23.12 | DKEYIQHNGVVQESYYRYVAREQSCRRPNAQR |
| DPI-23.5 | DEYIQHNGVVQESYYRYVAREQSCRRDD |
| DPI-23.6 | DEYIQHNGVVQESYYRYVAREQSSRRDD |
| DPI-23.7 | DEYIQHNGVVQESYYRYVAREQSCRRPD |
| DPI-23.8 | DEYIQHNGVVQESYYRYVAREQSSRRPD |
| DPI-23.9 | DEYIQHNGVVQESYYRYVAREQSE |
| DPI-23.15 | RYVAREQSCRRPNAQ |
| DPI-23.16 | RYVAREQSERRPNAQ |
| DPI-23.17 | RYVAREQSSRRPNAQ |
| DPI-26.2 | DEGIKDLDAFRHYDGRTIIQRDNGYQ |
| DPI-26.3 | IGIKDLDAFRHYD |
| DPI-26.4 | DAFRHYDGRTIIQ |
| DPI-26.5 | TIIQRDNGYQPNY |
| DPII-20.7 | DQVDVKDSANHEIKVLVPGSHGSEPK |
| DPII-22.6 | DKQLEAVFEANQNTKTAKIEIKASIDGLEVD |
| DPII-22.3 | DKQLEAVFEANQNTKTAKIEIKASIDGLEVK |
| DPII-22.4 | QLEAVFEANQNTKTAKIEIKASIDE |
| DPII-22.5 | DKQLEAVFEANQNTKTAKIEIKASIDE |
| DPII-22.7 | AKIEIKASIDGLE |
| DPII-22.8 | DKEQLEAVFEANQNTKTAKIEIKASIDE |
| DPII-22.9 | DKEQLEAVFEANQNTKTAKIEIKASIDEE |
| DPII-22.10 | LEAVFEANQNTKTAK |
| DPII-22.11 | LEAVFEANQATKTAK |
| DPII-25.3 | KTVKVLGDDGVLASAIATHAKIRD |
| DPII-25.4 | DTVKVLGDDGVLASAIATHAKIRD |

Fig. 29

| NAME | SEQUENCE | |
|---|---|---|
| DpI-23.32 | KKEYIQHNGVVQESYYRYVAREQSCRRPNAER | |
| DpI-23.33 | KKEYIQHNGVVQESYYRYVAREQSCRRPNAEK | |
| DpI-23.31 | DEEGVVQESYYRYVAREQSCRRPNAE | |
| DpI-23.34 | DKEGVVQESYYRYVAREQSCRRPNAKE | |
| DpI-23.35 | DEKEGVVQESYYRYVAREQSCRRPNADKE | |
| DpI-26.6 | DEGIKDLDAFRHYDGRTIIQRDNGYE | |
| DpII-20.9 | DQVDVKDCANHEIKKVLVPGCHGSE | |
| DpII-20.11 | DQVDVKDCANHEIKKVLVPGCHGSE | ox |
| DpII-20.10 | DQVDVKDCANHEIKKVLVPGCHGSEG | |
| DpII-20.8 | DQVDVKDCANHEIKKVLVPGCHGSEPK | |
| DpII-22.19 | DKELEAVFEANQNTKTAKIEIKAD | |
| DpII-22.20 | DKELEAVFEANQNTKTAKIEIKAK | |
| DpII-22.21 | DKELEAVFEANQNTKTAKIEIKD | |
| DpII-22.22 | DKELEAVFEANQNTKTAKIEIKK | |
| DpII-22.26 | DKELEAVFEANQNTKTAKIEIK | |
| DpII-22.23 | DKELEAVFEANQNTKTAKIED | |
| DpII-22.24 | DKELEAVFEANQNTKTAKIEK | |
| DpII-22.25 | DKELEAVFEANQNTKTAKIE | |
| DpII-22.14 | DKELEAVFEANQNTKTAKAE | |
| DpII-25.0 | TVKVMGDDGVLACAIATHAKIRD | |
| DfII-25.11 | TVKLVGDDGVLACAIATHAKIRD | |
| DpII-25.9 | DKTVKVMGDDGVLACAIATHAKIRDKE | |
| DfII-25.10 | DKTVKLVGDNGVLACAIATHAKIRDKE | |
| DfII-25.12 | DKTVKLVGDDGVLACA | |
| DfII-25.13 | DKTVKLVGDGVLACA | |
| DpII-25.14 | KKTVKVMGDDGVLACAIATHAKIRDKK | |
| DpII-25.15 | DEETVKVMGDDGVLACAIATHAKIRDEE | |
| DpII-25.16 | DKEKTVKVMGDDGVLACAIATHAKIRDKEK | |
| DpII-25.17 | KKTVKVMGDDGVLACAIATHAKKK | |
| DpII-25.18 | DKEKTVKVMGDDGVLACAIATHAKKK | |

Fig. 30

| NAME | SEQUENCE |
|---|---|
| DPI-21.2 | SINGNAPAEIDLRQMRTVTPIRMQ |
| DFI-22.2 | VAATESAYLAYRNTSLDLSEQELVD |
| DPI-23.31 | DEEGVVQESYYRYVAREQSCRRPNAE |
| DPI-26.6 | DEGIKDLDAFRHYDGRTIIQRDNGYE |
| DPII-20.9 | DQVDVKDCANHEIKKVLVPGCHGSE |
| DPII-22.14 | DKELEAVFEANQNTKTAKAE |
| DPII-25.15 | DEETVKVMGDDGVLACAIATHAKIRDEE |

Fig. 33

| PEPTIDE NAME | |
|---|---|
| DPI-1 (1-20) | TNACSING*NAPAEIDLRQMR |
| DPI-2 (13-39) | EIDLRQMRTVTPIRMQGGCGSCWAFSG |
| DPI-3 (21-49) | TVTPIRMQGGCGSCWAFSGVAATESAYLA |
| DPI-4 (40-60) | VAATESAYLAHRNQSLDLAEQ |
| DPI-11.1 (50-71) | HRNQSVDLAEQELVDCASQHGC |
| DPI-12.1 (61-81) | ELVDCASQHGCHGDTIPRGIE |
| DPI-5.1 (81-100) | EYIQHNGVVQESYYRYVARE |
| DPI-13 (85-109) | HNGVVQESYYRYVAREQSCRRPNAQ |
| DPI-14 (101-119) | QSCRRPNAQRFGISNYCQI |
| DPI-15 (110-131) | RFGISNYCQIYPPNANKIREAL |
| DPI-6.1 (120-143) | YPPNANKIREALAQTHSAIAVIIG |
| DPI-7.1 (132-157) | AQTHSAIAVIIGIKDLDAFRHYDGRT |
| DPI-8 (144-169) | IKDLDAFRHYDGRTIIQRDNGYQPNY |
| DPI-9 (158-180) | IIQRDNGYQPNYHAVNIVGYSNA |
| DPI-16 (170-191) | HAVNIVGYSNAQGVDYWIVRNS |
| DPI-10 (181-204) | QGVDYWIVRNSWDTNWGDNGYGYF |
| DPI-17 (197-222) | GDNGYGYFAANIDLMMIEEYPYVVIL |
| DPII-1 (1-20) | DQVDVKDCANHEIKKVLVPG |
| DPII-2 (11-35) | HEIKKVLVPGCHGSEPCIIHRGKPF |
| DPII-3.1 (22-50) | HGSEPCIIHRGKPFQLEAVFEANQNTKTA |
| DPII-4 (36-60) | QLEAVFEANQNTKTAKIEIKASIDG |
| DPII-5 (51-77) | KIEIKASIDGLEVDVPGIDPNACHYMK |
| DPII-6 (61-86) | LEVDVPGIDPNACHYMKCPLVKGQQY |
| DPII-7 (78-104) | CPLVKGQQYDIKYTWNVPKIAPKSENV |
| DPII-8 (87-112) | DIKYTWNVPKIAPKSENVVVTVKVMG |
| DPII-9 (105-129) | VVTVKVMGDDGVLACAIATHAKIRD |

Fig. 34

T CELL EPITOPES OF THE MAJOR ALLERGENS FROM DERMATOPHAGOIDES (HOUSE DUST MITE)

RELATED APPLICATIONS

This application is a divisional of U.S. Ser. No. 08/445,307, filed May 19, 1995, which is continuation-in-part of U.S. Ser. No. 08/227,772 filed Apr. 14, 1994. This application also claims priority to PCT/US95/04481 filed Apr. 12, 1995. All of the above identified cases are hereby incorporated herein by reference.

BACKGROUND OF THE INVENTION

Recent reports have documented the importance of responses to the Group I (e.g., Der p I and Der f I) and Group II (e.g., Der p II and Der f II) protein allergens in house dust mite allergy. For example, it has been documented that over 60% of patients have at least 50% of their anti-mite antibodies directed towards these proteins (e.g., Lind, P. et al., *Allergy.* 39:259–274 (1984); van der Zee, J. S. et al., *Journal Allergy and Clinical Immunology,* 81:884–896 (1988)). It is possible that children show a greater degree of reactivity to the Group I and Group II allergens (Thompson, P. J., et al., *Immunology,* 64:301–314 (1988)). Allergy to mites of the genus Dermatophagoides (D.) is associated with conditions such as asthma, rhinitis and ectopic dermatitis. Two species, *D. pteronyssinus* and *D. farinae,* predominate and, as a result, considerable effort has been expended in trying to identify the allergens produced by these two species.

A concerted effort has been made to characterize by gene cloning the major allergens from both *D. pteronyssinus* and *D. farinae.* Consequently, several publications have reported the complete nucleotide sequences of several allergens including Der p I (Thomas, W. R., et al., *International Archives of Allergy and Applied Immunology,* 85:127–129 (1988); and Chua, K. Y., et al., *Journal of Experimental Medicine,* 167:175–182 (1988)), Der p II (Chua, K. Y., et al., *International Archives of Allergy and Applied Immunology,* 91:118–123 (1990)), Der f I (Dilworth, R. J., et al., *Clinical and Experimental Allergy,* 21:25–32 (1891)), Der f II (Yuuki, T., et al., *Japan Journal Allergol.,* 39:557–461 (1990); and Trudinger, M., et al., *Clinical and Experimental Allergy,* 21:33–37 (1991)) and a low molecular weight allergen (Ovey, E. R., et al., *Journal of Experimental Medicine,* 170:1457–1462 (1989)).

The published nucleotide sequences of cDNAs encoding Der p I and Der f I demonstrate that these two proteins are highly homologous at the amino acid level (81% identity) and that the mature protein products are comprised of 222 and 223 residues, respectively (Chua, K. Y., et al., *Journal of Experimental Medicine,* 167:175–182 (1988); and Dilworth, R. J., et al., supra)). The protein allergens Der p II and Der f II are both comprised of 129 residues, and are also highly homologous (88% identity) in amino acid sequence (Trudinger, M., et al. supra; Yuuki, T., et al. supra); Chua, K. Y., et al, *International Archives of Allergy and Applied Immunology,* 91:118–123 (1990)).

The isolation of cDNAs clones encoding Der p I and Der p II has permitted antibody binding studies on the recombinant antigens (Green, W. K., et al., *International Archives of Allergy and Applied Immunology,* 92:30–38 (1990); Chua, K. Y., et al., *International Archives of Allergy and Applied Immunology,* 91:124–129 (1990)). Complementary DNA fragments of Der p I have been expressed in *E. coli* and IgE binding studies with pooled human mite allergic IgE sera have demonstrated binding and non-binding regions throughout the molecule (Thomas, W. R., et al., In: *Epitopes of Atopic Allergens, Proceedings of Workshop from XIV Congress of the European Academy of Allergy and Clinical Immunology,* Berlin, September 1989. pp 77–82). T cell epitopes of Der p I have been reported (O'Hehir, R. E., et al., *Annual Review Immunology,* 9:67–95 (1991); Stewart, G. A., et al., In: *Epitopes of Atopic Allergens, Proceedings of Workshop from XIV Congress of the European Academy of Allergy and Clinical Immunology.* Berlin, September 1989. pp 41–47; Yessel, H., et al., In: T cell Activation in Health and Disease: Discrimination Between Immunity and Tolerance, Conference 22–26 September, 1990, Trinity College, Oxford, U.K. and Hessel, H., et al., *Journal of Immunology,* 148(3): 738–745 (Feb. 1, 1992).

SUMMARY OF THE INVENTION

The present invention provides isolated peptides of the major protein allergens of the genus Dermatophagoides. Preferred peptides within the scope of the invention comprise at least one T cell epitope, and may comprise at least two T cell epitopes of a protein allergen selected from the allergens Der p I, Der p II, Der f I, or Der f II. The invention further provides peptides comprising at least two regions, each region comprising at least one T cell epitope of a mite protein allergen. The regions are derived from the same or from different protein allergens of the genus Dermatophagoides.

The invention also provides modified peptides having similar or enhanced therapeutic properties as the corresponding, naturally-occurring allergen or portion thereof, but having reduced side effects, as well as modified peptides having improved properties such as increased solubility and stability. Peptides of the invention are capable of modifying, in a house dust mite-sensitive individual to whom they are administered, the allergic response of the individual to a house dust mite allergen or an allergen immunologically cross-reactive with house dust mite allergen. Methods of treatment or of diagnosis of sensitivity to house dust mite in an individual and therapeutic compositions comprising one or more peptides of the invention are also provided.

The present invention further provides optimized therapeutic compositions and multipeptide formulations comprising "unique" peptides of the invention. Such therapeutic compositions have been optimized to accomodate and maintain the unique characteristics of the "unique" peptides of the invention, and at the same time provide maximum therapeutic effect when used in therapeutic regimens for the treatment of house dust mite allergy in humans.

BRIEF DESCRIPTION OF THE DRAWINGS

FIG. 2a shows adaptors used in the expression of Der p I and Der f I and FIG. 2b shows primers for amplification of Der f II and Der p II and a Der f II mutagenesis primer.

FIG. 3 shows various peptides of desired lengths derived from the Der p I and Der p II protein allergens.

FIG. 4 shows various peptides of desired lengths derived from the Der f I and Der f II protein allergens.

FIG. 14 is a graphic representation depicting the responses of T cell lines from 9 patients primed in vitro to the Der f I protein and analyzed for response to selected peptides of desired lengths derived from the Der f I protein allergen, by percent of responses with an S.I. of at least 2 within the individuals tested and the mean T cell stimulation index of positive responses for the peptide and the ranked sum of peptide responses.

FIG. 22 is a composite alignment of the amino acid sequences of five Der p I clones (a)–(e) which illustrates polymorphism in the Der p I protein. The numbering refers to the sequence of the Der p I(a) clone. The symbol (-) is used to indicate that the amino acid residue of a Der p I clone is identical to the corresponding amino acid sequences of Der p I(a) at that position. The amino acid sequences of these clones indicate that there may be significant variation in Der p I, with five polymorphic amino acid residues found in the five sequences.

FIG. 23 is a composite alignment of the amino acid sequences of three Der p II clones (c), (1) and (2) which illustrates polymorphism in the Der p II protein. The numbering refers to the sequence of the Der p II (c) clone. The symbol (.) is used to indicate that the amino acid residue of a Der p II clone is identical to the corresponding amino acid residue of Der p II (c) at that position.

FIG. 24 is a composite alignment of the amino acid sequences of six Der f II clones (i.e., pFL1 (SEQ ID NO: 157), pFL2 (SEQ ID NO: 158), MT3 (SEQ ID NO: 159), Mr5 (SEQ ID NO: 160), MT18 (SEQ ID NO: 161) and MT16 (SEQ ID NO: 162)) which illustrates polymorphism is the Der f II protein. The numbering refers to the sequences of the Der f pLF1 clone. The symbol (.) is used to indicate that the amino acid residue of a Der f II clone is identical to the corresponding amino acid residue of Der f II pFL1 at that position.

FIG. 25 shows the nucleotide and amino acid sequences of a selected peptide which comprises various regions derived from Der p I, Der p II and Der f I protein allergens.

FIG. 26 shows the nucleotide and amino acid sequences of a selected peptide which comprises various regions derived from Der p I, Der p II and Der f I protein allergens.

FIG. 27 shows the nucleotide and amino acid sequences of a selected peptide which comprises various regions derived from Der p I, Der p II and Der f I protein allergens.

FIG. 28 shows the amino acid sequences of modified peptides in accordance with the invention.

FIG. 29 shows the amino acid sequences of various modified peptides of the invention.

FIG. 30 shows the amino acid sequences of various modified peptides of the invention.

FIG. 33 shows the amino acid sequences of the "unique" peptides in accordance with the invention including the novel "unique" peptides of the invention.

FIG. 34 shows overlapping peptides derived from Der p I and Der p II protein allergens used in T cell studies described herein.

DETAILED DESCRIPTION OF THE INVENTION

Figure 1:
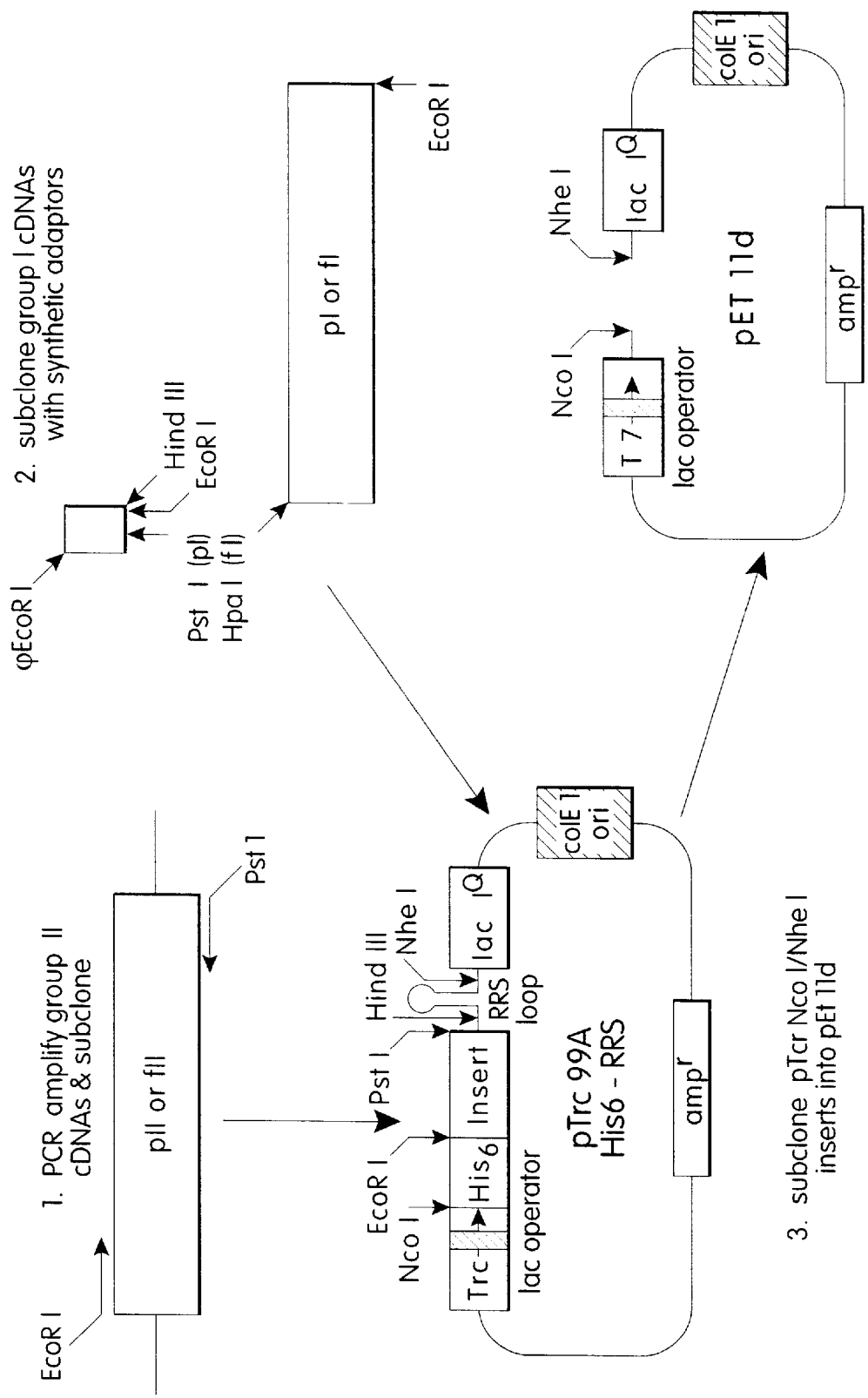
FIG. 1 shows the subcloning and expression of Group I and Group II allergens from *D. pteronyssinus* and *D. farinae.*
Figure 5:
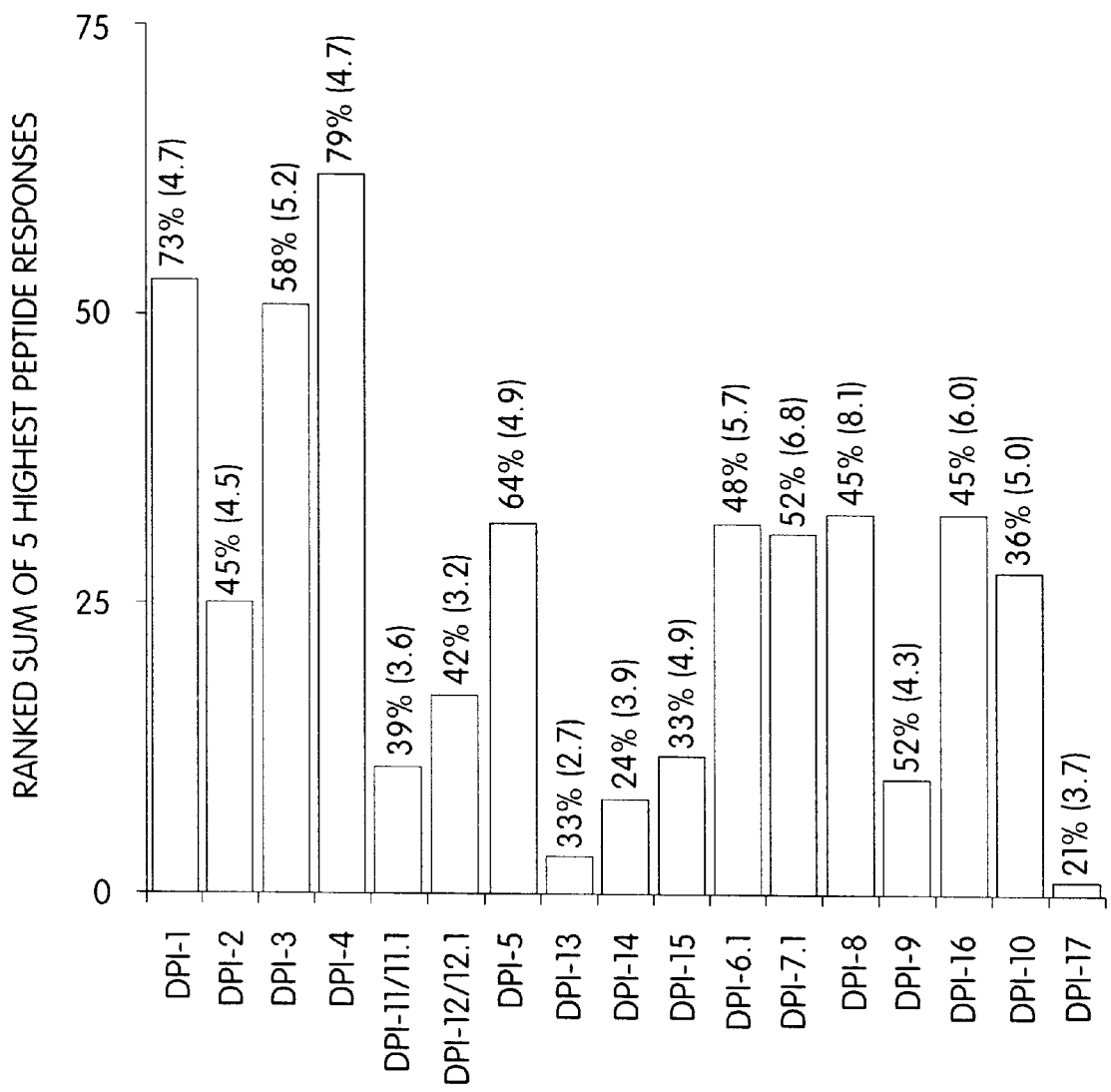
FIG. 5 is a graphic representation depicting the responses of T cell lines from 33 patients primed in vitro to either purified native (N) or recombinant (R) Der p I protein and analyzed for response to various overlapping Der p I peptides by percent of responses with a T cell Stimulation Index (S.I.) of at least 2 within the individuals tested, the mean T cell stimulation index of positive responses for the peptide and the ranked sum of peptide responses.

The present invention provides isolated peptides derived from the major protein allergens of the genus Dermatophagoides. As used herein, a "peptide" refers to an amino acid sequence having fewer amino acid residues than the entire amino acid sequence of the protein from which the peptide was derived. The term "peptide" also refers to any functional equivalents of a peptide or to any fragments or portions of a peptide. Peptides of the invention include peptides derived from Der p I (SEQ ID NO: 1 and 2), Der p II (SEQ ID NO: 3 and 4), Der f I (SEQ ID NO: 5 and 6) and Der f II (SEQ ID NO: 7 and 8) which are antigenic (i.e. have the ability to induce an immune response). Preferably, peptides of the invention comprise at least one T cell epitope of the allergen.

Peptides comprising at least two regions, each region comprising at least one T cell epitope of a protein allergen of the genus Dermatophagoides are also within the scope of the invention. Each region of such peptides is derived from the same or from different mite allergens. Isolated peptides or regions of isolated peptides, each comprising at least two T cell epitopes of a mite protein allergen are also desirable for therapeutic effectiveness. Peptides which are immunologically related (e.g., by antibody or T cell cross-reactivity) to peptides of the present invention are also within the scope of the invention. Peptides immunologically related by antibody cross-reactivity are bound by antibodies specific for a peptide of a protein allergen of the genus Dermatophagoides. Peptides immunologically related by T cell cross-reactivity are capable of reacting with the same T cells as a peptide of the invention.

The present invention also provides modified peptides. As used herein, the term "modified peptide" refers to a peptide derived from a protein allergen of the genus Dermatophagoides in which the amino acid sequence has been altered by amino acid substitution, deletion or addition. Modified peptides also include those peptides which are modifications or variations of peptides of the invention defined herein such as by amino acid substitution, deletion or addition.

Isolated peptides of the invention can be produced by recombinant DNA techniques in a host cell transformed with a nucleic acid having a sequence encoding such peptide. The isolated peptides of the invention can also be produced by chemical synthesis. In certain situations, isolated peptides can be produced by chemical cleavage of the protein allergen.

When a peptide is produced by recombinant techniques, host cells transformed with a nucleic acid of the invention (or the functional equivalent of the nucleic acid having a sequence encoding the peptide (or functional equivalent of the peptide) are cultured in a medium suitable for the cells. Peptides can be purified from cell culture medium, host cells, or both using techniques known in the art for purifying peptides and proteins including ion-exchange chromatography, gel filtration chromatography, ultrafiltration, electrophoresis or immunopurification with antibodies specific for the peptide, the protein allergen of the genus Dermatophagoides from which the peptide is derived, or a portion thereof. Isolated peptides of the invention are substantially free of cellular material or culture medium when produced by recombinant DNA techniques, or substantially free of chemical precursors or other chemicals when synthesized chemically or free of other materials and reagents when produced by chemical cleavage.

The term "nucleic acid" as used herein is intended to include fragments or equivalents of nucleic acids of the invention. Nucleic acid sequences used in any embodiment of this invention can be cDNA as described herein, or alternatively, can be any oligodeoxynucleotide sequence having all or a portion of a sequence represented herein, or their functional equivalents. Such oligodeoxynucleotide sequences can be produced chemically or mechanically, using known techniques. A functional equivalent of an oligonucleotide sequence is one which is 1) a sequence capable of hybridizing to a complementary oligonucleotide to which the sequence (or corresponding sequence portions) of SEQ ID NO: 1, SEQ ID NO: 3, SEQ ID NO: 5 and SEQ ID NO: 7, or fragments thereof hybridizes, or 2) the sequence (or corresponding sequence portion) complementary to SEQ ID NO: 1, SEQ ID NO: 3, SEQ ID NO: 5 and SEQ ID NO: 7 and/or 3 a sequence which encodes a product (e.g., a polypeptide or peptide) having the same functional characteristics of the product encoded by the sequence (or corresponding sequence portion) of SEQ ID NO: 1, SEQ ID NO: 3, SEQ ID NO: 5 and SEQ ID NO: 7. Whether a functional equivalent must meet one or more criteria will depend on its use (e.g., if it is to be used only as an oligoprobe, it need meet only the first or second criteria and if it is to be used to produce a peptide of the present invention, it need only meet the third criterion).

As used herein, the "functional equivalent" of a peptide includes peptides having the same or enhanced ability to bind MHC, peptides capable of stimulating the same T cell subpopulations, peptides having the same or increased ability to induce T cell responses such as stimulation (proliferation or cytokine secretion), peptides having the same or increased ability to induce T cell non-responsiveness or reduced responsiveness to a mite allergen, peptides having at least the same level of reduced IgE binding, and peptides which elicit at least the same minimal level of IgE synthesis stimulating activity. Minimal IgE stimulating activity refers to IgE synthesis stimulating activity that is less than the amount of IgE production elicited by a purified native mite allergen Preferred nucleic acids encode a peptide having at least about 50% homology to a peptide of the invention, more preferably at least about 60% homology and most preferably at least about 70% homology with a peptide of the invention. Nucleic acids which encode peptides having at least about 90%, more preferably at least about 95%, and most preferably at least about 98–99% homology with a peptide of the invention are also within the scope of the invention. Homology refers to sequence similarity between two peptides or between two nucleic acid molecules. Homology can be determined by comparing a position in each sequence which may be aligned for purposes of comparison. When a position in the compared sequence is occupied by the same base or amino acid, then molecules are homologous at that position. A degree of homology between sequences is a function of the number of matching or homologous positions shared by the sequences.

The present invention provides expression vectors and host cells transformed to express the nucleic acid sequences of the invention. A nucleic acid sequence coding for a peptide of the invention or at least one fragment or portion thereof may be expressed in bacterial cells such as *E. coli*, insect cells (baculovirus), yeast, or mammalian cells such as Chinese hamster ovary cells (CHO). Suitable expression vectors, promoters, enhancers, and other expression control elements may be found in Sambrook et al. *Molecular Cloning: A Laboratory Manual*, second edition, Cold Spring Harbor Laboratory Press, Cold Spring Harbor, N.Y. (1989). Other suitable expression vectors, promoters, enhancers, and other expression elements are known to those skilled in the art. Expression in mammalian, yeast or insect cells leads to partial or complete glycosylation of the recombinant material and formation of any inter- or intra-chain disulfide bonds. Suitable vectors for expression in yeast include YepSec1 (Baldari et al. (1987) *Embo J.*, 6: 229–234); pMFa (Kuijan and Herskowitz (1982) *Cell*, 30: 933–943); JRY88 (Schultz et al. (1987) *Gene*, 54: 113–123) and pYES2 (Invitrogen Corporation, San Diego, Calif.). These vectors are freely available. Baculovirus and mammalian expression systems are also available. For example, a baculovirus system is commercially available (PharMingen, San Diego, Calif.) for expression in insect cells while the pMSG vector is commerically available (Pharmacia, Piscataway, N.J.) for expression in mammalian cells.

For expression in *E. coli,* suitable expression vectors include, among others, pTRC (Amann et al. (1988) *Gene,* 69: 301–315); pGEX (Amrad Corp., Melbourne, Australia); pMAL (N.E. Biolabs, Beverly, Mass.); pRIT5 (Pharmacia, Piscataway, N.J.); pET-11d (Novagen, Madison, Wis.) Jameel et al., (1990) *J. Virol.,* 64:3963–3966; and pSEM (Knapp et al. (1990) *BioTechniques,* 8:280–281). The use of pTRC, and pET-11d, for example, will lead to the expression of unfused protein. The use of pMAL, pRIT5 pSEM and pGEX will lead to the expression of allergen fused to maltose E binding protein (pMAL), protein A (pRIT5), truncated β-galactosidase (PSEM), or glutathione S-transferase (pGEX). When a mite peptide of the invention is expressed as a fusion protein, it is particularly advantageous to introduce an enzymatic cleavage site at the fusion junction between the carrier protein and a mite peptide. A mite peptide of the invention may then be recovered from the fusion protein through enzymatic cleavage at the enzymatic site and biochemical purification using conventional techniques for purification of proteins and peptides. Suitable enzymatic cleavage sites include those for blood clotting Factor Xa or thrombin for which the appropriate enzymes and protocols for cleavage are commercially available from, for example, Sigma Chemical Company, St. Louis, Mo. and N.E. Biolabs, Beverly, Mass. The different vectors also have different promoter regions allowing constitutive or inducible expression with, for example, IPTG induction (PRTC, Amann et al., (1988) supra; pET-11d, Novagen, Madison, Wis.) or temperature induction (pRIT5, Pharmacia, Piscataway, N.J.). It may also be appropriate to express recombinant peptides of the invention in different *E. coli* hosts that have an altered capacity to degrade recombinantly expressed proteins (e.g. U.S. Pat. No. 4,758,512). Alternatively, it may be advantageous to alter the nucleic acid sequence to use codons preferentially utilized by *E. coli,* where such nucleic acid alteration would not affect the amino acid sequence of the expressed protein.

Host cells can be transformed to express the nucleic acid sequences of the invention using conventional techniques such as calcium phosphate or calcium chloride co-precipitation, DEAE-dextran-mediated transfection, or electroporation. Suitable methods for transforming the host cells may be found in Sambrook et al. supra, and other laboratory textbooks.

Inducible non-fusion expression vectors include pTrc (Amann et al., (1988) *Gene,* 69:301–315) and pET11d (Studier et al., *Gene Expression Technology: Methods in Enzymology,* 185, Academic Press, San Diego, Calif.(1990) 60–89). While target gene expression relies on host RNA polymerase transcription from the hybrid trp-lac fusion promoter in pTrc, expression of target genes inserted into pET11d relies on transcription from the T7 gn10-lac 0 fusion promoter mediated by coexpressed viral RNA polymerase (T7 gn1). This viral polymerase is supplied by host strains BL21 (DE3) or HMS174(DE3) from a resident λ prophage harboring a T7 gn1 under the transcriptional control of the lacUV 5 promoter.

One strategy to maximize recombinant expression of peptides of the invention in *E. coli* is to express the protein in a host bacteria with an impaired capacity to proteolytically cleave the recombinant peptide (Gottesman, S., *Gene Expression Technology: Methods in Enzymology,* 185, Academic Press, San Diego, Calif. (1990) 119–128). Another strategy would be to alter the nucleic acid sequence of the desired peptide to be inserted into an expression vector so that the individual codons for each amino acid would be those preferentially utilized in highly expressed *E. coli* proteins (Wadaet al., (1992) *Nuc. Acids Res..* 20:2111–2118). Such alteration of nucleic acid sequences of the invention could be carried out by standard DNA synthesis techniques.

The nucleic acids of the invention can also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071, incorporated by reference herein).

To obtain isolated peptides of the present invention, a mite allergen is divided into non-overlapping peptides of desired length or overlapping peptides of desired lengths as discussed in Example III which can be produced recombinantly, synthetically, or in certain situations, by chemical cleavage of the allergen. Peptides comprising at least one T cell epitope are capable of eliciting a T cell response, such as stimulation (i.e. proliferation or lymphokine secretion) and/or are capable of inducing T cell nonresponsiveness. To determine peptides comprising at least one T cell epitope, isolated peptides are tested by, for example, T cell biology techniques, to determine whether the peptides elicit a T cell response or induce T cell non-responsivenss. Those peptides found to elicit a T cell response or induce T cell non-responsiveness are defined as having T cell stimulating activity.

Screening peptides of the invention for human T cell stimulating acitivity can be accomplished using one or more of several different assays. For example, in vitro, T cell stimulatory activity is assayed by contacting a peptide of the invention with an antigen presenting cell which presents appropriate MHC molecules in a T cell culture. Presentation of a peptide of the invention in association with appropriate MHC molecules to T cells, in conjunction with the necessary costimulation has the effect of transmitting a signal to the T cell that induces the production of increased levels of cytokines, particularly of interleukin-2 and interleukin-4. The culture supernatant can be obtained and assayed for interleukin-2 or other known cytokines. For example, any one of several conventional assays for interleukin-2 can be employed, such as the assay described in *Proc. Natl. Acad. Sci USA.* 86:1333 (1989) the pertinent portions of which are incorporated herein by reference. A kit for an assay for the production of interferon is also available from Genzyme Corporation (Cambridge, Mass.).

A common assay for T cell proliferation entails measuring tritiated thymidine incorporation. The proliferation of T cells can be measured in vitro by determining the amount of $^3$H-labeled thymidine incorporated into the replicating DNA of cultured cells. Therefore, the rate of DNA synthesis and, in turn, the rate of cell division can be quantified.

A peptide may also be screened for the ability to reduce T cell responsiveness. The ability of a peptide known to stimulate T cells, to inhibit or completely block the activity of a purifed native Dermatophagoides protein allergen or portion thereof and induce a state of T cell nonresponsiveness or reduced T cell responsiveness, can be determined using subsequent attempts at stimulation of the T cells with antigen presenting cells that present a native Dermatophagoides allergen following exposure to a peptide of the invention. If the T cells are unresponsive to the subsequent activation attempts, as determined by interleukin-2 synthesis and T cell proliferation, a state of nonresponsiveness has been induced. See, e.g., Gimmi, et al. (1993) *Proc. Natl. Acad. Sci USA,* 90:6586–6590; and Schwartz (1990) *Science,* 248:1349–1356, for assay systems that can be used as the basis for an assay in accordance with the present invention.

Additionally, peptides comprising "cryptic epitopes" may be determined and are also within the scope of this invention. Cryptic epitopes are those determinants in a protein antigen which, due to processing and presentation of the native protein antigen to the appropriate MHC molecule, are not normally revealed to the immune system. However, a peptide comprising a cryptic epitope is capable of causing T cells to become non-responsive, and when a subject is primed with the peptide, T cells obtained from the subject will proliferate in vitro in response to the peptide or the protein antigen from which the peptide is derived. Peptides which comprise at least one cryptic epitope derived from a protein antigen are referred to herein as "cryptic peptides". To confirm the presence of cryptic epitopes in the above-described T cell proliferation assay, antigen-primed T cells are cultured in vitro in the presence of each peptide separately to establish peptide-reactive T cell lines. A peptide is considered to comprise at least one cryptic epitope if a T cell line can be established with a given peptide and T cells are capable of proliferation upon challenge with the peptide and the protein antigen from which the peptide is derived.

As discussed above and in the Examples, human T cell stimulating activity can be tested by culturing T cells obtained from an individual sensitive to a mite allergen, (i.e., an individual who has an IgE mediated immune response to a mite allergen) with a peptide derived from the allergen and determining whether proliferation of T cells occurs in response to the peptide as measured, e.g., by cellular uptake of tritiated thymidine. Stimulation indices for responses by T cells to peptides can be calculated as the maximum CPM in response to a peptide divided by the control CPM. A T cell stimulation index (S.I.) equal to or greater than two times the background level is considered "positive." Positive results are used to calculate the mean stimulation index for each peptide for the group of peptides tested. Preferred peptides of this invention comprise at least one T cell epitope and have a mean T cell stimulation index of greater than or equal to 2.0. A peptide having a T cell stimulation index of greater than or equal to 2.0 is considered useful as a therapeutic agent. Preferred peptides have a mean T cell stimulation index of at least 2.5, more preferably at least 3.5, even more preferably at least 4.0, and most preferably at least 5.0.

Figure 37:
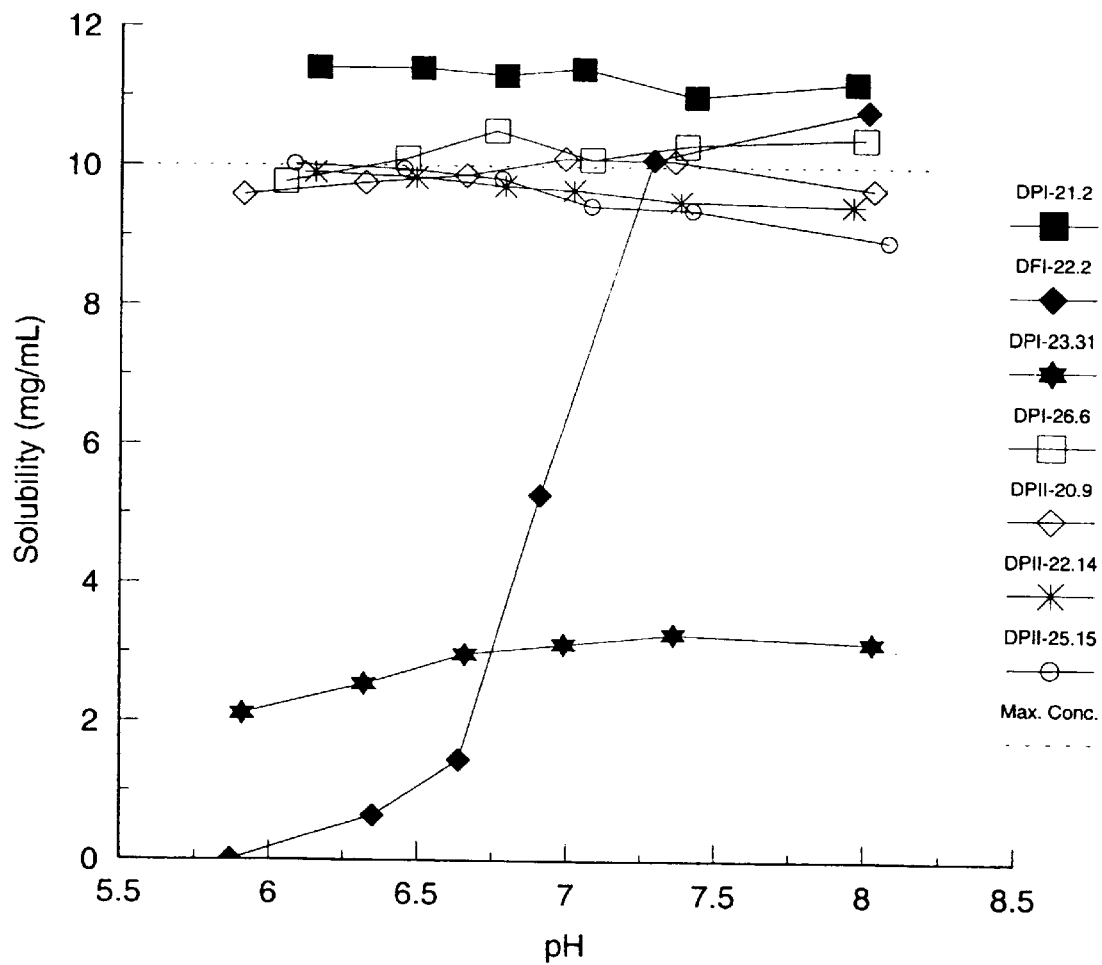
FIG. 37 is a pH-solubility profile of "unique" candidate peptides DPI-21.2 (SEQ. ID. NO. 28), DFI-22.2 (SEQ. ID. NO. 93), DFI-23.31(SEQ. ID. NO. 165), DFI-26.6 (SEQ. ID. NO. 168), DPII-20.9 (SEQ. ID. NO. 169), DPII-22.14 (SEQ. ID. NO. 180) and DPII-25.15 (SEQ. ID. NO. 188), in 50 mM sodium phosphate buffers with 5% mannitol. Solubility is measured in mg/ml (y axis) over a pH range of pH 5.5 to pH 8.5 at about 22° C.±2.

In addition, preferred peptides have a positivity index (P.I.) of at least about 100, more preferably at least 150, even more preferably at least about 200 and most preferably at least about 250. The positivity index for a peptide is determined by multiplying the mean T cell stimulation index by the percent of individuals, in a population of individuals sensitive to house dust mite (e.g., preferably at least 9 individuals, more preferably at least 16 individuals or more, more preferably at least 29 individuals or more, or even more preferably at least 30 individuals or more), who have T cells that respond to the peptide. Thus, the positivity index represents both the strength of a T cell response to a peptide (S.I.) and the frequency of a T cell response to a peptide in a population of individuals sensitive to house dust mite. For example, as shown in FIG. 37, peptide DP I-1 has a mean S.I. of 4.7 and 73% of positive responses in the group of individuals tested resulting in a positivity index of 343.1. As shown in FIG. 37, peptides of Der p I having a positivity index of at least about 150 and a mean T cell stimulation index of at least about 4 include: DP I-1 (SEQ ID NO: 9); DP I-21.1 (SEQ ID NO: 27); DP I-21.2 (SEQ ID NO: 28); DP I-23.1 (SEQ ID NO: 33); DP I-23.2 (SEQ ID NO: 34); DP I-25.2 (SEQ ID NO: 36); and DP I-26.1 (SEQ ID NO: 37).

Figure 31A:
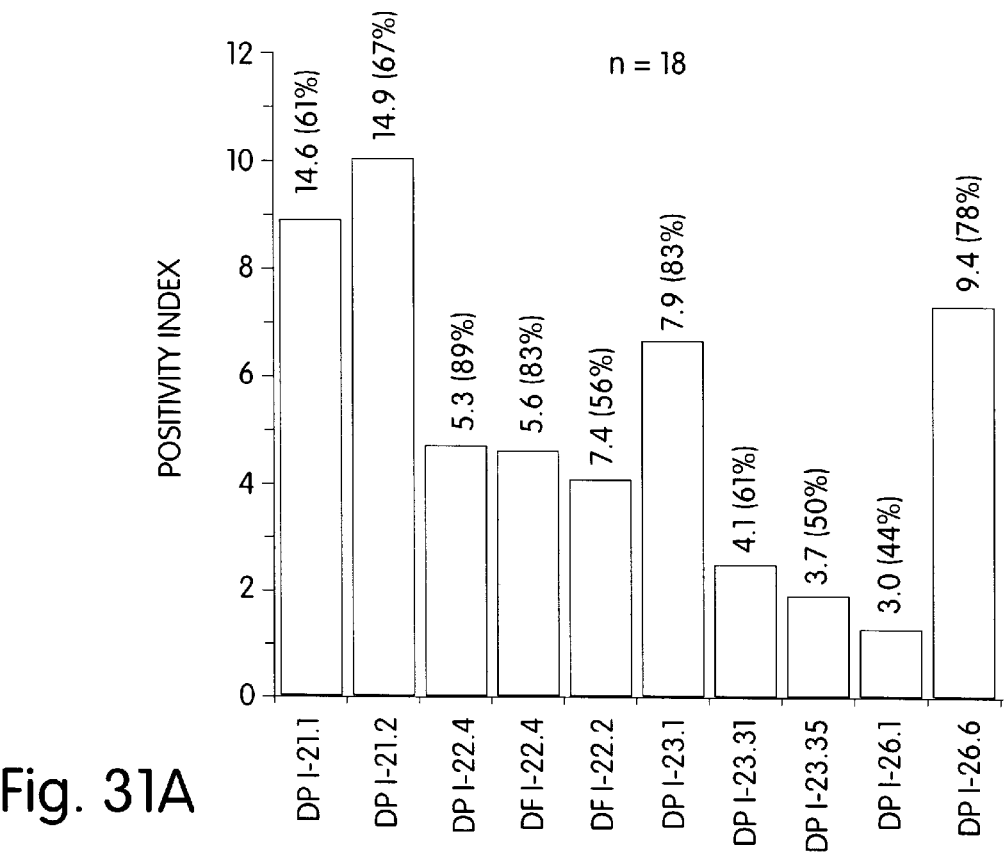
FIG. 31a and 31b are graphic representations depicting the responses of T cell lines from 18 patients (some matched) primed in vitro with mite group I allergen (Der p I) and analyzed for response to various peptides and modified peptides of the invention, the y axis indicates the positivity index for each peptide tested which is the mean S.I. multiplied by the percent of individuals tested responding to the peptide with a mean S.I. of at least 2.
Figure 31B:
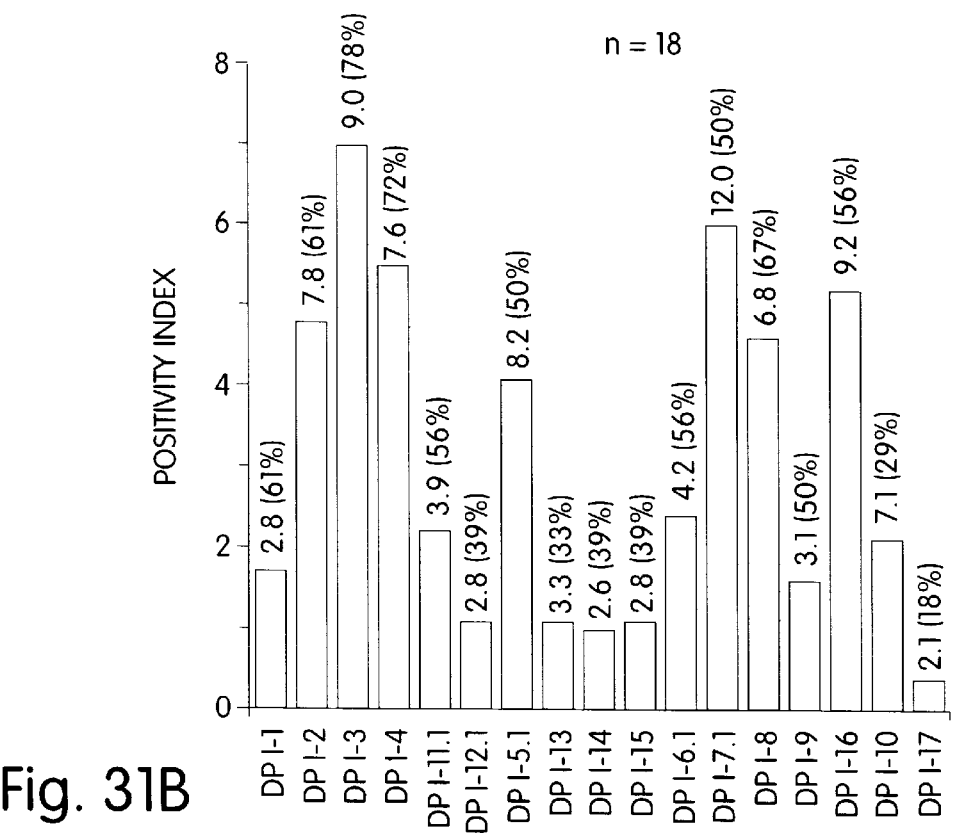

In order to determine precise T cell epitopes by, for example, fine mapping techniques, a peptide having T cell stimulating activity and thus comprising at least one T cell epitope as determined by T cell biology techniques is modified by addition or deletion of amino acid residues at either the amino or carboxy terminus of the peptide and tested to determine a change in T cell reactivity to the modified peptide. If two or more peptides which share an area of overlap in the native protein sequence are found to have human T cell stimulating activity, as determined by T cell biology techniques, additional peptides can be produced comprising all or a portion of such peptides and these additional peptides can be tested by a similar procedure. Following this technique, peptides are selected and produced recombinantly or synthetically or by chemical cleavage. Peptides are selected based on various factors, including the strength of the T cell response to the peptide (e.g., stimulation index), the frequency of the T cell response to the peptide in a population of individuals sensitive to house dust mite, and the potential cross-reactivity of the peptide with other allergens of the genus Dermatophagoides. The physical and chemical properties of these selected peptides (e.g., solubility, stability) are examined to determine whether the peptides are suitable for use in therapeutic compositions or whether the peptides require modification as described herein. The ability of the selected peptides or selected modified peptides to stimulate human T cells (e.g., induce proliferation, lymphokine secretion) is determined. Peptide DF I-22.2 (FIG. 36) is one example of the product of this process. This peptide is derived from amino acid residues 40–64 of Der f I. This peptide was constructed from information obtained during T cell studies of the initial overlapping peptides (Example III). These initial studies indicated that overlapping peptides DP I-4 and DP I-11.1, which together covered amino acid residues 40–60 of Der p I (which is homologous to Der f I in that region), both gave a positive response in the T cell assays, indicating that at least one epitope existed in that region (see Example V). Thus, several peptides were constructed (for "fine mapping" purposes) which covered the general region of overlapping peptides DP I-4 and DP I-11.1, including DF I-22.2, DF I-22.4 and DP I-22.4 among others. FIG. 31a–b shows the relationship of the peptides under the same assay conditions. FIG. 31b shows that overlapping peptides DP I-4 and DP I-11.1 give positive responses indicating the presence of T cell reactivity. FIG. 31a shows that peptides DF I-22.2, DP I-22.4 and DF I-22.4 (amino acid residues 36–64 of Der f I, and Der p I) which are all based on the general region covered by overlapping peptides DP I-4 and DP I-11.1, also have positive responses indicating that each of these peptides also comprises at least one T cell epitope. In addition, it may be desirable to further modify the "fine map" peptides such as DF I-22.2 for purposes of increasing solubility or stability. For example, peptide DF I-22.2 which has the amino acid sequence VAATESAYLAYRNTSLDLSE-QELVD may be further modified by removing the first amino acid, valine (V), from the amino terminus and also removing one or both of the the last two amino acid residues (valine (V) and aspartic acid (D)) from the carboxy terminus of the peptide. This modification may increase the stability or solubility of the peptide. In addition charged amino acids may replace the deleted amino acid residues to further increase the peptide's solubility.

The results in FIGS. 31a–b and 32a–b show a number of other successful examples of the fine mapping techniques combined with further modifications of the fine map peptides. For example, as shown in FIG. 31b, peptides DP I-1 and DP I-2 each give a positive response. Together these peptides cover amino acid residues 1–29 of Der p I. Peptides DP I-21.1 and DP I-21.2 were constructed as fine map peptides to cover this 1–29 region. Peptides DP I-21.1 and DP I-21.2 both give a positive response indicating that at least one epitope from the overlapping region covered by peptides DP I-1 and DP I-2 was preserved. Moreover, the results in FIG. 31a indicate that peptide DP I-21.2 has a higher positivity index then either of the overlapping peptides, DP I-1 and DP I-2 (FIG. 31b), which makes it a very useful peptide. It may be desirable to further modify DP I-21.2 to increase its solubility or stability for the purposes of including it in a therapeutic composition. Modified peptide DP I-21.7 is an example of such a modification in which the "core" of peptide DP I-21.2 remains essentially unchanged except a charged amino acid is added to the amino terminus and a methionine internal to the peptide is replaced with a leucine resulting in peptide DP I-21.7. Similarly positive T cell studies with other fine map peptides shown in FIGS. 31a and 32a (i.e. DP I-23.1, DP I-26.1 DP II-20.0, DP II-22, DP II-25) and modified forms S thereof (i.e. DP I-23.31, DP I-23.35, DP I-26.6, DP II-20.9, DP II-20.11, DP II-20.10, DPII-8, DP II-22.19, DP II-22.22, DP II-22.23, DP II-22.14, DP II-25.9) show that regions of reactivity can be identifed with overlapping peptides (FIGS. 31b and 32b), and fine map peptides may be constructed from those regions which preserve and perhaps enhance the T cell reactivity previously defined in the overlapping region, and using the amino acid sequences of the fine map peptides as a "core", further modifications may be made to the fine map peptides to impart other desired characteristics to the peptide such as increased solubility and stability, which is important if the peptide is to be used as a therpeutic composition. Examples of specific modifications to peptides for purposes of increased solubility, stability etc. are discussed later.

If a peptide of the invention is to be used for therapeutic purposes, it is preferred that the peptide does not bind immunoglobulin E (IgE) or binds IgE to a substantially lesser extent (i.e. at least 100-fold less binding and more preferably, at least 1,000-fold less binding) than the protein allergen from which the peptide is derived binds IgE. The major complications of standard immunotherapy are IgE-mediated responses such as anaphylaxis. Immunoglobulin E is a mediator of anaphylactic reactions which result from the binding and cross-linking of antigen to IgE on mast cells or basophils and the release of mediators (e.g., histamine, serotonin, eosinophil chemotacic factors) in allergic ("atopic") patients (see, Example XVI). Thus, anaphylaxis in a substantial percentage of a population of individuals sensitive to house dust mite could be avoided by the use in immunotherapy of a peptide or peptides which do not bind IgE in a substantial percentage (e.g., at least about 75%) of a population of individuals sensitive to a house dust mite allergen, or if the peptide binds IgE, such binding does not result ink the release of mediators from mast cells or basophils. The risk of anaphylaxis could be reduced by the use in immunotherapy of a peptide or peptides which have reduced IgE binding. Moreover, peptides which have minimal IgE stimulating activity are desirable for therapeutic effectiveness. Minimal IgE stimulating activity refers to IgE production that is less than the amount of IgE production and/or IL-4 production stimulated by the native protein allergen (e.g., Der p I).

If a peptide of the invention binds IgE, and is to be used as a therapeutic agent, it is preferable that such binding does not result in the release of mediators (e.g. histamines) from mast cells or basophils. To determine whether a peptide which binds IgE results in the release of mediators, a histamine release assay can be performed using standard reagents and protocols obtained for example, from Amac, Inc. (Westbrook, Me.). Briefly, a buffered solution of a peptide to be tested is combined with an equal volume of whole heparinized blood from an allergic subject. After mixing and incubation, the cells are pelleted and the supernatants are processed and analyzed using a radioimmunoassay to determine the amount of histamine released.

If a peptide of the invention is to be used as a diagnostic reagent, it is not necessary that the peptide or protein have reduced IgE binding activity compared to the native Dermatophagoides allergen (e.g. Der p I, Der p II, Der f I or Der f II). IgE binding activity of peptides can be determined by, for example, an enzyme linked immunosorbent assay (ELISA) using, for example, sera obtained from a subject, (i.e., an allergic subject) that has been previously exposed to the native Dermatophagoides allergen. Briefly, a peptide to be tested is coated onto wells of a microtiter plate. After washing and blocking the wells, antibody solution consisting of the plasma of an allergic subject who has been exposed to the peptide being tested or the protein from which it was derived is incubated in the wells. The plasma is generally depleted of IgG before incubation. A labeled secondary antibody is added to the wells and incubated. The amount of IgE binding is then quantified and compared to the amount of IgE bound by ai purified native Dermatophagoides protein allergen. Alternatively, the binding activity of a peptide can be determined by Western blot analysis. For example, a peptide to be tested is run on a polyacrylamide gel using SDS-PAGE. The peptide is then transferred to nitrocellulose and subsequently incubated with sera from an allergic subject. After incubation with the labeled secondary antibody, the amount of IgE bound is then determined and quantified.

Another assay which can be used to determine IgE binding activity of a peptide is a competition ELISA assay. Briefly, an IgE antibody pool is generated by combining plasma from house dust mite allergic subjects that have been shown by direct ELISA to have IgE reactive with native Dermatophagoides protein allergen. This pool is used in ELISA competition assays to compare IgE binding to native Dermatophagoides protein, allergen to the peptide tested. IgE binding for the native Dermatophagoides protein allergen and the peptide being tested is determined and quantified.

A peptide of the invention, when administered to a house dust mite-sensitive individual in a therapeutic regimen, is capable of modifying the allergic response of the individual to the allergen. Particularly, peptides of the invention comprising at least one T cell epitope of a mite allergen or at least two regions derived from a mite allergen, each comprising at least one T cell epitope, when administered to an individual sensitive to house dust mite are capable of modifying the T cell response, the B cell response or both the T cell and B cell response of the individual to the allergen. As used herein, modification of the allergic response of an individual sensitive to a house dust mite allergen can be defined as non-responsiveness or diminution in symptoms upon exposure to a mite allergen, as determined by standard clinical procedures (see e.g., Varney et al., *British Medical Journal*, 302:265–269 (1990)) including diminution in mite protein allergen induced asthmatic symptoms. As referred to herein, a diminution in symptoms includes any reduction in allergic response of an individual to the allergen after the individual has completed a treatment regimen with a peptide of the invention. This diminution may be subjective (i.e. the patient feels more comfortable in the presence of the allergen). Diminution in symptoms can be determined clinically as well, using standard skin tests as is known in the art.

As a result of the work described herein, peptides derived from mite allergens which have T cell stimulating activity and thus comprise at least one T cell epitope have been produced. T cell epitopes are believed to be involved in initiation and perpetuation of the immune response to a protein allergen which is responsible for the clinical symptoms of allergy. These T cell epitopes are thought to trigger early events at the level of the T helper cell by binding to an appropriate HLA molecule on the surface of an antigen presenting cell and stimulating the relevant T cell subpopulation. These events lead to T cell proliferation, lymphokine secretion, local inflammatory reactions, recruitment of additional immune cells to the site, and activation of the B cell cascade leading to production of antibodies. One isotype of these antibodies, IgE, is fundamentally important to the development of allergic symptoms and its production is influenced early in the cascade of events, at the level of the T helper cell, by the nature of the lymphokines secreted. A T cell epitope is the basic element or smallest unit of recognition by a T cell receptor, where the epitope comprises amino acids essential to receptor recognition. Amino acid sequences which mimic those of the T cell epitopes and which modify the allergic response to protein allergens are also within the scope of this invention.

Exposure of house dust mite patients to isolated peptides of the present invention which comprise at least one T cell epitope, and are derived from Dermatophatophagoides protein allergens, in a non-immunogenic form, may cause T cell non-responsiveness of appropriate T cell subpopulations such that they become unresponsive to the protein allergen and do not participate in stimulating an immune response upon such exposure or may cause reduced T cell responsiveness. In addition, administration of a peptide of the invention which comprises at least one T cell epitope may modify the lymphokine secretion profile as compared with exposure to the naturally-occurring protein allergen or portion thereof (e.g. result in a decrease of IL-4 and/or an increase in IL-2). Furthermore, exposure to such peptide may influence T cell subpopulations which normally participate in the response to the allergen such that these T cells are drawn away from the site(s) of normal exposure to the allergen (e.g., nasal mucosa, skin, and lung) towards the site(s) of therapeutic administration of the fragment or protein allergen. This redistribution of T cell subpopulations may ameliorate or reduce the ability of an individual's immune system to stimulate the usual immune response at the site of normal exposure to the allergen, resulting in a diminution in allergic symptoms.

The isolated peptides of the invention can be used in methods of diagnosing, treating and preventing allergic reactions to house dust mite allergen or a cross reactive protein allergen. Thus the present invention provides therapeutic compositions comprising peptides derived from house dust mite allergens and a pharmaceutically acceptable carrier or diluent. Administration of the therapeutic compositions of the present invention to an individual to be desensitized can be carried out using known techniques. Peptides of the invention may be administered to an individual in combination with, for example, an appropriate diluent, a carrier and/or an adjuvant or incomplete adjuvant. Pharmaceutically acceptable diluents include saline and aqueous buffer solutions. Pharmaceutically acceptable carriers include polyethylene glycol (Wie et al. (1981) *Int. Arch. Allergy Appl. Immunol.*, 64:84–99) and liposomes (Strejan et al. (1984) *J. Neuroimmunol.*, 7: 27).

The therapeutic compositions of the invention are administered to house dust mite allergen-sensitive individuals or individuals sensitive to an allergen which is immunologically cross-reactive with house dust mite allergen. For purposes of inducing T cell non responsiveness, therapeutic compositions of the invention are preferably administered in non-immunogenic form, e.g. which does not contain adjuvant. While not intending to be limited to any theory, it is believed that T cell non responsivness or reduced T cell responsiveness is induced as a result of not providing an appropriate costimulatory signal sometimes referred to as a "second signal" Briefly, it is believed that stimulation of T cells requires two types of signals, the first is the recognition by the T cell via the T cell receptor of appropriate MHC-associated processed antigens on antigen presenting cells (APCs) and the second type of signal is referred to as a costimulatory signal(s) or "second signal" which may be provided by certain competent APCs. When a composition of the invention is administered without adjuvant, it is believed that competent APCs which are capable of producing the second signal or costimulatory signal are not engaged in the stimulation of appropriate T cells therefore resulting in T cell nonresponsiveness or reduced T cell responsiveness. In addition, there are a number of antibodies or other reagents capable of blocking the delivery of costimulatory signals such as the "second signal" which include, but are not limited to B7 (including B7-1, B7-2, and BB-1), CD28, CTLA4, CD40 CD40L CD54 and CD11a/18 (Jenkins and Johnson, *Current Opinion in Immunology,* 5:361–367 (1993), and Clark and Ledbetter, *Nature,* 367:425–428 (1994)) Thus, a peptide of the invention may be administered in nonimmunogenic form as discussed above, in conjunction with a reagent capable of blocking costimulatory signals such that the level of T cell nonresponsiveness is enhanced.

Administration of the therapeutic compositions of the present invention to an individual to be desensitized can be carried out using known procedures at dosages and for periods of time effective to reduce sensitivity (i.e., reduce the allergic response) of the individual to the allergen. Effective amounts of the therapeutic compositions will vary according to factors such as the degree of sensitivity of the individual to Japanese cedar pollen, the age, sex, and weight of the individual, and the ability of the protein or fragment thereof to elicit an antigenic response in the individual. The active compound (i.e., protein or fragment thereof) may be administered in a convenient manner such as by injection (subcutaneous, intravenous, etc.), oral administration, inhalation, transdermal application, or rectal administration. Depending on the route of administration, the active compound may be coated within a material to protect the compound from the action of enzymes, acids and other natural conditions which may inactivate the compound.

For example, preferably about 1 $\mu$g–3 mg and more preferably from about 20– 500 $\mu$g of active compound (i.e., protein or fragment thereof) per dosage unit may be administered by injection. Dosage regimen may be adjusted to provide the optimum therapeutic response. For example, several divided doses may be administered daily or the dose may be proportionally reduced as indicated by the exigencies of the therapeutic situation.

To administer protein or peptide by other than parenteral administration, it may be necessary to coat the protein with, or co-administer the protein with, a material to prevent its inactivation. For example, protein or fragment thereof may be administered in an incomplete adjuvant, co-administered with enzyme inhibitors or in liposomes. Enzyme inhibitors include pancreatic trypsin inhibitor, diisopropylfluorophosphate (DEP) and trasylol. Liposomes include water-in-oil-in-water CGF emulsions as well as conventional liposomes (Strejan et al., (1984) *J. Neuroimmunol.*, 7:27).

The active compound may also be administered parenterally or intraperitoneally. Dispersions can also be prepared in glycerol, liquid polyethyline glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions of dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glyceral, propylene glycol, and liquid polyetheylene glycol, and the like), suitable mixtures thereof, and vegetable oils. The proper fluidity can be maintained, for example, by the use of a coating such as licithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thirmerosal, and the like. In many cases, it will be preferable to include isotonic agents, for example, sugars, polyalcohols such as manitol and sorbitol or sodium chloride in the composition. Prolonged absorption of the injectable compositions can be brought about, including in the composition, an agent which delays absorption, for example, aluminum monostearate and gelatin.

Sterile injectable solutions can be prepared by incorporating active compound (i.e., protein or peptide) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile indectable solutions, the preferred methods of preparation are vacuum drying and freeze-drying which yields a powder of the active ingredient (i.e., protein or peptide) plus any additional desired ingredient from a previously sterile-filtered solution thereof.

When a peptide is suitably protected, as described above, the peptide may be orally administered, for example, with an inert diluent or an assimilable edible carrier. The peptide and other ingredients may also be enclosed in a hard or soft shell gelatin capsule, compressed into tablets, or incorporated directly into the individual's diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the composition and preparations may, of course, be varied and may conveniently be between about 5 to 80% of the weight of the unit. The amount of active compound in such therapeutically useful compositions is such that a suitable dosage will be obtained. Preferred compositions or preparations according to the present invention are prepared so that an oral dosage unit contains between from about 10 $\mu$g to about 200 mg of active. compound.

The tablets, troches, pills, capsules and the like may also contain the following: a binder such as gum gragacanth, acacia, corn starch or gelatin; excipients such as dicalcium phosphate; a disintegrating agent such as corn starch, potato starch, alginic acid and the like; a lubricant such as magnesium stearate; and a sweetening agent such was sucrose, lactose or saccharin or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservative, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. Dosage unit from as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the novel dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

The invention further includes isolated allergenic proteins or fragments thereof that are immunologically related to a Dermatophagoides protein allergen or peptide thereof, such as by antibody cross-reactivity wherein the isolated allergenic proteins or fragments thereof are capable of binding to antibodies specific for the peptides of the invention, or by T cell cross-reactivity wherein the isolated allergenic proteins or fragments thereof are capable of stimulating T cells specific for the peptides of this invention.

Peptides encoded by the cDNA of the present invention can be used, for example as "purified" allergens. Such purified allergens are useful in the standardization of allergen extracts which are currently key reagents for the clinical diagnosis and treatment of sensitivity to house dust mite allergens.

Another aspect of the invention pertains to an antibody specifically reactive with a peptide of the invention. The antibodies of this invention can be used to standardize allergen extracts or to isolate the naturally-occurring or native forms of protein allergens derived from the genus Dermatophagoides or other immunologically related allergens.

The term antibody as used herein is intended to include fragments thereof which are also specifically reactive with a peptide of the invention. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments. The antibody of the present invention is further intended to include bispecific and chimeric molecules having an anti-Der p I, Der p II, Der f I or Der f II portion.

Another aspect of this invention provides isolated T cell clones and isolated soluble T cell receptors specifically reactive with peptides of the invention. Monoclonal T cell populations (i.e., T cells genetically identical to one another and expressing identical T cell receptors) can be derived from an individual sensitive to house dust mite protien allergen, followed by repetitive in vitro stimulation with house dust mite protein allergen in the presence of MHC-matched antigen-presenting cells. Single house dust mite protein allergen MHC responsive cells can then be cloned by limiting dilution and permanent lines expanded and maintained by periodic in vitro restimulation. Alternatively, house dust mite protein allergen specific T—T hybridomas can be produced by a technique similar to B cell hybridoma production. For example, a mammal, such as a mouse can be immunized with a peptide of the invention, T cells from the mammal can be purified and fused with an autonomously growing T cell tumor line. From the resulting hybridomas, cells responding to a peptide of the invention are selected and cloned. Procedures for propagating monoclonal T cell populations are described in *Cellular and Molecular Immunology* (Abul K. Abbas et al. ed.), W. B. Saunders Company, Philadelphia, Pa. (1991) page 139. Soluble T cell receptors specifically reactive with a peptide of the invention or fragments thereof can be obtained by immunoprecipitation using an antibody against the T cell receptor as described in *Immunology: A Synthesis* (Second Edition), Edward S. Golub et al., ed., Sinauer Associates, Inc., Sunderland, Mass. (1991) pages 366–269.

T cell clones specifically reactive with a peptide of the invention can be used to isolate and molecularly clone the gene encoding the relevant T cell receptor. In addition, a soluble T cell receptor specifically reactive with a peptide of the invention can be used to interfere with or inhibit antigen-dependent activation of the relevant T cell subpopulation, for example, by administration to an individual sensitive to house dust mite protein allergen. Antibodies specifically reactive with such a T cell receptor can be produced according to known techniques. Such antibodies can be used to block or interfere with the T cell interaction with peptides presented by MHC.

Through use of the peptides of the present invention, preparations of consistent, well-defined composition and biological activity can be made and administered for therapeutic purposes (e.g. to modify the allergic response of a house dust mite sensitive individual). Administration of such peptides or protein may, for example, modify B-cell response to a house dust mite protein allergen, T-cell response to a house dust mite protein allergen, or both responses. Isolated peptides can also be used to study the mechanism of immunotherapy of house dust mite protein allergy and to design modified derivatives or analogues useful in immunotherapy.

Work by others has shown that high doses of allergens generally produce the best results (i.e., best symptom relief). However, many people are unable to tolerate large doses of allergens because of allergic reactions to the allergens. A peptide can be designed in such a manner to have the same or enhanced therapeutic properties as the corresponding naturally-occurring allergen but have reduced side effects (especially anaphylactic reactions) can be produced. These can be, for example, a peptide of the present invention.

It is also possible to modify the structure of a peptide of the invention for such purposes as increasing solubility, enhancing therapeutic or preventive efficacy, or stability (e.g., shelf life ex vivo, and resistance to proteolytic degradation in vivo). A modified peptide can be produced in which the amino acid sequence has been altered, such as by amino acid substitution, deletion, or addition, to modify immunogenicity and/or reduce allergenicity, or to which a component has been added for the same purpose.

For example, a peptide can be modified so that it maintains the ability to induce T cell anergy and bind MHC proteins without the ability to induce a strong proliferative response or possibly, any proliferative response when administered in immunogenic form. In this instance, critical binding residues for the T cell receptor can be determined using known techniques (e.g., substitution of each residue and determination of the presence or absence of T cell reactivity). Those residues shown to be essential to interact with the T cell receptor can be modified by replacing the essential amino acid with another, preferably similar amino acid residue (a conservative substitution) whose presence is shown to enhance, diminish but not eliminate, or not effect T cell reactivity. In addition, those amino acid residues which are not essential for T cell receptor interaction can be modified by being replaced by another amino acid whose incorporation may enhance, diminish or not effect T cell reactivity but does not eliminate binding to relevant MHC.

Additionally, peptides of the invention can be modified by replacing an amino acid shown to be essential to interact with the MHC protein complex with another, preferably similar amino acid residue (conservative substitution) whose presence is shown to enhance, diminish but not eliminate or not effect T cell activity. In addition, amino acid residues which are not essential for interaction with the MHC protein complex but which still bind the MHC protein complex can be modified by being replaced by another amino acid whose incorporation may enhance, not effect, or diminish but not eliminate T cell reactivity. Preferred amino acid substitutions for non-essential amino acids include, but are not limited to substitutions with alanine, glutamic acid, or a methyl amino acid.

Another example of a modification of peptides is substitution of cysteine residues preferably with serine, threonine, leucine or glutamic acid to minimize dimerization via disulfide linkages. For example, the stability of a peptide of Der p II or Der f II which includes the first ten amino acid residues of either allergen can be enhanced by replacing the cysteine located at the 8th amino acid residue, preferably with alanine, or glutamic acid, or alternatively with serine or threonine.

In order to enhance stability and/or reactivity, peptides can also be modified to incorporate one or more polymorphisms in the amino acid sequence of a protein allergen resulting from natural allelic variation as shown in FIGS. 25–27. Additionally, D-amino acids, non-natural amino acids or non-amino acid analogues can be substituted or added to produce a modified peptide within the scope of this invention. Furthermore, peptides of the present invention can be modified using the polyethylene glycol (PEG) method of A. Sehon and co-workers (Wie et al. s to produce a peptide conjugated with PEG. In addition, PEG can be added during chemical synthesis of a peptide of the invention. Modifications of peptides or portions thereof can also include reduction/alkylation (Tarr in: *Methods of Protein Microcharacterization,* J. E. Silver ed. Humana Press, Clifton, N.J., pp 155–194 (1986)); acylation (Tarr, supra); esterification (Tarr, supra); chemical coupling to an appropriate carrier (Mishell and Shiigi, eds, *Selected Methods in Cellular Immunology,* W H Freeman, San Francisco, Calif. (1980); U.S. Pat. No. 4,939,239); or mild formalin treatment (Marsh *International Archives of Allergy and Applied Immunology,* 41:199–215 (1971)).

In another embodiment, peptides within an allergen group can be modified to enhance T cell reactivity. Given the cross-reactivity within the Group I and Group II allergens, a peptide of one group allergen which may be less reactive than a peptide of another group allergen corresponding in amino acid position can have one or more amino acids substituted with one or more amino acids from the corresponding peptide (e.g., peptide DF II-1, residue seventeen [methionine] in the Der f II amino acid sequence can be substituted with the amino acid located at residue seventeen in Der p II [leucine] to enhance the reactivity of the Der f II peptide). Additionally, peptides can be modified to incorporate a polymorphism in the amino acid sequence of a protein allergen resulting from natural allelic variation. Modification of peptides to include one or more of these polymorphisms may result in enhanced stability and/or reactivity.

To facilitate purification and potentially increase solubility of peptides of the invention, it is possible to add reporter group(s) to the peptide backbone. For example, polyhistidine can be added to a peptide to purify the peptide on immobilized metal ion affinity chromatography (Hochuli, E. et al., *Bio/Technology,* 6:1321–1325 (1988)). In addition, specific endoprotease cleavage sites can be introduced, if desired, between a reporter group and amino acid sequences of a peptide to facilitate isolation of peptides free of irrelevant sequences.

In order to successfully desensitize an individual to a peptide, it may be necessary to increase the solubility of a peptide for use in buffered aqueous solutions, such as pharmaceutically acceptable carriers or diluents, by adding functional groups to the peptide, terminal portions of the peptide, or by not including hydrophobic T cell epitopes or regions containing hydrophobic epitopes in the peptides or hydrophobic regions of the protein or peptide. For example, to increase solubility, charged amino acids or charged amino acid pairs or triplets may be added to the carboxy or amino terminus of the peptide. Examples of charged amino acids include, arginine (R), lysine (K), histidine (H), glutamic acid (E), and aspartic acid (D).

To potentially aid proper antigen processing of T cell epitopes within a peptide, canonical protease sensitive sites can be recombinantly or synthetically engineered between regions, each comprising at least one T cell epitope. For example, charged amino acid pairs, such as KK or RR, can be introduced between regions within a peptide during recombinant construction of the peptide. The resulting peptide can be rendered sensitive to cathepsin and/or other trypsin-like enzymes cleavage to generate portions of the peptide containing one or more T cell epitopes. In addition, such charged amino acid residues can result in an increase in solubility of a peptide.

Site-directed mutagenesis of DNA encoding a peptide of the invention can be used to modify the structure of the peptide. Such methods may involve PCR (Ho et al., *Gene,* 77:51–59 (1989)) or total synthesis of mutated genes (Hostomsky, Z., et al., *Biochem. Biophys. Res. Comm.,* 161:1056–1063 (1989)). To enhance bacterial expression, the aforementioned methods can be used in conjunction with other procedures to change the eucaryotic codons in DNA constructs encoding peptides of the invention to ones preferentially used in *E. coli.*

Specific examples of peptides of the invention modified in accordance with one or more of the modification procedures discussed above include but are not limited to modifications to peptide DPI-23.1 as shown in FIG. 28 and to peptide DPII-22 as shown in FIG. 28. More specifically, modifications to peptides 23.1 include the addition of charged amino acids (23.1.2) charged amino acid pairs (23.1.1) to increase solubility and replacement of a cysteine residue with serine 23.1.3 or glutamic acid (23.1.4) to increase solubility. Changes to peptide 22 include the addition of charged amino acid pairs (22.1 and 22.2) to increase solubility.

It is now also possible to design an agent or a drug capable of blocking or inhibiting the ability of house dust mite allergen to induce an allergic reaction in house dust mite allergen-sensitive individuals. Such agents could be designed, for example, in such a manner that they would bind to relevant anti-Der p or Der f protein allergen IgEs, thus preventing IgE-allergen binding and subsequent mast cell degranulation. Alternatively, such agents could bind to cellular components of the immune system, resulting in suppression or desensitization of the allergic response to house dust mite allergens.

Peptides of the present invention can also be used for detecting and diagnosing sensitivity to house dust mite protein allergens. For example, this could be done by combining blood or blood products obtained from an individual to be assessed for sensitivity to house dust mite protein allergens with an isolated antigenic peptide or peptides of the invention, under conditions appropriate for binding of components in the blood (e.g., antibodies, T cells, B cells) with the peptide(s) and determining the extent to which such binding occurs. Other diagnostic methods for allergic diseases which the peptides of the present invention can be used include radio-allergergosorbent test (RAST), paper radioimmunosorbent test (PRIST), enzyme linked immunosorbent assay (ELISA), radioimmunoassays (RIA), immuno-radiometric assays (IRMA), luminescence immunoassays (LIA), histamine release assays and IgE immunoblots.

The presence in individuals of IgE specific for at least one protein allergen of the genus Dermatophagoides and the ability of T cells of the individuals to respond to T cell epitope(s) of the protein allergen can be determined by administering to the individuals an Immediate Type Hypersensitivity test and a Delayed Type Hypersensitivity test. The individuals are administered an Immediate Type Hypersensitivity test (see e.g. *Immunology* (1985) Roitt, I. M., Brostoff, J., Male, D. K. (eds), C. V. Mosby Co., Gower Medical Publishing, London, N.Y., pp. 19.2–19.18; pp. 22.1–22.10) utilizing a peptide of the protein allergen, or a modified form of the peptide, each of which binds IgE specific for the allergen. The same individuals are administered a Delayed Type Hypersensitivity test prior to, simultaneously with, or subsequent to administration of the Immediate Type Hypersensitivity test. Of course, if the Immediate Type Hypersensitivity test is administered prior to the Delayed Type Hypersensitivity test, the Delayed Type Hypersensitivity test would be given to those individuals exhibiting a specific Immediate Type Hypersensitivity reaction. The Delayed Type Hypersensitivity test utilizes a modified form of the protein allergen or a portion thereof, the protein allergen produced recombinantly, or peptide derived from the protein allergen, each of which has human T cell stimulating activity and each of which does not bind IgE specific for the allergen in a substantial percentage of the population of individuals sensitive to the allergen (e.g., at least about 75%). Those individuals found to have both a specific Immediate Type Hypersensitivity reaction and a specific Delayed Type Hypersensitivity reaction are diagnosed as having sensitivity to house dust mite protein allergen and may, if need be, administered a therapeutically effective amount of a therapeutic composition of the invention. The therapeutic composition may comprise a peptide of the invention and a pharmaceutically acceptable carrier or diluent.

For therapeutic purposes, isolated peptides of the invention comprise at least one T cell epitope of a protein allergen of the genus Dermatophagoides and accordingly, the peptide comprises at least approximately seven amino acid residues of the protein allergen. Therapeutic compositions of the invention may comprise at least two T cell epitopes of a mite allergen. Accordingly, isolated peptides of the invention comprising at least two T cell epitopes comprise at least approximately eight amino acid residues, and preferably fifteen amino acid residues. Additionally, therapeutic compositions of the invention preferably comprise a sufficient percentage of the T cell epitopes of the entire protein allergen (i.e.at least about 40% and more preferably about 60% of the T cell reactivity to Der p and/or Der f allergens) are included in the composition such that a therapeutic regimen of administration of the composition to an individual sensitive to house dust mite, results in T cells of the individual being rendered nonresponsive to the protein allergen or protein allergens. Synthetically produced peptides of the invention comprising up to approximately forty-five amino acid residues in length, and most preferably up to approximately thirty amino acid residues in length are particularly desirable as increases in length may result in difficulty in peptide synthesis as well as retention of an undesirable property (e.g., immunoglobulin binding or enzymatic activity) due to maintenance of conformational similarity between the peptide and the protein allergen from which it is derived Preferred peptides comprise all or a portion of the areas of major T cell reactivity within the Der p I, Der f I, Der p II and Der f II protein allergens, i.e., Region 1, Region 2, Region 3, Region 4, Region 5, Region 6a, Region 6b, Region 7, Region 8, Region 9 and Region 10. Each area is defined as follows: Region 1 comprises amino acid residues 1–28 of the Der p I and Der f I protein allergens; Region 2 comprises amino acid residues 36–68 of the Der p I and Der f I protein allergens; Region 3 comprises amino acid residues 74–109 of the Der p I and Der f I protein allergens; Region 4 comprises amino acid residues 118–139 of the Der p I and Der f I protein allergens; Region 5 comprises amino acid residues 141–166 of the Der p I and Der f I protein allergens; Region 6a comprises amino acid residues 161–185 of the Der p I and Der f I protein allergens; Region 6b comprises amino acid 173–201 of the Der p I and Der f I allergens; Region 7 comprises amino acid residues 1–26 of the Der p II and Der f II protein allergens; Region 8 comprises amino acid residues 33–67 of the Der p II and Der f II protein allergens; Region 9 comprises amino acid residues 79–104 of the Der p II and Der f II protein allergens and Region 10 comprises amino acid residues 107–129 of the Der p II and Der f II protein allergens.

Figure 13:
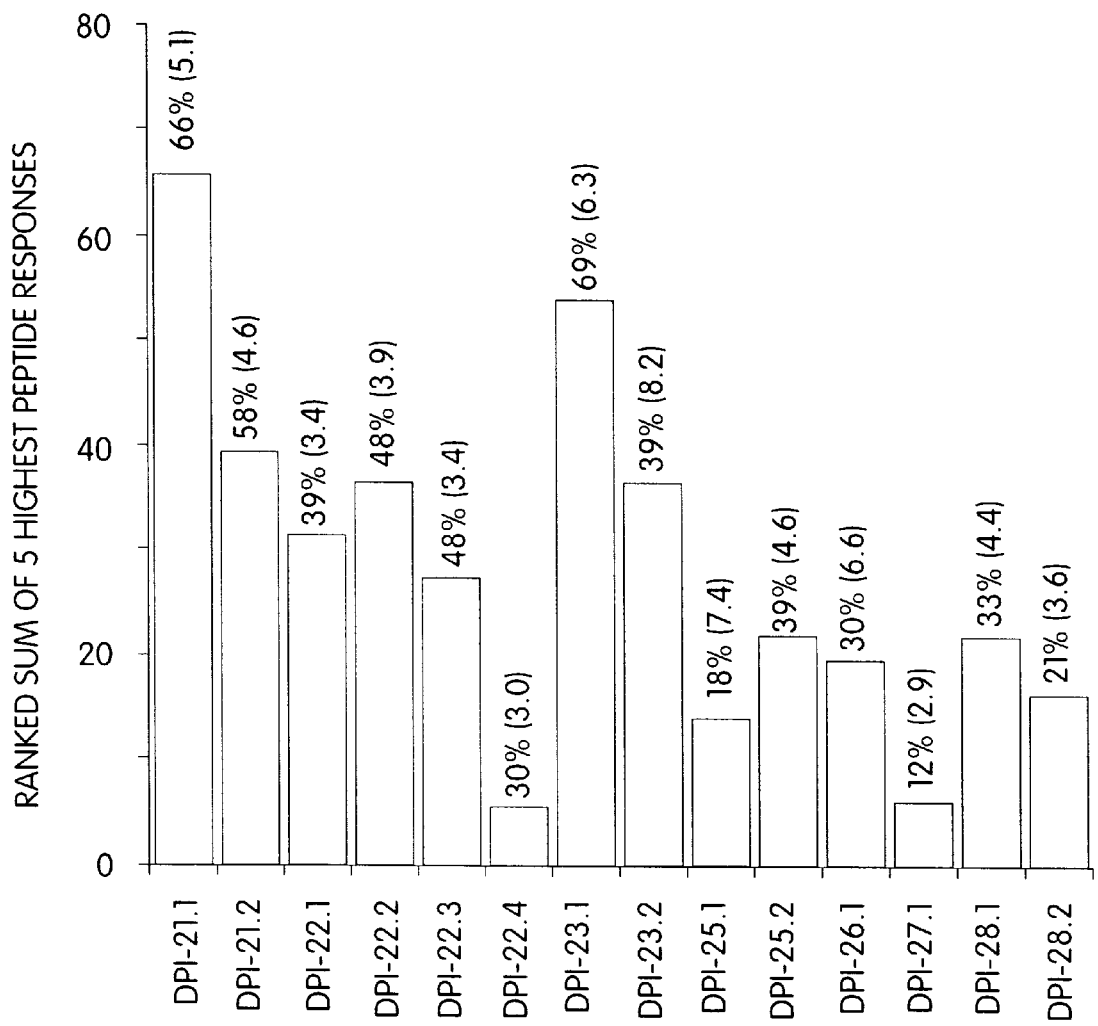
FIG. 13 is a graphic representation depicting the responses of T cell lines from 33 patients primed in vitro to the Der p I protein and analyzed for response to selected peptides of desired lengths derived from the Der p I protein allergen by percent of responses with an S.I. of at least 2 within the individuals tested, the mean T cell stimulation index of positive responses for the peptide and the ranked sum of peptide responses.

Preferred peptides derived from the Der p I protein comprise all or a portion of the following peptides: DP I-1 (SEQ ID NO: 9); DP I-2 (SEQ ID NO: 10); DP I-3 (SEQ ID NO: 11); DP I-4 (SEQ ID NO: 12); DPI-11.1 (SEQ ID NO: 13); DP I-12.1 (SEQ ID NO: 14); DP I-5 (SEQ ID NO: 15); DP I-13 (SEQ ID NO: 17); DP I-14 (SEQ ID NO: 18); DP I-15 (SEQ ID NO: 19); DP I-6.1 (SEQ ID NO: 20); DP I-7.1 (SEQ ID NO: 21); DP I-8 (SEQ ID NO: 22); DP I-9 (SEQ ID NO: 23); DP I-16 (SEQ ID NO: 24); DP I-10 (SEQ ID NO: 25); DP I-17 (SEQ ID NO: 26); DP I-21.1 (SEQ ID NO: 27); DP I-21.2 (SEQ ID NO: 28); DP I-22.1 (SEQ ID NO: 29); DP I-22.2 (SEQ ID NO: 30); DP I-22.3 (SEQ ID NO: 31); DP I-22.4 (SEQ ID NO: 32); DP I-23.1 (SEQ ID NO: 33); DP I-23.2 (SEQ ID NO: 34); DP I-25.1 (SEQ ID NO: 35); DP I-25.2 (SEQ ID NO: 36); DP I-26.1 (SEQ ID NO: 37); DP I-27.1 (SEQ ID NO: 38); DP I-28.1 (SEQ ID NO: 39); and DP I-28.2 (SEQ ID NO: 40), wherein the portion of the peptide has a mean T cell stimulation index substantially equivalent to, or greater than the mean T cell stimulation index of the peptide from which it is derived as shown in FIG. 37 and FIG. 13. More preferably, peptides derived from the Der p I protein comprise all or a portion of the following peptides: DP I-21.2, DP I-22.2, DPI-23.1, DP I-25.2, DPI-26.1, DPI-27.1 and DP I-28.1, and most preferably, peptides derived from the Der p I protein comprises all or a portion of DP I-21.2, DP I-23.1 and DP I-26.1, wherein the portion of the peptide has a mean T cell stimulation index substantially equivalent to, or greater than the mean T cell stimulation index of the peptide from which it is derived as shown in FIG. 37 and FIG. 13.

Preferred peptides derived from the Der f I, the Der p II and the Der f II proteins include: DF I-1 (SEQ ID NO: 72); DF I-2.1 (SEQ ID NO: 73); DF I-3 (SEQ ID NO: 74); DF I-4 (SEQ ID NO: 75); DF I-11 (SEQ ID NO: 76); DF I-12 (SEQ ID NO: 77); DF I-5 (SEQ ID NO: 78); DF I-13 (SEQ ID NO: 79); DF I-14 (SEQ ID NO: 80); DF I-15 (SEQ ID NO: 81); DF I-6 (SEQ ID NO: 82); DF I-7 (SEQ ID NO: 83); DF I-8.1 (SEQ ID NO: 84); DF I-8 (SEQ ID NO: 85); DF I-9 (SEQ ID NO: 86); DF I-16 (SEQ ID NO: 87); DF I-10 (SEQ ID NO: 88); DF I-17 (SEQ ID NO: 89); DF I-21.1 (SEQ ID NO: 90); DF I-21.2 (SEQ ID NO: 91); DF I-22.1 (SEQ ID NO: 92); DF I-22.2 (SEQ ID NO: 93); DF I-22.4 (SEQ ID NO: 94); DF I-23.1 (SEQ ID NO: 95); DF I-23.2 (SEQ ID NO: 96); DF I-25.1 (SEQ ID) NO: 97); DF I-25.2 (SEQ ID NO: 98); DF I-26.1 (SEQ ID NO: 99); DF I-27.1 (SEQ ID NO: 100); DF I-28.1 (SEQ ID NO: 101); DF I-28.2 (SEQ ID NO: 102); DP II-20 (SEQ ID NO: 50); DP II-20.1 (SEQ ID NO: 51); DP II-20.2 (SEQ ID NO: 52); DP II-20.3 (SEQ ID NO: 53); DP II-20.4 (SEQ ID NO: 54); DP II-20.5 (SEQ ID NO: 55); DP II-20.6 (SEQ ID NO: 56); DP II-1 (SEQ ID NO: 41); DP II-2 (SEQ ID NO: 42); DP II-3.1 (SEQ ID NO: 43); DP II-4 (SEQ ID NO: 44); DP II-5 (SEQ ID NO: 45); DP II-6 (SEQ ID NO: 46); DP II-7 (SEQ ID NO: 47); DP II-8 (SEQ ID NO: 48); DP II-9 (SEQ ID NO: 49); DP II-1.1 (SEQ ID NO: 57); DP II-1.2 (SEQ ID NO: 58); DP II-2.1 (SEQ ID NO: 59); DP II-2.2 (SEQ ID NO: 60); DP II-2.3 (SEQ ID NO: 61); DP II-21 (SEQ ID NO: 62); DP II-22 (SEQ ID NO: 63); DP II-26 (SEQ ID NO: 64); DP II-26.1 (SEQ ID NO: 65); DP II-23 (SEQ ID NO: 66); DP II-23.1 (SEQ ID NO: 67); DP II-24 (SEQ ID NO: 68); DP II-25 (SEQ ID NO: 69); DP II-25.1 (SEQ ID NO: 70); DP II-25.2 (SEQ ID NO: 71); DF II-1 (SEQ ID NO: 103); DF II-2 (SEQ ID NO: 104); DF II-13.1 (SEQ ID NO: 105); DF II-3.1 (SEQ ID NO: 106); DF II-4.5 (SEQ ID NO: 107); DF II-4.3 (SEQ ID NO: 108); DF II-15 (SEQ ID NO: 109); DF II-16 (SEQ ID NO: 110); DF II-17 (SEQ ID NO: 111); DF II-18 (SEQ ID NO: 112); DF II-19 (SEQ ID NO: 113); DF II-19.1 (SEQ ID NO: 114); DF II-21 (SEQ ID NO: 115); and DF II-22 (SEQ ID NO: 116), or portions of the peptides comprising at least one T cell epitope. Preferably, a portion of a peptide derived from Der f I, Der p II and Der f II has a mean T cell stimulation index equivalent to or greater than the mean T cell stimulation index of the peptide from which it is derived as shown in FIG. 10, FIG. 15a, FIG. 15b and FIG. 16. More preferably, peptides derived from the Der p II and Der f I proteins comprise all or a portion of the following peptides: DF I-22.2 (ID SEQ NO: 93 ), DP II-20.6 (ID SEQ NO: 56 ), DP II-20.0 (ID SEQ NO: 50), DP II-22 (ID SEQ NO: 63 ), DP II-24 (ID SEQ NO: 68 ) and DP II-25.2 (ID SEQ NO: 71 ).

Preferred modified peptides derived from Der p I, Der p II, and Der f II protein allergens include: DP I-21.7 (SEQ ID NO: 120), DP I-23.10 (SEQ ID NO: 121), DP I-23.11 (SEQ ID NO: 124), DP I-23.12 (SEQ ID NO: 125), DP I-23.5 (SEQ ID NO: 126), DP I-23.6 (SEQ ID NO: 127), DP I-23.7 (SEQ ID NO: 128), DP I-23.8 (SEQ ID NO: 129), DP I-23.9 (SEQ ID NO: 130), DP I-26.2 (SEQ ID NO: 134), DP II-20.7 (SEQ ID NO: 138), DP II-22.6 (SEQ ID NO: 139), DP II-22.3 (SEQ ID NO: 140), DP II-22.4 (SEQ ID NO: 141), DP II-22.5 (SEQ ID NO: 142), DP II-25.3 (SEQ ID NO: 148), DP II-25.4 (SEQ ID NO: 149), DP I-23.13 (SEQ ID NO: 122), DP I-23.14 (SEQ ID NO: 123), DP I-23.15 (SEQ ID NO: 131), DP I-23.16 (SEQ ID NO: 132), DP I-23.17 (SEQ ID NO: 133), DP I-26.3 (SEQ ID NO: 135), DP I-26.4 (SEQ ID NO: 136), DP I-26.5 (SEQ ID NO: 137), DP II-22.7 (SEQ ID NO: 143), DP II-22.8 (SEQ ID NO: 144), DP II-22.9 (SEQ ID NO: 145), DP II-22.10 (SEQ ID NO: 146), DP II-22.11 (SEQ ID NO: 147), DP I-23.32 (SEQ ID NO: 163), DPI-23.33 (SEQ ID NO: 164) DP I-23.31 (SEQ ID NO: 165), DP I-23.34 (SEQ ID NO: 166), DP I-23.35 (SEQ ID NO: 167), DP I-26.6 (SEQ ID NO: 168), DP II-20.9 (SEQ ID NO: 169), DP II-20.11 (SEQ ID NO: 169), DP II-20.10 (SEQ ID NO: 170) DP II-20.8 (SEQ ID NO: 171), D,P II-22.19 (SEQ ID NO: 172), DP II-22.20 (SEQ ID NO: 173), DP II-22.21 (SEQ ID NO: 174), DP II-22.22 (SEQ ID NO: 175), DP II-22.26 (SEQ ID NO: 176), DP II-22.23 (SEQ ID NO: 177), DP II-22.24 (SEQ ID NO: 178), DP II-22.25 (SEQ ID NO: 179), DP II-22.14 (SEQ ID NO: 180), DF II-25.11 (SEQ ID NO: 182), DP II-25.9 (SEQ ID NO: 183), DF II-25.10 (SEQ ID NO: 184), DF II-25.13 (SEQ ID NO: 186), DP II-25.14 (SEQ ID NO: 187), DP II-25.15 (SEQ ID NO: 188), DP II-25.16 (SEQ ID NO: 189), DP II-25.17 (SEQ ID NO: 190), DP II-25.18 (SEQ ID NO: 191) all as shown in FIGS. 29 and 30.

Preferably modified peptides derived from Der p I, Der p II, and Der f II protein allergens include: DP I-21.7 (SEQ ID NO: 120), DP I-23.31 (SEQ ID NO: 165), DP I-23.35 (SEQ ID NO: 167), DP I-26.6 (SEQ ID NO: 168), DP II-20.9 (SEQ ID NO: 169), DP II 20.11 (SEQ ID NO: 169), DP II-20.10 (SEQ ID NO: 170), DP II-8 (SEQ ID NO: 171), DP II-22.19 (SEQ ID NO: 172), DP II-22.22 (SEQ ID NO: 175), DP II-22.23 (SEQ ID NO: 177), DP II-22.14 (SEQ ID NO: 180), DP II-25.9 (SEQ ID NO: 183), DP II-25.14 (SEQ ID NO: 187), DP II-25.15 (SEQ ID NO: 188), DP II-25.16 (SEQ ID NO: 189), DP II-25.17 (SEQ ID NO: 190), and DP II-25.18 (SEQ ID NO: 191).

One embodiment of the present invention features a peptide of a protein allergen of the genus Dermatophagoides. The peptide or portion thereof comprises at least one T cell epitope of the protein allergen and has a formula $X_n$—Y—$Z_m$. According to the formula, Y is an amino acid sequence selected from the group consisting of: DF I-21.1 (SEQ ID NO: 90); DF I-21.2 (SEQ ID NO: 91); DF I-22.1 (SEQ ID NO: 92); DF I-22.2 (SEQ ID NO: 93); DF I-22.4 (SEQ ID NO: 94); DF I-23.1 (SEQ ID NO: 95); DF I-23.2 (SEQ ID NO: 96); DF I-25.1 (SEQ ID NO: 97); DF I-25.2 (SEQ ID NO: 98); DF I-26.1 (SEQ ID NO: 99); DF I-27.1 (SEQ ID NO: 100); DF I-28.1 (SEQ ID NO: 101); DF I-28.2 (SEQ ID NO: 102); DF I-1 (SEQ ID NO: 72); DP II-20 (SEQ ID NO: 50); DP II-20.1 (SEQ ID NO: 51); DP II-20.2 (SEQ ID NO: 52); DP I-20.3 (SEQ ID NO: 53); DP II-20.4 (SEQ ID NO: 54); DP II-20.5 (SEQ ID NO: 55); DP II 20.6 (SEQ ID NO: 56); DP II-1 (SEQ ID NO: 41); DP II-1.1 (SEQ ID NO: 57); DP II-1.2 (SEQ ID NO: 58); DP II-2.1 (SEQ ID NO: 59); DP II-2.2 (SEQ ID NO: 60); DP II-2.3 (SEQ ID NO: 61); DP II-21 (SEQ ID NO: 62); DP II-22 (SEQ ID NO: 63); DP II-26 (SEQ ID NO: 64); DP II-26.1 (SEQ ID NO:65); DP II-23 (SEQ ID NO: 66); DP II-23.1 (SEQ ID NO: 67); DP II-24 (SEQ ID NO: 68); DP II-25 (SEQ ID NO: 69); DP II-25.1 (SEQ ID NO: 70); DP II-25.2 (SEQ ID NO: 71); DF II-1 (SEQ ID NO: 103); DF II-2 (SEQ ID NO: 104); DF II-13.1 (SEQ ID NO: 105); DF II-3.1 (SEQ ID NO: 106); DF II-4.5 (SEQ ID NO: 107); DF II-4.3 (SEQ ID NO: 108); DF II-15 (SEQ ID NO: 109); DF II-16 (SEQ ID NO: 110); DF II-17 (SEQ ID NO: 111); DF II-18 (SEQ ID NO: 112); DF II-19 (SEQ ID NO: 113); DF II-19.1 (SEQ ID NO: 114); DF II-21 (SEQ ID NO: 115); and DF II-22 (SEQ ID NO: 116). In addition, $X_n$ are amino acid residues contiguous to the amino terminus of Y in the amino acid sequence of the protein allergen and $Z_m$ are amino acid residues contiguous to the carboxy terminus of. Y in the amino acid sequence of the protein allergen. Preferably, the amino acids comprising the amino terminus of X and the carboxy terminus of Z are selected from charged amino acids, i.e., arginine (R), lysine (K), histidine (H), glutamic acid (E) or aspartic acid (D); amino acids with reactive side chains, e.g., cysteine (C), asparagine (N) or glutamine (Q); or amino acids with sterically small side chains, e.g., alanine (A) or glycine (G). In the formula, n is preferably 0–30 and m is preferably 0–30. Preferably n and m are 0–5, and most preferably n+m is less than 10. Preferably, the peptide or portion thereof has a mean T cell stimulation index equivalent to or greater than the mean T cell stimulation index of Y (see Examples and Figs).

In the above equation, Y may also be selected from the group of modified peptides consisting of: DP I-21.7 (SEQ ID NO: 120); DP I-23.10 (SEQ ID NO: 121); DP I-23.11 (SEQ ID NO: 124); DP I-23.12 (SEQ ID NO: 125); DP I-23.5 (SEQ ID NO: 126); DP I-23.6 (SEQ ID NO: 127); DP I-23.7 (SEQ ID NO: 128); DP I-23.8 (SEQ ID NO: 129); DP I-23.9 (SEQ ID NO: 130); DP I-26.2 (SEQ ID NO: 134); DP II-20.7 (SEQ ID NO: 138); DP II-22.6 (SEQ ID NO: 139); DP II-22.3 (SEQ ID NO: 140); DP II-22.4 (SEQ ID NO: 141); DP II-22.5 (SEQ ID NO: 142); DP II-25.3 (SEQ ID NO: 148); DP II-25.4 (SEQ ID NO: 149); DP I-23.13 (SEQ ID NO: 122); DP I-23.14 (SEQ ID NO: 123); DP I-23.15 (SEQ ID NO: 131); DP I-23.16 (SEQ ID NO: 132); DP I-23.17 (SEQ ID NO: 133); DP I-26.3 (SEQ ID NO: 135); DP I-26.4 (SEQ ID NO: 136); DP I-26.5 (SEQ ID NO: 137); DP II-22.7 (SEQ ID NO: 143); DP II-22.8 (SEQ ID NO: 144); DP II-22.9 (SEQ ID NO: 145); DP II-22.10 (SEQ ID NO: 146); DP II-22.11 (SEQ ID NO: 147); DP I-23.32 (SEQ ID NO: 163), DPI-23.33 (SEQ ID NO: 164), DP I-23.31 (SEQ ID NO: 165), DP I-23.34 (SEQ ID NO: 166), DP I-23.35 (SEQ ID NO: 167), DP I-26.6 (SEQ ID NO: 168), DP II-20.9 (SEQ ID NO: 169), DP II-20.11 (SEQ ID NO: 169), DP II-20.10 (SEQ ID NO: 170), DP II-20.8 (SEQ ID NO: 171), D,P II-22.19 (SEQ ID NO: 172), DP II-22.20 (SEQ ID NO: 173), DP II-22.21 (SEQ ID NO: 174), DP II-22.22 (SEQ ID NO: 175), DP II-22.26 (SEQ ID NO: 176), DP II-22.23 (SEQ ID NO: 177), DP II-22.24 (SEQ ID NO: 178), DP II-22.25 (SEQ ID NO: 179), DP II-22.14 (SEQ ID NO: 180), DF II-25.11 (SEQ ID NO: 182), DP II-25.9 (SEQ ID NO: 183), DF II-25.10 (SEQ ID NO: 184), DF II-25.13 (SEQ ID NO: 186), DP II-25.14 (SEQ ID NO: 187), DP II-25.15 (SEQ ID NO: 188), DP II-25.16 (SEQ ID NO: 189), DP II-25.17 (SEQ ID NO: 190), DP II-25.18 (SEQ ID NO: 191) all as shown in FIGS. 29 and 30.

Another embodiment of the present invention provides peptides comprising at least two regions, each region comprising at least one T cell epitope of a protein allergen of the genus Dermatophagoides and accordingly, each region comprises at least approximately seven amino acid residues). These peptides comprising at least two regions can comprise as many amino acid residues as desired and preferably comprise at least about 14, even more preferably about 30, and most preferably at least about 40 amino acid residues of a mite allergen. Each region of such peptide preferably comprises up to 45 amino acid residues in length, more preferably up to 40 residues in length and most preferably up to 30 amino acid residues in length as increases in length of a region may result in difficulty in peptide synthesis as well as retention of an undesirable property (e.g., immunoglobulin binding or enzymatic activity) due to maintenance of conformational similarity between the peptide and the protein allergen from which it is derived. If desired, the amino acid sequences of the regions can be produced and joined by a linker to increase sensitivity to processing by antigen-presenting cells. Such linker can be any non-epitope amino acid sequence or other appropriate liking or joining agent. To obtain preferred peptides comprising at least two regions, each comprising at least one T cell epitope, the regions are arranged in a configuration different from a naturally-occurring configuration of the regions in the allergen or a combination of different mite protein allergens. For example, the regions containing T cell epitope(s) can be arranged in a noncontiguous configuration and can preferably be derived from the same protein allergen or a combination of protein allergens. Noncontiguous is defined as an arrangement of regions containing T cell epitope(s) which is different than that of an amino acid sequence present in the protein allergen from which the regions are derived. Furthermore, the noncontiguous regions containing T cell epitopes can be arranged in a nonsequential order (e.g., in an order different from the order of the amino acids of the native protein allergen from which the region containing T cell epitope(s) are derived in which amino acids are arranged from an amino terminus to a carboxy terminus). A peptide can comprise at least 15%, at least 30%, at least 50% or up to 100% of the T cell epitopes of a mite allergen but does not comprise the whole protein sequence of the allergen.

The individual peptide regions can be produced and tested to determine which regions bind immunoglobulin E specific for a mite allergen and which of such regions would cause the release of mediators (e.g., histamine) from mast cells or basophils. Those peptide regions found to bind immunoglobulin E and cause the release of mediators from mast cells or basophils in greater than approximately 10–15% of the allergic sera tested are preferably not included in the peptide regions arranged to form peptides of the invention.

Preferred peptides of the invention comprise two or more regions derived from the same or from different mite allergens (e.g. Der p I, Der p II, Der f I and Der f II). For example, one region can be derived from Der p I and one region can be derived from Der p II; one region can be derived from Der p I and one region can be derived from Der f I; one region can be derived from Der p II and one region can be derived from Der f I; one region can be derived from Der p II and one region can be derived from Der f II; one region can be derived from Der p I and one region can be derived from Der f II; and one region can be derived from Der f I and one region can be derived from Der f II. In addition, the regions can be derived from the same protein allergen, e.g., Der p I and Der p I, etc.

Regions of a peptide of the invention preferably comprise all or a portion of the above discussed preferred areas of major T cell reactivity within each mite allergen (i.e., Regions I-6a-6b of Der p I and Der f I and Regions 7–10 of Der p II and Der f II). For example, one region can comprise all or a portion of Region 1 (amino acid residues 1–28 of Der p I or Der f I) and one region can comprise all or a portion of Region 2 (amino acid residues 36–68 of Der p I or Der f I). Peptides of the invention can comprise all or a portion of two or more of these Regions (i.e., Regions 1–10) and preferred resulting peptides do not bind IgE and cause the release of mediators from mast cells or basophils. Preferred peptides derived from Der p I and Der f I comprise all or a portion of Region 1, Region 2, Region 3 and optionally Region 4. Preferred peptides derived from Der p II and Der f II comprise all or a portion of Region 7 and Region 8 and, Region 10. Further, if one of these Regions is found to bind IgE and cause the release of mediators from mast cells or basophils, then it is preferred that the peptide not comprise such Regions but rather comprises various Regions derived from such Regions which do not bind IgE or cause release of mediators from mast cells or basophils.

Examples of preferred regions include all or a portion of the following amino acid sequences: DP I-21.1 (SEQ ID NO: 27); DP I-21.2 (SEQ ID NO: 28); DP I-22.1 (SEQ ID NO: 29); DP I-22.2 (SEQ ID NO: 30); DP I-22.3 (SEQ ID NO: 31); DP I-22.4 (SEQ ID NO: 32); DP I-23.1 (SEQ ID NO: 33); DP I-23.2 (SEQ ID NO: 34); DP I-25.1 (SEQ ID NO: 35); DP I-25.2 (SEQ ID NO: 36); DP I-26.1 (SEQ ID NO: 37); DP I-27.1 (SEQ ID NO: 38); DP I-28.1 (SEQ ID NO: 39); DP I-28.2 (SEQ ID NO: 40); DP I-1 (SEQ ID NO: 9); DF I-1 (SEQ ID NO: 72); DF I-21.1 (SEQ ID NO: 90); DF I-21.2 (SEQ ID NO: 91); DF I-22.1 (SEQ ID NO: 92); DF I-22.2 (SEQ ID NO: 93); DF I-22.4 (SEQ ID NO: 94); DF I-23.1 (SEQ ID NO: 95); DF I-23.2 (SEQ ID NO: 96); DF I-25.1 (SEQ ID NO: 97); DF I-25.2 (SEQ ID NO: 98); DF I-26.1 (SEQ ID NO: 99); DF I-27.1 (SEQ ID NO: 100); DF I-28.1 (SEQ ID NO: 101); DF I-28.2 (SEQ ID NO: 102); DP II-20 (SEQ ID NO: 50); DP II-20.1 (SEQ ID NO: 51); DP II-20.2 (SEQ ID NO: 52); DP II-20.3 (SEQ ID NO: 53); DP II-20.4 (SEQ ID NO: 54); DP II-20.5 (SEQ ID NO: 55); DP II 20.6 (SEQ ID NO: 56); DP II-1 (SEQ ID NO: 41); DP II-1.1 (SEQ ID NO: 57); DP II-1.2 (SEQ ID NO: 58); DP II-2.1 (SEQ ID NO: 59); DP II-2.2 (SEQ ID NO: 60); DP II-2.3 (SEQ ID NO: 61); DP II-21 (SEQ ID NO: 62); DP II-22 (SEQ ID NO: 63); DP II-26 (SEQ ID NO: 64); DP II-26.1 (SEQ ID NO: 65); DP II-23 (SEQ ID NO: 66); DP II-23.1 (SEQ ID NO: 67); DP II-24 (SEQ ID NO: 68); DP II-25 (SEQ ID NO: 69); DP II-25.1 (SEQ ID NO: 70); DP II-25.2 (SEQ ID NO: 71); DF II-1 (SEQ ID NO: 103) DF II-2 (SEQ ID NO: 104); DF II-13.1 (SEQ ID NO: 105); DF II-3.1 (SEQ ID NO: 106); DF II-4.5 (SEQ ID NO: 107); DF II-4.3 (SEQ ID NO: 108); DF II-15 (SEQ ID NO: 109); DF II-16 (SEQ ID NO: 110); DF II-17 (SEQ ID NO: 111); DF II-18 (SEQ ID NO: 112); DF II-19 (SEQ ID NO: 113); DF II-19.1 (SEQ ID NO: 114); DF II-21 (SEQ ID NO: 115); and DF II-22 (SEQ ID NO: 116), the amino acid sequences of such regions being shown in FIG. 3 and FIG. 36, or portions of said regions comprising at least one T cell epitope.

Figure 36:
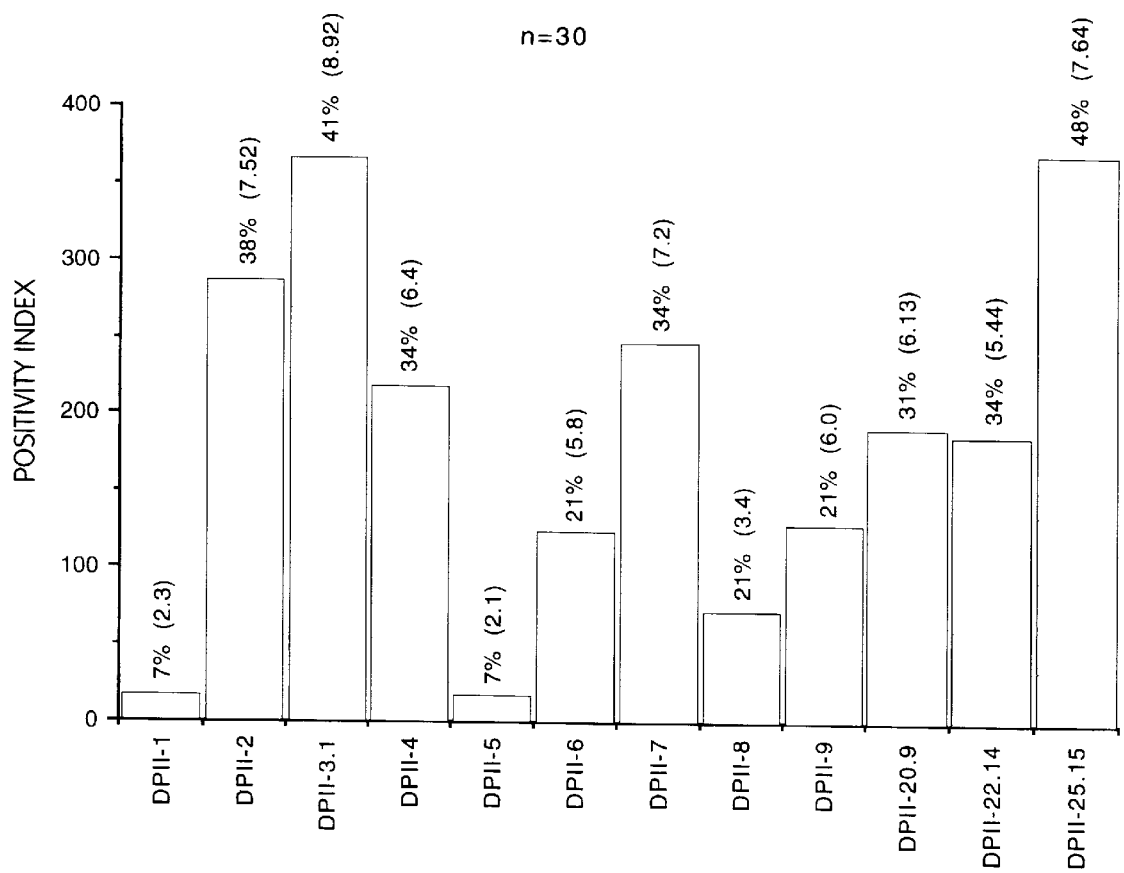
FIG. 36 is a graphic representation depicting T cell responses to the overlapping Der p II peptides, DPII-20.9 (SEQ. ID. NO. 169), DPII-22.14 (SEQ. ID. NO. 180), and DPII-25.15 (SEQ. ID. NO. 188), shown in FIG. 2 and the Der p II "unique" peptides shown in FIG. 2. The mean S.I. shown above each bar (in parenthesis) as well as the percentage of responses, the positivity index (mean S.I. multiplied by percentage of responses), is the Y axis.

Preferred peptides comprise various combinations of two or more regions, each region comprising all or a portion of the above-discussed preferred areas of major T cell reactivity. Preferred peptides comprise a combination of two or more regions (each region having an amino acid sequence as shown in FIG. 3 and FIG. 36) including: DP I-22.1 (SEQ ID NO: 29) and DP I-25.1 (SEQ ID NO: 35); DP I-21.1 (SEQ ID NO: 27) and DP I-25.2 (SEQ ID NO: 36); DP I-22.1 (SEQ ID NO: 29) and DP I-1 (SEQ ID NO: 9); DP I-21.1 (SEQ ID NO: 27), DP I-22.1 (SEQ ID NO: 29), and DP I-25.2 (SEQ ID NO: 36); DP I-21.2 (SEQ ID NO: 28), DP I-22.1 (SEQ ID NO: 29), and DP I-23.1 (SEQ ID NO: 39); DP I-1 (SEQ ID NO: 9), DP I-22.1 (SEQ ID NO: 29), and DP I-23.1 (SEQ ID NO: 33); DP I-1 (SEQ ID NO: 9), DP I-22.1 (SEQ ID NO: 29), and DP I-25.2 (SEQ ID NO: 36); DP I-21.1 (SEQ ID NO: 27), DP I-22.1 (SEQ ID NO: 29), DP I-23.1 (SEQ ID NO: 33), and DP I-25.2 (SEQ ID NO: 36); DP I-21.2 (SEQ ID NO: 28), DP I-22.1 (SEQ ID NO: 29), and DP I-25.2 (SEQ ID NO: 36); DP I-21.2 (SEQ ID NO: 27), DP I-22.1 (SEQ ID NO: 29), DP I-25.2 (SEQ ID NO: 36), and DP I-26.1 (SEQ ID NO: 37); DF I-21.2 (SEQ ID NO: 91) and DF I-22.1 (SEQ ID NO: 92); DF I-21.1 (SEQ ID NO: 90), DF I-22.1 (SEQ ID NO: 92), and DF I-25.1 (SEQ ID NO: 97); DF I-21.2 (SEQ ID NO: 91), DF I-22.1 (SEQ ID NO: 92), and DF I-25.1 (SEQ ID NO: 97); DF I-1 (SEQ ID NO: 72) and DF I-22.1 (SEQ ID NO: 92); DF I-1 (SEQ ID NO: 72), DF I-22.1 (SEQ ID NO: 92), and DF I-25.1 (SEQ ID NO: 97); DF I-22.1 (SEQ ID NO: 29), and DF I-25.1 (SEQ ID NO: 35); DF I-21.1 (SEQ ID NO: 90), DF I-22.1 (SEQ ID NO: 92), and DF I-23.1 (SEQ ID NO: 95); DP I-21.1 (SEQ ID NO: 27), and DF I-22.1 (SEQ ID NO: 92); DP I-1 (SEQ ID NO: 9), DP I-23.1 (SEQ ID NO: 33), DP I-25.1 (SEQ ID NO: 35), and DF I-1 (SEQ ID NO: 72); t) DP I-1 (SEQ ID NO: 9), DP I-25.1 (SEQ ID NO: 35), DP I-23.1 (SEQ ID NO: 33), and DF I-21.2 (SEQ ID NO: 91); DP I-1 (SEQ ID NO: 9), DP I-25.1 (SEQ ID NO: 35), DP I-23.1 (SEQ ID NO: 33), and DF I-21.1 (SEQ ID NO: 90); DP II-22 (SEQ ID NO: 63), and DP II-25.2 (SEQ ID NO: 71); DP II-22 (SEQ ID NO: 63), DP II-25.2 (SEQ ID NO: 71), and DP I-21.1 (SEQ ID NO: 27) and DP I-22.1 (SEQ ID NO: 29); DP II-22 (SEQ ID NO: 63), DP II-25.2 (SEQ ID NO: 71), DP II-20.6 (SEQ ID NO: 56), DP I-22.1 (SEQ ID NO: 29), DP I-21.1 (SEQ ID NO: 27), and DP I-23.1 (SEQ ID NO: 33); DP II-22 (SEQ ID NO: 63), DP II-25.2 (SEQ ID NO: 71), DP II-20.6 (SEQ ID NO: 56), DP I-21.1 (SEQ ID NO: 27), DP I-22.1 (SEQ ID NO: 29), and DP I-25.2 (SEQ ID NO: 36); DP II-22 (SEQ ID NO: 63), DP II-25.2 (SEQ ID NO: 71), DP I-21.1 (SEQ ID NO: 27), DP I-22.1 (SEQ ID NO: 29), and DP I-25.2 (SEQ ID NO: 36); DP II-22 (SEQ ID NO: 63), DP II-25.2 (SEQ ID NO: 71), DP I-21.1 (SEQ ID NO: 27), DP I-22.1 (SEQ ID NO: 29), and DP I-23.1 (SEQ ID NO: 33); DP II-22 (SEQ ID NO: 63), DP II-25.2 (SEQ ID NO: 71), DP I-1 (SEQ ID NO: 9), and DP I-22.1 (SEQ ID NO: 29); DF II-4.5 (SEQ ID NO: 107) and DF II-2 (SEQ ID NO: 104); DF II-4.5 (SEQ ID NO: 107) and DF II-19.1 (SEQ ID NO: 114); DF II-4.5 (SEQ ID NO: 107), DF II-2 (SEQ ID NO: 104), and DF II-19.1 (SEQ ID NO: 114); DF II-4.5 (SEQ ID NO: 107), DF II-2 (SEQ ID NO: 104), and DF II-9 (SEQ ID NO: 86); DF II-4.5 (SEQ ID NO: 107); and DF I-21.1 (SEQ ID NO: 90); DF II-4.5 (SEQ ID NO: 107), DP II-22 (SEQ ID NO: 63), and DP II-25.2 (SEQ ID NO: 71); and DF II-4.5 (SEQ ID NO: 107), DF II-2 (SEQ ID NO: 104), and DP II-22 (SEQ ID NO: 63).

Additional preferred peptides comprising a combination of two or more Regions include the following combinations: DP I-21.2 (SEQ ID NO:28), DP I-23.1 (SEQ ID NO:33), DP I-26.1 (SEQ ID NO:37), DP II-20.6 (SEQ ID NO:56), DP II-22 (SEQ ID NO:63), DP II-25.2 (SEQ ID NO:71) and DP II-22.2 (SEQ ID NO:156); DP I-21.2 (SEQ ID NO:91); DP II-22.2 (SEQ ID NO:156); DP I-21.2 (SEQ ID NO:28), DP I-22.2 (SEQ ID NO:93), DP I-23.1 (SEQ ID NO:95), DP I-25.2 (SEQ ID NO:36), DP I-26.1 (SEQ ID NO:37), DP I-27.1 (SEQ ID NO:38), DP II-20.6 (SEQ ID NO:56), DP II-22 (SEQ ID NO:63), DP II-24 (SEQ ID NO:68), and DP II-25.2; DP I-23.1, DP I-21.2, DP I-22, DF I-22.2, DP II-20.6, and DP II-25.2 (SEQ ID NO:71); DP I-23.1 (SEQ ID NO:33), DP I-21.2 (SEQ ID NO:28), DP I-22.1 (SEQ ID NO:29), DF I-22.2 (SEQ ID NO:93); DP II-20.6 (SEQ ID NO:56), and DP II-25.2 (SEQ ID NO:71); DP I-23.1 (SEQ ID NO:33), DP I-21-2 (SEQ ID NO:28); DF I-22.2 (SEQ ID NO:93) and DP II-20.6 (SEQ ID NO:56), and DP II-25.2 (SEQ ID NO:71); DP I-23.1 (SEQ ID NO:33), DF I-22.1 (SEQ ID NO:92), and DP II-20.6 (SEQ ID NO:56); DP I-26.1 (SEQ ID NO:37), DF I-22.2 (SEQ ID NO:93), and DP II-25.2 (SEQ ID NO:71); DP I-21.2 (SEQ ID NO:28), DF I-22.2 (SEQ ID NO:93), and DP II-22 (SEQ ID NO:63); and DP I-21.2 (SEQ ID NO:28) and DP II-22 (SEQ ID NO:63) all as shown in FIG. 29 and FIG. 30.

Other preferred peptides comprise a combination of two or more regions (each region having an amino acid sequence as shown in FIG. 3 and FIG. 36) derived from mite allergens Der p I, Der p II, and Der f I each of said preferred peptides having the following specific sequential arrangement of amino acid sequences as shown in FIGS. 25–27: DPI-26.1, DPII-25.2, DFI-22.2, DP II-22, DP I-23.1, DPII-20.6 and DPI-21.2 (SEQ ID NO:193) respectively; DPII-25.2, DFI-22.2, DPI-23.1, DPII-22, DPI-21.2 and DPII-20.6 (SEQ ID NO:195) respectively; and DPII-25.2, DPI-21.2, DPI-23.1, DPI-26.1, DPII-22, DPII-20.6 and DFI-22.2 (SEQ ID NO: 197) respectively. The nucleic acid and amino acid sequences of the above peptides are shown in FIGS. 25 (SEQ ID NOS:192 and 193), 26 (SEQ ID NOS:194 and 195) and 27 (SEQ ID NOS:196 and 197) respectively.

Other preferred peptides comprise various combinations of two or more regions, each region comprising at least one T cell epitope of a protein allergen of the genus Dermatophagoides, the regions may be derived from the same or different protein allergens of the genus Dermatophagoides, wherein at least one region comprises an amino acid sequence selected from the following group: DP I-21.1 (SEQ ID NO: 27); DP I-21.2 (SEQ ID NO: 28); DP I-22.1 (SEQ ID NO: 29); DP I-23.1 (SEQ ID NO: 33); DP I-25.2 (SEQ ID NO: 36); DP I-26.1 (SEQ ID NO: 37); DP I-28.1 (SEQ ID NO: 39); DP I-1 (SEQ ID NO: 9); DF I-1 (SEQ ID NO: 72); DF I-21.1 (SEQ ID NO: 90); DF I-22.1 (SEQ ID NO: 92); DF I-23.1 (SEQ ID NO: 95); DF I-25.1 (SEQ ID NO: 97); DP II-1 (SEQ ID NO: 41); DP II-1.2 (SEQ ID NO: 58); DP II-2.0 (SEQ ID NO: 56); DP II-20.3 (SEQ ID NO: 53); DP II-21 (SEQ ID NO: 62); DP II-22 (SEQ ID NO: 63); DP II-25 (SEQ ID NO: 69); DP II-25.2 (SEQ ID NO: 71); DF II-2 (SEQ ID NO: 104); DF II-4.5 (SEQ ID NO: 107); DF II-15 (SEQ ID NO: 109); DF II-17 (SEQ ID NO: 111); DF II-19.1 (SEQ ID NO: 114); DF I-22.2 (SEQ ID NO:93); DP II-20.0 (SEQ ID NO: 50) and DP II-20.6 (SEQ ID NO:56), all as shown in FIGS. 3–4 and wherein at least one region comprises an amino acid sequence selected from the following group: DP I-21.7 (SEQ ID NO: 120); DP I-23.10 (SEQ ID NO: 121); DP I-23.11 (SEQ ID NO: 124); DP I-23.12 (SEQ ID NO: 125); DP I-23.5 (SEQ ID NO: 126); DP I-23.6 (SEQ ID NO: 127);

DP I-23.7 (SEQ ID NO: 128); DP I-23.8 (SEQ ID NO: 129); DP I-23.9 (SEQ ID NO: 130); DP I-26.2 (SEQ ID NO: 134); DP II-20.7 (SEQ ID NO: 138); DP II-22.6 (SEQ ID NO: 139); DP II-22.3 (SEQ ID NO: 140); DP II-22.4 (SEQ ID NO: 141); DP II-22.5 (SEQ ID NO: 142); DP II-25.3 (SEQ ID NO: 148); DP II-25.4 (SEQ ID NO: 149); DP I-23.13 (SEQ ID NO: 122); DP I-23.14 (SEQ ID NO: 123); DP I-23.15 (SEQ ID NO: 131); DP I-23.16 (SEQ ID NO: 132); DP I-23.17 (SEQ ID NO: 133); DP I-26.3 (SEQ ID NO: 135); DP I-26.4 (SEQ ID NO: 136); DP I-26.5 (SEQ ID NO: 137); DP II-22.7 (SEQ ID NO: 143); DP II-22.8 (SEQ ID NO: 144); DP II-22.9 (SEQ ID NO: 145); DP II-22.10 (SEQ ID NO: 146); DP II-22.11 (SEQ ID NO: 147); DP I-23.32 (SEQ ID NO: 163), DPI-23.33 (SEQ ID NO: 164) DP I-23.31 (SEQ ID NO: 165), DP I-23.34 (SEQ ID NO: 166), DP I-23.35 (SEQ ID NO: 167), DP I-26.6 (SEQ ID NO: 168), DP II-20.9 (SEQ ID NO: 169), DP II-20.11 (SEQ ID NO: 169), DP II-20.10 (SEQ ID NO: 170) DP II-20.8 (SEQ ID NO: 171), D,P II-22.19 (SEQ ID NO: 172), DP II-22.20 (SEQ ID NO: 173), DP II-22.21 (SEQ ID NO: 174), DP II-22.22 (SEQ ID NO: 175), DP II-22.26 (SEQ ID NO: 176), DP II-22.23 (SEQ ID NO: 177), DP II-22.24 (SEQ ID NO: 178), DP II-22.25 (SEQ ID NO: 179), DP II-22.14 (SEQ ID NO: 180), DF II-25.11 (SEQ ID NO: 182), DP II-25.9 (SEQ ID NO: 183), DF II-25.10 (SEQ ID NO: 184), DF II-25.13 (SEQ ID NO: 186), DP II-25.14 (SEQ ID NO: 187), DP II-25.15 (SEQ ID NO: 188), DP II-25.16 (SEQ ID NO: 189), DP II-25.17 (SEQ ID NO: 190), DP II-25.18 (SEQ ID NO: 191) all as shown in FIGS. 29 and 30.

Additional preferred peptides comprise a combination of two or more regions (each region having an amino acid sequence as shown in FIG. 3, FIG. 36, and FIG. 29) including: DP I-21.7 (SEQ ID NO: 120), DF I-22.2 (SEQ ID NO:93), DP I-23.13 (SEQ ID NO:122), DP I-26.1 (SEQ ID NO:37), DP II-20.6 (SEQ ID NO:56), DP II-22.3 (SEQ ID NO:140), and DP II-25.2 (SEQ ID NO:71); DP I-21.2 (SEQ ID NO:28), DF I-22.2 (SEQ ID NO:93), DP I-23.10 (SEQ ID NO:121), DP I-26.2 (SEQ ID NO:134), DP II-20.6 (SEQ ID NO:56), DP II-22.4 (SEQ ID NO: 141), and DP II-25.3 (SEQ ID NO:148), DP I-21.7 (SEQ ID NO:120), DF I-22.2 (SEQ ID NO:93), DP I-23.11 (SEQ ID NO: 124), DP I-26.3 (SEQ ID NO:135), DP II-20.7 (SEQ ID NO:138), DP II-22.5 (SEQ ID NO:142), and DP II-25.4 (SEQ ID NO:149); DP I-21.7 (SEQ ID NO: 120), DF I-22.2 (SEQ ID NO:93), DP I-23.12 (SEQ ID NO:125), DP I-26.4 (SEQ ID NO: 136), DP II-20.6 (SEQ ID NO:56), DP II-22.6 (SEQ ID NO:139), and DP II-25.2 (SEQ ID NO:71); DP I-21.7 (SEQ ID NO: 120), DF I-22.2 (SEQ ID NO:93), DP I-23.5 (SEQ ID NO: 126), DP I-26.5 (SEQ ID NO:137), DP II-20.7 (SEQ ID NO:138), DP II-22.7 (SEQ ID NO:143), and DP II-25.3 (SEQ ID NO:148); DP I-21.7 (SEQ ID NO: 120), DF I-22.2 (SEQ ID NO:93), DP I-23.6 (SEQ ID NO: 127), DP I-26.2 (SEQ ID NO:134), DP II-20.6 (SEQ ID NO:56), DP II-22.8 (SEQ ID NO:144), and DP II-25.4 (SEQ ID NO: 149); DP I-21.7 (SEQ ID NO:120), DF I-22.2 (SEQ ID NO:93), DP I-23.7 (SEQ ID NO:128), DP I-26.3 (SEQ ID NO:135), DP II-20.7 (SEQ ID NO:138), DP II-22.9 (SEQ ID NO: 145), and DP II-25.3 (SEQ ID NO:148); DP I-21.7 (SEQ ID NO: 120), DF I-22.2 (SEQ ID NO:93), DP I-23.8 (SEQ ID NO: 129), DP I-26.4 (SEQ ID NO:136), DP II-20.6 (SEQ ID NO:56), DP II-22.3 (SEQ ID NO:140) and DP II-25.4 (SEQ ID NO: 149); DP I-21.7 (SEQ ID NO:120), DF I-22.2 (SEQ ID NO:93), DP I-23.9 (SEQ ID NO:130), DP I-26.1 (SEQ ID NO:37), DP I-20.7 (SEQ ID NO:138), DP II-22.4 (SEQ ID NO:141), and DP I-25.3 (SEQ ID NO:148); DP I-21.7 (SEQ ID NO:120), DF I-22.2 (SEQ ID NO:93), DP I-23.13(SEQ ID NO:122), DP I-26.2 (SEQ ID NO:134), DP II-20.6 (SEQ ID NO:56), DP I-22.5 (SEQ ID NO:142), and DP II-25.4 (SEQ ID NO:149); DP I-21.7 (SEQ ID NO:120), DF I-22.2 (SEQ ID NO:93), DP I-23.14 (SEQ ID NO:123), DP I-26.3 (SEQ ID NO:135), DP II-20.7 (SEQ ID NO:138), DP II-22.6 (SEQ ID NO:139), and DP II-25.3 (SEQ ID NO:148); DP I-21.7 (SEQ ID NO:120), DF I-22.2 (SEQ ID NO:93), DP I-23.15 (SEQ ID NO:131), DP I-26.4 (SEQ ID NO:136), DP II-20.6 (SEQ ID NO:56), DP II-22.6 (SEQ ID NO:139), and DP II-25.3 (SEQ ID NO:148); DP I-21.7 (SEQ ID NO: 120), DF I-22.2 (SEQ ID NO:93), DP I-23.16 (SEQ ID NO:132), DP I-26.5 (SEQ ID NO:137), DP II-20.6 (SEQ ID NO:56), DP II-22.3 (SEQ ID NO: 140), and DP II-25.4 (SEQ ID NO: 149); DP I-21.7 (SEQ ID NO:120), DF I-22.2 (SEQ ID NO:93), DP I-23.17 (SEQ ID NO:133), DP I-26.2 (SEQ ID NO:134), DP II-20.6 (SEQ ID NO:56), DP II-22.4 (SEQ ID NO: 141), and DP II-25.3 (SEQ ID NO:148); DP I-21.7 (SEQ ID NO:120), DF I-22.2 (SEQ ID NO:93), DP I-23.8 (SEQ ID NO: 129), DP I-26.3 (SEQ ID NO: 135), DP II-20.6 (SEQ ID NO:56), DP II-22.5 (SEQ ID NO:142), and DP II-25.4 (SEQ ID NO:149); DP I-21.7 (SEQ ID NO:120), DF I-22.2 (SEQ ID NO:93), DP I-23.9 (SEQ ID NO:130), DP I-26.4 (SEQ ID NO: 136), DP II-20.6 (SEQ ID NO:56), DP II-22.6 (SEQ ID NO:139) and DP II-25.3 (SEQ ID NO: 148); and DP I-21.7 (SEQ ID NO: 120), DF I-22.2 (SEQ ID NO:93), DP I-23.5 (SEQ ID NO: 126), DP I-26.1 (SEQ ID NO:37), DP II-20.6 (SEQ ID NO:56), DP II-22.7 (SEQ ID NO:143), and DP II-25.4 (SEQ ID NO:149).

Additional preferred peptides comprise at least two of the following combination of regions in any arrangement: X,Y, Z,A,B,C,D, wherein X is DP I-21.2 (SEQ ID NO: 27) or DP I-21.7 (SEQ ID NO: 120); Y is DF I-22.2 (SEQ ID NO:93); Z is DP I-23.1 (SEQ ID NO:33), DP I-23.10 (SEQ ID NO:121), DP I-23.11 (SEQ ID NO:124), DP I-23.12 (SEQ ID NO:125), DP I-23.13 (SEQ ID NO:122), DP I-23.14 (SEQ ID NO:123), DP I-23.15 (SEQ ID NO:131), DP I-23.16 (SEQ ID NO:132), DP I-23.17 (SEQ ID NO:133), DP I-23.5 (SEQ ID NO:126), DP I-23.6 (SEQ ID NO: 127), DP I-23.7 (SEQ ID NO:128), DP I-23.8 (SEQ ID NO: 129), DP I-23.9 (SEQ ID NO:130), DP I-23.32 (SEQ ID NO:163), DP I-23.33 (SEQ ID NO:164), DP I-23.31 (SEQ ID NO: 165), DP I-23.34 (SEQ ID NO: 166), or DP I-23.35 (SEQ ID NO:167); A is DP I-26.1 (SEQ ID NO:37), DP I-26.2 (SEQ ID NO:134), DP I-26.3 (SEQ ID NO: 135), DP I-26.4 (SEQ ID NO:136), DP I-26.5 (SEQ ID NO:137) or DP I 26.6 (SEQ ID NO:168); B is DP II-20.0 (SEQ ID NO:50), DP II-20.6 (SEQ ID NO:56), DP II-20.7 (SEQ ID NO:138), DP II-20.9 (SEQ ID NO:169), DP II-20.11 (SEQ ID NO:169), DP II-20.10 (SEQ ID NO:170), or DP II-20.8 (SEQ ID NO: 171); C is DP II-22 (SEQ ID NO:63), DP II-22.6 (SEQ ID NO:139), DP II-22.7 (SEQ ID NO: 143), DP II-22.8 (SEQ ID NO:144), DP II-22.9 (SEQ ID NO:145), DP I-22.10 (SEQ ID NO: 146), DP II-22.11 (SEQ ID NO: 147), DP II-22.3 (SEQ ID NO:140), DP II-22.4 (SEQ ID NO:141), DP II-22.5 (SEQ ID NO:142), DP II-22.19 (SEQ ID NO: 172), DP II-22.20 (SEQ ID NO: 173), DP II-22.21 (SEQ ID NO:174), DP II-22.22 (SEQ ID NO: 175), DP II-22.26 (SEQ ID NO:176), DP II-22.23 (SEQ ID NO:177), DP II-22.24 (SEQ ID NO:178), DP II-22.25 (SEQ ID NO: 179), or DP II-22.14 (SEQ ID NO:180); and D is DP II-25.2 (SEQ ID NO:71), DP II-25.3 (SEQ ID NO: 148), DP II-25.4 (SEQ ID NO: 149), DF II-25.11 (SEQ ID NO:182), DP II-25.9 (SEQ ID NO:183), DF II-25.10 (SEQ ID NO:184), or DF II-25.13 (SEQ ID NO:186), DP II-25-14 (SEQ ID NO:187), DP II-25.15 (SEQ ID NO:188), DP II-25.16 (SEQ ID NO:189), DP II-25.17 (SEQ ID NO: 190), DP II-25.18 (SEQ ID NO:191); with the proviso that X, Y, Z, A, B, C, D is not the following combination of regions: DP I-21.2 (SEQ ID NO:

91), DF I-22.2 (SEQ ID NO: 93), DP I-23.1 (SEQ ID NO: 95), DP I-26.1 (SEQ ID NO: 99), DP II-20.6 (SEQ ID NO: 56), DP II-22 (SEQ ID NO: 63), and DP II-25.2 (SEQ ID NO: 71). Preferably, a preferred peptide comprises at least one region from each of X, Y, Z, A, B, C, and D.

Another preferred peptide comprises a specific sequential arrangement of amino acid sequences, said specific sequential arrangement having the formula:

ADYCZBX wherein X is DP I-21.2 (SEQ ID NO: 27) or DP I-21.7 (SEQ ID NO:120); Y is DF I-22.2 (SEQ ID NO:93); Z is DP I-23.1 (SEQ ID NO:33), DP I-23.10 (SEQ ID NO: 121), DP I-23.11 (SEQ ID NO:124), DP I-23.12 (SEQ ID NO:125), DP I-23.13 (SEQ ID NO:122), DP I-23.14 (SEQ ID NO:123), DP I-23.15 (SEQ ID NO: 131), DP I-23.16 (SEQ ID NO: 132), DP I-23.17 (SEQ ID NO:133), DP I-23.5 (SEQ ID NO: 126), DP I-23.6 (SEQ ID NO:127), DP I-23.7 (SEQ ID NO:128), DP I-23.8 (SEQ ID NO:129), DP I-23.9 (SEQ ID NO:130), DP I-23.32 (SEQ ID NO:163), DP I-23.33 (SEQ ID NO:164), DP I-23.31 (SEQ ID NO:165), DP I-23.34 (SEQ ID NO:166), or DP I-23.35 (SEQ ID NO:167); A is DP I-26.1 (SEQ ID NO:37), DP I-26.2 (SEQ ID NO:134), DP I-26.3 (SEQ ID NO:135), DP I-26.4 (SEQ ID NO:136), DP I-26.5 (SEQ ID NO:137) or DP I 26.6 (SEQ ID NO: 168); B is DP II-20.0 (SEQ ID NO:50), DP II-20.6 (SEQ ID NO:56), DP II-20.7 (SEQ ID NO:138), DP II-20.9 (SEQ ID NO:169), DP II-20.11 (SEQ ID NO:169), DP II-20.10 (SEQ ID NO:170), or DP II-20.8 (SEQ ID NO:171); C is DP II-22 (SEQ ID NO:63), DP II-22.6 (SEQ ID NO:139), DP II-22.7 (SEQ ID NO:143), DP II-22.8 (SEQ ID NO:144), DP II-22.9 (SEQ ID NO:145), DP II-22.10 (SEQ ID NO: 146), DP II-22.11 (SEQ ID NO:147), DP II-22.3 (SEQ ID NO:140), DP II-22.4 (SEQ ID NO:141), DP II-22.5 (SEQ ID NO: 142), DP II-22.19 (SEQ ID NO:172), DP II-22.20 (SEQ ID NO:173), DP II-22.21 (SEQ ID NO: 174), DP II-22.22 (SEQ ID NO:175), DP II-22.26 (SEQ ID NO: 176), DP II-22.23 (SEQ ID NO: 177), DP II-22.24 (SEQ ID NO:178), DP II-22.25 (SEQ ID NO: 179), or DP II-22.14 (SEQ ID NO:180); and D is DP II-25.2 (SEQ ID NO:71), DP II-25.3 (SEQ ID NO:148), DP II-25.4 (SEQ ID NO: 149), DF II-25.11 (SEQ ID NO:182), DP II-25.9 (SEQ ID NO:183), DF II-25.10 (SEQ ID NO:184), or DF II-25.13 (SEQ ID NO:186), DP II-25-14 (SEQ ID NO:187), DP II-25.15 (SEQ ID NO:188), DP II-25.16 (SEQ ID NO:189), DP II-25.17 (SEQ ID NO:190), DP II-25.18 (SEQ ID NO:191), with the proviso that ADYCZBX is not DP I-26.1 (SEQ ID NO: 37), DP II-25.2 (SEQ ID NO: 71), DF I-22.2 (SEQ ID NO: 93), DP II-22 (SEQ ID NO: 63), DP I-23.1 (SEQ ID NO: 95), DP II-20.6 (SEQ ID NO: 56) and DP I-21.2 (SEQ ID NO:91) respectively.

Another preferred peptide comprises a specific sequenctial arrangement of amino acid sequences, said specific sequential arrangement having the formula:

DYZCAXB wherein X is DP I-21.2 (SEQ ID NO: 27) or DP I-21.7 (SEQ ID NO: 120); Y is DF I-22.2 (SEQ ID NO:93); Z is DP I-23.1 (SEQ ID NO:33), DP I-23.10 (SEQ ID NO:121), DP I-23.11 (SEQ ID NO:124), DP I-23.12 (SEQ ID NO:125), DP I-23.13 (SEQ ID NO: 122), DP I-23.14 (SEQ ID NO:123), DP I-23.15 (SEQ ID NO:131), DP I-23.16 (SEQ ID NO:132), DP I-23.17 (SEQ ID NO:133), DP I-23.5 (SEQ ID NO:126), DP I-23.6 (SEQ ID NO:127), DP I-23.7 (SEQ ID NO: 128), DP I-23.8 (SEQ ID NO: 129), DP I-23.9 (SEQ ID NO:130), DP I-23.32 (SEQ ID NO:163), DP I-23.33 (SEQ ID NO:164), DP I-23.31 (SEQ ID NO:165), DP I-23.34 (SEQ ID NO:166), or DP I-23.35 (SEQ ID NO:167); A is DP I-26.1 (SEQ ID NO:37), DP I-26.2 (SEQ ID NO:134), DP I-26.3 (SEQ ID NO:135), DP I-26.4 (SEQ ID NO:136), DP I-26.5 (SEQ ID NO: 137) or DP I 26.6 (SEQ ID NO:168); B is DP II-20.0 (SEQ ID NO:50), DP II-20.6 (SEQ ID NO:56), DP II-20.7 (SEQ ID NO:138), DP II-20.9 (SEQ ID NO:169), DP II-20.11 (SEQ ID NO: 169), DP II-20.10 (SEQ ID NO: 170), or DP II-20.8 (SEQ ID NO: 171); C is DP II-22 (SEQ ID NO:63), DP II-22.6 (SEQ ID NO:139), DP II-22.7 (SEQ ID NO:143), DP II-22.8 (SEQ ID NO:144), DP II-22.9 (SEQ ID NO: 145), DP II-22.10 (SEQ ID NO:146), DP II-22.11 (SEQ ID NO:147), DP II-22.3 (SEQ ID NO: 140), DP II-22.4 (SEQ ID NO:141), DP II-22.5 (SEQ ID NO: 142), DP II-22.19 (SEQ ID NO: 172), DP II-22.20 (SEQ ID NO:173), DP II-22.21 (SEQ ID NO: 174), DP II-22.22 (SEQ ID NO: 175), DP II-22.26 (SEQ ID NO: 176), DP II-22.23 (SEQ ID NO:177), DP II-22.24 (SEQ ID NO:178), DP II-22.25 (SEQ ID NO: 179), or DP II-22.14 (SEQ ID NO: 180); and D is DP II-25.2 (SEQ ID NO:71), DP II-25.3 (SEQ ID NO:148), DP II-25.4 (SEQ ID NO:149), DF II-25.11 (SEQ ID NO:182), DP II-25.9 (SEQ ID NO:183), DF II-25.10 (SEQ ID NO:184), or DF II-25.13 (SEQ ID NO:186), DP II-25-14 (SEQ ID NO:187), DP II-25.15 (SEQ ID NO:188), DP II-25.16 (SEQ ID NO:189), DP II-25.17 (SEQ ID NO:190), DP II-25.18 (SEQ ID NO:191); with the proviso that DYZCAXB is not DP II-25.2 (SEQ ID NO: 71), DF I-22.2 (SEQ ID NO: 93), DP I-23.1 (SEQ ID NO: 95), DP II-22 (SEQ ID NO: 63), DP I-26.1 (SEQ ID NO: 37), DP I-21.2 (SEQ ID NO: 91) and DP II-20.6 (SEQ ID NO: 56) respectively.

Yet another preferred peptide has a specific arrangement of amino acid sequences, said specific sequential arrangement having the formula:

DXZACBY wherein X is DP I-21.2 (SEQ ID NO: 27) or DP I-21.7 (SEQ ID NO:120); Y is DF I-22.2 (SEQ ID NO:93); Z is DP I-23.1 (SEQ ID NO:33), DP I-23.10 (SEQ ID NO: 121), DP I-23.11 (SEQ ID NO:124), DP I-23.12 (SEQ ID NO:125), DP I-23.13 (SEQ ID NO:122), DP I-23.14 (SEQ ID NO:123), DP I-23.15 (SEQ ID NO:131), DP I-23.16 (SEQ ID NO:132), DP I-23.17 (SEQ ID NO: 133), DP I-23.5 (SEQ ID NO:126), DP I-23.6 (SEQ ID NO:127), DP I-23.7 (SEQ ID NO: 128), DP I-23.8 (SEQ ID NO: 129), DP I-23.9 (SEQ ID NO: 130), DP I-23.32 (SEQ ID NO:163), DP I-23.33 (SEQ ID NO:164), DP I-23.31 (SEQ ID NO:165), DP I-23.34 (SEQ ID NO:166), or DP I-23.35 (SEQ ID NO:167); A is DP I-26.1 (SEQ ID NO:37), DP I-26.2 (SEQ ID NO:134), DP I-26.3 (SEQ ID NO:135), DP I-26.4 (SEQ ID NO: 136), DP I-26.5 (SEQ ID NO: 137) or DP I 26.6 (SEQ ID NO:168); B is DP II-20.0 (SEQ ID NO:50), DP II-20.6 (SEQ ID NO:56), DP II-20.7 (SEQ ID NO:138), DP II-20.9 (SEQ ID NO:169), DP II-20.11 (SEQ ID NO: 169), DP II-20.10 (SEQ ID NO: 170), or DP II-20.8 (SEQ ID NO: 171); C is DP II-22 (SEQ ID NO:63), DP II-22.6 (SEQ ID NO:139), DP II-22.7 (SEQ ID NO:143), DP II-22.8 (SEQ ID NO:144), DP II-22.9 (SEQ ID NO: 145), DP II-22.10 (SEQ ID NO:146), DP II-22.11 (SEQ ID NO:147), DP II-22.3 (SEQ ID NO: 140), DP II-22.4 (SEQ ID NO:141), DP II-22.5 (SEQ ID NO: 142), DP II-22.19 (SEQ ID NO: 172), DP II-22.20 (SEQ ID NO:173), DP II-22.21 (SEQ ID NO: 174), DP II-22.22 (SEQ ID NO: 175), DP II-22.26 (SEQ ID NO: 176), DP II-22.23 (SEQ ID NO:177), DP II-22.24 (SEQ ID NO:178), DP II-22.25 (SEQ ID NO: 179), or DP II-22.14 (SEQ ID NO: 180); and D is DP II-25.2 (SEQ ID NO:71), DP II-25.3 (SEQ ID NO:148), DP II-25.4 (SEQ ID NO:149), DF II-25.11

(SEQ ID NO: 182), DP II-25.9 (SEQ ID NO: 183), DF II-25.10 (SEQ ID NO:184), or DF II-25.13 (SEQ ID NO:186), DP II-25-14 (SEQ ID NO:187), DP II-25.15 (SEQ ID NO:188), DP II-25.16 (SEQ ID NO:189), DP II-25.17 (SEQ ID NO: 190), DP II-25.18 (SEQ ID NO:191); with the proviso that DXZACBY is not DP II-25.2 (SEQ ID NO: 71), DP I-21.2 (SEQ ID NO: 91), DP I-23.1 (SEQ ID NO: 95), DP I-26.1 (SEQ ID NO: 37), DP II-22 (SEQ ID NO: 63), DP II-20.6 (SEQ ID NO: 56), and DF I-22.2 (SEQ ID NO: 93) respectively.

In yet another aspect of the present invention, a composition is provided comprising at least two peptides (e.g., a physical mixture of at least two peptides), each comprising at least one T cell epitope of a protein allergen of the genus Dermatophagoides. The peptides or modified peptides may be derived from the same or from different mite allergens. Such compositions can be administered in the form of a therapeutic composition with a pharmaceutically acceptable carrier of diluent. A therapeutically effective amount of one or more of such compositions can be administered simultaneously or sequentially to an individual sensitive to house dust mite. In addition, peptides derived from the same or different mite allergens can be administered simultaneously or sequentially. Such combinations of peptides may comprise therapeutic compositions comprising only one peptide or more peptides if desired. Such compositions may be administered simultaneously or sequentially in preferred combinations.

Preferred compositions and preferred combinations of peptides which can be administered simultaneously or sequentially (comprising peptides having amino acid sequences shown in FIG. 3 and FIG. 36) include the following combinations: DP I-22.1 (SEQ ID NO: 29) and DP I-25.1 (SEQ ID NO: 35); DP I-21.1 (SEQ ID NO: 27) and DP I-25.2 (SEQ ID NO: 36); DP I-22.1 (SEQ ID NO: 29) and DP I-1 (SEQ ID NO: 9); DP I-21.1 (SEQ ID NO: 27), DP I-22.1 (SEQ ID NO: 29), and DP I-25.2 (SEQ ID NO: 36); DP I-21.2 (SEQ ID NO: 28), DP I-22.1 (SEQ ID NO: 29), and DP I-23.1 (SEQ ID NO: 39); DP I-1 (SEQ ID NO: 9), DP I-22.1 (SEQ ID NO: 29), and DP I-23.1 (SEQ ID NO: 33); DP I-1 (SEQ ID NO: 9), DP I-22.1 (SEQ ID NO: 29), and DP I-25.2 (SEQ ID NO: 36); DP I-21.1 (SEQ ID NO: 27), DP I-22.1 (SEQ ID NO: 29), DP I-23.1 (SEQ ID NO: 33), and DP I-25.2 (SEQ ID NO: 36); DP I-21.2 (SEQ ID NO: 28), DP I-22.1 (SEQ ID NO: 29), and DP I-25.2 (SEQ ID NO: 36); DP I-21.2 (SEQ ID NO: 27), DP I-22.1 (SEQ ID NO: 29), DP I-25.2 (SEQ ID NO: 36), and DP I-26.1 (SEQ ID NO: 37); DF I-21.2 (SEQ ID NO: 91) and DF I-22.1 (SEQ ID NO: 92); DF I-21.1 (SEQ ID NO: 90), DF I-22.1 (SEQ ID NO: 92), and DF I-25.1 (SEQ ID NO: 97); DF I-21.2 (SEQ ID NO: 91), DF I-22.1 (SEQ ID NO: 92), and DF I-25.1 (SEQ ID NO: 97); DF I-1 (SEQ ID NO: 72) and DF I-22.1 (SEQ ID NO: 92); DF I-1 (SEQ ID NO: 72), DF I-22.1 (SEQ ID NO: 92), and DF I-25.1 (SEQ ID NO: 97); DF I-22.1 (SEQ ID NO: 29), and DF I-25.1 (SEQ ID NO: 35); DF I-21.1 (SEQ ID NO: 90), DF I-22.1 (SEQ ID NO: 92), and DF I-23.1 (SEQ ID NO: 95); DP I-21.1 (SEQ ID NO: 27), and DF I-22.1 (SEQ ID NO: 92); DP I-1 (SEQ ID NO: 9), DP I-23.1 (SEQ ID NO: 33), DP I-25.1 (SEQ ID NO: 35), and DF I-1 (SEQ ID NO: 72); DP I-1 (SEQ ID NO: 9), DP I-25.1 (SEQ ID NO: 35), DP I-23.1 (SEQ ID NO: 33), and DF I-21.2 (SEQ ID NO: 91); DP I-1 (SEQ ID NO: 9), DP I-25.1 (SEQ ID NO: 35), DP I-23.1 (SEQ ID NO: 33), and DF I-21.1 (SEQ ID NO: 90); DP II-22 (SEQ ID NO: 63), and DP II-25.2 (SEQ ID NO: 71); DP II-22 (SEQ ID NO: 63), DP II-25.2 (SEQ ID NO: 71), and DP I-21.1 (SEQ ID NO: 27) and DP I-22.1 (SEQ ID NO: 29); DP II-22 (SEQ ID NO: 63), DP II-25.2 (SEQ ID NO: 71), DP II-20.6 (SEQ ID NO: 56), DP I-22.1 (SEQ ID NO: 29), DP I-21.1 (SEQ ID NO: 27), and DP I-23.1 (SEQ ID NO: 33); DP II-22 (SEQ ID NO: 63), DP II-25.2 (SEQ ID NO: 71), DP II-20.6 (SEQ ID NO: 56), DP I-21.1 (SEQ ID NO: 27), DP I-22.1 (SEQ ID NO: 29), and DP I-25.2 (SEQ ID NO: 36); DP II-22 (SEQ ID NO: 63), DP II-25.2 (SEQ ID NO: 71), DP I-21.1 (SEQ ID NO: 27), DP I-22.1 (SEQ ID NO: 29), and DP I-25.2 (SEQ ID NO: 36); DP II-22 (SEQ ID NO: 63), DP II-25.2 (SEQ ID NO: 71), DP I-21.1 (SEQ ID NO: 27), DP I-22.1 (SEQ ID NO: 29), and DP I-23.1 (SEQ ID NO: 33); DP II-22 (SEQ ID NO: 63), DP II-25.2 (SEQ ID NO: 71), DP I-1 (SEQ ID NO: 9), and DP I-22.1 (SEQ ID NO: 29); DF II-4.5 (SEQ ID NO: 107) and DF II-2 (SEQ ID NO: 104); DF II-4.5 (SEQ ID NO: 107) and DF II-19.1 (SEQ ID NO: 114); DF II-4.5 (SEQ ID NO: 107), DF II-2 (SEQ ID NO: 104), and DF II-19.1 (SEQ ID NO: 114); DF II-4.5 (SEQ ID NO: 107), DF II-2 (SEQ ID NO: 104), and DF II-9 (SEQ ID NO: 86); DF II-4.5 (SEQ ID NO: 107); and DF I-21.1 (SEQ ID NO: 90); DF II-4.5 (SEQ ID NO: 107), DP II-22 (SEQ ID NO: 63), and DP II-25.2 (SEQ ID NO: 71); and DF II-4.5 (SEQ ID NO: 107), DF II-2 (SEQ ID NO: 104), and DP II-22 (SEQ ID NO: 63); and DP I-26.1 (SEQ ID NO: 65), DP II-25.2 (SEQ ID NO: 71), DF I-22 (SEQ ID NO: 63), DP II-20.6 (SEQ ID NO: 56) and DP I-21.2 (SEQ ID NO: 91).

Other preferred therapeutic compositions comprising a pharmaceutically acceptable carrier or diluent and at least two peptides each comprising at least one T cell epitope, comprise at least one peptide selected from the group consisting of: DP I-1 (SEQ ID NO: 9); DP I-2 (SEQ ID NO: 10); DP I-3 (SEQ ID NO: 11); DP I-4 (SEQ ID NO: 12); DP I-11.1 (SEQ ID NO: 13); DP I-12.1 (SEQ ID NO: 14); DP I-5 (SEQ ID NO: 15); DP I-13 (SEQ ID NO: 17); DP I-14 (SEQ ID NO: 18); DP I-15 (SEQ ID NO: 19); DP I-6.1 (SEQ ID NO: 20); DP I-7.1 (SEQ ID NO: 21); DP I-8 (SEQ ID NO: 22); DP I-9 (SEQ ID NO: 23); DP I-16 (SEQ ID NO: 24); DP I-10 (SEQ ID NO: 25); DP I-17 (SEQ ID NO: 26); DP I-21.1 (SEQ ID NO: 27); DP I-21.2 (SEQ ID NO: 28); DP I-22.1 (SEQ ID NO: 29); DP I-22.2 (SEQ ID NO: 30); DP I-22.3 (SEQ ID NO: 31); DP I-22.4 (SEQ ID NO: 32); DP I-23.1 (SEQ ID NO: 33); DP I-23.2 (SEQ ID NO: 34); DP I-25.1 (SEQ ID NO: 35); DP I-25.2 (SEQ ID NO: 36); DP I-26.1 (SEQ ID NO: 37); DP I-27.1 (SEQ ID NO: 38); DP I-28.1 (SEQ ID NO: 39); DP I-28.2 (SEQ ID NO: 40), DF I-1 (SEQ ID NO: 72); DF I-2.1 (SEQ ID NO: 73); DF I-3 (SEQ ID NO: 74); DF I-4 (SEQ ID NO: 75); DF I-11 (SEQ ID NO: 76); DF I-12 (SEQ ID NO: 77); DF I-5 (SEQ ID NO: 78); DF I-13 (SEQ ID NO: 79); DF I-14 (SEQ ID NO: 80); DF I-15 (SEQ ID NO: 81); DF I-6 (SEQ ID NO: 82); DF I-7 (SEQ ID NO: 83); DF I-8.1 (SEQ ID NO: 84); DF I-8 (SEQ ID NO: 85); DF I-9 (SEQ ID NO: 86); DF I-16 (SEQ ID NO: 87); DF I-10 (SEQ ID NO: 88); DF I-17 (SEQ ID NO: 89); DF I-21.1 (SEQ ID NO: 90); DF I-21.2 (SEQ ID NO: 91); DF I-22.1 (SEQ ID NO: 92); DF I-22.2 (SEQ ID NO: 93); DF I-22.4 (SEQ ID NO: 94); DF I-23.1 (SEQ ID NO: 95); DF I-23.2 (SEQ ID NO: 96); DF I-25.1 (SEQ ID NO: 97); DF I-25.2 (SEQ ID NO: 98); DF I-26.1 (SEQ ID NO: 99); DF I-27.1 (SEQ ID NO: 100); DF I-28.1 (SEQ ID NO: 101); DF I-28.2 (SEQ ID NO: 102); DP II-20 (SEQ ID NO: 50); DP II-20.1 (SEQ ID NO: 51); DP II-20.2 (SEQ ID NO: 52); DP II-20.3 (SEQ ID NO: 53); DP II-20.4 (SEQ ID NO: 54); DP II-20.5 (SEQ ID NO: 55); DP II 20.6 (SEQ ID NO: 56); DP II-1 (SEQ ID NO: 41); DP II-2 (SEQ ID NO: 42); DP II-3.1 (SEQ ID NO: 43); DP II-4 (SEQ ID NO: 44); DP II-5 (SEQ ID NO: 45); DP II-6 (SEQ ID NO: 46); DP II-7 (SEQ ID NO: 47); DP II-8 (SEQ ID NO: 48); DP II-9 (SEQ ID NO: 49); DP II-1.1 (SEQ ID NO: 57); DP II-1.2 (SEQ ID NO: 58); DP II-2.1 (SEQ ID NO: 59); DP II-2.2 (SEQ ID NO: 60); DP II-2.3 (SEQ ID NO: 61); DP II-21 (SEQ ID NO: 62); DP II-22 (SEQ ID NO: 63); DP II-26 (SEQ ID NO: 64); DP II-26.1 (SEQ ID NO: 65); DP II-23 (SEQ ID NO: 66); DP II-23.1 (SEQ ID NO: 67); DP II-24 (SEQ ID NO: 68); DP II-25 (SEQ ID NO: 69); DP II-25.1 (SEQ ID NO: 70); DP II-25.2 (SEQ ID NO: 71); DF II-1 (SEQ ID NO: 103); DF II-2 (SEQ ID NO: 104); DF II-13.1 (SEQ ID NO: 105); DF II-3.1 (SEQ ID NO: 106); DF II-4.5 (SEQ ID NO: 107); DF II-4.3 (SEQ ID NO: 108); DF II-15 (SEQ ID NO: 109); DF II-16 (SEQ ID NO: 110); DF II-17 (SEQ ID NO: 111); DF II-18 (SEQ ID NO: 112); DF II-19 (SEQ ID NO: 113); DF II-19.1 (SEQ ID NO: 114); DF II-21 (SEQ ID NO: 115); and DF II-22 (SEQ ID NO: 116), DP I-23.1.1, DP I-23.1.2, DP I-23.1.3, DP I-23.1.4, DP II-22.1, DP II-22.2 (all as shown in FIGS. 3, 4, and 25), and at least one modified peptide selected from the following group: DP I-21.7 (SEQ ID NO: 120); DP I-23.10 (SEQ ID NO: 121); DP I-23.11 (SEQ ID NO: 124); DP I-23.12 (SEQ ID NO: 125); DP I-23.5 (SEQ ID NO: 126); DP I-23.6 (SEQ ID NO: 127); DP I-23.7 (SEQ ID NO: 128); DP I-23.8 (SEQ ID NO: 129); DP I-23.9 (SEQ ID NO: 130); DP I-26.2 (SEQ ID NO: 134); DP II-20.7 (SEQ ID NO: 138); DP II-22.6 (SEQ ID NO: 139); DP II-22.3 (SEQ ID NO: 140); DP II-22.4 (SEQ ID NO: 141); DP II-22.5 (SEQ ID NO: 142); DP II-25.3 (SEQ ID NO: 148); DP II-25.4 (SEQ ID NO: 149); DP I-23.13 (SEQ ID NO: 122); DP I-23.14 (SEQ ID NO: 123); DP I-23.15 (SEQ ID NO: 131); DP I-23.16 (SEQ ID NO: 132); DP I-23.17 (SEQ ID NO: 133); DP I-26.3 (SEQ ID NO: 135); DP I-26.4 (SEQ ID NO: 136); DP I-26.5 (SEQ ID NO: 137); DP II-22.7 (SEQ ID NO: 143); DP II-22.8 (SEQ ID NO: 144); DP II-22.9 (SEQ ID NO: 145); DP II-22.10 (SEQ ID NO: 146); DP II-22.11 (SEQ ID NO: 147); DP I-23.32 (SEQ ID NO: 163), DPI-23.33 (SEQ ID NO: 164) DP I-23.31 (SEQ ID NO: 165), DP I-23.34 (SEQ ID NO: 166), DP I-23.35 (SEQ ID NO: 167), DP I-26.6 (SEQ ID NO: 168), DP II-20.9 (SEQ ID NO: 169), DP II-20.11 (SEQ ID NO: 169), DP II-20.10 (SEQ ID NO: 170) DP II-20.8 (SEQ ID NO: 171), D,P II-22.19 (SEQ ID NO: 172), DP II-22.20 (SEQ ID NO: 173), DP II-22.21 (SEQ ID NO: 174), DP II-22.22 (SEQ ID NO: 175), DP II-22.26 (SEQ ID NO: 176), DP II-22.23 (SEQ ID NO: 177), DP I-22.24 (SEQ ID NO: 178), DP II-22.25 (SEQ ID NO: 179), DP II-22.14 (SEQ ID NO: 180), DF II-25.11 (SEQ ID NO: 182), DP II-25.9 (SEQ ID NO: 183), DF II-25.10 (SEQ ID NO: 184), DF II-25.13 (SEQ ID NO: 186), DP II-25.14 (SEQ ID NO: 187), DP II-25.15 (SEQ ID NO: 188), DP II-25.16 (SEQ ID NO: 189), DP II-25.17 (SEQ ID NO: 190), DP II-25.18 (SEQ ID NO: 191) all as shown in FIGS. 29 and 30.

Even more preferred therapeutic compositions comprising a pharmaceutically acceptable carrier or diluent and at least two peptides each comprising at least one T cell epitope, comprise at least one peptide selected from the group consisting of: DP I-21.7 (SEQ ID NO: 120); DP I-23.10 (SEQ ID NO: 121); DP I-23.11 (SEQ ID NO: 124); DP I-23.12 (SEQ ID NO: 125); DP I-23.5 (SEQ ID NO: 126); DP I-23.6 (SEQ ID NO: 127); DP I-23.7 (SEQ ID NO: 128); DP I-23.8 (SEQ ID NO: 129); DP I-23.9 (SEQ ID NO: 130); DP I-26.2 (SEQ ID NO: 134); DP II-20.7 (SEQ ID NO: 138); DP II-22.6 (SEQ ID NO: 139); DP II-22.3 (SEQ ID NO: 140); DP II-22.4 (SEQ ID NO: 141); DP II-22.5 (SEQ ID NO: 142); DP II-25.3 (SEQ ID NO: 148); DP II-25.4 (SEQ ID NO: 149); DP I-23.13 (SEQ ID NO: 122); DP I-23.14 (SEQ ID NO: 123); DP I-23.15 (SEQ ID NO: 131); DP I-23.16 (SEQ ID NO: 132); DP I-23.17 (SEQ ID NO: 133); DP I-26.3 (SEQ ID NO: 135); DP I-26.4 (SEQ ID NO: 136); DP I-26.5 (SEQ ID NO: 137); DP II-22.7 (SEQ ID NO: 143); DP II-22.8 (SEQ ID NO: 144); DP II-22.9 (SEQ ID NO: 145); DP II-22.10 (SEQ ID NO: 146); DP II-22.11 (SEQ ID NO: 147); DP I-23.32 (SEQ ID NO: 163), DPI-23.33 (SEQ ID NO: 164) DP I-23.31 (SEQ ID NO: 165), DP I-23.34 (SEQ ID NO: 166), DP I-23.35 (SEQ ID NO: 167), DP I-26.6 (SEQ ID NO: 168), DP II-20.9 (SEQ ID NO: 169), DP II-20.11 (SEQ ID NO: 169), DP II-20.10 (SEQ ID NO: 170) DP II-20.8 (SEQ ID NO: 171), D,P II-22.19 (SEQ ID NO: 172), DP II-22.20 (SEQ ID NO: 173), DP II-22.21 (SEQ ID NO: 174), DP II-22.22 (SEQ ID NO: 175), DP II-22.26 (SEQ ID NO: 176), DP II-22.23 (SEQ ID NO: 177), DP II-22.24 (SEQ ID NO: 178), DP II-22.25 (SEQ ID NO: 179), DP II-22.14 (SEQ ID NO: 180), DF II-25.11 (SEQ ID NO: 182), DP II-25.9 (SEQ ID NO: 183), DF II-25.10 (SEQ ID NO: 184), DF II-25.13 (SEQ ID NO: 186), DP II-25.14 (SEQ ID NO: 187), DP II-25.15 (SEQ ID NO: 188), DP II-25.16 (SEQ ID NO: 189), DP II-25.17 (SEQ ID NO: 190), DP II-25.18 (SEQ ID NO: 191) all as shown in FIGS. 29 and 30, wherein said composition comprises a sufficient percentage of the T cell epitopes of at least one protein allergen such that upon administration of the composition to an individual sensitive to a house dust mite allergen, T cells of the individual are tolerized to said at least one protein allergen.

Other preferred compositions of the invention comprise the following combination of peptides and/or modified peptides and a pharmaceutically acceptable carrier or diluent: DP I-21.7 (SEQ ID NO:120), DF I-22.2 (SEQ ID NO:93), DP I-23.13 (SEQ ID NO:122), DP I-26.1 (SEQ ID NO:37), DP II-20.6 (SEQ ID NO:56), DP II-22.3 (SEQ ID NO: 140), and DP II-25.2 (SEQ ID NO:71); DP I-21.2 (SEQ ID NO:28), DF I-22.2 (SEQ ID NO:93), DP I-23.10 (SEQ ID NO:121), DP I-26.2 (SEQ ID NO:134), DP II-20.6 (SEQ ID NO:56), DP II-22.4 (SEQ ID NO: 141), and DP II-25.3 (SEQ ID NO: 148), DP I-21.7 (SEQ ID NO:120), DF I-22.2 (SEQ ID NO:93), DP I-23.11 (SEQ ID NO:124), DP I-26.3 (SEQ ID NO:135), DP II-20.7 (SEQ ID NO:138), DP II-22.5 (SEQ ID NO: 142), and DP II-25.4 (SEQ ID NO: 149); DP I-21.7 (SEQ ID NO: 120), DF I-22.2 (SEQ ID NO:93), DP I-23.12 (SEQ ID NO:125), DP I-26.4 (SEQ ID NO:136), DP II-20.6 (SEQ ID NO:56), DP II-22.6 (SEQ ID NO:139), and DP II-25.2 (SEQ ID NO:71); DP I-21.7 (SEQ ID NO:120), DF I-22.2 (SEQ ID NO:93), DP I-23.5 (SEQ ID NO:126), DP I-26.5 (SEQ ID NO:137), DP II-20.7 (SEQ ID NO:138), DP II-22.7 (SEQ ID NO: 143), and DP II-25.3 (SEQ ID NO:148); DP I-21.7 (SEQ ID NO: 120), DF I-22.2 (SEQ ID NO:93), DP I-23.6 (SEQ ID NO: 127), DP I-26.2 (SEQ ID NO:134), DP II-20.6 (SEQ ID NO:56), DP II-22.8 (SEQ ID NO:144), and DP II-25.4 (SEQ ID NO:149); DP I-21.7 (SEQ ID NO:120), DF I-22.2 (SEQ ID NO:93), DP I-23.7 (SEQ ID NO:128), DP I-26.3 (SEQ ID NO:135), DP II-20.7 (SEQ ID NO:138), DP II-22.9 (SEQ ID NO: 145), and DP II-25.3 (SEQ ID NO: 148); DP I-21.7 (SEQ ID NO: 120), DF I-22.2 (SEQ ID NO:93), DP I-23.8 (SEQ ID NO:129), DP I-26.4 (SEQ ID NO:136), DP II-20.6 (SEQ ID NO:56), DP II-22.3 (SEQ ID NO: 140) and DP II-25.4 (SEQ ID NO:149); DP I-21.7 (SEQ ID NO:120), DF I-22.2 (SEQ ID NO:93), DP I-23.9 (SEQ ID NO:130), DP I-26.1 (SEQ ID NO:37), DP II-20.7 (SEQ ID NO:138), DP II-22.4 (SEQ ID NO:141), and DP II-25.3 (SEQ ID NO:148); DP I-21.7 (SEQ ID NO:120), DF I-22.2 (SEQ ID NO:93), DP I-23.13 (SEQ ID NO:122), DP I-26.2 (SEQ ID NO:134), DP II-20.6 (SEQ ID NO:56), DP II-22.5 (SEQ ID NO: 142), and DP II-25.4 (SEQ ID NO:149); DP I-21.7 (SEQ ID NO:120), DF I-22.2 (SEQ ID NO:93), DP I-23.14 (SEQ ID NO:123), DP I-26.3 (SEQ ID NO: 135), DP II-20.7 (SEQ ID NO:138), DP II-22.6 (SEQ ID NO:139), and DP II-25.3 (SEQ ID NO:148); DP I-21.7 (SEQ ID NO:120), DF I-22.2 (SEQ ID NO:93), DP I-23.15 (SEQ ID NO:131), DP I-26.4 (SEQ ID NO:136), DP II-20.6 (SEQ ID NO:56), DP II-22.6 (SEQ ID NO:139), and DP II-25.3 (SEQ ID NO:148); DP I-21.7 (SEQ ID NO: 120), DF I-22.2 (SEQ ID NO:93), DP I-23.16 (SEQ ID NO:132), DP I-26.5 (SEQ ID NO:137), DP II-20.6 (SEQ ID NO:56), DP II-22.3 (SEQ ID NO:140), and DP II-25.4 (SEQ ID NO:149); DP I-21.7 (SEQ ID NO:120), DF I-22.2 (SEQ ID NO:93), DP I-23.17 (SEQ ID NO:133), DP I-26.2 (SEQ ID NO: 134), DP II-20.6 (SEQ ID NO:56), DP II-22.4 (SEQ ID NO: 141), and DP II-25.3 (SEQ ID NO:148); DP I-21.7 (SEQ ID NO:120), DF I-22.2 (SEQ ID NO:93), DP I-23.8 (SEQ ID NO:129), DP I-26.3 (SEQ ID NO:135), DP II-20.6 (SEQ ID NO:56), DP II-22.5 (SEQ ID NO:142), and DP II-25.4 (SEQ ID NO: 149); DP I-21.7 (SEQ ID NO:120), DF I-22.2 (SEQ ID NO:93), DP I-23.9 (SEQ ID NO:130), DP I-26.4 (SEQ ID NO:136), DP II-20.6 (SEQ ID NO:56), DP II-22.6 (SEQ ID NO:139) and DP II-25.3 (SEQ ID NO: 148); and DP I-21.7 (SEQ ID NO:120), DF I-22.2 (SEQ ID NO:93), DP I-23.5 (SEQ ID NO: 126), DP I-26.1 (SEQ ID NO:37), DP II-20.6 (SEQ ID NO:56), DP II-22.7 (SEQ ID NO: 143), and DP II-25.4 (SEQ ID NO: 149).

In yet another aspect of the invention a composition is provided comprising a pharmaceutically acceptable carrier or diluent and at least two, preferably at least four, more preferably at least six, even more preferably at least seven of the following combination of peptides: X, Y, Z, A, B, C, D, wherein X is DP I-21.2 (SEQ ID NO: 27) or DP I-21.7 (SEQ ID NO:120); Y is DF I-22.2 (SEQ ID NO:93); Z is DP I-23.1 (SEQ ID NO:33), DP I-23.10 (SEQ ID NO:121), DP I-23.11 (SEQ ID NO:124), DP I-23.12 (SEQ ID NO:125), DP I-23.13 (SEQ ID NO:122), DP I-23.14 (SEQ ID NO:123), DP I-23.15 (SEQ ID NO:131), DP I-23.16 (SEQ ID NO:132), DP I-23.17 (SEQ ID NO:133), DP I-23.5 (SEQ ID NO:126), DP I-23.6 (SEQ ID NO:127), DP I-23.7 (SEQ ID NO:128), DP I-23.8 (SEQ ID NO: 129), DP I-23.9 (SEQ ID NO:130), DP I-23.32 (SEQ ID NO:163), DP I-23.33 (SEQ ID NO: 164), DP I-23.31 (SEQ ID NO:165), DP I-23.34 (SEQ ID NO: 166), or DP I-23.35 (SEQ ID NO:167); A is DP I-26.1 (SEQ ID NO:37), DP I-26.2 (SEQ ID NO:134), DP I-26.3 (SEQ ID NO: 135), DP I-26.4 (SEQ ID NO: 136), DP I-26.5 (SEQ ID NO: 137) or DP I 26.6 (SEQ ID NO: 168); B is DP II-20.0 (SEQ ID NO:50), DP II-20.6 (SEQ ID NO:56), DP II-20.7 (SEQ ID NO:138), DP II-20.9 (SEQ ID NO:169), DP II-20.11 (SEQ ID NO:169), DP II-20.10 (SEQ ID NO:170), or DP II-20.8 (SEQ ID NO: 171); C is DP II-22 (SEQ ID NO:63), DP II-22.6 (SEQ ID NO:139), DP II-22.7 (SEQ ID NO: 143), DP II-22.8 (SEQ ID NO: 144), DP II-22.9 (SEQ ID NO:145), DP II-22.10 (SEQ ID NO:146), DP II-22.11 (SEQ ID NO: 147), DP II-22.3 (SEQ ID NO: 140), DP II-22.4 (SEQ ID NO:141), DP II-22.5 (SEQ ID NO: 142), DP II-22.19 (SEQ ID NO: 172), DP II-22.20 (SEQ ID NO: 173), DP II-22.21 (SEQ ID NO: 174), DP II-22.22 (SEQ ID NO:175), DP II-22.26 (SEQ ID NO:176), DP II-22.23 (SEQ ID NO:177), DP II-22.24 (SEQ ID NO: 178), DP II-22.25 (SEQ ID NO:179), or DP II-22.14 (SEQ ID NO:180); and D is DP II-25.2 (SEQ ID NO:71), DP II-25.3 (SEQ ID NO: 148), DP II-25.4 (SEQ ID NO:149), DF II-25.11 (SEQ ID NO:182), DP II-25.9 (SEQ ID NO:183), DF II-25.10 (SEQ ID NO:184), or DF II-25.13 (SEQ ID NO:186), DP II-25-14 (SEQ ID NO:187), DP II-25.15 (SEQ ID NO:188), DP II-25.16 (SEQ ID NO:189), DP II-25.17 (SEQ ID NO:190), DP II-25.18 (SEQ ID NO:191); with the proviso that X, Y, Z, A, B, C, D is not the following combination of peptides: DP I-21.2 (SEQ ID NO:91), DF I-22.2 (SEQ ID NO: 93), DP I-23.1 (SEQ ID NO: 95), DP I-26.1 (SEQ ID NO: 99), DP II-20.6, (SEQ ID NO: 56) DP II-22 (SEQ ID NO: 63), and DP II-25.2 (SEQ ID NO: 71).

The present invention also provides novel modified Der p I, Der f I, and Der p II peptides which are a part of a preformulation scheme to develop an optimized drug product for therapeutic treatment of humans suffering from allergy to house dust mite allergen. Such peptides and modified peptides possess certain unique characteristics which render them particularly suitable for drug product formulation, and may be referred to herein as "unique" peptides.

In accordance with pharmaceutical chemistry, preformulation is the process of optimizing a drug through determination and/or definition of those physical and chemical properties considered important in the formulation of a stable, effective, and safe dosage form. The possible interactions with the various components intended for use in the final drug product are also considered. Preformulation is an intensive effort that includes the study of such parameters as solubility, pH profile of stability, and drug-excipient interactions, which may have a profound effect on a drug's physiological availability and physical and chemical stability. The data obtained from such studies are integrated with those obtained from preliminary pharmacological and biochemical studies of the active drug component thus providing information that permits the selection of the best drug form, and the most desirable excipients for use in its development.

The development of an optimum formulation of active drug component and excipients is complex and many factors influence formulation properties. The high degree of uniformity, the physiological availability and the therapeutic quality expected of pharmaceuticals can only be achieved by considerable effort and expertise. Flexibility is also an important factor in preformulation. Numerous excipients, stabilizers counter ions and the like may have to be tested in order to find those compatible with the active drug component of the formulation. Multiple modifications of the active component may become necessary to successfully formulate a drug product. Such modifications must not effect the overall therapeutic effectiveness of the drug but at the same time, must render the drug more suitable for formulation.

As a part of a preformulation scheme to provide an optimized drug product suitable for use in humans and other mammals for treating sensitivity to house dust mite, it was determined that the active component (referred to herein as a "peptide" or "candidate peptide" or "unique peptide") in such formulation should possess the following characteristics which would render such peptides "unique" among all of the possible peptides derived from the Der p I, Der p II and Der f I protein allergen sequences. First, a unique peptide should alone or in combination with other unique peptides comprise a sufficient percentage of the T cell reactivity of the Der p and Der f protein allergens to induce T cell nonresponsiveness or reduced T cell responsiveness in a substantial percentage of the individuals sensitive to house dust mite allergen. Second, the candidate peptide should possess the characteristic of "superior solubility" which is defined herein as solubility of greater than 3 mg/ml at a pH in a pH range of pH 6 to pH 8 in an aqueous buffer. Third, the peptide is stable in an aqueous buffer at a pH in a pH range from pH 6 to pH 8. Candidate peptides derived from Der p and Der f protein allergens which have been determined to be "unique" peptides of the invention are DPI-21.2 (SEQ. ID. NO. 28), DFI-22.2 (SEQ. ID. NO. 93), DFI-23.31

(SEQ. ID. NO. 165), DFI-26.6 (SEQ. ID. NO. 168), DPII-20.9 (SEQ. ID. NO. 169), DPII-22.14 (SEQ. ID. NO. 180) and DPII-25.15 (SEQ. ID. NO. 188) all as shown in FIG. 33.

In accordance with the first characteristic, Those peptides found to elicit a T cell response such as T cell proliferation or lymphokine secretion (i.e. comprise at least one T cell epitope), or induce T cell non-responsiveness or reduced T cell responsiveness are understood to have T cell reactivity. It is believed that exposure of house dust mite allergic patients to isolated house dust mite Group I and Group II protein allergen peptides which comprise at least one T cell epitope may cause T cell non-responsiveness of appropriate T cell subpopulations such that they become unresponsive or have reduced responsiveness to the protein allergen and do not participate in stimulating an immune response upon such exposure for example, via anergy, tolerance, or apoptosis, the ability to modify the lymphokine secretion profile as compared with exposure to the naturally occurring autoantigen; and /or the ability to cause induction of T suppresser cells.

As discussed earlier, to determine peptides having T cell reactivity and comprising at least one T cell epitope, isolated peptides are tested by, for example, T cell biology techniques, to determine whether the peptides elicit a T cell response or induce T cell non-responsiveness. As discussed in the Examples human T cell stimulating activity can be tested by culturing T cells obtained from an individual sensitive to house dust mite allergen, (i.e., an individual who has an IgE mediated immune response to house dust mite allergen) with a peptide or modified peptide derived from a Der p or Der f Group I or Group II protein allergen and determining whether proliferation of T cells occurs in response to the peptide as measured, e.g., by cellular uptake of tritiated thymidine. Stimulation indices for responses by T cells to peptides can be calculated as the maximum counts per minute (CPM) in response to a peptide divided by the control CPM. A stimulation index (S.I.) equal to or greater than two times the background level is considered "positive". Positive results are used to calculate the mean stimulation index for each peptide for the group of patients tested. Peptides suitable as candidates for formulation into a final drug product have a mean T cell stimulation index of greater than or equal to 2.0 and preferably higher, (e.g. at least 2.5, more preferably at least 3.5, more preferably at least 4.0, more preferably at least 5, even more preferably at least 7 and most preferably at least about 9).

For therapeutic purposes, candidate peptides are recognized by at least 10%, more preferably at least 20%, more preferably at least 30% and even more preferably at least 40% or more of individuals in a population of individuals sensitive to house dust mite allergen. In addition, preferred candidate peptides have a positivity index (P.I.) of at least about 100, more preferably at least about 250 and most preferably at least about 350. The positivity index for a peptide is determined by multiplying the mean T cell stimulation index by the percent of individuals, in a population of individuals sensitive to house dust mite allergen (e.g., preferably at least 15 individuals, more preferably at least 30 individuals or more), who have a T cell stimulation index to such peptide of at least 2.0. Thus, the positivity index represents both the strength of a T cell response to a peptide (S.I.) and the frequency of a T cell response to a peptide in a population of individuals sensitive to house dust mite allergen.

To determine whether a peptide (candidate peptide) or a combination of candidate peptides are likely to comprise a sufficient percentage of the T cell reactivity of house dust mite protein allergens, to induce T cell nonresponsiveness in a substantial percentage of a population of individuals sensitive to house dust mite allergen, an algorithm can be used. In accordance with one such algorithm, a set of overlapping peptides is produced by systematically dividing the protein allergen(s) of interest into al least two overlapping peptide regions of desired lengths (e.g., of about 12–30 amino acid residues in length, preferably not longer than about 25 amino acid residues in length with about 5–15 amino acid residues of overlap). This division into peptide regions can be arbitrary, can be made according to an algorithm, or can be wholly or partially based on regions of house dust mite Group I and/or Group II protein allergens known to comprise at least one T cell epitope. Preferably, at least 50% of the entire house dust mite protein allergen sequence and more preferably, the entire house dust mite protein allergen sequence is divided into two or more peptides. A human T cell stimulation index is determined for each of the peptides in an in vitro T cell proliferation assay as described herein for each individual tested in a population of individuals sensitive to the protein antigen. For example both WO93/08279 and WO94/24281 disclose T cell studies with overlapping peptides derived from Der p I, Der p II, Der f I and Der f II. A candidate peptide or combination of candidate peptides is selected based, at least in part, on the mean human T cell stimulation index of the candidate peptide in the set of peptides tested and the positivity index of the candidate peptide in the set of peptides tested (see, FIGS. 3 and 4). The human T cell stimulation index for the candidate peptide(s) is summed. For each individual, the human T cell stimulation index for the candidate peptide(s) is divided by the sum of the human T cells stimulation indices of the remaining peptides in the set of peptides tested to determine a percent of T cell reactivity as shown below:

$$\% \text{ T Cell Reactivity of a candidate peptide(s)} = \frac{\text{Candidate S.I.}}{\text{Sum of S.I. of the set of Overlapping peptides}} \times 100 \quad (1)$$

Alternatively, the presence of T cell epitopes in the candidate peptide dependent on amino acids residues in an overlapping peptide located at either the N-terminus or C-terminus of the candidate peptide in the amino acid sequence of the protein antigen, but which epitopes are not present in the candidate peptide can be considered in calculating the percent of T cell reactivity in the candidate peptide by use of the following formula:

$$\% \text{ T Cell Reactivity of a candidate peptide(s)} = \frac{N_T \text{ flanking peptide S.I.} + \text{Candidate peptide S.I.} + C_T \text{ flanking peptide S.I.}}{\text{Sum of S.I. of the set of overlapping peptides}} \times 100 \quad (2)$$

In this formula, "$N_T$ flanking peptide" refers to a peptide which comprises amino acid residues which overlap with amino acid residues located at the N-terminus of the candidate peptide in the amino acid sequence of the protein antigen from which the peptide is derived; "$C_T$ flanking peptide" refers to a peptide which comprises amino acid residues which overlap with amino acid residues located a the C-terminus of the candidate peptide in the amino acid sequence of the protein antigen from which the peptide is derived. In this calculation stimulation indices for the candidate peptide, the N-terminal flanking peptide and the C-terminal flanking peptide are added and divided by the sum total of the stimulation indices for the entire set of overlapping peptides obtain a percent of T cell reactivity for the candidate peptide. If a combination of two or more candidate peptides is selected each of which contains amino acid residues which overlap, this calculation cannot be used to determine a percent of T cell reactivity for each candidate peptide separately. However, a total percent of T cell reactivity for the combination of candidate peptides can be obtained. In this situation, the stimulation indices for all of the candidate peptides which overlap is included in the calculation.

The values obtained for the percentage of T cell reactivity for the candidate peptide or combination of peptides in each individual tested can be expressed as a range of the lower and higher values of the results of the above described calculations. By either of the above calculations, the percent is obtained for at least about twenty (20) and preferably at least about thirty (30) individuals sensitive to the protein antigen and a mean percent is determined. For use in the compositions of the invention, the candidates peptide or combination of candidate peptides has the following criteria: (1) the candidate peptide or combination of candidate peptides has a mean percent of at least about 10%, preferably at least about 20%, more preferably at least about 30%, more preferably at least about 40% and more preferably at least about 50–60% or greater; and (2) in the population of individuals tested at least about 60%, preferably at least about 75%, and more preferably at least about 90–100% have positive T call responses (S.I. equal to or greater than 2.0) in response to the candidate peptide or combination of candidate peptides. A candidate peptide or combination of candidate peptides meeting the above criteria is likely to comprise a sufficient percentage of the T cell reactivity to house dust mite protein allergen to induce T cell non-responsiveness or reduced T cell responsiveness in a substantial percentage of a population of individuals sensitive to house dust mite.

As an illustrative embodiment of the above-described algorithm, a set of overlapping peptides and candidate peptides derived from Der p I and Der p II respectfully were produced and tested. Secondary T cell cultures determined to be reactive with Der p I protein allergen were derived from 39 house dust mite-allergic subjects and analyzed for reactivity to an overlapping set of peptides, as well as candidate peptides derived from Der p I and Der f I protein allergen, DPI-21.2 (SEQ. I). NO. 28), DFI-22.2 (SEQ. ID. NO. 93), DFI-23.31(SEQ. ID. NO. 165) and DFI-26.6 (SEQ. ID. NO. 168), in an in vitro T cell proliferation assay as described herein. The results are shown in FIG. 3. The highest stimulation index greater than or equal to 2.0 in response to each peptide was recorded for each subject tested. The data were then analyzed by the equations above. The results and calculations of the percent of T cell reactivity for a single dust mite-allergic subject are shown below using formulas (1) and (2).

| T CELL REACTIVITY FOR PATIENT 1733 PEPTIDE STIMULATION INDEX | |
|---|---|
| DPI-21.2 (SEQ. ID. NO. 28) | 3.6 |
| DPI-3 (SEQ. ID. NO. 11) | 3.9 |
| DPI-22.2 (SEQ. ID. NO. 30) | 3.1 |
| DPI-12.1 (SEQ. ID. NO. 14) | 2.2 |
| DPI-5.1 (SEQ. ID. NO. 205) | 3.5 |

| -continued | |
|---|---|
| T CELL REACTIVITY FOR PATIENT 1733 PEPTIDE STIMULATION INDEX | |
| DFI-23.31 (SEQ. ID. NO. 165) | 5.7 |
| DPI-14 (SEQ. ID. NO. 18) | 2.3 |
| DPI-15 (SEQ. ID. NO.) | 2.8 |
| DPI-6.1 (SEQ. ID. NO. 19) | 2.1 |
| DPI-7.1 (SEQ. ID. NO. 21) | 2.2 |
| DFI-26.6 (SEQ. ID. NO. 168) | 5.0 |
| DPI-9 (SEQ. ID. NO. 23) | 2.4 |
| DPI-16 (SEQ. ID. NO. 24) | 2.0 |
| DPI-10 (SEQ. ID. NO. 25) | 0 |
| DPI-17 (SEQ. ID. NO. 26) | 0 |
| SUM OF STIMULATION INDICES | 40.8 (DENOMINATOR) |

% Reactivity of Peptide DFI-26.6 (SEQ. ID. NO. 168) for patient 1733 is $$(1) \quad \frac{\text{DPI-26.6 (S.I.)}}{40.8} = \frac{5.0}{40.8} \times 100 = 12.3\%$$

$$(2) \quad \frac{\text{DPI-7.1} + \text{DPI-26.6} + \text{DPI-9}}{40.8} = \frac{2.2 + 5.0 + 2.4}{40.8} \times 100 = 24\%$$

Therefore the estimated range of T cell reactivity for Peptide DFI-26.6 (SEQ. ID. NO; 168) for this patient is 12.3%–24% of the total reactivity of the Der p I protein. The above calculation is repeated for any potential candidate peptides for each patient tested. In the population of 39 Cry j I-allergic subjects tested the following results were obtained:

| Candidate Peptides | Range of mean percentage T Cell Reactivity | Frequency of response at least one peptide |
|---|---|---|
| DPI-21.2 (SEQ. ID. NO. 28), DFI-22.2 (SEQ. ID. NO. 93) DPI-23.31 (SEQ. ID. NO. 165), DPI-26.6 (SEQ. ID. NO. 168) | 38–67% | 82% |

Thus, the combination of the four candidate peptides are well within the desired range for possessing, in combination, sufficient T cell reactivity of Group I protein allergen of Der f and Der p, and meet the first characteristic of a "unique" peptide of the invention.

The same calculations were determined for the Group II, Der p protein allergen. Secondary T cell cultures determined to be reactive with Der p I protein allergen were derived from 30 house dust mite-allergic subjects and analyzed for reactivity to an overlapping set of peptides, as well as candidate peptides derived from Der p II, DPII-20.9 (SEQ. ID. NO. 169), DPII-22.14 (SEQ. ID. NO. 180)and DPII-25.15 (SEQ. ID. NO. 188), in an in vitro T cell proliferation assay as described herein. The results are shown in FIG. 4. The highest stimulation index greater than or equal to 2.0 in response to each peptide was recorded for each subject tested. The data were then analyzed by the equations above. In the population of 30 house dust mite-allergic subjects tested the following results were obtained:

| Candidate Peptides | Range of mean percentage T Cell Reactivity | Frequency of response at least one peptide |
|---|---|---|
| DPII-20.9 (SEQ. ID. NO. 169), DPII-22.14 (SEQ. ID. NO. 180) DPII-25.15 (SEQ. ID. NO. 188) | 37–51% | 63% |

Thus, the combination of the three Der p II candidate peptides of the invention are well within the desired range for possessing, in combination, sufficient T cell reactivity of Group II house dust mite protein allergen of Der p, and meet the first characteristic of a "unique" peptide of the invention.

For the treatment of allergy in accordance with the methods of the invention, it is preferred that a peptide used in conjunction therewith does not bind immunoglobulin E (IgE) or binds IgE to a substantially lesser extent (i.e. at least 100-fold less binding and more preferably, at least 1,000-fold less binding) than the respective house dust mite protein allergen from which the peptide is derived binds IgE. Experiments to date indicate that candidate peptides DPI-21.2 (SEQ. ID. NO. 28), DFI-22.2 (SEQ. ID. NO. 93), DFI-23.31(SEQ. ID. NO. 165), DFI-26.6 (SEQ. ID. NO. 168), DPII-20.9 (SEQ. ID. NO. 169), DPII-22.14 (SEQ. ID. NO. 180) and DPII-25.15 (SEQ. ID. NO. 188) exhibit negative IgE reactivity or histamine release (data not shown).

The second characteristic for a unique peptide is that of "superior solubility" which was defined earlier as being solubility of greater than 3 mg/ml at a pH in a range of pH 6 to pH 8. Solubility in a physiologically acceptable pH range (e.g. pH 6 to pH 8) is particularly important when formulating a multipeptide therapeutic for injection. Administration of a soluble drug product in a physiologically acceptable pH range by intravenous or subcutaneous injection provides about 100% bioavailability of the drug component to the physiological system into which the drug is being introduced. Thus, it is necessary that a drug product intended for injection be fluid to the extent that easy syringability exists, and the active component be soluble as well if maximum therapeutic effect is to be achieved. Solubility is also useful when formulating compositions to be administered via other modes of administration such as by oral administration (tablet, aerosol, sublingual), or sustained release preparations and formulations.

Proteins and peptides may be difficult to formulate into soluble compositions as a peptide may not be soluble in any desirable pH range or may be soluble in only a narrow pH range. It is particularly difficult when multiple peptides are being formulated together into a single multipeptide formulation, as each peptide may be soluble in a pH range which does not overlap with those of the other peptides in the formulation. As a result, it is the requirement of "superior solubility" which requires the most formulation flexibility in that considerable modification of the targeted candidate peptides may be necessary to successfully formulate a multipeptide drug product.

Some of the unique peptides of the invention are the product of multiple amino acid modifications of the original targeted candidate peptide sequence ("parent") from which the modified unique peptides of the invention were originally derived. Such modified "unique" peptides of the invention include DFI-23.31(SEQ. ID. NO. 165), DFI-26.6 (SEQ. ID. NO. 168), DPII-20.9 (SEQ. ID. NO. 169), DPII-22.14 (SEQ. ID. NO. 180) and DPII-25.15 (SEQ. ID. NO. 188) all as shown in FIG. 33. For example, the amino acid sequence of DPII-22.14 (SEQ. ID. NO. 180) was derived from the protein sequence of Der p II by first identifying those regions of the native protein with high T-cell reactivity using a set of overlapping peptides that covered the entire protein sequence. Several peptides were found to exhibit high T-cell reactivity, corresponding to three different locations/areas in the protein. One of these areas were covered by three adjacent peptides each being about 25–29 amino acids long and with 10–15 amino acids overlap, DpII-3.1 (SEQ. ID. NO. 206), Dp-II4 (SEQ. ID. NO. 44)and DpII-5 (SEQ. ID. NO. 45) (FIG. 34) that all exhibited high T-cell reactivity. Based on this T-cell map a new peptide was synthesized, with the amino acid sequence QLEAVFEANQNTKTAKIEIKASIDGLEV (SEQ. ID. NO. 207), 28 amino acids long, which exhibits most of the reactivity found in the individual peptides (data not shown) and contains all of DpII-4 (SEQ. ID. NO. 44)and parts of DpII-3.1 (SEQ. ID. NO. 206) and DpII-5 (SEQ. ID. NO. 45). However, this peptide did not meet the "superior solubility" requirement of 3 mg/ml for a "unique peptide of the invention nor did it meet the stability requirement. Therefore two analogs were made with addition of one or two charged residues at each end, DpII-22.2 KQLEAVFEANQNTKTAKIEIKASIDGLEVK (SEQ. ID. NO. 93) and DpII-22.6 DKQLEAVFEANQNTKTAKIEIKASIDGLEVD (SEQ. ID. NO. 139) and the stability improved substantially but the solubility did not reach the standard of a "superior solubility". In the second attempt a series of truncated analogs with up to five charged amino acid residues added to the ends (Table 1).

TABLE 1

| | |
|---|---|
| Dpll-22 (SEQ. ID. NO. 63) | QLEAVFEANQNTKTAKIEIKASIDGLEV |
| Dpll-22.2 (SEQ. ID. NO. 93) | KQLEAVFEANQNTKTAKIEIKASIDGLEVK |
| Dpll-22.6 (SEQ. ID. NO. 139) | DKQLEAVFEANQNTKTAKIEIKASIDGLEVD |
| Dpll-22.4 (SEQ. ID. NO. 141) | QLEAVFEANQNTKTAKIEIKASIDE |
| Dpll-22.5 (SEQ. ID. NO. 142) | DKQLEAVFEANQNTKTAKIEIKASIDE |
| Dpll-22.8 (SEQ. ID. NO. 144) | DKEQLEAVFEANQNTKTAKIEIKASIDE |
| Dpll-22.9 (SEQ. ID. NO. 145) | DKEQLEAVFEANQNTKTAKIEIKASIDEE |
| Dpll-22.12 (SEQ. ID. NO. 198) | DKQLEAVFEANQATKTAKIEIKASIDE |
| Dpll-22.16 (SEQ. ID. NO. 199) | DKELEAVFEANQNTKTAKIEIKASD |
| Dpll-22.19 (SEQ. ID. NO. 200) | DKELEAVFEANQNTKTAKIEIKAD |
| Dpll-22.20 (SEQ. ID. NO. 201) | DKELEAVFEANQNTKTAKIEIKAK |
| Dpll-22.21 (SEQ. ID. NO. 202) | DKELEAVFEANQNTKTAKIEIKD |
| Dpll-22.22 (SEQ. ID. NO. 175) | DKELEAVFEANQNTKTAKIEIKK |

TABLE 1-continued

| Name | Sequence |
|---|---|
| Dp11-22.26 (SEQ. ID. NO. 176) | DKELEAVFEANQNTKTAKIEIK |
| Dp11-22.23 (SEQ. ID. NO. 177) | DKELEAVFEANQNTKTAKIED |
| Dp11-22.24 (SEQ. ID. NO. 178) | DKELEAVFEANQNTKTAKIEK |
| Dp11-22.25 (SEQ. ID. NO. 179) | DKELEAVFEANQNTKTAKIE |
| DP11-22.14 (SEQ. ID. NO. 180) | DKELEAVFEANQNTKTAKAE |
| Dp11-22.10 (SEQ. ID. NO. 146) | LEAVFEANQNTKTAK |
| Dp11-22.11 (SEQ. ID. NO. 147) | LEAVFEANQATKTAK |
| Dp11-22.18 (SEQ. ID. NO. 203) | DKTAKIEIKASIDGLE |
| Dp11-22.15 (SEQ. ID. NO. 204) | KTAKIEIKASIDGLE |

Of these the DpII-22.5, DKQLEAVFEANQNTKTAKIE-IKASIDE (SEQ. ID. NO. 142), was promising since it retained the T-cell reactivity of the "parent" peptide, DPII-22, (SEQ. ID. NO. 63)and was very soluble, but it was very difficult to synthesized. The difficulties in synthesizing this sequence were found to disappear with the replacement of the hydrophobic isoleucine with the less hydrophobic alanine and simultaneously the solubility increased by an order of magnitude. Peptide DpII-22.14, DKELEAVFEANQNT-KTAKAE (SEQ. ID. NO. 180), was found to possess almost the same T-cell reactivity as the "parent" peptide DpII-22 (SEQ. ID. NO. 63)as well as being soluble at greater than 3 mg/ml at a pH in the pH range 6.0 to 8.0, and was easy to synthesize and purify. Therefore, DPII-22 (SEQ. ID. NO. 63) was chosen as a "unique" peptide when it was determined to be stable at a pH in the range of 6.0 to 8.0. The development of the other modified "unique" peptides, DFI-23.31(SEQ. ID. NO. 165), DFI-26.6 (SEQ. ID. NO. 168) and DPII-25.15 (SEQ. ID. NO. 188), followed a process similar to that described above for DPII-22.14 (SEQ. ID. NO. 180). All of the unique candidates are novel peptides of this invention.

The third criteria which the unique peptides of this invention must meet is stability, particularly solution stability, in a physiologically acceptable pH range of pH 6 to pH 8. It must be stable under the conditions of manufacture and storage, and under conditions of reconstitution if necessary. Stability testing establishes the time period for which the integrity, quality and purity of the drug product is preserved in its finished dosage form. Stability testing may be performed concurrently with solubility studies as discussed in Example 3. An equal concentration composition comprising each of the candidate peptides of the invention remained stable (e.g. no significant degradation) in solution at a common "window" within the pH range from pH 6-pH 8 at about room temperature and at about 5° C. for at least 24 hours (see, FIG. 6).

Therefore, candidate peptides DPI-21.2 (SEQ. ID. NO. 28), DFI-22.2 (SEQ. ID. NO. 93), DFI-23.31(SEQ. ID. NO. 165), DFI-26.6 (SEQ. ID. NO. 168), DPII-20.9 (SE(t. ID. NO. 169), DPII-22.14 (SEQ. ID. NO. 180) and DPII-25.15 (SEQ. ID. NO. 188) possess each of the three required "unique" characteristics outlined above, indicating that this combination of peptides is suitable for formulation as an optimized therapeutic drug product for administration to humans for treatment of allergy to house dust mite allergen.

Highly purified peptides of this invention, may be produced synthetically by chemical synthesis using standard techniques. Various methods of chemically synthesizing peptides are known in the art such as solid phase synthesis which has been fully or semi automated on commercially available peptide synthesizers. Synthetically produced peptides may then be purified to homogeneity (i.e. at least 90%, more preferably at least 95% and even more preferably at least 97% purity), free from all other polypeptides and contaminants using any number of techniques known in the literature for protein purification.

In accordance with one procedure for producing highly purified homogenous peptides of the invention, a peptide produced by synthetic chemical means (either anchored to a polymer support "solid phase synthesis" or by conventional homogenous chemical reactions "solution synthesis") may be purified by preparative reverse phase chromatography. In this method, the synthetically produced peptide in "crude" form is dissolved in an appropriate solvent (typically an aqueous buffer) and applied to a separation column (typically a reverse phase silica based media, in addition, polymer or carbon based media may be used). Peptide is eluted from the column by increasing the concentration of an organic component (typically acetonitrile or methanol) in an aqueous buffer (typically TFA, triethylamine phosphate, acetate or similar buffer). Fractions of the eluate will be collected and analyzed by appropriate analytical methods (typically reverse phase HPLC or CZE chromatography). Those fractions having the required homogeneity will be pooled. The counter ion present may be changed by additional reverse phase chromatography in the salt of choice or by ion exchange resins. The peptide may then be isolated as its acetate or other appropriate salt. The peptide is then filtered and the water removed (typically by lyophilization) to give a homogenous peptide composition containing at least 90%, more preferably at least 95% and even more preferably at least 97% of the required peptide component. Optionally, or in conjunction with reverse phase HPLC as described above, purification may be accomplished by affinity chromatography, ion exchange, size exclusion, counter current or normal phase separation systems, or any combination of these methods. Peptide may additionally be concentrated using ultra filtration, rotary evaporation, precipitation, dialysis or other similar techniques.

The highly purified homogenous peptide composition is then characterized by any of the following techniques or combinations thereof: a) mass spectroscopy to determine molecular weight to check peptide identity; b) amino acid analysis to check the identity of the peptide via amino acid composition; c) amino acid sequencing (using an automated protein sequencer or manually) to confirm the defined sequence of amino acid residues; d) HPLC (multiple systems if desired) used to check peptide identity and purity (i.e. identifies peptide impurities); e) water content to determine the water concentration of the peptide compositions; f) ion content to determine the presence of salts in the peptide composition; and g) residual organics to check for the presence of residual organic reagents, starting materials, and/or organic contaminants.

A peptide of the invention may also be produced by recombinant DNA techniques in a host cell transformed with a nucleic acid sequence coding for such peptide as described earlier.

In certain limited circumstances, peptides of this invention may also be produced by chemical or enzymatic cleavage of a highly purified full length or native protein of which the sites of chemical digest or enzymatic cleavage have been predetermined and the resulting digest is reproducible. Peptides having defined amino acid sequences can be highly purified and isolated free of any other poly peptides or contaminants present in the enzymatic or chemical digest by any of the procedures described above for highly purified, and isolated synthetically or recombinantly produced peptides.

The present invention also pertains to therapeutic compositions and multipeptide therapeutic formulations comprising the unique peptides of the invention. Therapeutic compositions of the invention may comprise one or more of the unique peptides of the invention which may be administered simultaneously or sequentially as single treatment episode for treatment of allergy to house dust mite allergen in a human or other mammal. Such a treatment regimen may not necessarily be a physical mixture of more than one peptide of the invention, but does comprise a combination of such peptides administered simultaneously or sequentially as a single treatment episode in order to achieve the maximum therapeutic effect the combination of the unique peptides, DPI-21.2 (SEQ. ID. NO. 28), DFI-22.2 (SEQ. ID. NO. 93), DFI-23.31(SEQ. ID. NO. 165), DFI-26.6 (SEQ. ID. NO. 168), DPII-20.9 (SEQ. ID. NO. 169), DPII-22.14 (SEQ. ID. NO. 180) and DPII-25.15 (SEQ. ID. NO. 188) provide (e.g. solubility and stability in acceptable physiological pH range as well as having a range of T cell reactivity of 38–67% of the total T cell reactivity of the Group I house dust mite protein allergen and a frequency of response of 91% for at least one Der p I peptide tested in a population of individuals allergic to house dust mite and similarly, have a range of T cell reactivity of 37–51% of the total T cell reactivity of the Group II house dust mite protein allergen and a frequency of response of 63% for at least one Der p II peptide tested in a population of individuals allergic to house dust mite).

Therapeutic compositions of the invention comprise one or more of peptides DPI-21.2 (SEQ. ID. NO. 28), DFI-22.2 (SEQ. ID. NO. 93), DPI-23.31(SEQ. ID. NO. 29), DFI-26.6 (SEQ. ID. NO. 168), DPII-20.9 (SEQ. ID. NO. 169), DPII-22.14 (SEQ. ID. NO. 180) and DPII-25.15 (SEQ. ID. NO. 188) also comprise one or more pharmaceutically acceptable carriers such as excipients which are compatible with peptide or peptides present in a single composition. When the composition is a multipeptide formulation, the pharmaceutically acceptable carrier must be compatible with all of the peptides in the multipeptide formulation. Preferred excipients include but are not limited to sterile water, sodium phosphate, mannitol, or both sodium phosphate and mannitol or any combination thereof. Other suitable excipients include but are not limited to sorbitol, sucrose, dextrose, lactose dextran and PVP. Additionally, due to the potential for dimerization of the peptides in a mutlipeptide formulation, there may also be included an agent such as EDTA to prevent dimerization. Alternatively, any other material or procedures known in the art to prevent dimerization may be used. In addition, pharmaceutically acceptable counter ions may be added during the preparation of the multipeptide formulation. Examples of pharmaceutically acceptable counter ions include acetate, HCl, and citrate.

A therapeutic composition of the invention should be sterile, stable under conditions of manufacture, storage, distribution and use and should be preserved against the contaminating action of microorganisms such as bacteria and fungi. A preferred means for manufacturing a therapeutic compositions of the invention in order to maintain the integrity of the composition (i.e. prevent contamination, prolong storage, etc.) is to prepare the formulation of peptide and pharmaceutically acceptable carrier(s) such that the composition may be in the form of a lyophilized powder which is reconstituted in a pharmaceutically acceptable carrier, such as sterile water, just prior to use. In the case of sterile powders for the preparation of sterile injectable solutions, the preferred methods of preparation are vacuum drying, freeze-drying or spin drying which, yields a powder of the active ingredient plus any additional desired ingredient from a previously sterile-filtered solution thereof.

A preferred multipeptide formulation comprises the following unique peptides DPI-21.2 (SEQ. ID. NO. 28), DFI-22.2 (SEQ. ID. NO. 93), DFI-23.31(SEQ. ID. NO. 165), DFI-26.6 (SEQ. ID. NO. 168), DPII-22.14 (SEQ. ID. NO. 180) and DPII-25.15 (SEQ. ID. NO. 188) and sodium phosphate and mannitol, and optionally may further comprise DPII-20.9 (SEQ. ID. NO. 169). For this embodiment, EDTA is added to the formulation. A suitable counter ion such as acetate may also be added during the preparation of the formulation. The formulation is preferably prepared in the form of a lyophilized powder which is reconstituted in a physiologically acceptable carrier, such is. sterile water, prior to use. Several non-limiting examples of a preferred multipeptide formulations of this invention are described below. The unique house dust mite protein allergen peptides will preferably be combined during manufacturing with the appropriate counter ion to produce one vial containing a sterile, pyrogen free, and preferably lyophilized powder of the desired formulation:

Active: Der p I, Der f I and Der p II peptides DPI-21.2 (SEQ. ID. NO. 27), DFI-22.2 (SEQ. ID. NO. 93), DPI-23.31 (SEQ. ID. NO. 29), DFI-26.6 (SEQ. ID. NO. 168), DPII-22.14 (SEQ. ID. NO. 32) and DPII-25.15 (SEQ. ID. NO. 188) In concentration of 0.75 mg per peptide Inactives: 0.05 M Sodium Phosphate U.S.P. 5% w/v Mannitol, U.S.P. 0.1 mg/ml EDTA disodium dihydrate U.S.P. Final pH 7.2–7.4

Diluent: Sterile Water for Injection, U.S.P.

Optionally 0.75 mg of DPII-20.9 (SEQ. ID. NO. 169) may be added to the active ingredients.

A preferred combination of multipeptide formulations suitable for administration simultaneously or sequentially as a single treatment episode and contained in two separate sterile, pyrogen free vials preferably in the form of lyophilized powders include,, the following formulations:

Vial #1

Active: Der p I, Der f I and Der p II peptides DFI-22.2 (SEQ. ID. NO. 28), DFI-23.31(SEQ. ID. NO. 165), and DPII-22.14 (SEQ. ID. NO. 32) In concentration of 0.75 mg per peptide Inactives: 0.05 M Sodium Phosphate U.S.P. 5% w/v Mannitol, U.S.P. 0.1 mg/ml EDTA disodium dihydrate Final pH 7.0

Diluent: Sterile Water for Injection, U.S.P.

Vial #2

Active: Der p I, and Der p II peptides DPI-21.2 (SEQ. ID. NO. 28), DFI-26.6 (SEQ. ID. NO. 168), DPII 20.9 (SEQ. ID. NO. 31), DPII-25.15 (SEQ. ID. NO. 188) In concentration of 0.75 mg per peptide Inactives: 0.05 M Sodium Phosphate U.S.P. 5% w/v Mannitol, U.S.P. 0.1 mg/ml EDTA disodium dihydrate U.S.P. Final pH 6.2

Diluent: Sterile Water for Injection, U.S.P.

The multipeptide formulations of the invention may also be provided in the form of a kit, including instructions for use.

Administration of the therapeutic compositions and multipeptide formulations described above to an individual, preferably in non-immunogenic form, can be carried out using known procedures at dosages and for periods of time effective to cause down regulation of the house dust mite-specific immune response (i.e., reduce the allergic symptoms caused by house dust mite protein allergen of the individual. Down regulation of the allergic immune response to house dust mite allergen in humans may be determined clinically whenever possible (see e.g., Varney et al, *British Medical Journal,* 302:265–269 (1990), or may be determined subjectively (i.e. the patient feels as if some or all of the allergic symptoms caused by house dust mite allergens have been alleviated).

One of the unique characteristics of each unique peptide in accordance with the invention is that each peptide possesses "superior solubility". Therefore, compositions and multipeptide formulations of the invention are particularly suitable for administration by injection (e.g. subcutaneous, or intravenous). However, optimized compositions and multipeptide formulations of the invention may be administered in any convenient manner wherein solubility of the active drug component is either desirable or acceptable, such as by injection (subcutaneous, intravenous, etc.), oral administration, sublingual, inhalation, transdermal application, rectal administration, or any other route of administration known in the art for administering soluble therapeutic agents. It may be desirable to administer simultaneously or sequentially a therapeutically effective amount of one or more of the therapeutic compositions of the invention to an individual as a single treatment episode. Each of such compositions for administration simultaneously or sequentially as a single treatment episode, may comprise only one unique peptide of the invention or may comprise an optimized multipeptide formulation in accordance with the invention.

For subcutaneous injection of one or more therapeutic compositions and multipeptide formulations of the invention, preferably about 1 mg–3 mg and more preferably from about 20mg–1.5 mg, and even more preferably about 50 mg–750 mg of each active component (peptide) per dosage unit may be administered. It is especially advantageous to formulate parenteral compositions in unit dosage form for ease of administration and uniformity of dosage. Unit dosage form as used herein refers to physically discrete units suited as unitary dosages for human subjects to be treated; each unit containing a predetermined quantity of active compound calculated to produce the desired therapeutic effect in association with the desired pharmaceutical carrier. The specification for the novel unit dosage forms of the invention are dictated by and directly dependent on (a) the unique characteristics of the active compound and the particular therapeutic effect to be achieved, and (b) the limitations inherent in the art of compounding such an active compound for the treatment of human subjects.

Effective amounts of the optimized drug compositions of the invention will vary according to factors such as the degree of sensitivity of the individual to the antigen, the age, sex, and weight of the individual, and the ability of peptide to cause down regulation of the antigen specific immune response in the individual. Dosage regimen may be adjusted to provide the optimum therapeutic response. For example, several divided doses may be administered over the course of days, weeks, months or years, or the dose may be proportionally increased or reduced with each subsequent injection as indicated by the exigencies of the therapeutic situation. In one preferred therapeutic regimen, subcutaneous injections of therapeutic compositions are given once a week for 3–6 weeks. The dosage may remain constant for each injection or may increase or decrease with each subsequent injection. A booster injection may be administered at intervals of about three months to about one year after initial treatment and may involve only a single injection or may involve another series of injections similar to that of the initial treatment.

This invention is further illustrated by the following non-limiting examples.

EXAMPLE I

Native Mite Allergen Purification

What follows is a description of the work done to purify the group I and group II allergens of the house dust mites *Dermatophagoides pteronyssinus* and *Dermatophagoides farinae* in their native form as primary antigens for human T-cell epitope mapping.

All four protein allergens, Der f I, Der p I, Der f II, and Der p II, were immunoaffinity purified from spent mite culture media obtained from either Commonwealth Sera Laboratories Melbourne, Australia or Dr. Larry G. Arlian at Wright State University Dayton, Ohio. A 10% (wt./vol.) aqueous extract of dessicated spent mite culture media was prepared in PBS (phosphate Buffered Saline) with stirring overnight at 4° C. Insoluble material was removed by centrifugation at 10,000×g for 1 hour at 4° C. The supernatant was then filtered on a vacuum manifold through Whatman #1 paper, and re-centrifuged at 15,000×g for 1 hour at 4° C. A final filtration was carried out through a 0.45 m cellulose acetate filter.

Monoclonal antibodies 4C1 and 6D6 (University of Virginia, North Carolina) were used for immunoaffinity purification of group I or group II mite allergens respectively (Chapman et al., *J. Allergy Clin. Immunol.,* 80:1479–1484 (1987); Heymann et al., L *Allergy Clin. Immunol.,* 83:1055–1067 (1989)). The 4C1 monoclonal antibody reacts with an epitope shared by both the Der f I and Der p I proteins; similarly, the 6D6 monoclonal antibody reacts with both the Der f II and Der p II proteins.

For each monoclonal antibody, ascites fluid was cut in 50% ammonium sulfate and the antibodies coupled to CNBr-activated Sepharose 4B (Pharmacia) in 100 mM NaHCO$_3$, 500 mM NaCl, pH 8.3, overnight at 4° C.

Monoclonal antibody columns were equilibrated in PBS and the filtered extracts loaded at 15 ml per hour. The column was then washed in 20 volumes of PBS, after which a more stringent wash of 20 column volumes was carried out with PBS supplemented with 500 mM NaCl. Proteins were eluted in 500 mM NaCl, 100 mM glycine pH 11.0, and fractions evaluated for protein content by spectrophotometric absorbance at 280 nm. Peak fractions were pooled and dialyzed extensively against PBS, concentrated with a negative pressure dialysis device (obtained from Amicon, Beverly Mass.) and were used in T-cell epitope mapping studies of the mite group I and group II allergens. Recovered proteins were obtained at purities ranging from 80% (group 11) to 90% (group I).

Reverse Phase HPLC chromatography was applied to further purify the immunoaffinity purified group II mite protein allergen according to the conditions in Heymann et al., *J. Allergy Clin. Immunol.,* 83:1055–1067 (1989). Briefly, immunoaffinity purified protein was applied to a 5 μm 300 Å C-8 column (Applied Biosystems Inc.) in 0.1% vol./vol. TFA/H$_2$O. The flow rate for the column was 1 ml/min. with a gradient of 0–60% acetonitrile/0.1% TFA over 60 minutes. Group II proteins eluted around 45% acetonitrile/0.1% TFA. Fractions were analyzed for purity by SDS-polyacrylamide gel electrophoresis followed by densitometric scanning. Those fractions with group II protein of purity greater than 90% were subsequently utilized for human T-cell mapping of the allergen.

EXAMPLE II

Recombinant Mite Allergen Expression

What follows is a description of the work done to produce the group I and group II allergens of the house dust mites *Dermatophagoides pteronyssinus* and *Dermatophagoides farinae* as recombinant proteins in *E. coli*.

All four protein allergens, Der f I, Der p I, Der f II, and Der p II, were fused at their mature amino termini with the leader sequence MGHHHHHHEF (SEQ ID NO: 150) (where amino acids EF are encoded by the EcoR I restriction site GAATTC).

Since the H$_6$ stretch of amino acids coordinates Ni$^{++}$ ions on NTA agarose columns (Diagen GmbH), this activity was exploited in the purification of the recombinant proteins (Hochuli et al., *Biotechnology,* 86:1321–1325 (1988)). Ultimately, all four allergens were subcloned into the expression vector pET 11d (Studier et al., *Methods In Enzymology,* 185:60–88 (1990)) under the transcriptional control of the phage T7 gn 10 promoter.

The cDNAs encoding the group I allergens from *D. pteronyssinus* and *D. farinae* were obtained from Dr. Wayne Thomas in plasmid form as subclones from λgt11 (Chua et al., *J. Exp. Med.,* 167:175–182 (1988); Dilworth et al., *Clin. Exp. Allergy,* 21:25–32(1991)). The Der p I cDNA had been subcloned from an M13 RF plasmid as an EcoRI fragment into pUC18 by Dr. Roland Buelow at ImmuLogic (Palo Alto), while the Der f I cDNA was manipulated directly from the M13mp19 RF plasmid Df I(1).

Initially the cDNAs were subcloned into the expression vector pTrc99A His$_6$ Insert RRRS which is a modified version of pTrc99A (Amann et al., *Gene,* 69:301–315 (1988)). The original vector was modified by the addition of a synthetic adaptor (consisting of two complimentary oligonucleotides) encoding the leader sequence MGHHH-HHHEF (SEQ ID NO: 150) between its NcoI (MG) and EcoRI (EF) sites at the 5' end of the polylinker, and an RRS metro Regulatory Sequence) into its Hind III site at the polylinker's 3' end. The leader sequence was used as a purification aid as described above, while the RRS was added to enhance recombinant message stability and thereby increase recombinant protein yield (Skoglund et al., *Gene,* 88:1–5 (1990)). Lasdy, an insert, in this case an Amb a I.1 cDNA encoding the major allergen of the short ragweed (Rafnar et al., *J. Biol. Chem.,* 226:1229–1236 (1991)) was subcloned in frame with the H$_6$ leader as an EcoRI to PstI fragment.

To express the mite group I allergens, the Amb a I.1 cDNA was excised by EcoRI/Hind III digestion and replaced by adaptors with φEcoRI/Hind III overhangs (composed of a pair of complimentary oligonucleotides). These adaptors (FIG. 2*a*) encoded the first 5 amino acids, up to the Pst I site, of the mature Der p I NH$_2$ terminus, and the first 10 amino acids, up to the HpaI site, of the mature Der f I NH$_2$ terminus. Upon ligation of the EcoRI site of the vector and the φEcoRI site in the adaptors, the EcoRI site in the vector was destroyed, leaving the EcoRI site encoded internal to the adaptor as the sole EcoRI site in the intermediate constructs pTrc99A His$_6$ 5' p1 RRS and pTrc99A His$_6$ 5' f1 RRS. The Der p I cDNA was inserted as a PstI/EcoRI fragment into PstI/EcoRI digested pTrc99A His$_6$ 5' p1 RRS, while the Der f I cDNA was inserted as a HpaI/EcoRI fragment into Hpa1/EcoRI digested pTrc99A His$_6$ 5' f1 RRS. The sequence of the 5' end of each construct, pTrc99A His$_6$ 5' p1 RRS and pTrc99A His$_6$ f1 RRS, was verified by dideoxy chain termination DNA sequencing using a Sequenase™ II kit (U.S. Biochemicals). Both the H$_6$ P1 and H$_6$ f1 coding cassettes were excised by NcoI/NheI digestion (an NheI site existed at the 3' end of the RRS adaptor) and inserted into NcoI/NheI digested pET11d. These two constructs, pET11d His$_6$ p1 RRS and pET11d His$_6$ f1 RRS, were transformed into competent BL21 [DE3] bacteria for expression of the recombinant proteins. BL21 [DE3] contains a recombinant phage λ lysogen, DE 3, with a phage T7 RNA polymerase gene under the transcriptional control of the lac UV5 promoter. T7 RNA polymerase gene expression is induced by the addition of IPTG (Isopropyl-B-D-thiogalactopyrano- side), which in turn leads to high level expression of the recombinant gene subcloned 3' of the pET vector's T7 gn 10 promoter.

The cDNAs encoding the group II allergens from *D. pteronyssinus* and *D. farinae* were also obtained from Dr. Wayne Thomas in plasmid form as subclones from λgt11 (Chua et al., *Int Arch. Appl. Immun.,* 91:118–123 (1990); Trudinger et al., *Clin. Exp. Allergy,* 21:33–37 (1991)). The original Der p II cDNA was subcloned from an M13RF plasmid into the pCA and pGEX vectors by Dr. Roland Buelow at ImmuLogic (Palo Alto). Dr. Thomas' group had supplied the Der f I cDNA as a subclone in pGEX. Both pGEX plasmids harboring group II cDNAs were used as templates for PCR amplification with the same 5' sense/3' antisense primer pair (FIG. 2*b*). The primers were designed to fuse an EcoRI site (GAATTC encoding the amino acids EF) in frame with the NH$_2$ terminus of the mature group II proteins and place a PstI site 3' of the group II coding region. An MJ Research Thermal Controller with a program of 30× (94° C. 1 min./55°1 min. 30 sec./72° C. 2 min.) was used in conjunction with reagents from a Perkin Elmer—Cetus Gene Amp kit for PCR amplification. The PCR products were EcoRI/PstI digested and subcloned into EcoRI/PstI digested M13mp19RF. DNA sequence analysis was performed to verify the sequence of the PCR products. Correct M13RF were EcoRI/PstI digested, their group II cDNA inserts isolated, and subcloned into EcoRI/PstI digested pTrc99A His$_6$ Amb a I.1 RRS (which served to exchange the group II cDNAs with the ragweed cDNA (FIG. 33)).

The Der f II cDNA possessed a sequence polymorphism at position 54 (i.e., threonine residue in place of isoleucine). To alter this polymorphism, site directed mutagenesis of the T$_{54}$ residue in the Der f II cDNA was performed using a MutaGene kit from Bio-Rad Laboratories, based on the method of Kunkel, *Proc. Natl. Acad. Sci. USA,* 82:488–492 (1985). The original M13mp19RF with the T$_{54}$ Der f II cDNA was transformed into CJ236 bacteria, which tolerate the incorporation of uracil in place of thymidine during DNA replication, and single stranded phage DNA prepared as template. A mutagenic 17 base pair primer (FIG. 2*b*) was annealed to the phage template DNA. T4 DNA polymerase was used to copy the template DNA primed by the mutagenic oligonucleotide, and T4 DNA ligase served to seal gaps in the DNA strand. The reaction was transformed into MV1190 bacteria, which are wild type for the editing of uracil residues from DNA and therefore selectively replicate the mutagenized (non-uracil containing) strand, and single stranded phage DNA prepared from recombinant (white) plaques. Several recombinants were subjected to DNA sequence analysis and Der f II cDNAs with the corrected $I_{54}$ sequence subcloned as EcoRI/PstI fragments into EcoRI/PstI digested pTrc99A $His_6$ Amb a I.1 RRS.

Since one previous work had shown that the pET11d vector was, in most cases, capable of expressing recombinant proteins at higher levels than the pTrc99A vector, the two mite group II cDNAs were subcloned as $H_6$ fusion proteins into T7 vector. pTrc ppA $His_6$ f II RRS and pTrc99A $His_6$ p II RRS were NcoI/NheI digested, the cDNA inserts isolated, and subcloned into NcoI/NheI digested pET11d $His_6$ p1 (FIG. 33). Recombinant plasmids were transformed into BL 21 [DE3] bacteria for expression.

BL21 DE3 host bacteria harboring the pET11d mite allergen expression constructs were freshly streaked onto a BHI agar plate (3.7% wt./vol. Difco Brain Heart Infusion; 1.5% wt./vol. Difco agar) supplemented with 200 μg/ml ampicillin and incubated overnight at 37° C. A single colony was innoculated into a 2 ml of 200 μg/ml ampicillin/BH1 media (3.7% wt./vol. Difco Brain Heart Infusion) and shaken at 300 rpm at 37° C. until turbid but not saturated. The 2 ml culture was then added to 100 ml of 200 μg/ml ampicillin/BH1 media, shaken at 300 rpm at 37° C. until turbid but not saturated, at which point the culture was divided into 18×500 ml (9 litres) of 200 μg/ml ampicillin/BH1 media and shaken at 300 rpm at 37° C. When the $OD_{595}$ of the culture reached 1.0, expression of the recombinant molecules was induced by the addition of IPTG to 400 μM, and allowed to continue for two hours.

Bacteria were harvested by centrifugation at 10,000× g for 15 minutes, and resuspended in $\frac{1}{20}^{th}$ volume of lysis buffer (0.2 mg/ml lysozyme, 100 mM $NaPO_4$ pH 8.0, 50 mM NaCl), incubated on ice for 30 minutes, and frozen at −70° C. The frozen bacteria were fractured by a quick thaw at 37° C. and then sonicated 5 times for 20 seconds at 30 second intervals. The sonicated samples were centrifuged at 15,000× g to separate soluble and particulate bacterial proteins. The soluble proteins were poured off, and the pelleted protein resuspended in 6 M guanidine HCl, 100 mM 2-mercaptoethanol, 100 mM $NaPO_4$, 10 mM Tris pH 8.0. This suspension was subjected to centrifugation at 15,000× g, and the supernatant removed, adjusted to pH 8.0 with 10 N NaOH, and applied to an NTA agarose column that had been equilibrated in 6 M guanidine HCl, 100 mM $NaPO_4$, 10 mM Tris pH 8.0. The column was washed in 6 M guanidine HCl, 100 mM $NaPO_4$, 10 mM Tris pH 8.0 until the $OD_{280}$ of the effluent reached background. The column buffer was then switched to 8 M urea, 100 mM $NaPO_4$, 10 mM Tris pH 8.0. After equilibration, a more stringent wash was performed in 8 M urea, 100 mM NaOAc, 10 mM Tris pH 6.3 until the $OD_{280}$ of the effluent reached background. Recombinant mite protein (as an $H_6$ fusion) was then eluted in 8 M urea, 100 mM NaOAc, 10 mM Tris pH 4.5 and collected in aliquots whose $OD_{280}$ profile was monitored. The protein peak was dialyzed 3 times into 500 volumes of PBS for human T-cell analysis. Yield ranged from 10 to 70 mg of recombinant protein per liter with purity (as determined by densitometric scanning) ranging from 80 (Der f II) to 95%.

To further purify the recombinant Der f II protein allergen, Reverse Phase HPLC chromatography was applied. Approximately 100 mg of $His_6$-Der f II protein was reduced in 20 mM DTT at 36° C. for 30 minutes and then applied to a Pharmacia PRO RPC HR 10/10 column in 0.1% vol./vol. $TFA/H_2O$. The flow rate for the column was 1.5 ml/min. with a gradient of 0–70% acetonitrile in 0.1% TFA over 40 minutes, followed by a gradient of 70–100% acetonitrile in 0.1% TFA. $His_6$-Der f II protein eluted between 54–96% acetonitrile. Fractions detected at 214 nm and 280 nm were analyzed for purity by SDS-polyacrylamide gel electrophoresis/densitometric scanning. Those fractions with $His_6$-Der f II protein of purity greater than 95% were subsequently utilized for human T-ell mapping of the allergen. Yield from the preparative Reverse Phase HPLC was approximately 69%.

Determination of Nucleotide Sequence Polymorphisms in the Der p I, Der p II and Der f II Allergens It was expected that there were sequence polymorphisms in the nucleic acid sequence coding for Der p I, Der p II, Der f I and Der f_II, due to natural allelic variation among individual mites. Several nucleotide and resulting amino acid sequence polymorphisms have been discovered during the sequencing of different Der p I_Der p II and Der f II clones. The amino acid sequence polymorphisms are shown in FIGS. 22, 23 and 24.

EXAMPLE III

Synthesis of Overlapping Peptides

Der p I, Der f I, Der p II, and Der f II overlapping peptides as shown in FIGS. 3 and 4 were synthesized using standard Fmoc/tBoc synthetic chemistry and purified by dialysis or Reverse Phase HPLC. The amino acid residues of the synthesized peptides are in brackets by the peptide name and the amino acid sequence (in single letter code) is next to the peptide name. The peptide names are consistent throughout the Figures. The Der p I, Der f I, Der p II and Der f II proteins were divided into overlapping peptides in such a way that the overlapping peptides of Der p I and Der f I as well as for Der p II and Der f II have corresponding amino acid residue numbers, e.g. DP I-1 and DF I-1 both contain amino acid residues I-20 of the Der p I and Der f I allergens, respectively. This correspondence in amino acid position between the Der p and Der f peptides was done purposefully in order to best test for cross-reactivity of Der p and Der f T cell epitopes and, thus, determine peptides which, upon administration to an individual sensitive to dust mite, would treat sensitivity to both Der p and Der f allergens. In the design of the overlapping peptides the relationship of the Group I and Group II allergens at the level of T cell cross-reactivity was considered. In addition, the function of the Group I allergens as serine proteases was considered and the amino acid sequences of other known serine proteases, e.g., papain, actinidin, were examined to identify similar conserved and variable regions within the Group I allergens. It was expected that conserved regions within the Group I allergens would contain "shared" T cell epitopes.

EXAMPLE IV

Mite Allergic Patient Primary T Cell Responses to Der p I and Der p II Proteins and Peptides Peripheral blood mononuclear cells (PBMC) were purified by Ficoll-Hypaque centrifugation of a peripheral blood specimen from mite-allergic patient R.B. and were assayed for proliferation in response to various antigens, i.e., affinity-purified Der p I, affinity purified Der p II, various Der p I and Der p II peptides. For assay, $5 \times 10^4$ PBMC were cultured in triplicate microwells for 7 days at 37° C. in the presence of various concentrations of antigen in 200 μl RPMI-1640 containing 5% human AB serum. Each well then received 1 μCi tritiated thymidine for 16 hours. The counts incorporated were collected onto glass fiber filters and processed for liquid scintillation counting. Table I shows the results of this assay. The CPM +/− standard deviation are shown. The stimulation index of each response (S.I.) is the ratio of the $^3$H-thymidine CPM incorporated by the cells in response to antigen divided by the $^3$H-thymidine CPM incorporated by cells in medium only. The results indicate that this patient responds with an S.I. of at least 2.0 to peptides DP I-1, DP I-3, DP I-8, DP I-10, DP I-5.2, DP II-4 and DP II-9. Thus, these peptides contain Der p I or Der p II T cell epitopes recognized by T cells from this particular allergic patient.

TABLE I

| Antigen | Concentration μg/ml | CPM ± S.D. | S.I. |
|---|---|---|---|
| Medium | — | 1071 ± 30 | — |
| Der p I | 10 | 920 ± 15 | 0.9 |
|  | 30 | 2122 ± 93 | 2.0 |
|  | 100 | 1492 ± 13 | 1.4 |
| DP I-1 | 10 | 1099 ± 48 | 1.0 |
|  | 30 | 3527 ± 73 | 3.3 |
|  | 100 | 2746 ± 81 | 2.6 |
| DP I-2 | 10 | 1395 ± 47 | 1.3 |
|  | 30 | 1283 ± 34 | 1.5 |
|  | 100 | 1486 ± 38 | 1.4 |
| DP I-3 | 10 | 2608 ± 52 | 2.4 |
|  | 30 | 1561 ± 13 | 1.5 |
|  | 100 | 5252 ± 67 | 4.9 |
| DP I-8 | 10 | 1439 ± 32 | 1.3 |
|  | 30 | 1045 ± 32 | 1.0 |
|  | 100 | 2272 ± 40 | 2.1 |
| DP I-10 | 10 | 1936 ± 50 | 1.8 |
|  | 30 | 3042 ± 89 | 2.8 |
|  | 100 | 2644 ± 63 | 2.5 |
| DP I-5.2 | 10 | 1374 ± 20 | 1.3 |
|  | 30 | 2241 ± 87 | 2.1 |
|  | 100 | 3132 ± 111 | 2.9 |
| Der p II | 10 | 1113 ± 35 | 1.0 |
|  | 30 | 2104 ± 43 | 2.0 |
|  | 100 | 1057 ± 27 | 1.0 |
| DP II-4 | 10 | 2126 ± 25 | 2.0 |
|  | 30 | 1979 ± 94 | 1.8 |
|  | 100 | 2314 ± 116 | 2.2 |
| DP II-9 | 10 | 3970 ± 87 | 3.7 |
|  | 30 | 4464 ± 86 | 4.2 |
|  | 100 | 2237 ± 53 | 2.1 |

EXAMPLE V

T Cell Epitope Studies with Der p I

Peripheral blood mononuclear cells (PBMC) were purified by Ficoll-Hypaque centrifugation of 60 ml of heparinized peripheral blood from house dust mite-allergic individuals who exhibited clinical symptoms of mite allergy and who were skin test positive for house dust mite.

$10^7$ PBMC from individual 543 were cultured in 10 ml RPMI-1640 containing 5% pooled human AB serum and supplemented with glutamine, penicillin, streptomycin and HEPES buffer in the presence of 20 μg/ml purified native Der p I/ml at 37° C. for 7 days. Viable cells were then purified by Ficoll-Hypaque centrifugation and cultured for 2 additional weeks in RPMI-1640/5% AB serum containing 5 units recombinant human IL-2/ml and 5 units recombinant human IL-4/ml. The resting T cells were then tested in a secondary proliferation assay to assess T cell responses to various house dust mite proteins and peptides. For assay, $2 \times 10^4$ resting T cells were cultured in 200 μl of RPMI-1640/ 5% AB serum for 3 days at 37° C. in the presence of $2 \times 10^4$ autologous Epstein-Barr virus transformed B cells (20,000 Rads) as antigen presenting cells with various concentrations of purified native Der p I or synthetic Der p I peptides. Each well then received 1 μCi tritiated thymidine for 16 hours. The counts incorporated were collected onto glass fiber filters and processed for liquid scintillation counting. Medium alone, acting as negative control, contained no allergen or peptide. The results of this experiment indicate that this particular patient responds with an S.I. of at least 2.0 to several peptides derived from the Der p I protein, including DP I-1, DP I-2, DP I-4, DP I-11, DP I-5, DP I-13, DP I-15, DP I-6.1, DP I-8, DP I-9, DP I-16, DP I-10 and DP I-17 (data not shown).

The above procedure was followed with a number of other house dust mite allergic individuals except a) in individual cases, the length of time of cultivation with IL-2 and IL-4 varied; b) in individual cases, the T cells were primed with either purified native (N) or recombinant (R) Der p I protein at either 20 μg/ml or 10 μg/ml; and c) in individual cases, x-irradiated (3500 Rads) autologous PBMC were used as antigen presenting cells in the secondary proliferation assay. In addition, three peptides (DP I-11 (SEQ ID NO: 117), DP I-12 (SEQ ID NO: 118), and DP II-3 (SEQ ID NO: 119)) were found to contain a low number of conservative changes from the native sequence in their amino acid sequence. Three additional peptides (DP I-11.1 (SEQ ID NO: 13), DP I-12.1 (SEQ ID NO: 14) and DP II-3.1 (SEQ ID NO: 43) were synthesized with no changes from the native sequence. Some T cell analysis was done with the original peptides (i.e., DP I-11, DP I-12 and DP II-3). Following T cell analysis conducted with the additional peptides (i.e., DP I-11.1, DP I-12.1 and DP II-3.1) no significant difference in mean S.I. or percentage of positive responses between the original peptides and the additional peptides was detected. Thus, the data from both groups of peptides was pooled.

Individual results were considered positive and used if the individual responded to the Der p I protein and at least one peptide derived from Der p I at an S.I. of 2.0 or greater. A summary of the results of 33 positive experiments is shown in FIG. 37. The resting T cell lines primed with recombinant or native Der p I-stimulated PBMC were tested for reactivity to synthetic Der p I peptides. The maximum response for each peptide in a titration of the antigen is expressed as the T cell stimulation index (S.I.). The S.I. is the counts-per-minute (CPM) incorporated by cells in response to the peptide divided by the CPM incorporated by cells in medium only. An S.I. value greater than the background level indicates that the peptide contains a T cell epitope. However, only individual S.I. values greater than or equal to 2.0 (a response two-fold or greater over background), referred to herein as "positive" results, were used in calculating mean T cell stimulation indices for each peptide for the patient or group of patients tested. In parentheses above each bar on the histogram are the mean T cell stimulation indices calculated after discarding the highest and lowest positive responses for each peptide to minimize the effect of extreme outliers. The T cell stimulation index is calculated by:

$$\frac{(\text{CPM of T cell} + \text{APC} + \text{Antigen})}{\text{CPM of T cell} + \text{APC} + \text{Control}}$$

The bar represents the cumulative rank of the peptide response in the group of patients. To determine the cumulative rank, the 5 peptides with the highest S.I. in each individual were determined and assigned a numerical rank in descending order, with 5 representing the strongest response. The ranks for each peptide were then summed in the group of patients to determine the cumulative rank for the peptide. Above each bar is the percent of positive responses with an S.I. of at least 2 to the peptide in the group of patients tested. Given the percent positive and the mean T cell stimulation index, the positivity index (P.I.) for each peptide can be calculated. The P.I. for each individual is determined by multiplying the mean S.I. by the percent of individuals, in a population of individuals sensitive to house dust mite (e.g. preferably at least 15 individuals, more preferably at least 30 individuals or more) who responded with an S.I. of at least 2.0 to that peptide (e.g., for DP I-1 in FIG. 37, the P.I. would be about 343 (73%×4.7). The P.I. therefore represents both the strength of a T cell response to a peptide (S.I.) and the frequency of a T cell response to a peptide in a population of individuals sensitive to house dust mite. FIG. 37 demonstrates that peptides DP I-1, DP I-2, DP I-3, DP I-4, DP I-5, DP I-6.1, DP I-7.1, DP I-8, DP I-9, DP I-16, and DP I-10 contain significant regions of T cell reactivity in this panel of patients.

EXAMPLE VI

T Cell Epitope Studies with Der f I

Experiments similar to those of Example V were performed to determine. the T cell-reactive areas of the Der f I protein. For example, PBMC from house dust mite-allergic patient 783 were isolated as described in Example V and were stimulated in vitro with recombinant purified Der f I at 20 µg/ml. The results of the proliferation assay with Der f I peptides using x-irradiated (3500 Rads) autologous PBMC as antigen presenting cells indicate that T cells from this patient respond to the peptides DF I-8.1, DF I-9, DF I-6, DF I-10, DF I-2.1, DF I-3, DF I-11, DF I-5, DF I-1, and DF I-17 (data not shown).

Figure 6:
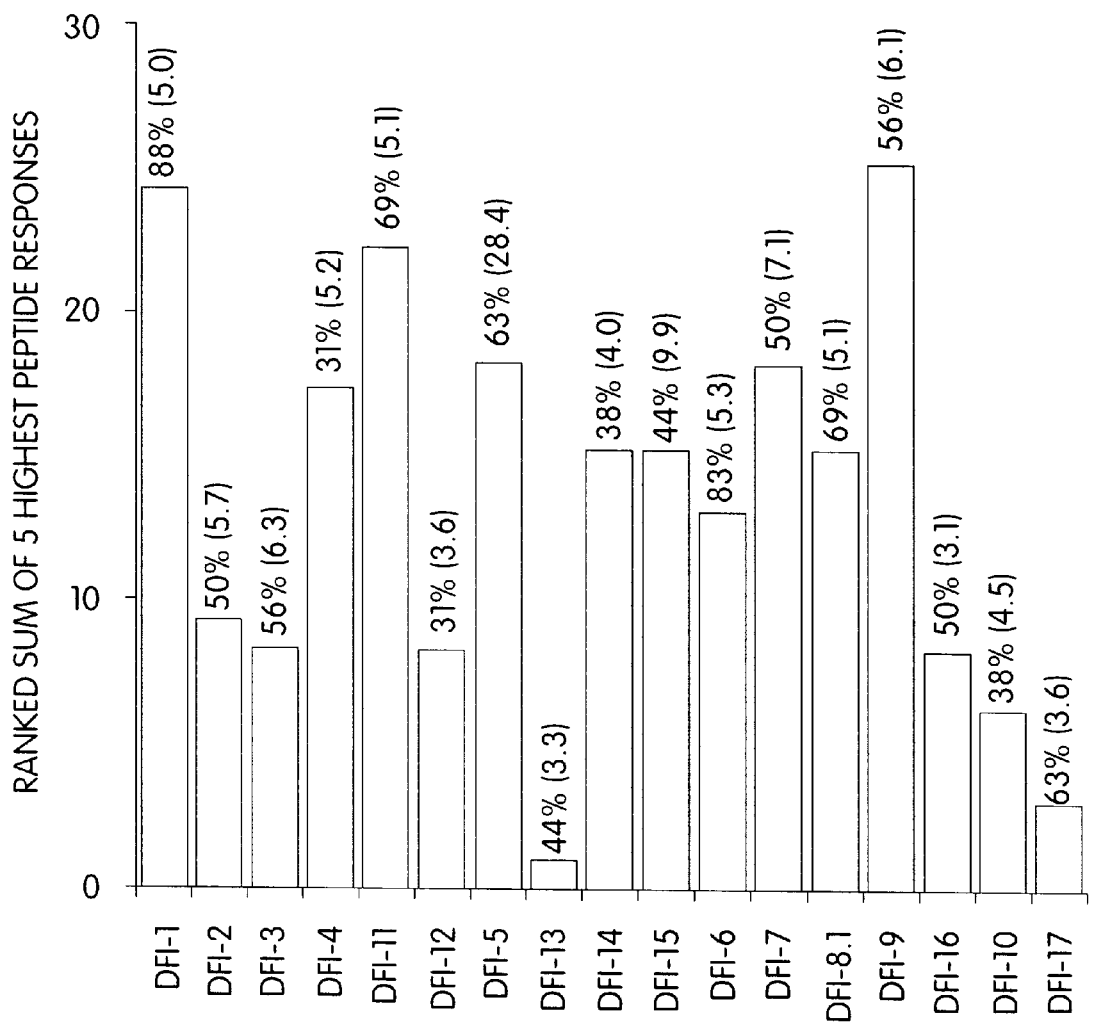
FIG. 6 is a graphic representation depicting the responses of T cell lines from 16 patients primed in to the Der f I protein and analyzed for response to various overlapping Der f I peptides by percent of responses with an (S.I.) of at least 2 within the individuals tested, the mean T cell stimulation index of positive responses for the peptide and the ranked sum of peptide responses.

The above procedure was followed in a number of patients except in individual cases, T cell lines were primed with affinity purified Der f I at 20 µg/ml or at 10 µg/ml and x-irradiated (25,000 Rads) autologous Epstein-Barr virus transformed B cells were used as antigen presenting cells. A summary of the results of 16 positive experiments is shown in FIG. 6. The data was analyzed as described in Example V. The data indicate that significant areas of T cell reactivity in the Der f I protein are found in the peptides DF I-1, DF I-2, DF I-3, DF I-4, DF I-11, DF I-5, DF I-6, DF I-7, DF I-14, DF I-5, DF I-8.1 and DF I-9.

EXAMPLE VII

A Study Indicating the Cross-reactivity of Der p I and Der f I T Cell Epitopes

Figure 7:
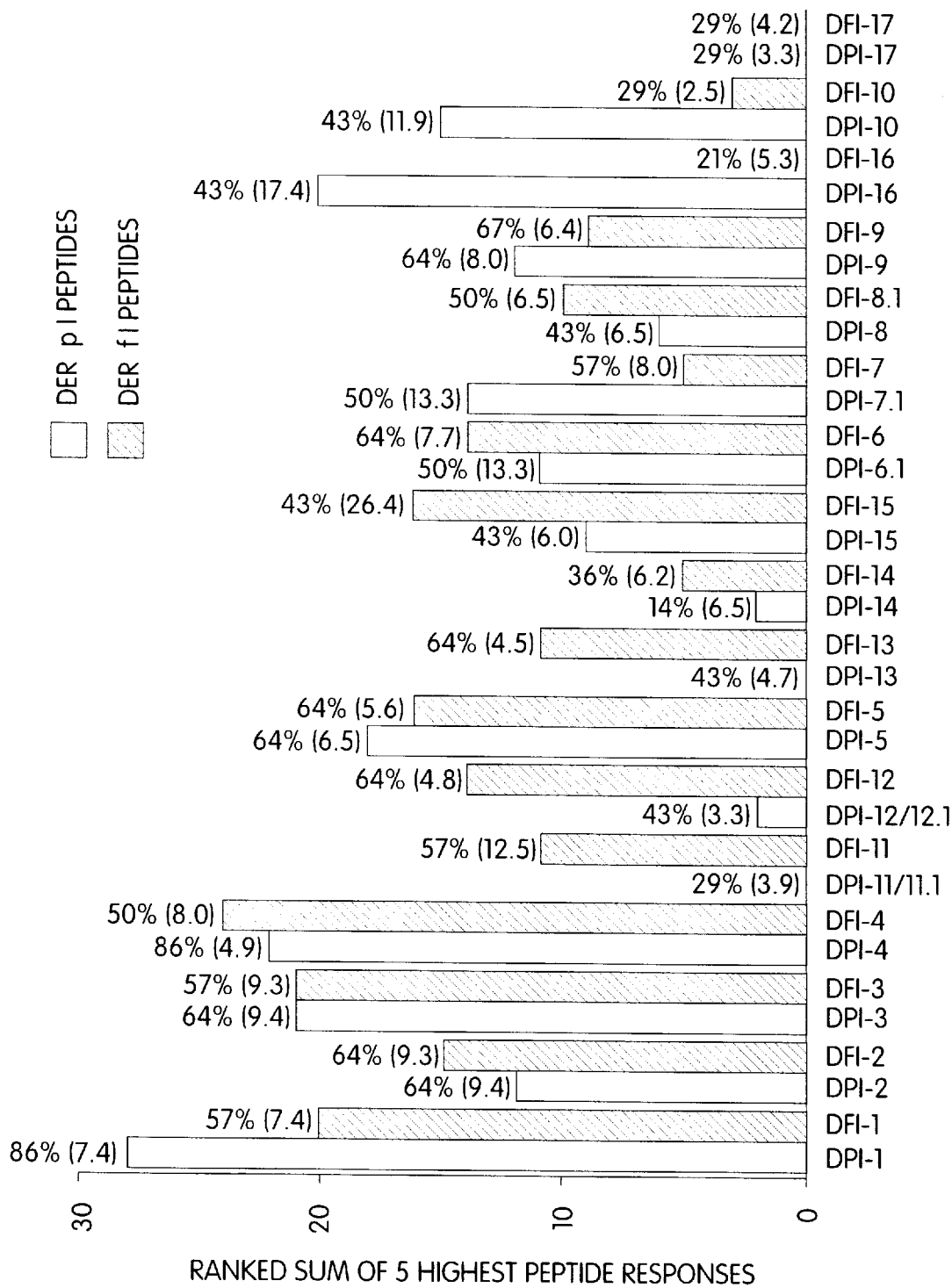
FIG. 7 is a graphic representation depicting the responses of T cell lines from 14 patients primed in vitro to the Der p I protein and analyzed for response to various overlapping Der p I peptides and substantially matching Der f I peptides by percent of responses with an S.I. of at least 2 within the individuals tested, the mean T cell stimulation index of positive responses for the peptide and the ranked sum of peptide responses.
Figure 8:
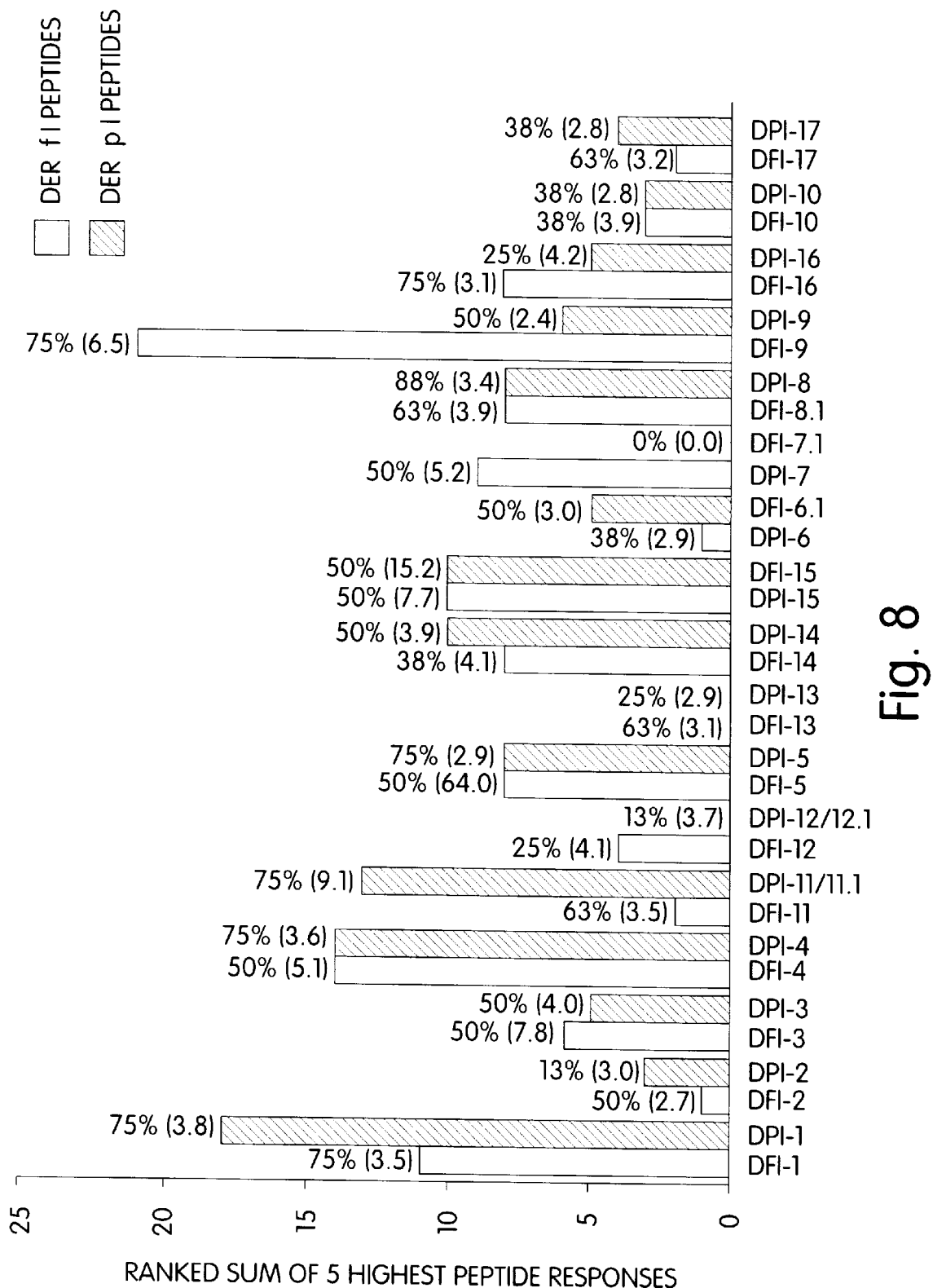
FIG. 8 is a graphic representation depicting the responses of T cell lines from 8 patients primed in vitro to the Der f I protein and analyzed for response to various overlapping Der f I peptides and substantially matching Der p I peptides by percent of responses with an S.I. of at least 2 within the individuals tested, the mean T cell stimulation index of positive responses for the peptide and the ranked sum of peptide responses.

The Der p I and Der f I proteins are very homologous (81% identity). Thus, experiments, similar to those of Example V, were carried out to determine the T cell responses of Der p I primed T cell lines when challenged with various Der p I peptides and substantially matching Der f II peptides. T cell lines were primed in vitro as described in Example V and tested for response to a set of substantially matching Der p I and Der f I peptides (e.g., DP I-1 (amino acid residues 1–20 of Der p I) or DF I-1 (amino acid residues 1–20 of Der f I). The data was analyzed as described in Example V except the highest and lowest S.I. values of the positive responses to each peptide were not omitted from the mean S.I. calculations. A summary of a number of such experiments is shown in FIG. 7. The results of 14 positive experiments indicate that Der p I-primed T cells respond to various Der f I peptides indicating cross-reactivity within the Group I allergens. Der p I primed T cells respond significantly to peptides DF I-1, DF I-2, DF I-3, DF I-4, DF I-11, DF I-12, DF I-15, DF I-8, DF I-9, DF I-15 and DF I-6. In some patients, the Der f I peptide was a more potent stimulator of Der p I-primed T cells than the corresponding Der p I peptide. FIG. 8 shows the results of inverse experiments in which T cells from a number of patients were primed in vitro to the Der f I protein and analyzed for response to various Der p I peptides and a set of substantially matching Der f I peptides. The results of 8 positive experiments indicate that Der f I primed T cells respond significantly to peptides DP I-1, DP I-3, DP I-4, DP I-11/11.1, DP I-14, DP I-5, DP I-15, and DP I-8.

EXAMPLE VIII

T Cell Epitope Studies with Der p II

Experiments similar to those of Example V were performed to determine the T cell-reactive areas of the Der p II protein. For example, PBMC from house dust mite-allergic patient 348 were isolated as described in Example V and were stimulated in vitro with 20 µg/ml purified native Der p II. The results of a proliferation assay using x-irradiated (25,000 Rads) Epstein-Barr virus transformed autologous B cells as antigen-presenting cells with various Der p II peptides demonstrate that this particular patient responds well to peptides DP II-1, DP II-7, DP II-8, DP II-2, and DP II-9 (data not shown).

Figure 9:
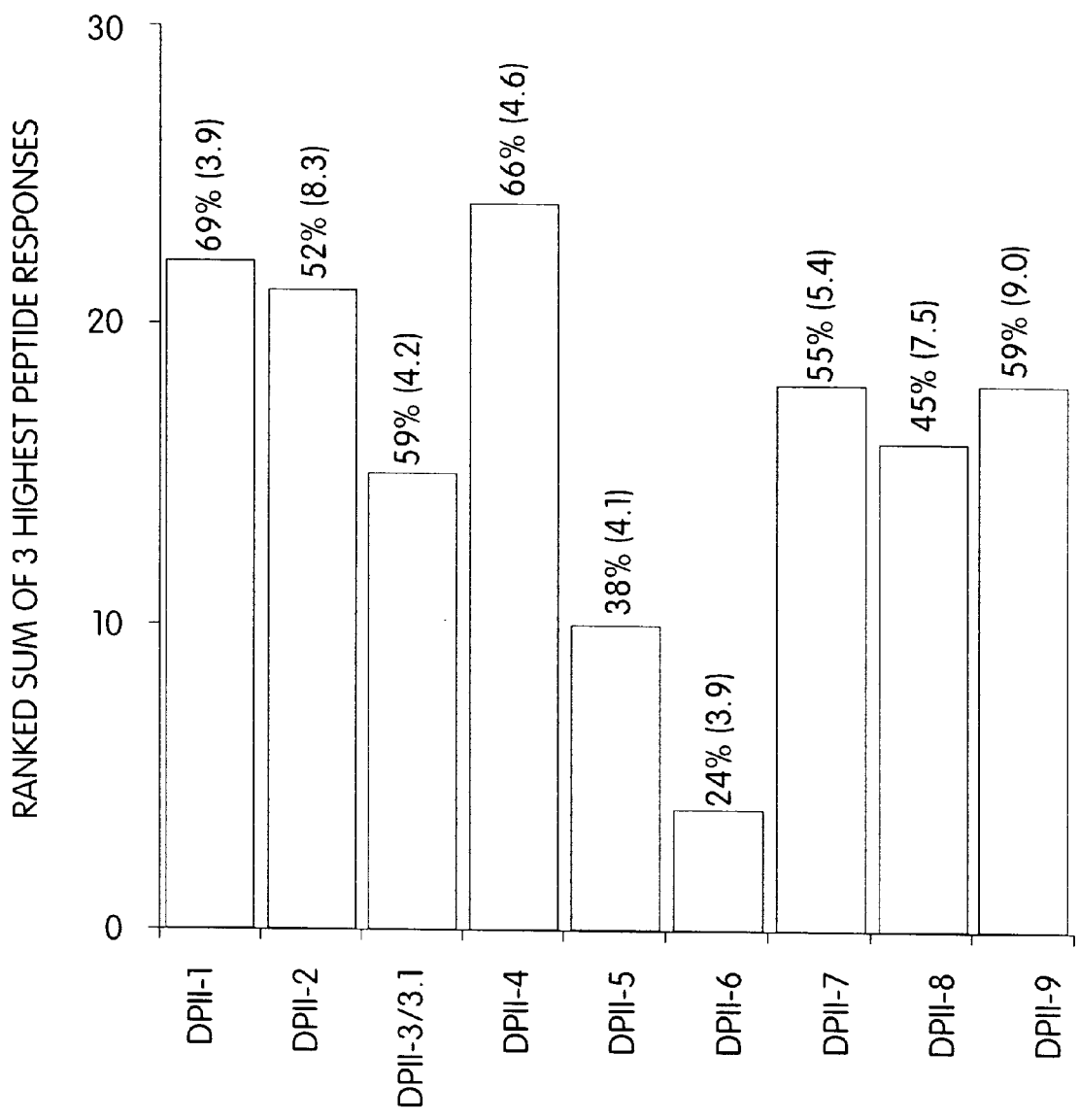
FIG. 9 is a graphic representation depicting the responses of T cell lines from 29 patients primed in vitro to the Der p II protein and analyzed for response to various overlapping Der p II peptides by percent of responses with an S.I. of at least 2 within the individuals tested, the mean T cell stimulation index of positive responses for the peptide and the ranked sum of peptide responses.

The above procedure was followed with a number of patients except in individual cases, T cell lines were primed with recombinant Der p II at 20 µg/ml or at 3 µg/ml and x-irradiated (3500 Rads) autologous PBMC were used as antigen-presenting cells. A summary of the results of 26 positive experiments is shown in FIG. 9. The data was analyzed as described in Example V, except the ranked sum of peptide responses was analyzed assigning a value of 3, 2 or 1 to the three highest S.I. responses. Areas of significant T cell reactivity within the Der p II protein for this panel of patients are found in peptides DP II-1, DP II-2, DP II-3, DP II-4, DP II-7, DP II-8 and DP II-9.

EXAMPLE IX

T Cell Epitope Studies with Der f II

Experiments similar to those of Example V were performed to determine the T cell-reactive areas of the Der f II protein. For example, PBMC from house dust mite-allergic patient 384 were stimulated in vitro with purified recombinant Der f II and the T cell line was then challenged in the presence of x-irradiated (25,000 Rads) autologous Epstein-Barr virus transformed B cells as antigen presenting cells with various overlapping Der f II peptides. The results of this proliferation assay indicate that T cells from this particular patient respond well to peptides DF II-1, DF II-2, DF II-3.1, DF II-4.5, DF II-15, DF II-16, and DF I-19.1 (data not shown).

Figure 10:
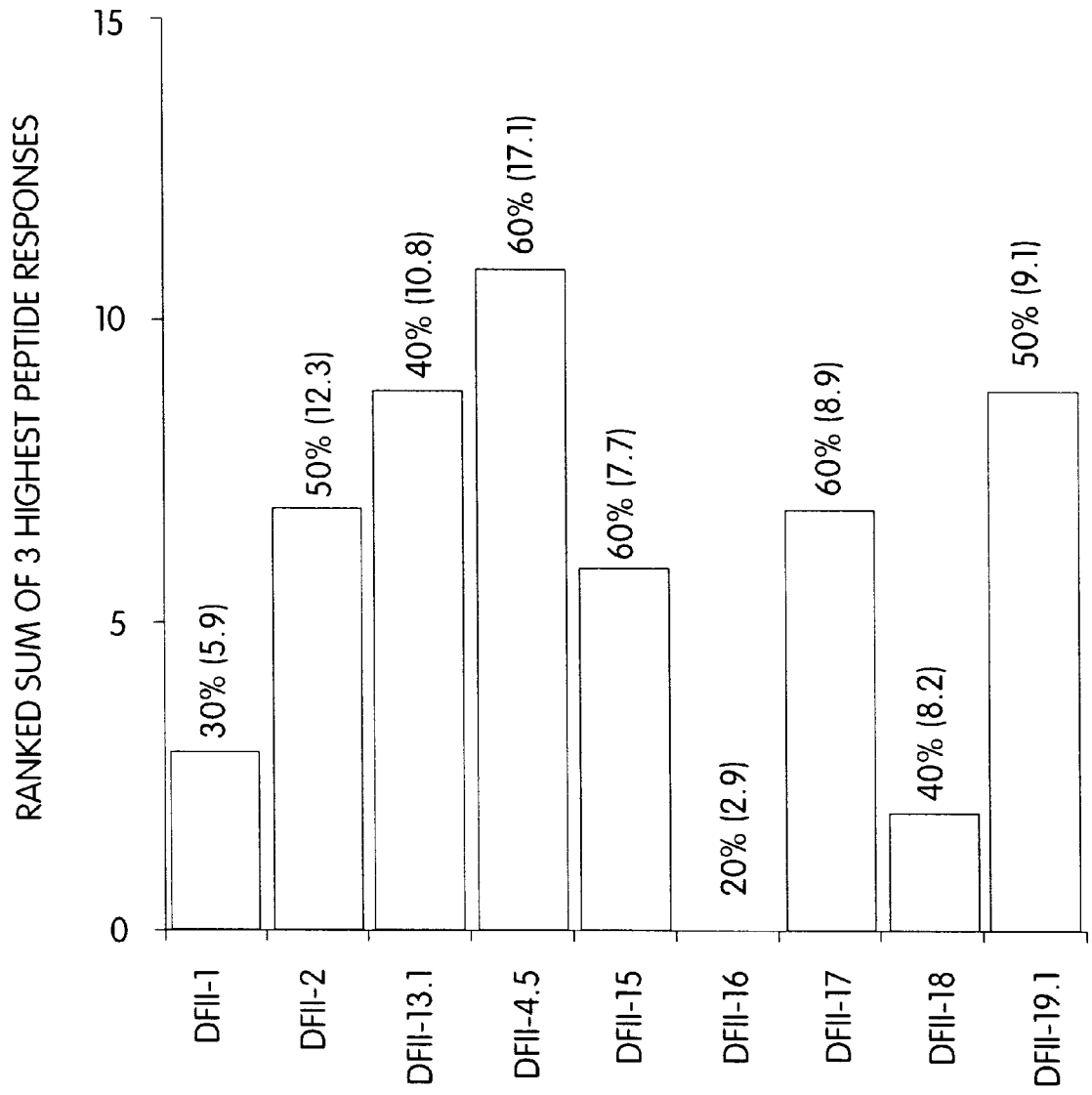
FIG. 10 is a graphic representation depicting the responses of T cell lines from 10 patients primed in vitro to the Der f II protein and analyzed for response to various overlapping Der f II peptides by percent of responses with an S.I. of at least 2 within the individuals tested, the mean T cell stimulation index of positive responses for the peptide and the ranked sum of peptide responses.

The above procedure was followed with 10 patients, except in individual cases, T cell lines were primed by stimulating the patient PBMC with 20 µg/ml or 3 µg/ml purified native Der f II, and were assayed in the presence of x-irradiated (3500 Rads) autologous PBMC as antigen-presenting cells. A summary of the results of 10 positive experiments is shown in FIG. 10. The data was analyzed as detailed in Example IX, except the highest and lowest S.I. values of the positive responses to each peptide were not omitted from the calculations. The data indicate that significant areas of T cell reactivity within the Der f II protein are found in peptides DF II-1, DF II-2, DF II-13.1, DF II-4.5, DF II-15, DF II-17, and DF II-19.1.

EXAMPLE X

Figure 11:
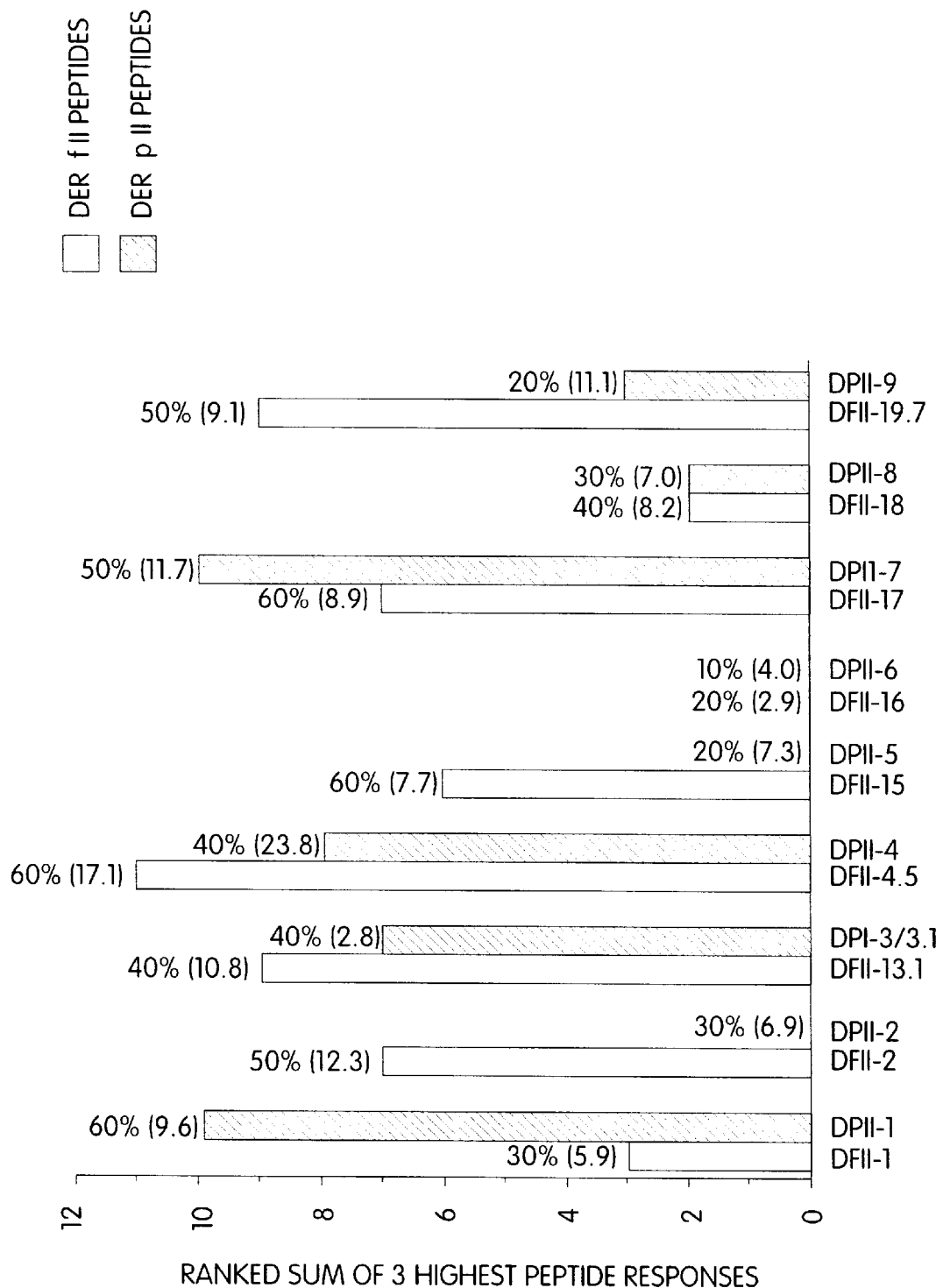
FIG. 11 is a graphic representation depicting the responses of T cell lines from 10 patients primed in vitro to the Der f II protein and analyzed for response to various overlapping Der f II peptides and substantially matching Der p II peptides by percent of responses with an S.I. of at least 2 within the individuals tested, the mean T cell stimulation index of positive responses for the peptide and the ranked sum of peptide responses.
Figure 12:
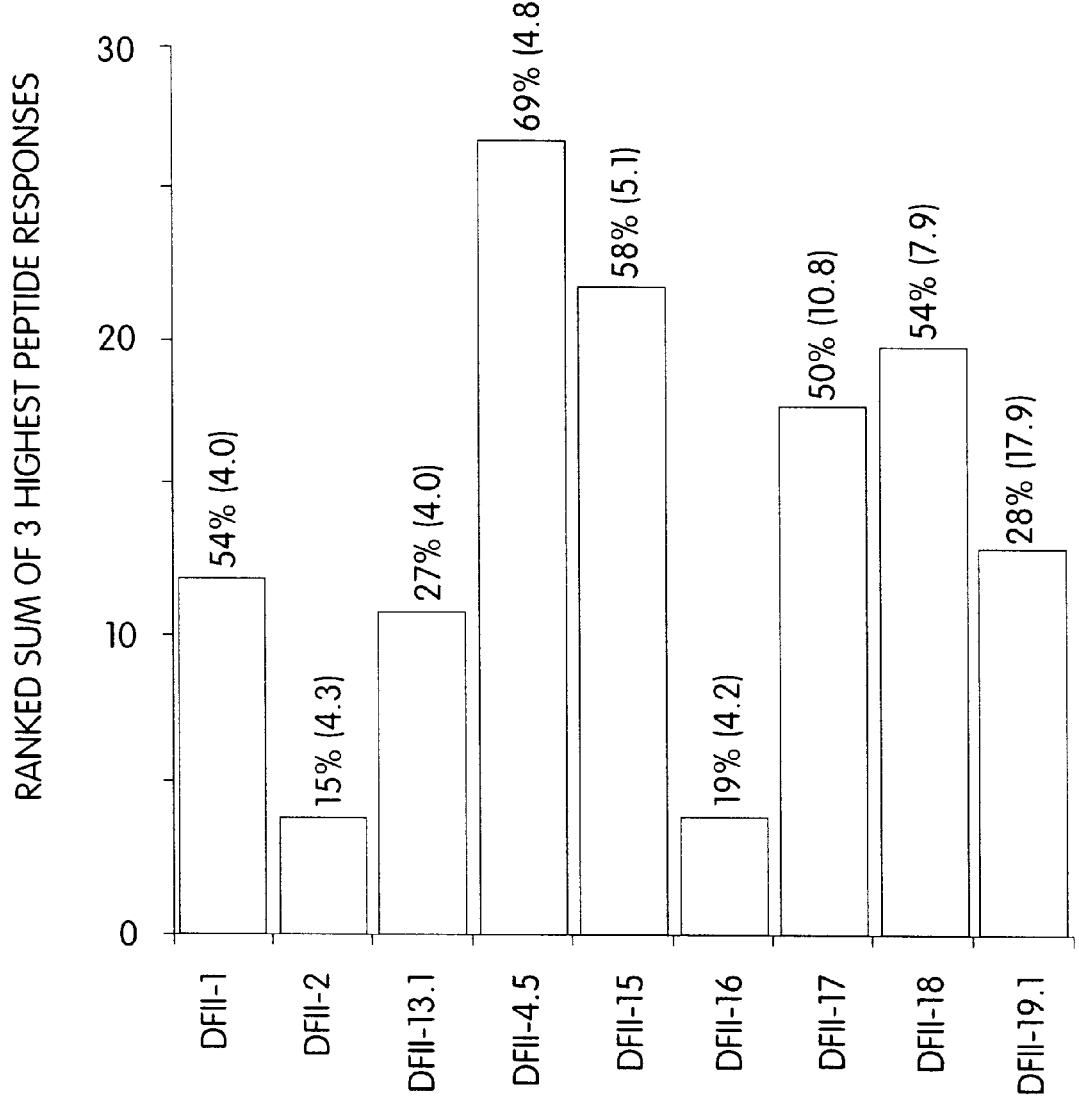
FIG. 12 is a graphic representation depicting the responses of T cell lines from 26 patients primed in vitro to the Der p II protein and analyzed for response to various overlapping Der f II peptides by percent of responses with an S.I. of at least 2 within the individuals tested, the mean T cell stimulation index of positive responses for the peptide and the ranked sum of peptide responses.

A Study Indicating the Cross-Reactivity of Der p II and Der f II T Cell Epitopes A study similar to that described in Example VII was carried out to determine the T cell cross-reactivity of the Der p II and Der f II proteins. T cells primed with the Der f II protein were challenged with various Der f II peptides and a set of substantially matching Der p II peptides. A summary of the results of 10 positive experiments is shown in FIG. 11. The results indicate that Der f II primed T cells respond significantly to peptides DP II-1, DP II-3/3.1, DP II-4, and DP II-7. FIG. 12 shows the results of inverse experiments in which T cells from a number of patients were primed in vitro to the Der p II protein and analyzed for response to various Der f II peptides. The results of 26 positive experiments indicate that Der p II primed T cells respond significantly to peptides DF II-1, DF II-4.5, DF II-15, DF II-17, DF II-18 and DF II-19.1.

EXAMPLE XI

Synthesis of Dominant Peptides

Based on the analyses described in Examples V–X, major areas of T cell reactivity within Der p I, Der p II, Der f I and Der f II were identified. In each study, all of the patients tested responded to the protein allergen (e.g., Der p I) and at least one peptide derived from a major area of T cell reactivity within the protein. Seven regions (Region 1, Region 2, Region 3, Region 4, Region 5, Region 6a and Region 6b) of major T cell reactivity were identified in the Der p I and Der f I proteins. These regions are defined as follows: Region 1, amino acid residues 1–28 of the Der p I and Der f I proteins; Region 2, amino acid residues 36–68 of the Der p I and Der f I proteins; Region 3, amino acid residues 74–109 of the Der p I and Der f I proteins; Region 4, amino acid residues 118–139 of the Der p I and Der f I proteins; Region 5, amino acid residues 141–166 of the Der p I and Der f I proteins; and Region 6a, amino acid residues 161–185 of the Der p I and Der f I proteins and Region 6b, amino acid residues 173–201 of the Der p I and Der f I proteins.

Similarly, four regions of major T cell reactivity (Region 7, Region 8, Region 9, and Region 10) were identified in the Der p II and Der f II proteins. These regions are defined as follows: Region 7, amino acid residues 1–26 of the Der p II and Der f II proteins; Region 8, amino acid residues 33–67 of the Der p II and Der f II proteins; Region 9, amino acid residues 79–104 of the Der p II and Der f II proteins; and Region 10, amino acid residues 107–129 of the Der p II and Der f II proteins. Based in part on the T cell reactivity described in Examples V–X, peptides derived from Der p I, Der f I, Der p II, and Der f I were selected and modified by addition or deletion of amino acid residues at either the 5' or 3' end of the peptide. In designing these selected peptides, various factors were considered, including the ranked sum of the overlapping peptides, the percentage of responses with an S.I. of at least 2.0 to the peptides, the potential cross-reactivity of the peptides, the difficulty of manufacture of the peptides, etc. T cell studies similar to those described in Examples V–X were performed using these selected peptides to more precisely define the major areas of T cell reactivity within Regions I-6a and 6b of the Der p I and Der f I protein and Regions 7–10 of the Der p II and Der f II protein.

The results of T cell studies using selected peptides derived from the Der p I, the Der f I, the Der p II and the Der f II proteins are shown in FIGS. 13–18a–d. The procedure described in Example V was followed with T cell lines from a number of patients primed a vitro to the Der p I protein then analyzed for response to selected peptides derived from the Der p I sequence. The results of 33 positive experiments shown in FIG. 13 indicate that the Der p I primed T cells respond significantly to peptides found in peptides DP I-21.1, DP I-21.2, DP I-22.2, DP I-25.2, DP I-22.1, DP I-23.1, DP I-23.2, DP I-26.1, and DP I-28.1.

Similarly, the procedure described in Example VI was followed with T cell lines from 9 patients primed in vitro to the Der f I protein then analyzed for response to selected peptides derived from the protein. The data was analyzed as described in Example VI. The results of the 9 patients shown in FIG. 14 demonstrate T cell reactivity to selected peptides from Der f I.

Figure 15A:
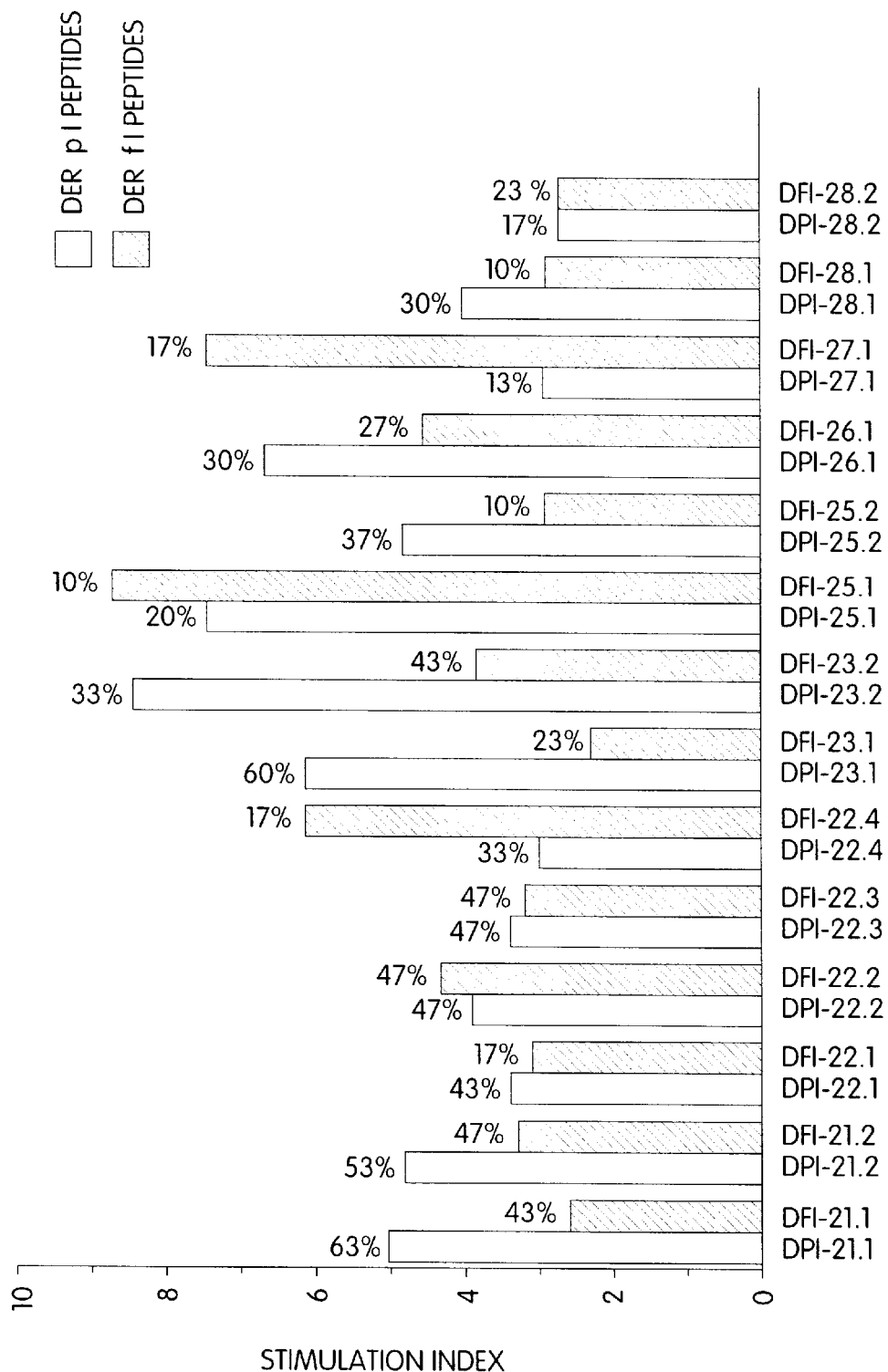
FIG. 15a is a graphic representation depicting the responses of T cell lines from 30 matched patients primed i it to the Der p I protein and analyzed for response to selected peptides of desired lengths derived from the Der p I and the Der f I protein allergens, by percent of responses with an S.I. of at least 2 within the individuals tested and the mean T cell stimulation index of positive responses for the peptide.
Figure 15B:
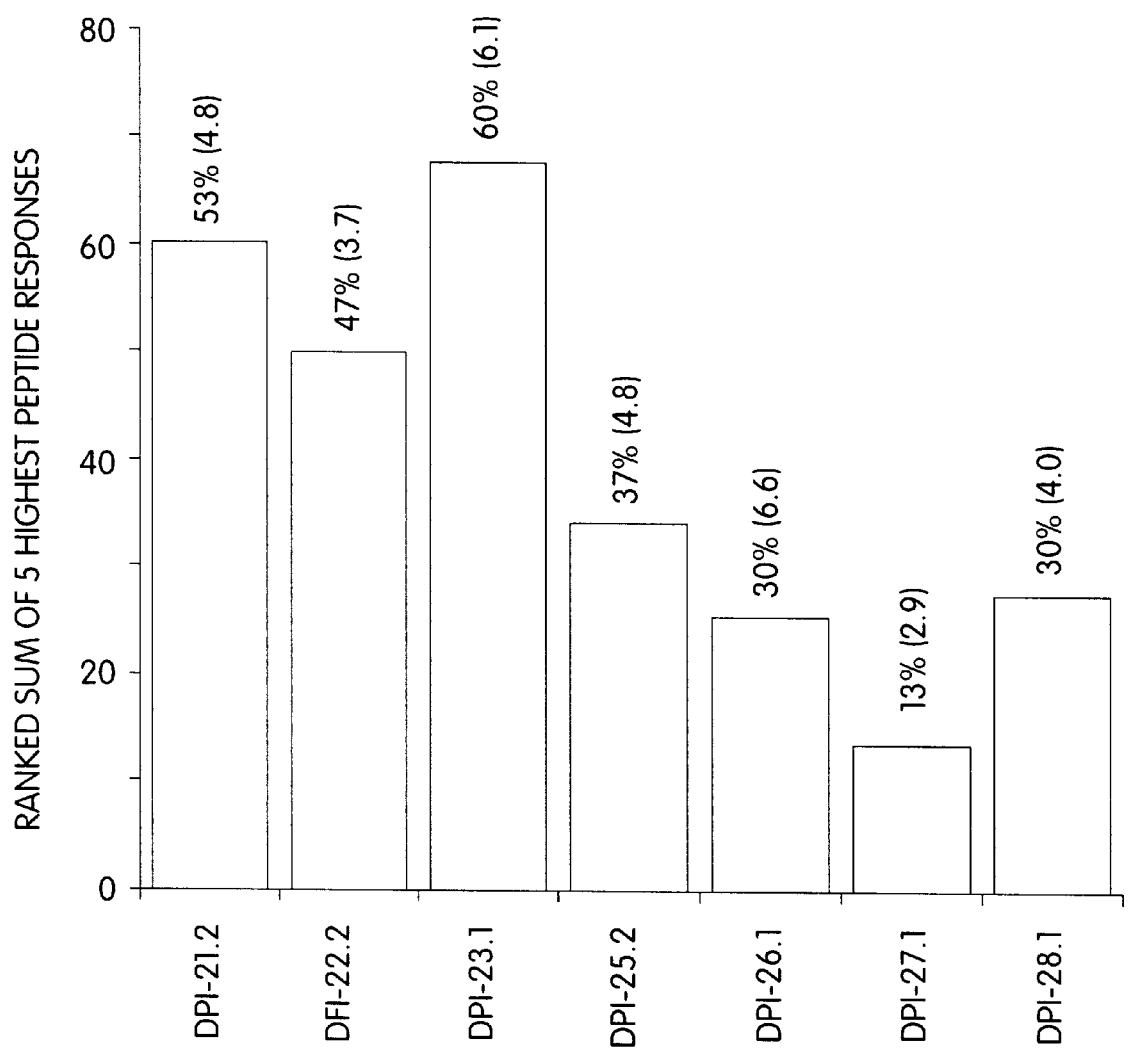
FIG. 15b is a graphic representation derived from the same data shown in FIG. 15a showing the response of Der p I primed T cells to preferred Der p I peptides analyzed by percent of response with an S.I. of at least two within the individuals tested (above each bar), the mean T cell stimulation index (above each bar in parenthesis) and the ranked sum of peptide responses.
Figure 16A:
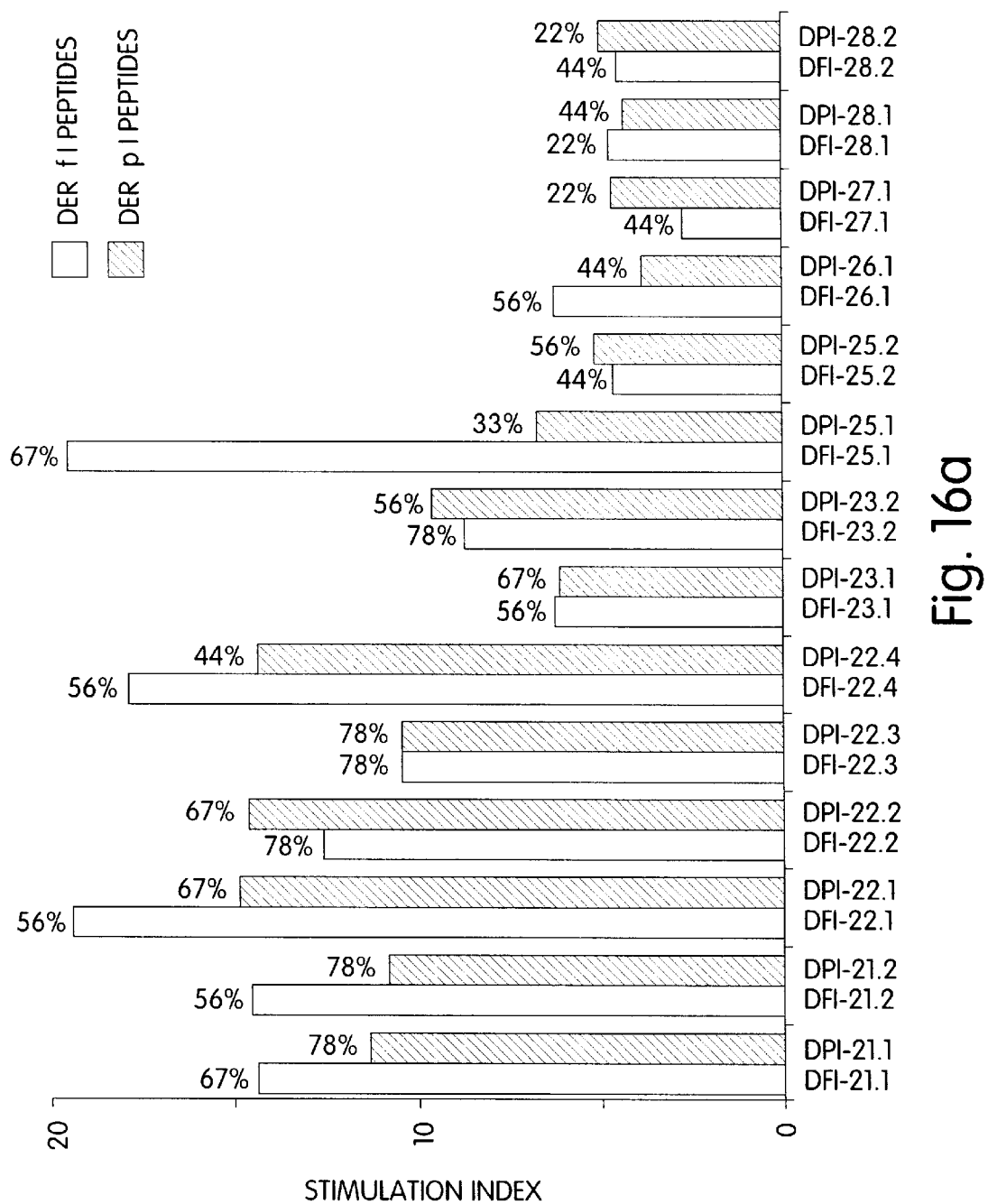
FIG. 16a is a graphic representation depicting the responses of T cell lines from 9 patients primed in vitro to the Der f I protein and analyzed for response to selected peptides of desired lengths derived from the Der f I and Der p I protein allergens, by percent of responses with an S.I. of at least 2 within the individuals tested and the mean T cell stimulation index of responses with an S.I. of at least 2 for the peptide.
Figure 16B:
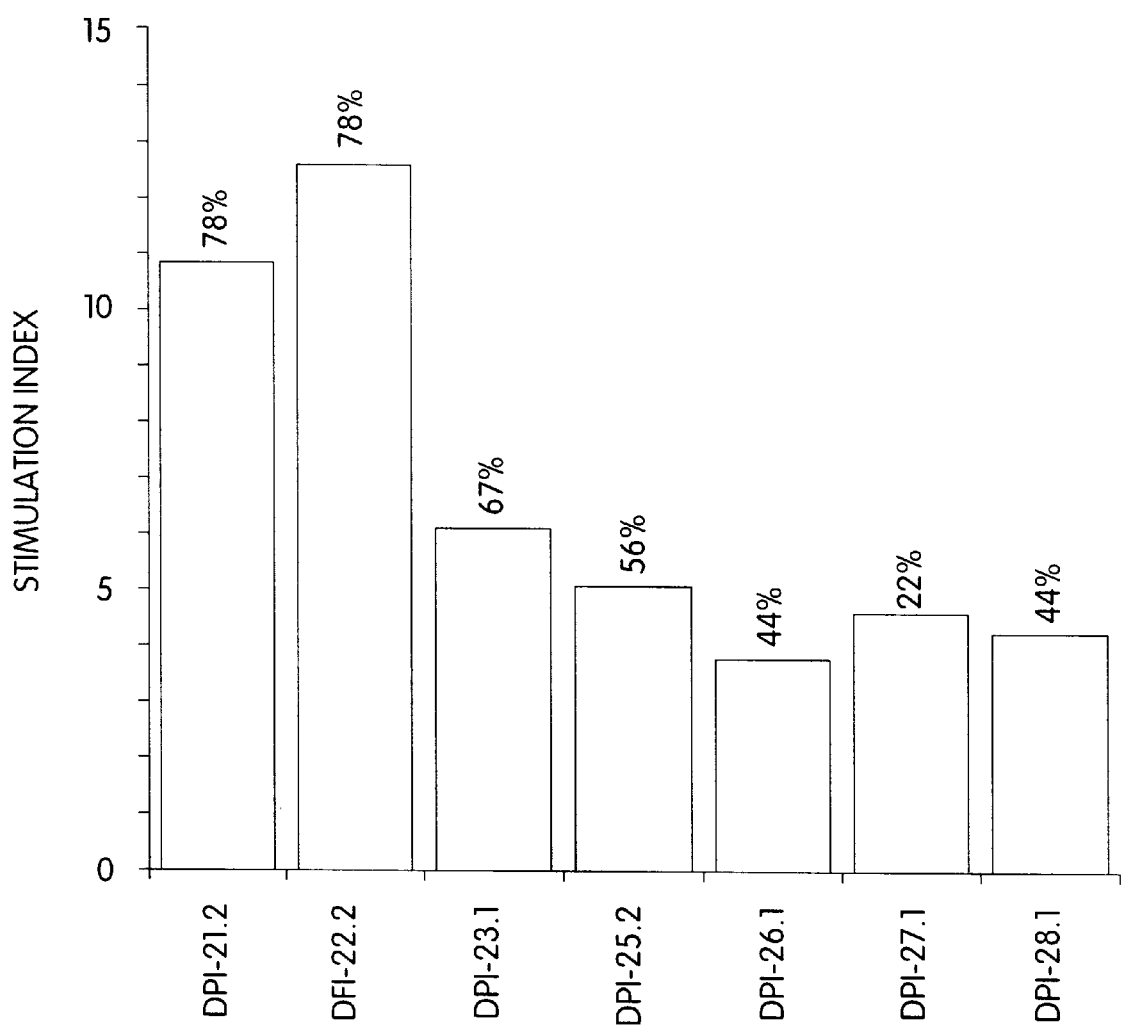
FIG. 16b is a graphic representation derived from the same data shown in FIG. 16a showing the response of Der p I primed T cell lines to preferred Der f I and Der p I peptides by percent of responses with an S.I. of at least 2 within the individuals tested and the mean T cell stimulation index of responses with an S.I. of at least 2 for the peptide.

In another experiment, the T cell lines from a number of patients were primed in vitro to the Der p I protein and analyzed for response to selected peptides derived from the Der p I protein and a set of substantially matching peptides derived from the Der f I protein. The data from 30 positive experiments was analyzed as described in Example V. As shown in FIG. 15a, the Der p I primed T cells respond significantly to peptides DF I-21.1, DF I-21.2, DF I-23.1, DF I-22.2, DF I-22.3, DF I-22.4, DF I-23.2, DF I-25.1, DF I-26.1 and DF I-27.1. FIG. 15b is a subset of the data shown in FIG. 15a and shows the response of Der p I primed T cells to peptides analyzed by ranked sum. FIG. 15b shows that DPI-23.1 has the highest ranked sum of this group of peptides in this study. FIG. 16a shows the results of the inverse experiment in which T cells from 9 patients were primed in vitro to the Der f I protein and challenged with selected Der f I peptides and a set of substantially matching Der p I peptides. The results indicate that Der f I primed T cells from 9 patients respond to selected peptides from Der p I. FIG. 16a shows that DF I-22.1 and DF I-25.1 have the highest stimulation indexes of this group of peptides. FIG. 16b is a subset of the same data as shown in FIG. 16a and shows the response of preferred Der f I and Der p I peptides is shown. FIG. 16b shows that DFI-22.2 has the highest stimulation index of this group of preferred peptides in this experiment.

Figure 17A:
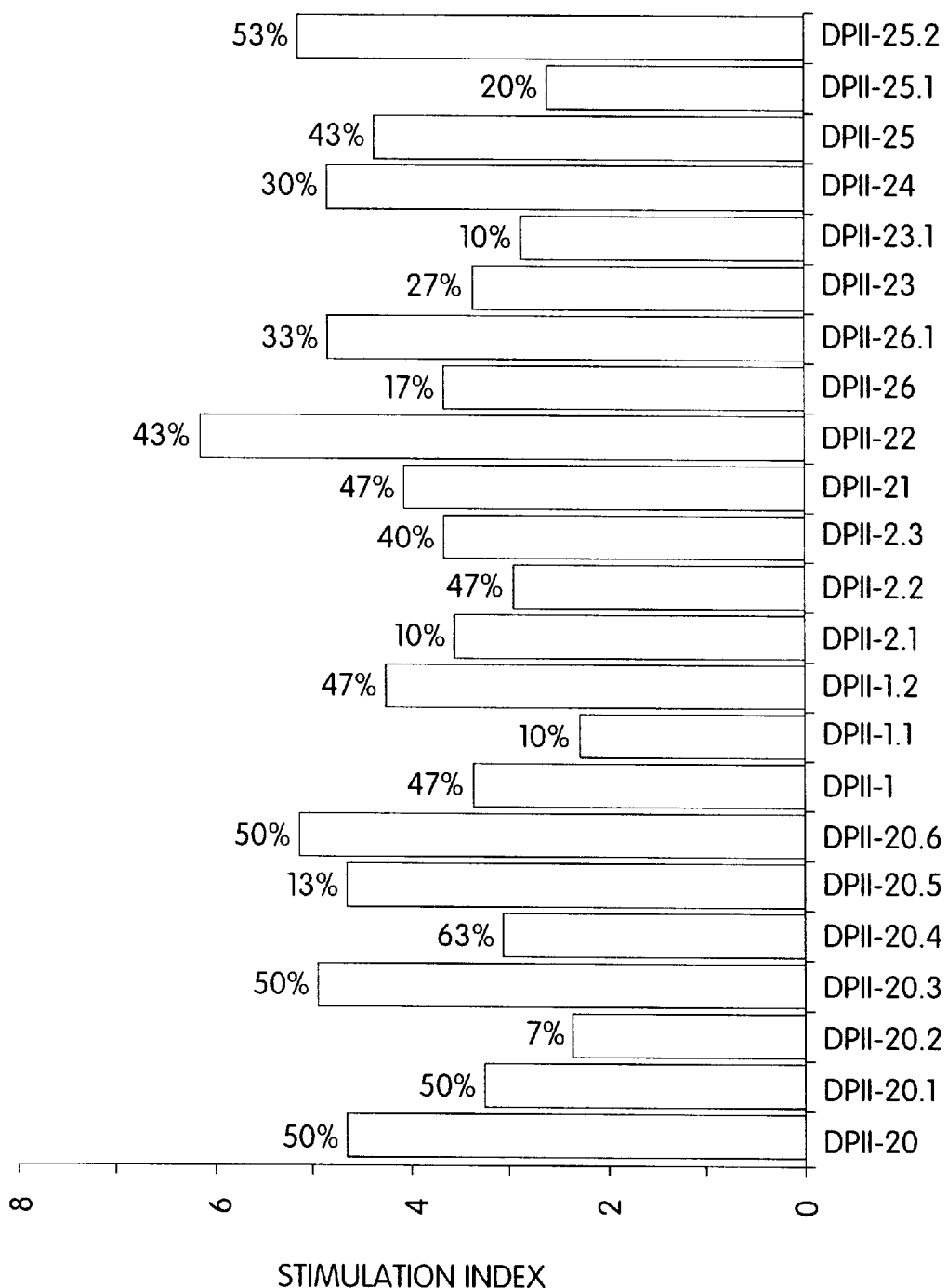
FIG. 17a is a graphic representation depicting the response of T cells from 29 patients primed in vitro to the Der p II protein and analyzed for response to selected peptides of desired lengths derived from the Der p II protein, by the T cell stimulation index of a response with an S.I. of at least 2 for the peptide.
Figure 17B:
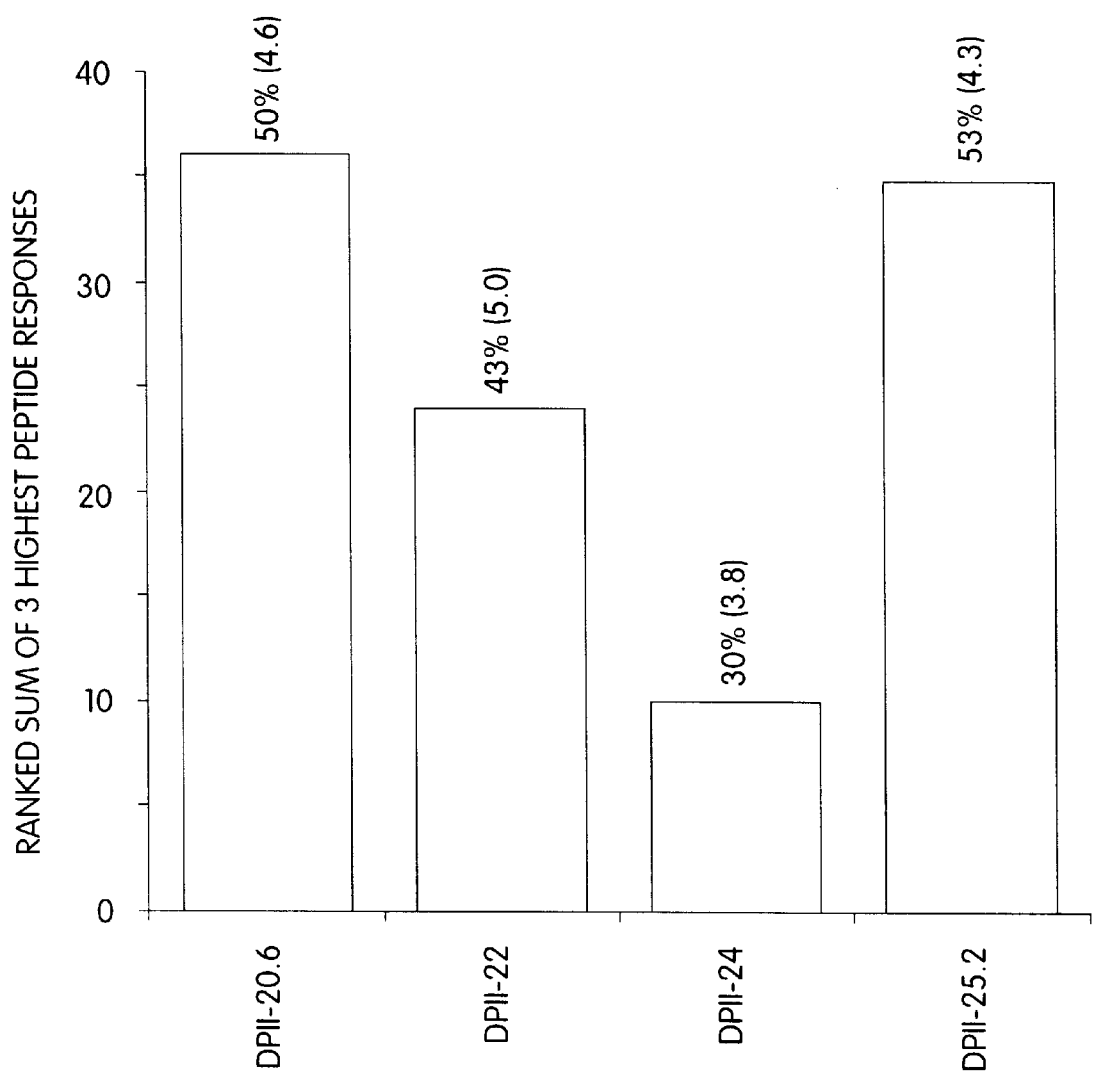
FIG. 17b is a graphic representation depicting the response of 30 patients primed in vitro to the Der p II protein and analyzed for response to selected peptides derived from the Der p II protein by percent of responses with an S.I. of at least 2 within the individuals tested (above each bar), the mean T cell stimulation index (above each bar in parenthesis) and the ranked sum of peptide response (X-axis).
Figure 18A:
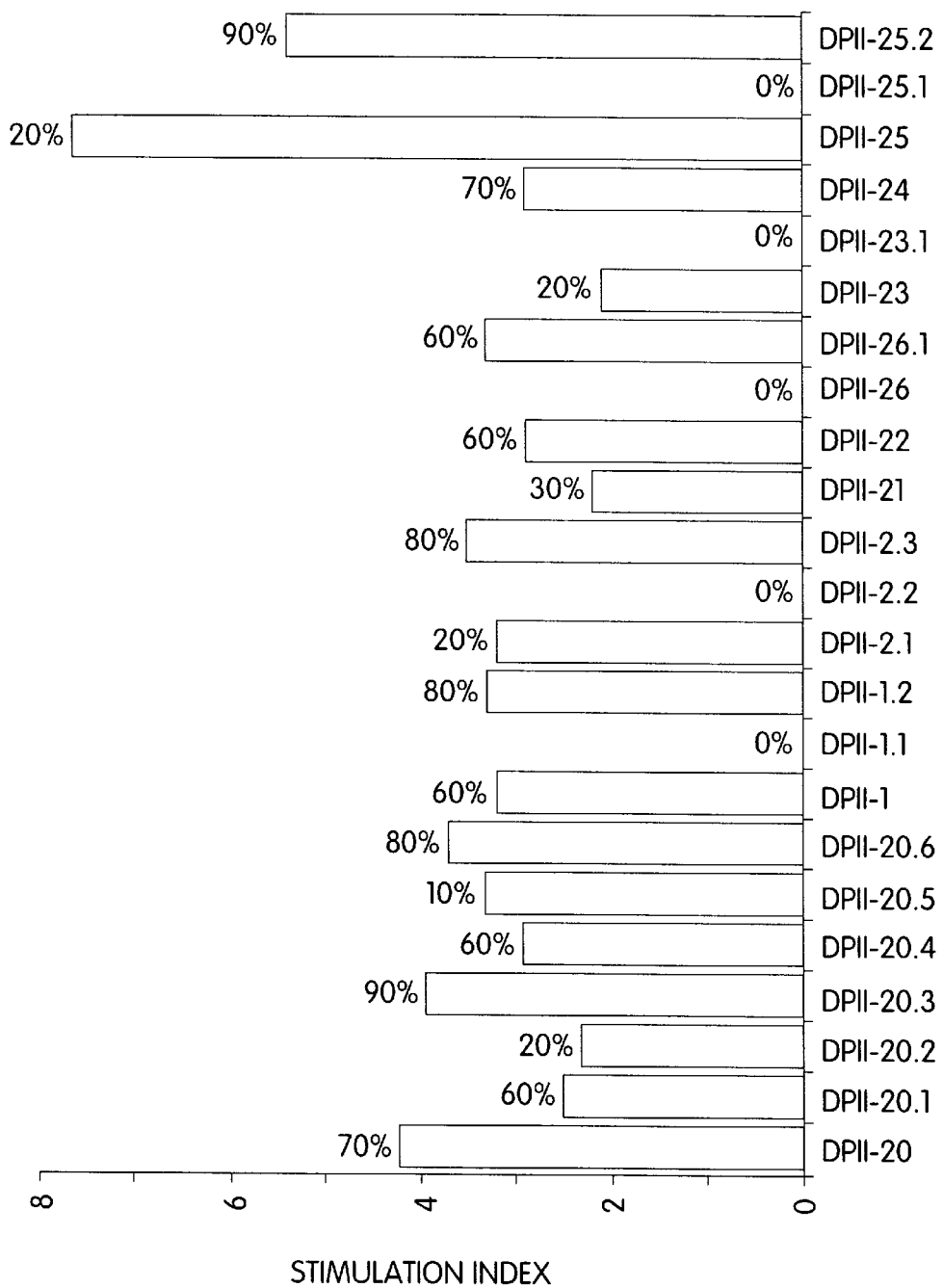
FIG. 18a is a graphic representation depicting the response of T cells from 10 patients primed in vitro to the Der f II protein and analyzed for response to selected peptides of desired lengths derived from the Der p II and Der f II protein, by the T cell stimulation index of a response with an S.I. of at least 2 for the peptide.
Figure 18B:
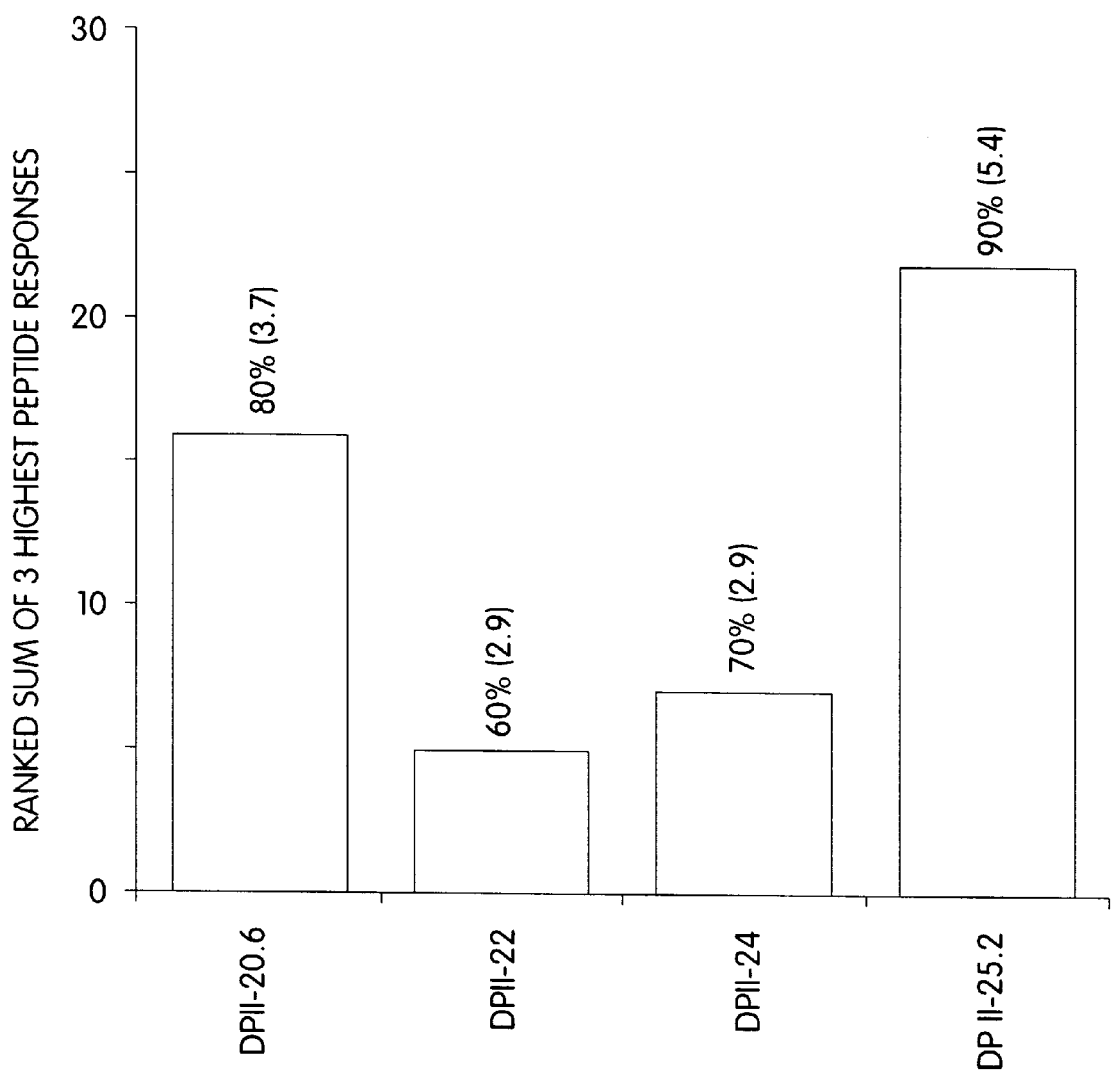
FIG. 18b is a graphic representation derived from the same data shown in FIG. 18a showing the response of Der f II primed T cell lines to preferred Der p II peptides analyzed by percent responses with an S.I. of at least 2 within the individuals tested (above each bar), the mean T cell stimulation index (above each bar in parenthesis) and the ranked sum of peptide responses (X-axis).
Figure 18C:
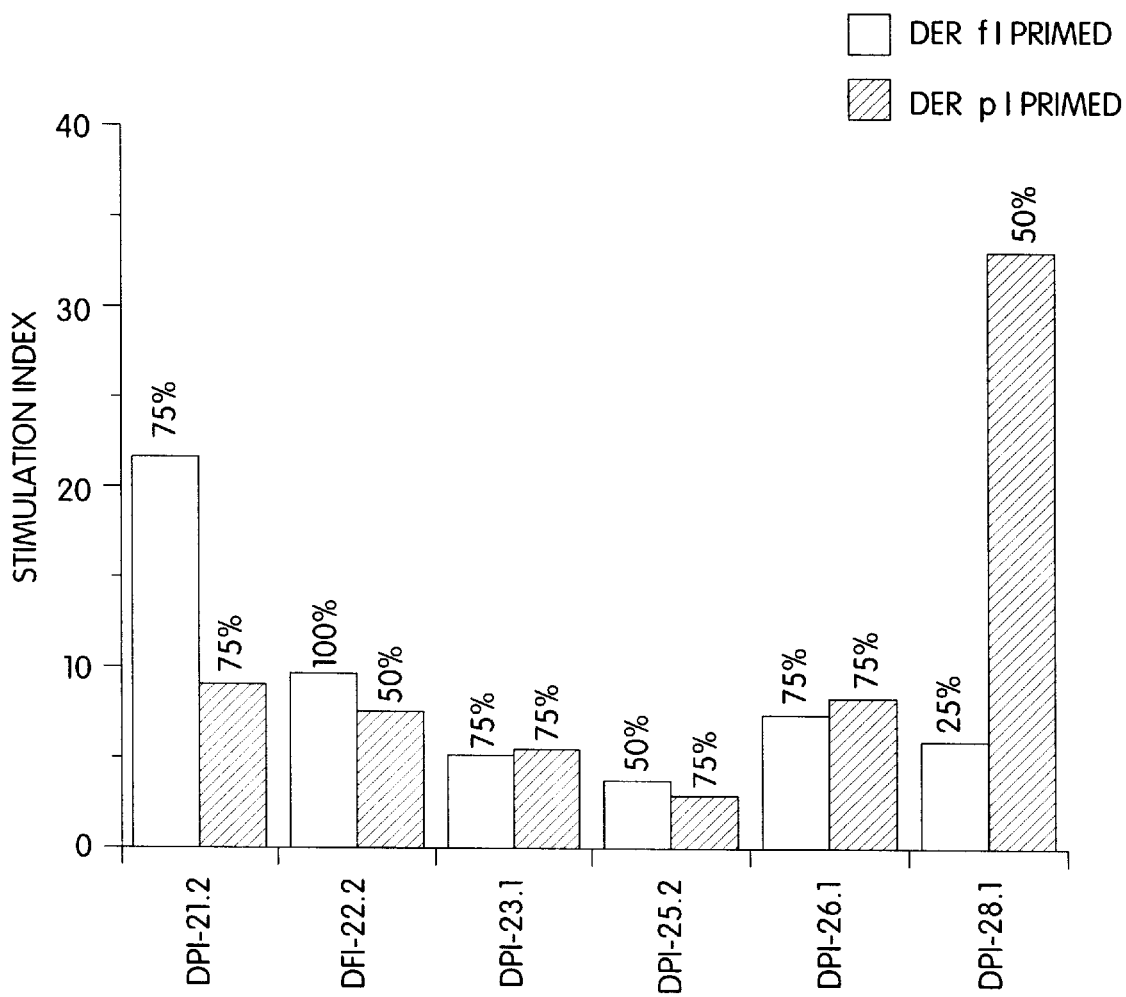
FIG. 18c is a graphic representation depicting the responses of T cell lines from 4 matched patients primed in vitro with mite group I allergen and analyzed for response to preferred Der p I and Der f I peptides by percent of responses with an S.I. of at least 2 within the individuals tested and the mean T cell stimulation index of positive responses for the peptide.

Another experiment following the procedure described in Example VIII analyzed the response of 29 patients primed in vitro to the Der p II protein and challenged with selected peptides derived from the Der p II sequence. FIG. 17a shows that Der p II primed T cells from one patient respond to selected peptides from Der p II. FIG. 17b shows the results from an experiment similar to that shown in FIG. 17a with a set of 30 patients and with the high and low omitted from the mean. FIG. 17b shows that DPII-20.6 has the highest ranked sum of this group of preferred peptides in this study. FIG. 18a shows the inverse experiment in which T cells from 1 patient were primed in vitro to the Der f II protein and challenged with selected peptides derived from the Der p II sequence. FIG. 18a shows that Der f II primed T cells from 10 patients respond to selected peptides from Der p II. As shown in FIG. 18a DP II-25 has the highest stimulation index. FIG. 18b is a subset of the same data shown in FIG. 18a and shows the response of native Der f II primed T cell lines to preferred Der p II peptides analyzed by ranked sum. As is shown in FIG. 18b, DPII-25.2 has the highest ranked sum of the preferred peptides in this study.

EXAMPLE XII

Study Indicating Cross-reactivity of Selected Group I and Group II Epitopes

A study similar to that described in Example VII was carried out with T cells from 4 matched patients primed in vitro with Group I proteins from Der f and Der p then analyzed for response to selected preferred peptides from Der p I and Der f I. The results in FIG. 18c demonstrate that T cell reactivity to a number of the selected preferred Der p I peptides was essentially equivalent for their Der f I counterpart and vice-versa.

Figure 18D:
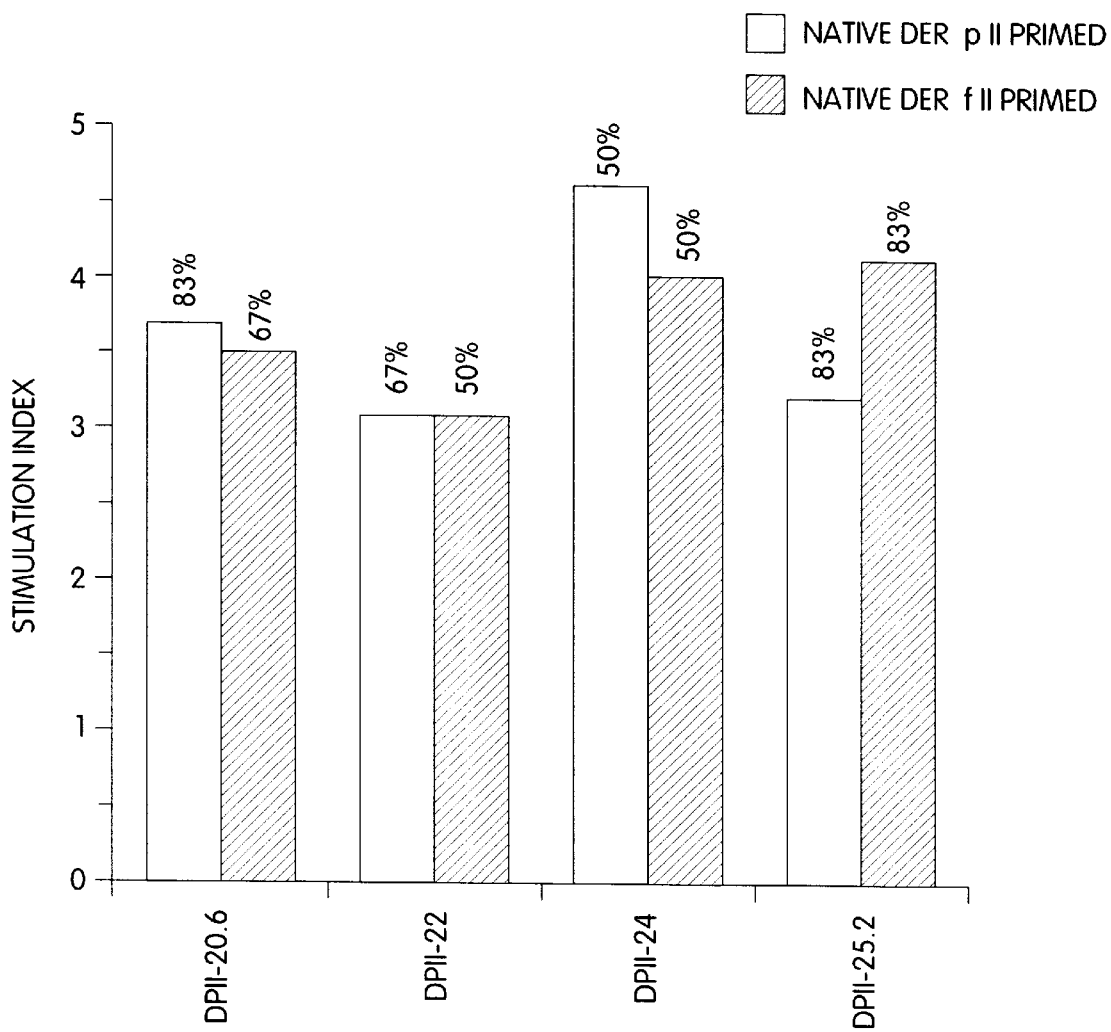
FIG. 18d is a graphic representation depicting the responses of T cell lines from 6 matched patients primed in vitro with mite group II allergen and analyzed for response to preferred Der p II peptides by percent of responses with an S.I. of at least 2 within the individuals tested and the mean stimulation index of positive responses for the peptide.

FIG. 18d shows the results of a similar study with T cells from 6 matched patients primed in vitro with Group II proteins from Der p and Der f, then analyzed for response to selected preferred Der p II and Der f II peptides. Similar to the results in FIG. 18c, T cell reactivity to a number of the selected preferred peptides of_Der p II are essentially equivalent to their Der f II counterparts and vice-versa.

EXAMPLE XIII

Direct Binding Assay of IgE to Mite Allergen Proteins and Peptides

Figure 19A:
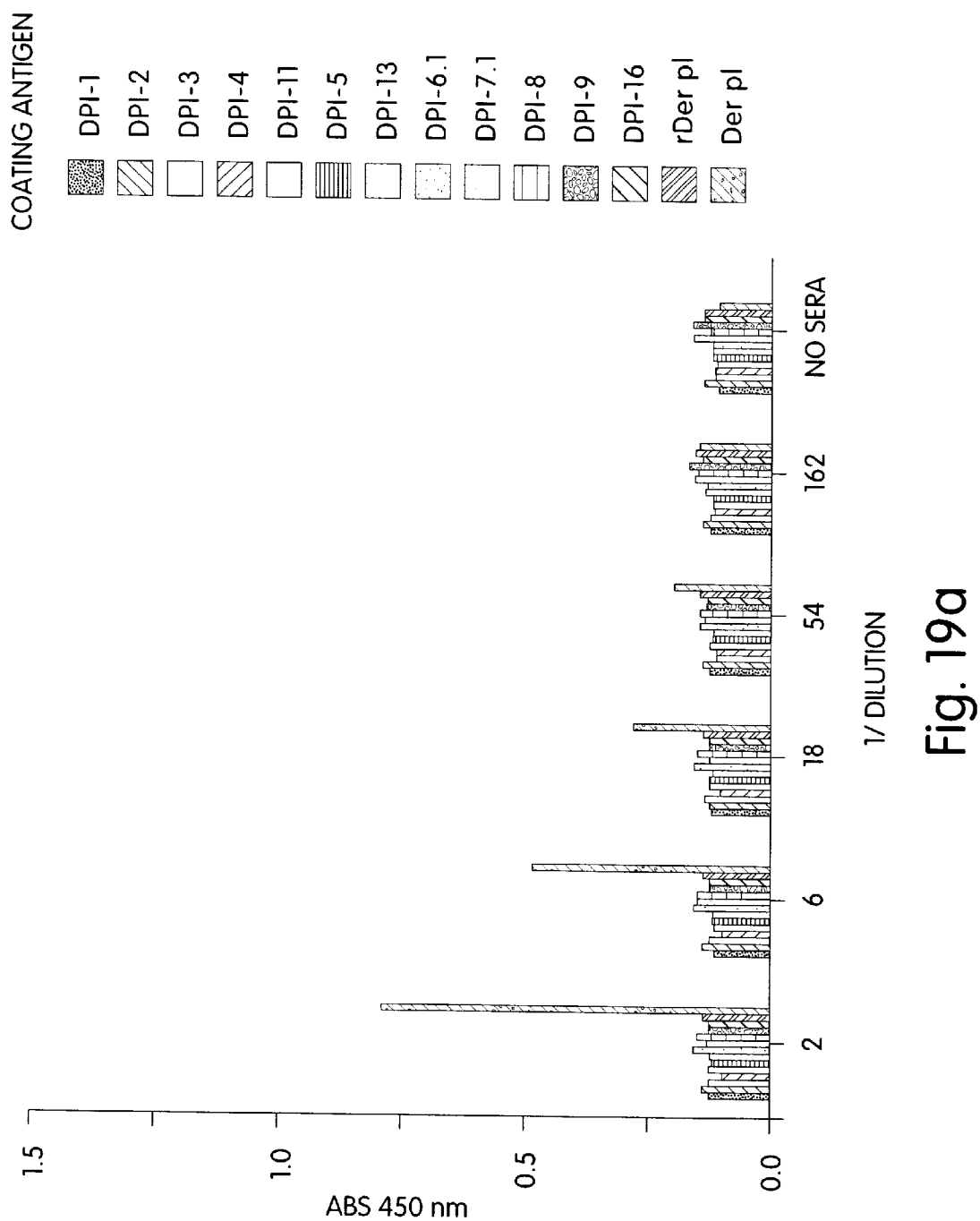
FIG. 19a–19b are graphic representations of the results of a direct binding assay of IgE to affinity purified and recombinant Der p I and Der p II proteins and certain Der p I and Der p II overlapping peptides.
Figure 19B:
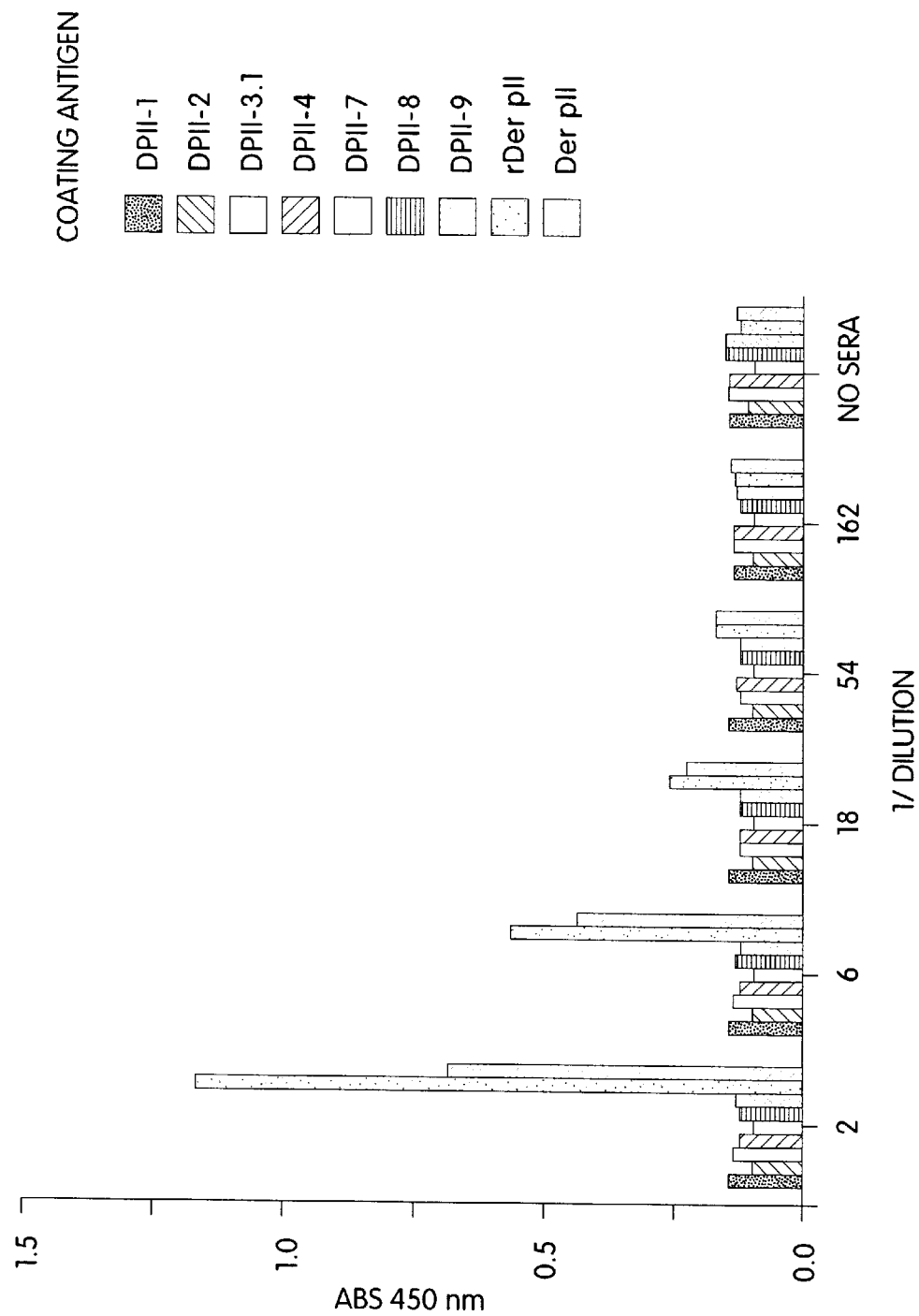
Figure 20A:
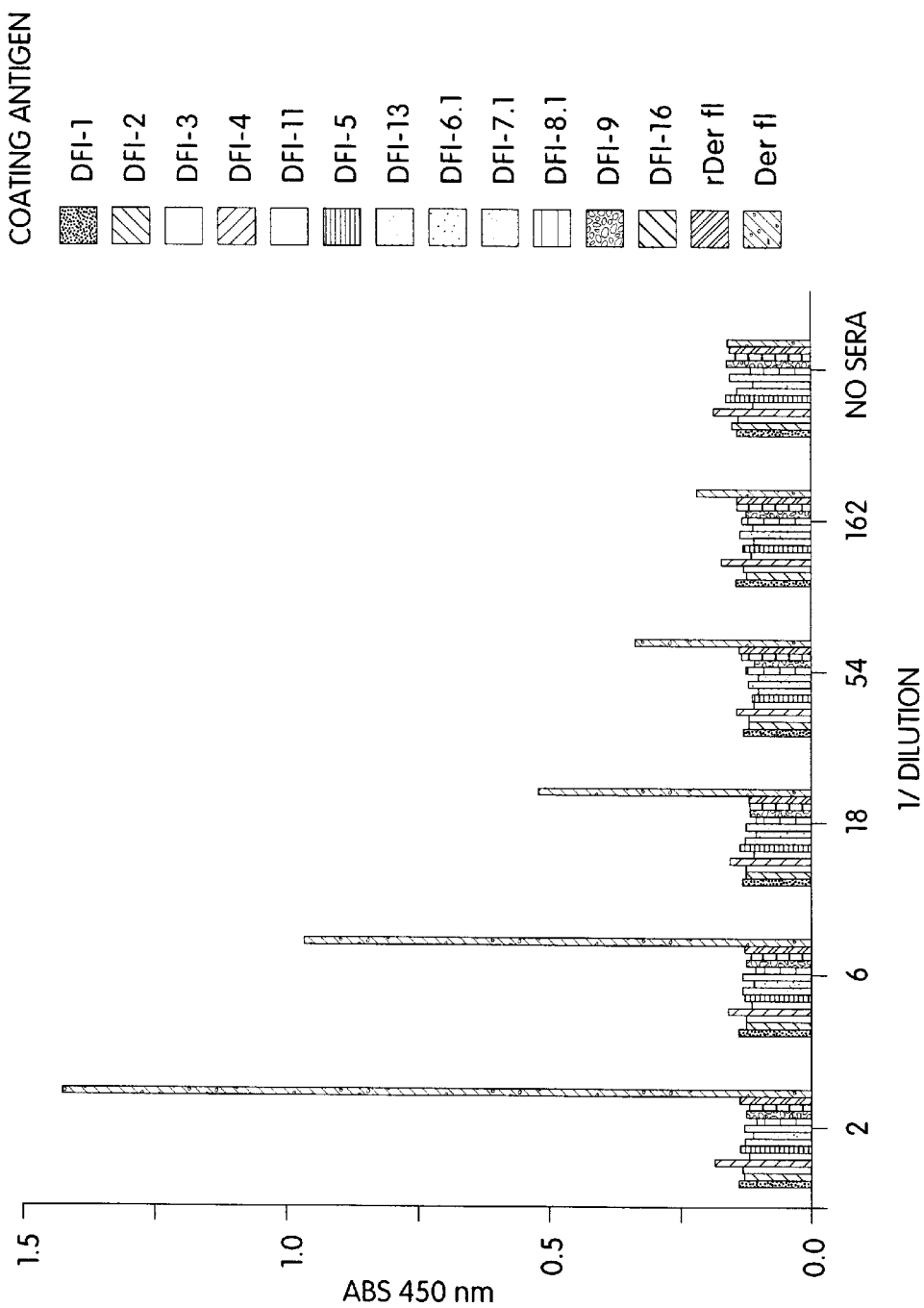
FIG. 20a–20b are graphic representations of the results of a direct binding assay of IgE to affinity purified and recombinant Der f I and Der f II proteins and certain Der f I and Der f II overlapping peptides.
Figure 20B:
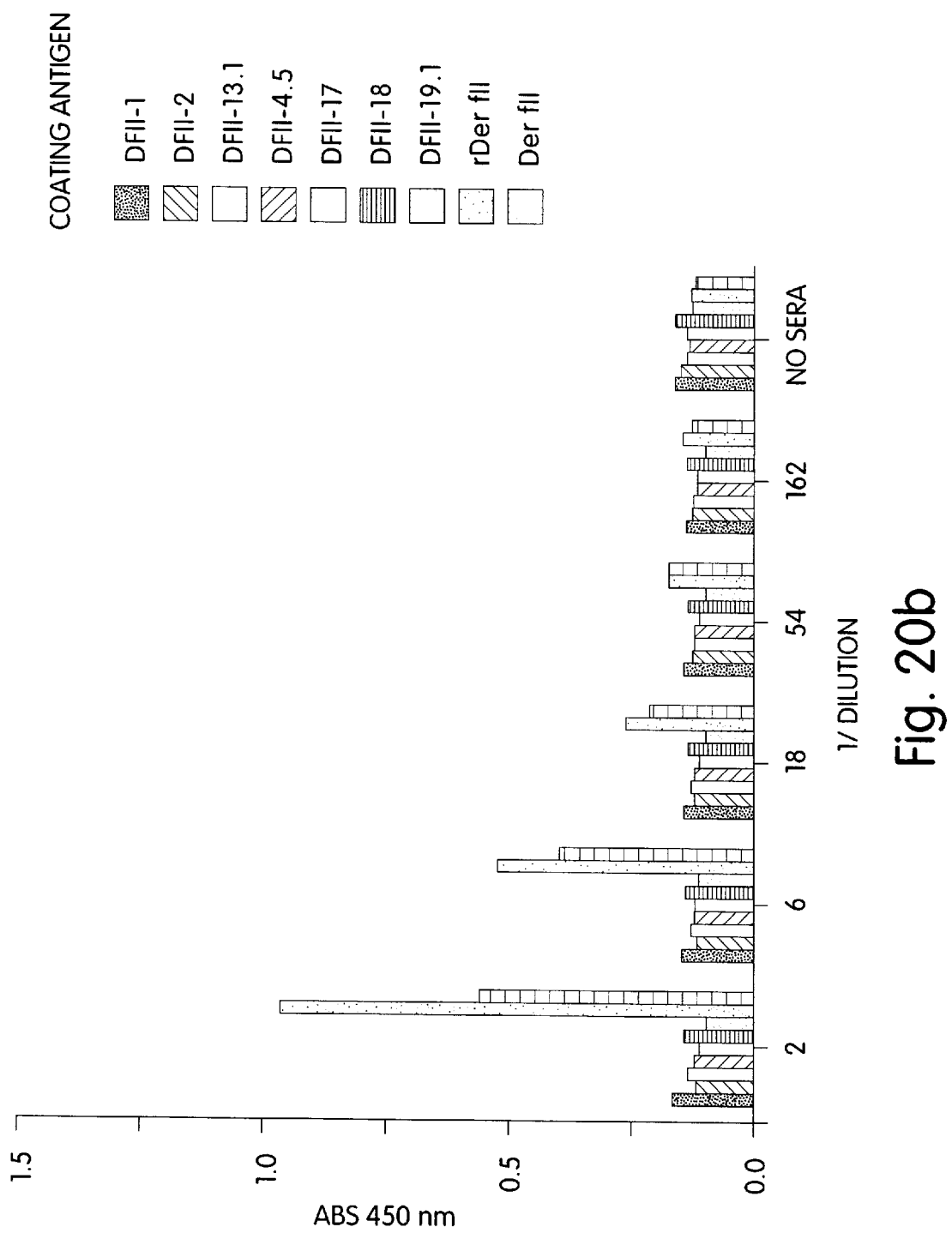
Figure 21A:
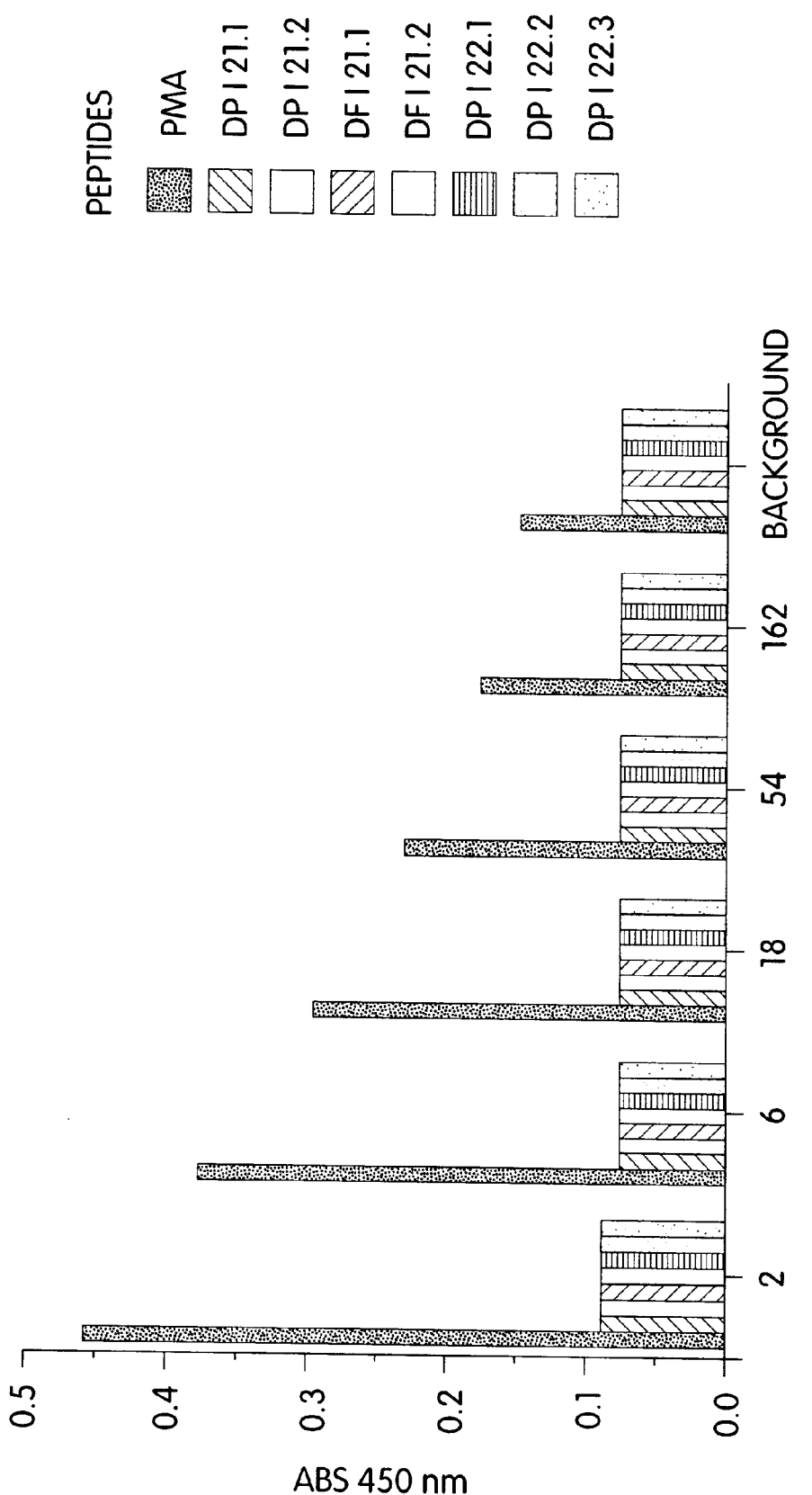
FIG. 21a–21h are graphic representations of the results of a direct binding assay of IgE to a mixture of biochemically purified mite allergens (PMA) and various peptides derived from Der p I, Der f I, Der p II and Der f II.
Figure 21B:
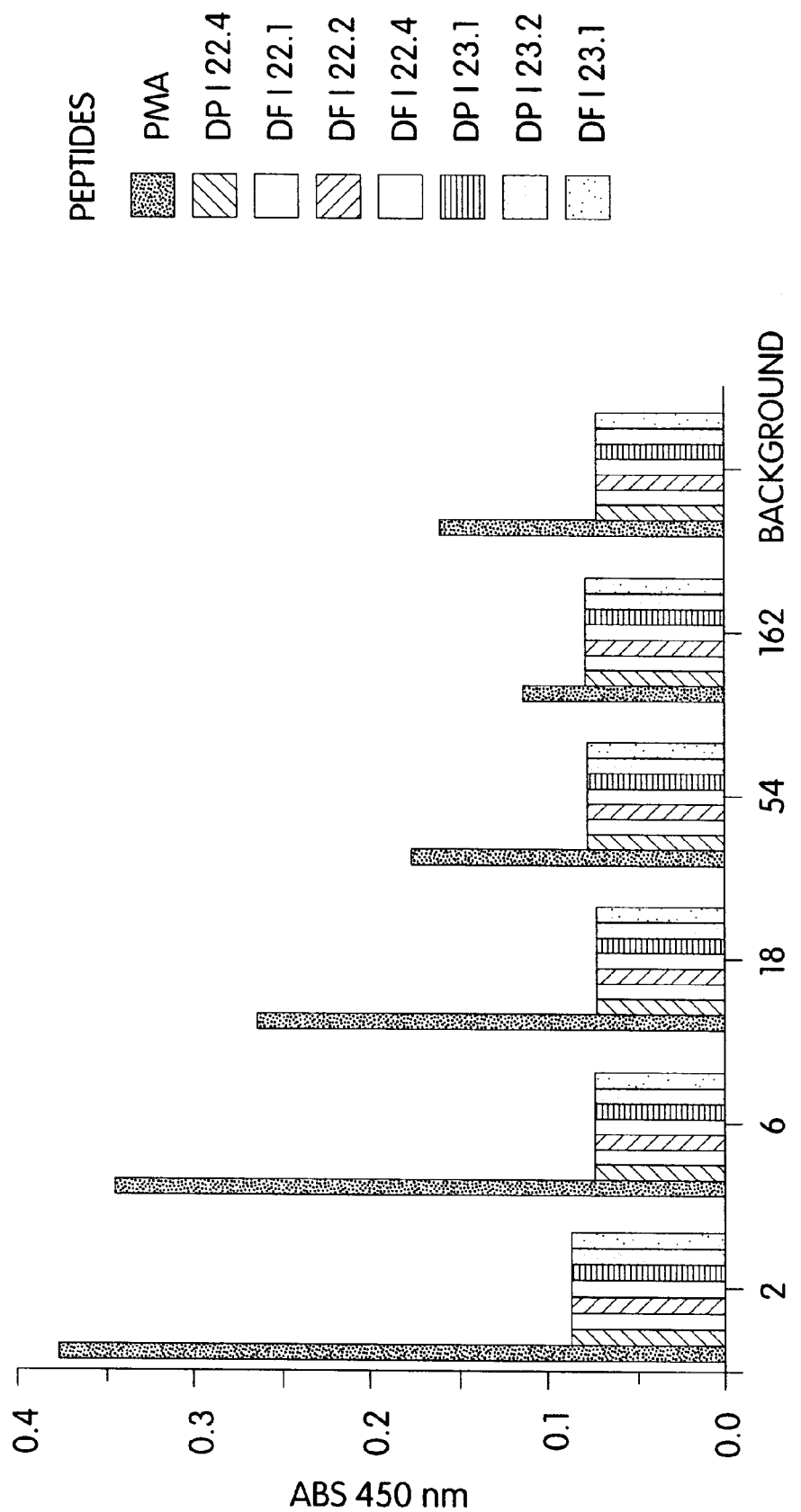
Figure 21C:
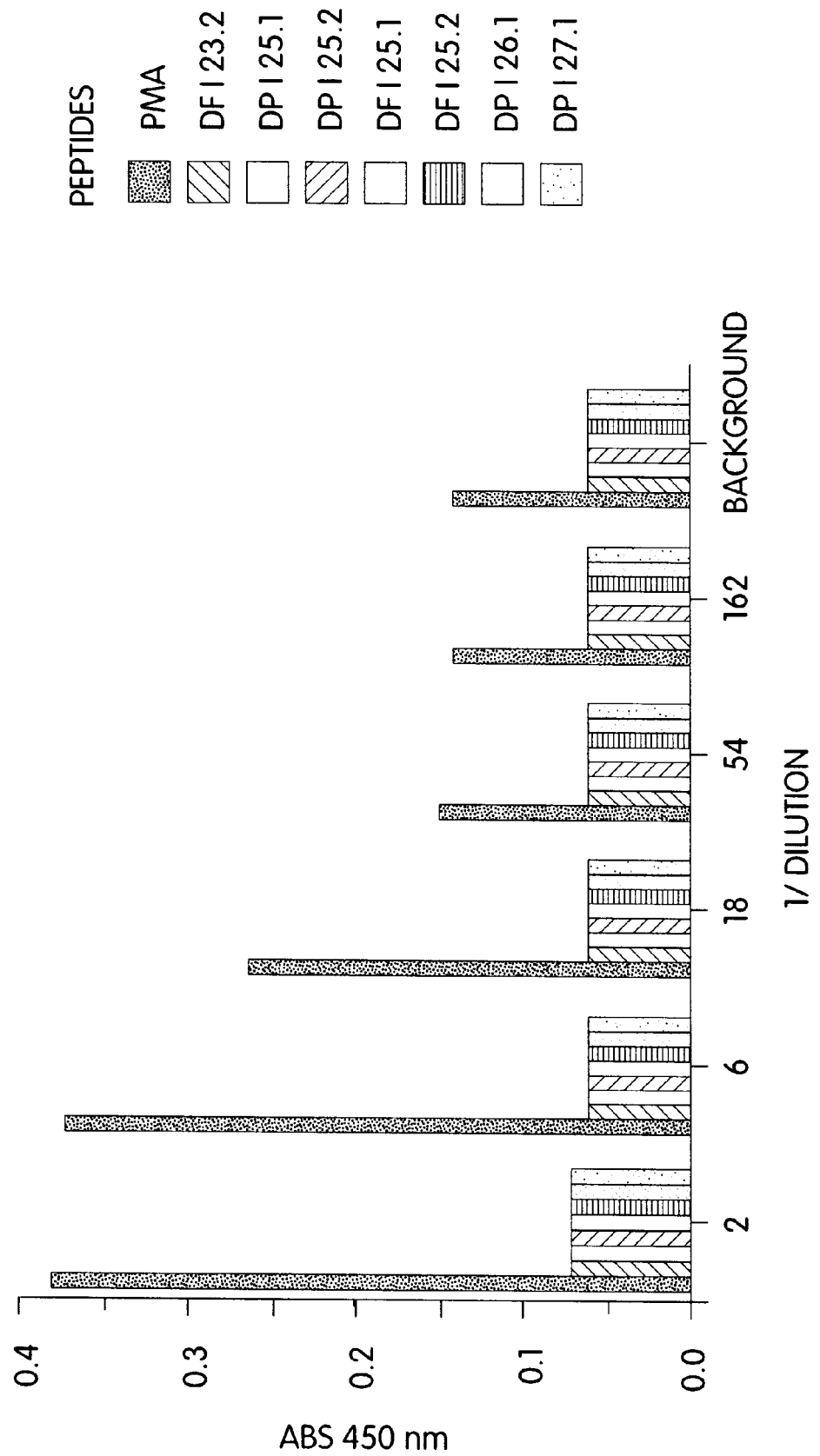
Figure 21D:
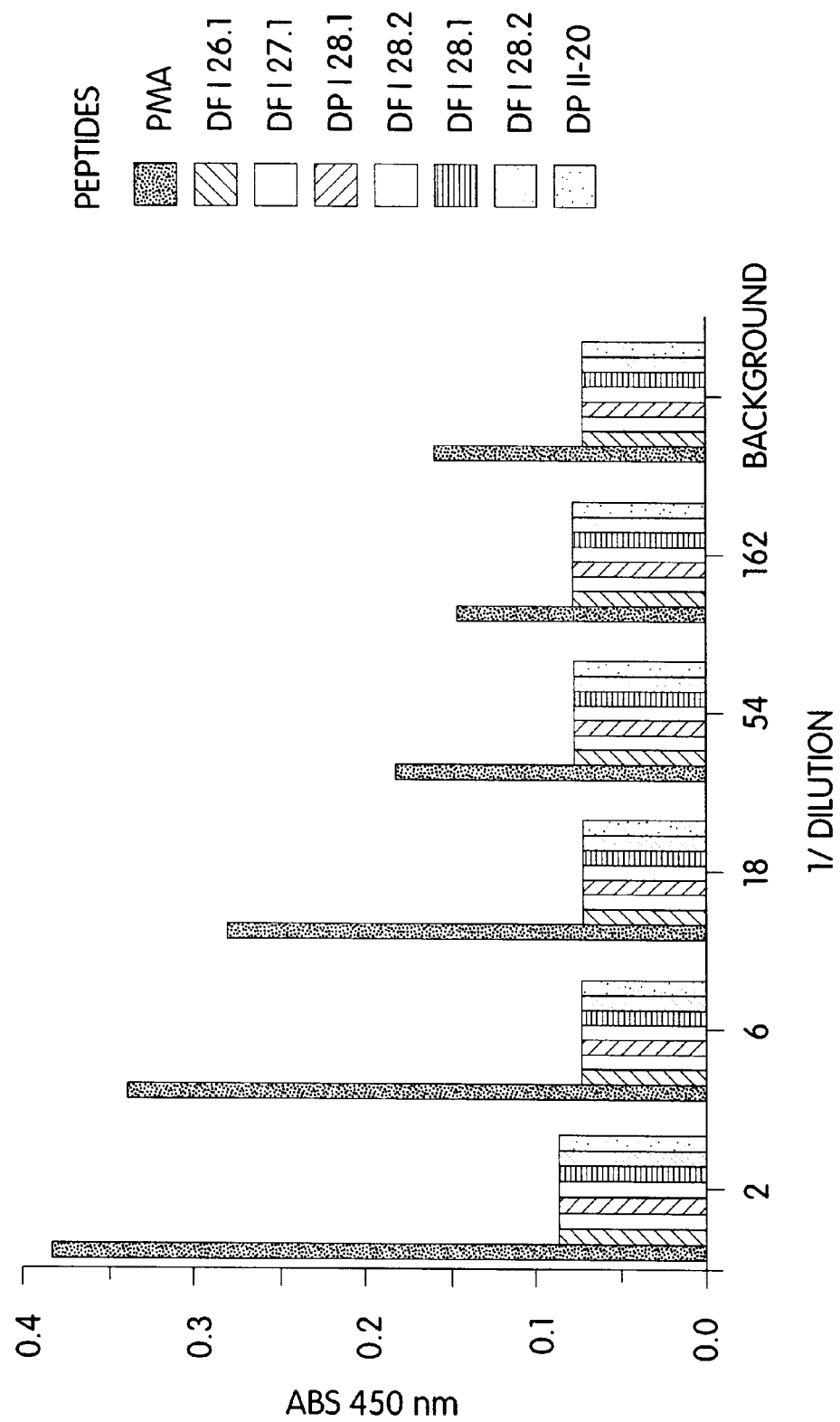
Figure 21E:
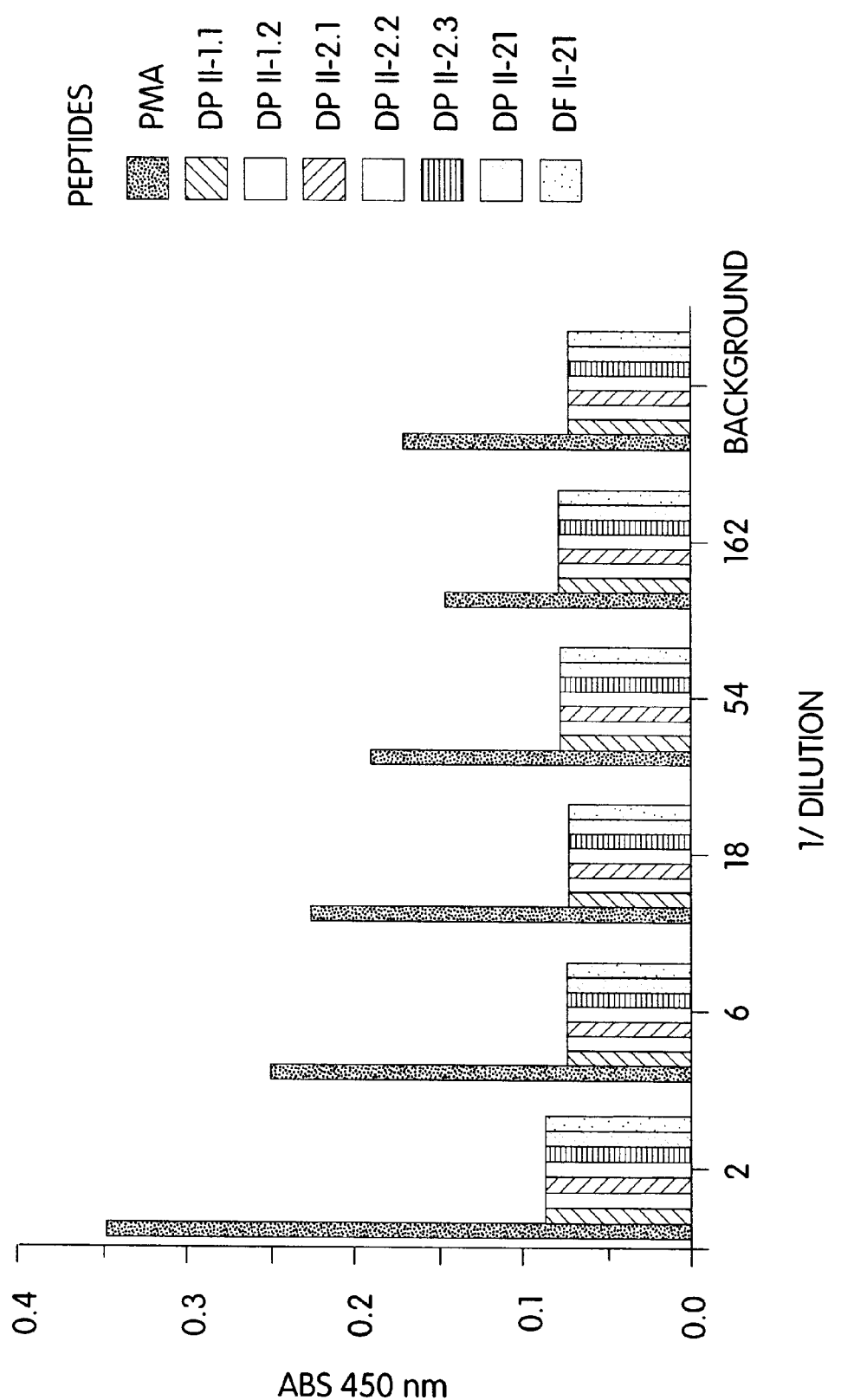
Figure 21F:
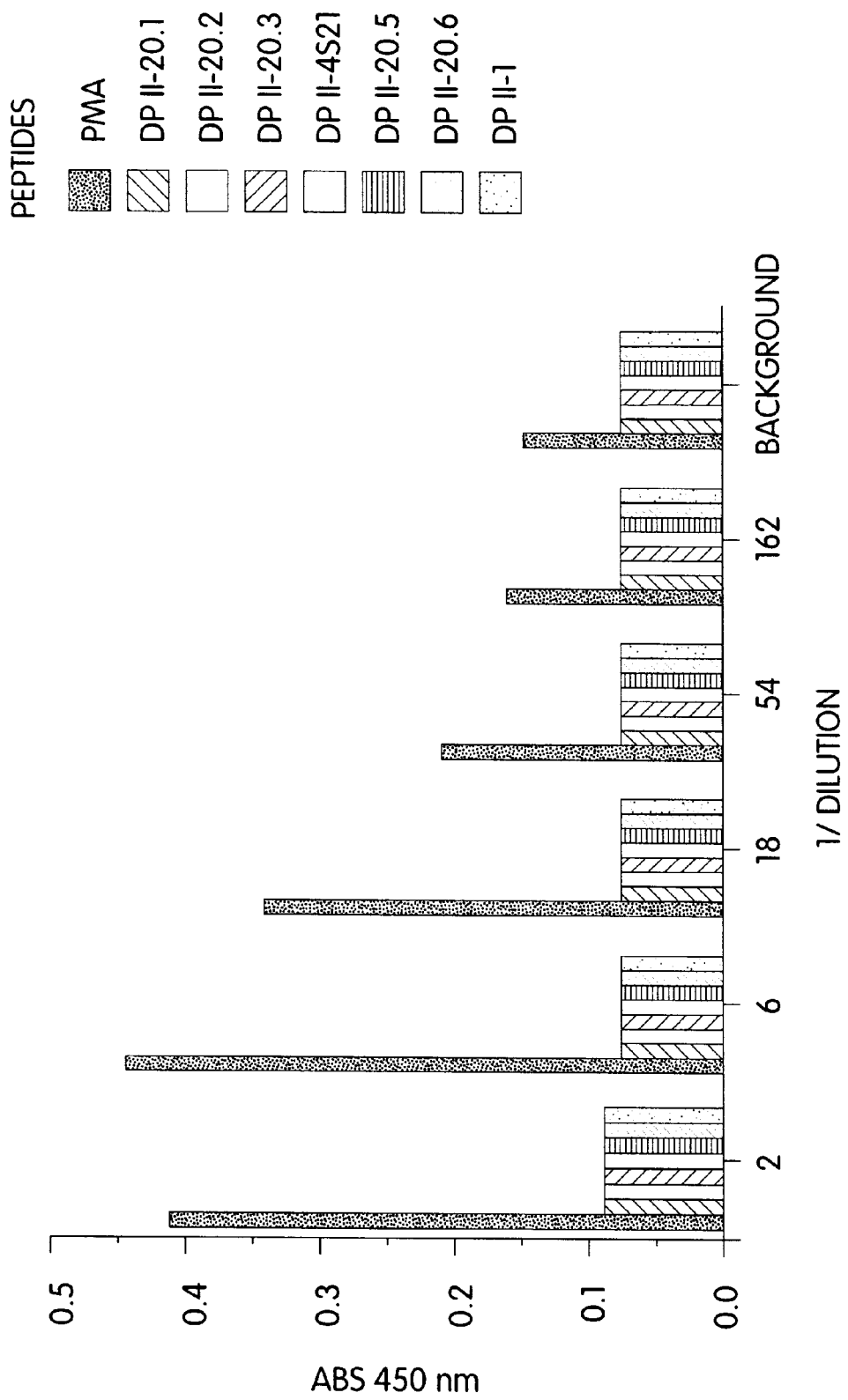
Figure 21G:
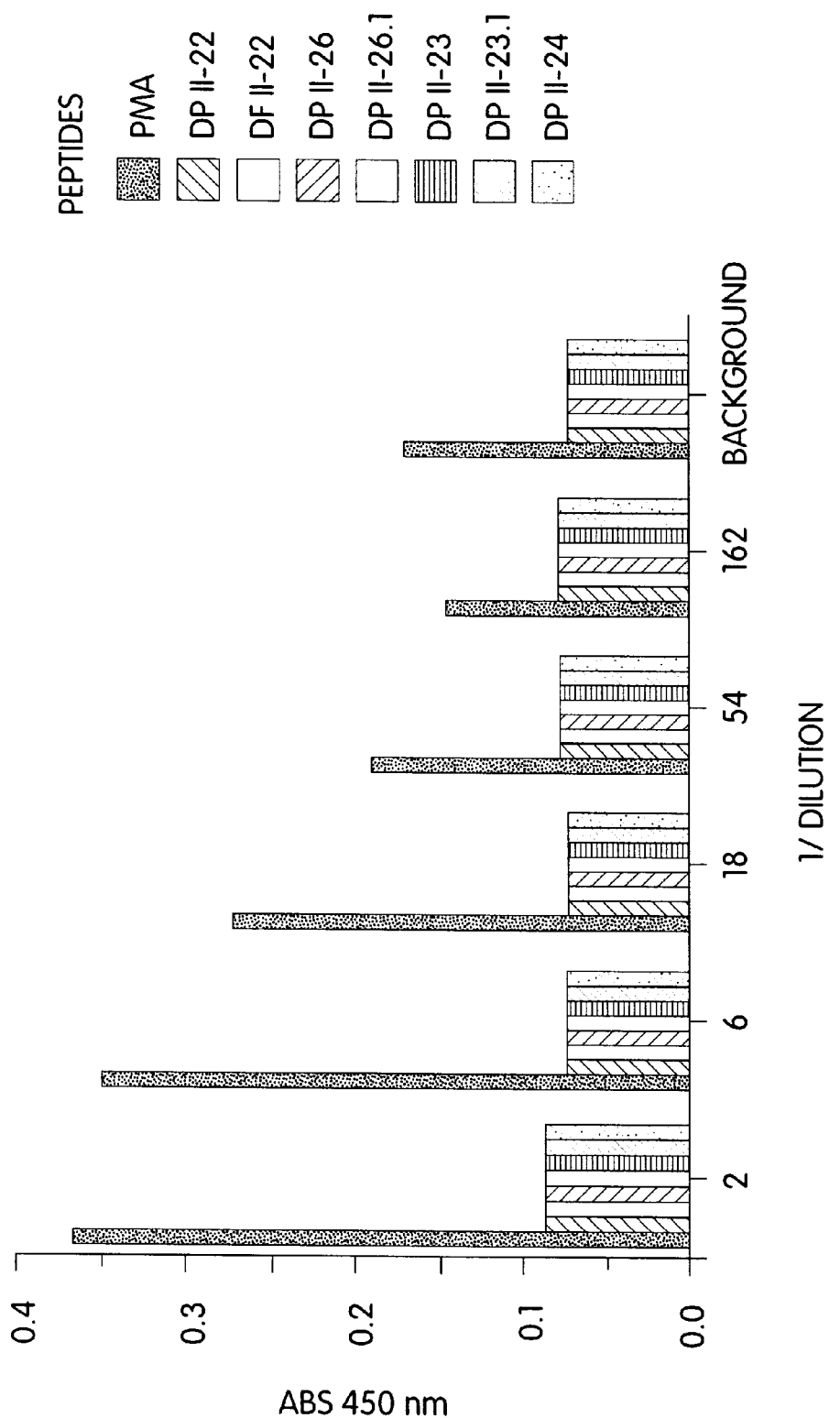
Figure 21H:
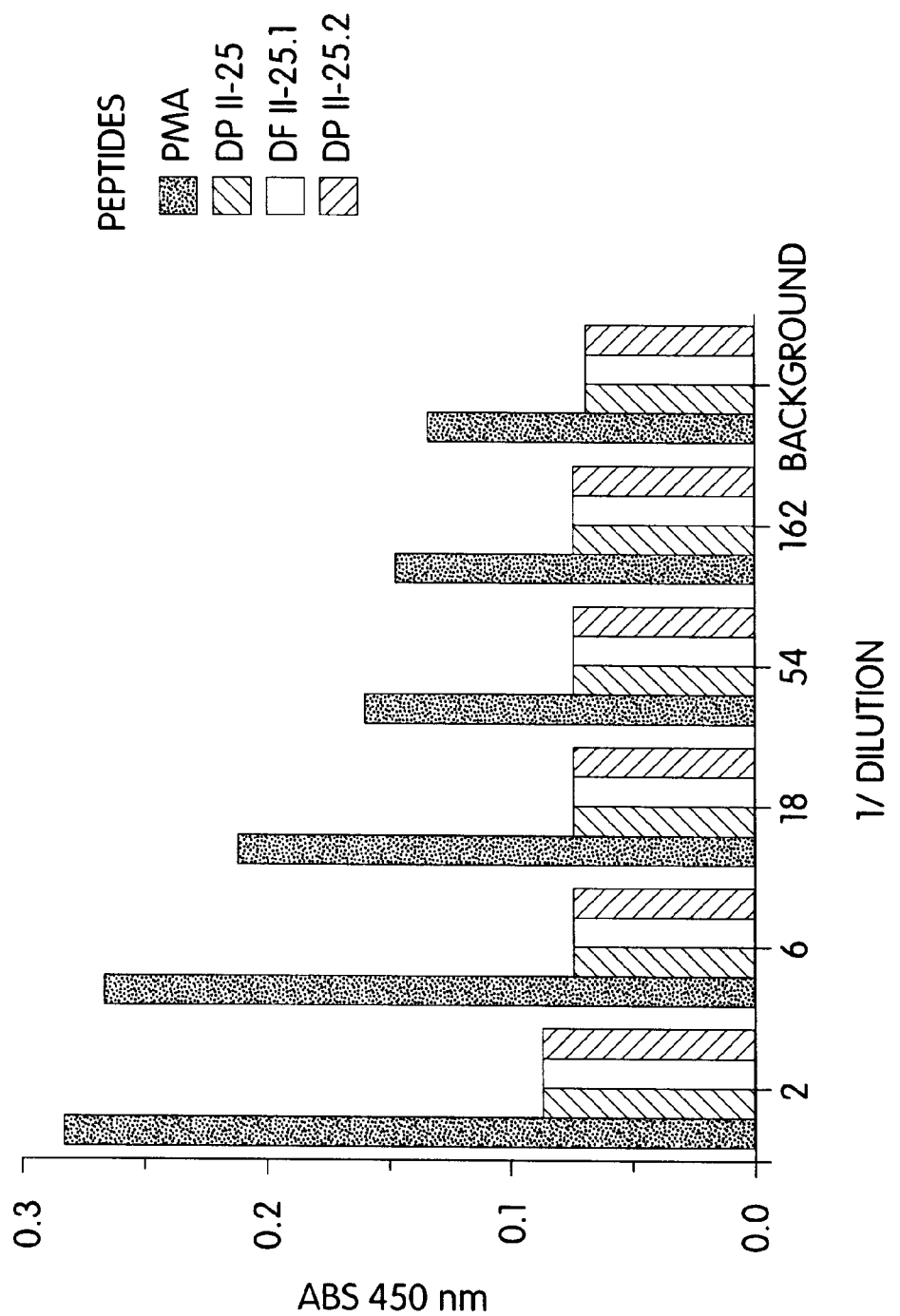

Corning assay plates (#25882-96) were coated with 5 μg/ml of each coating antigen listed in FIGS. 19, 20 and 21 at 50 μl/100 ml/well and incubated overnight at 4° C. The coating antigens were removed and the wells are blocked with 0.5% gelatin in PBS, 300 μl/well for 2 hours at room temperature. Pooled human plasma (a mix of plasma samples from 20 patients that were skin test positive for commerical mite extract) was serially diluted with PBS-Tween 20 (PBS with 0.05% nonionic detergent Tween-20 Sigma, St. Louis, Mo.) and 100 μl/well a\was added and incubated overnight at 4° C. (plasma dilutions were tested in duplicate). The second antibody (biotinylated goat anti-Human IgE, 1:1000, Kirkegaard & Perry Laboratories Inc, Gaithersburg, Md.), was added at 100 μl/well for one hour at room temperature. This solution was removed and streptavidin-HRPO, 1:10000, (Southern Biotechnology Associates, Inc., Birmingham, Ala.) was then added at 100 μl/well for one hour at room temperature (all wells are washed three times with PBS-Tween between each incubation step). TMB Membrane Peroxidase Substrate system (Kirkegaard & Perry Laboratories) was freshly miced, and added at 100 ml/well. The color was allowed to develop for 2–5 minutes. The reaction was stopped by the addition of 100 ml/well of 1M phosphoric acid. Plates were read on a Microplate IL310 Autoreader (Biotech Instruments, Winooski, Vt.) with a 450 nm filter. The absorbance levels of duplicate wells were averaged. The graphed results (log of the dilution versus absorbance) of the ELISA assays are shown in FIGS. 19a–b, 20a–b and 21a–h. The order of coating antigens listed vertically in these figure legends corresponds in orDer from left to right to the coating antigens listed for each histogram.

The results of the ELISA assay shown in FIG. 19b demonstrate good binding of both biochemically purified Der p II and recombinant Der p II (rDer p II) with human IgE and no detectable binding to the Der p II peptides. The IgE binding to the Der p set of peptides and proteins (FIGS. 20a and 20b) shows the same pattern of reactivity as the Der f set. That is, no detectable binding to Der f I or Der f II peptides or recombinant Der f I with binding to only biochemically purified Der f_I and recombinant and biochemically purified Der f II. In both cases there appears to be better binding to recombinant Der p II or Der f_II than to the biochemically purified forms. All the conclusions derived from the above ELISA assay data were corraborated by another assay method, dot blots on nitrocellulose paper, using the same set of antibody and antigen reagents.

The antigen preparation that was used as a positive control was a mixture of the four major biochemically purified mite allergens (term PMA for Purified Mite Allergen); Der f I, Der f II, Der p I and Der p II. The stock was generated at a concentration of 100 μgs of each protein per millimeter or 400 μgs total protein/ml. This preparation was used on each coated ELISA plate. The results from these ELISA assays are shown in FIGS. 21a–h. There is clear binding to either the purified or recombinant protein or the PMA antigen preparation on each plate indicating good IgE reactivity. However, the PMA antigen preparation, does exhibit a high degree of non-specific reactivity shown in the background dilution where no first antibody solution was added. This non-specific reactivity occurs between the PMA antigen and the biotinyulated second antibody and does not compromise the finding of specific IgE reactivity to the antigen. Using a quantitative value of two-fold over background at the highest plasma concentration as a positive reading, there is no detectable IgE reactivity to any one of the 56 peptides screened by this assay method.

EXAMPLE XIV

T Cell Epitope Studies with Modified Peptides
Synthesis of Peptides

Modified Der p I, Der p II, and Der f II peptides were synthesized using standard Fmoc/tBoc synthetic chemistry and purified by Reverse Phase HPLC. FIG. 30 shows the modified house dust mite peptides used in these studies. These modified peptides were constructed for enhanced solubility as compared to the peptides from which they were derived. In almost all cases, these modified peptides exhibited enhanced solubility as compared to the peptides from which they were derived (data not shown). Other peptides used in these studies and which are shown in FIGS. 31a–b and 32a–b may be found in FIGS. 3 and 4 and are discussed in Examples III–IX and XI. The peptide names; are consistent throughout.

T Cell Responses to Cedar Pollen Antigen Peptides

Peripheral blood mononuclear cells (PBMC) were purified by lymphocyte separation medium (LSM) centrifugation of 60 ml of heparinized blood from house dust mite allergic patients who exhibited clinical symptoms of seasonal rhinitis and/or were MAST and/or skin test positive for house dust mite protein allergen. Long term T cell lines were established by stimulation of $2\times10^6$ PBL/ml in bulk cultures of complete medium (RPMI-1640, 2 mM L-glutamine, 100 U/ml penicillin/streptomycin, $5\times10^{-5}$M 2-mercaptoethanol, and 10 mM HEPES supplemented with 5% heat inactivated human AB serum) with 30 μg/ml of purified native Der p I or Der p II for 5–6 days at 37° C. in a humidified 5% $CO_2$ incubator to select for house dust mite protein allergen reactive T cells. This amount of priming antigen was determined to be optimal for the activation of T cells from house dust mite allergic patients. Viable cells were purified by LSM centrifugation and cultured in complete medium supplemented with 5 units recombinant human IL-2/ml and 5 units recombinant human IL-4/ml for up to three weeks until the cells no longer responded to lymphokines and were considered "rested". The ability of the T cells to proliferate to selected peptides, purified Der p I or Der p II, or positive (PHA) controls or negative controls (medium only) was then assessed. For assay, $2 \times 10^4$ rested cells were restimulated in the presence of $2 \times 10^4$ autologous Epstein-Barr virus (EBV)-transformed B cells (prepared as described below) (gamma-irradiated with 25,000 RADS) or with $5 \times 10^4$ autologous PBMs (gamma-irradiated with 3500 RADS), with 2–50 $\mu$g/ml of purified native Der p I or Der p II in a volume of 200 $\mu$l complete medium in duplicate or triplicate wells in 96-well round bottom plates for 3 days. Each well then received 1 $\mu$Ci tritiated thymidine for 16–20 hours. The counts incorporated were collected onto glass fiber filter mats and processed for liquid scintillation counting. Titrations using T cells from one individual were conducted which showed the effect of varying antigen dose in assays with purified native Der p I or Der p II and several of the peptides synthesized as described above. The titrations were used to optimize the dose of peptides in T cell assays.

The maximum response in a titration of each peptide is expressed as the stimulation index (S.I.). The S.I. is the counts per minute (CPM) incorporated by cells in response to peptide, divided by the CPM incorporated by cells in medium only. An S.I., value equal to or greater than 2 times the background level is considered "positive" and indicates that the peptide contains a T cell epitope. The positive results were used in calculating mean stimulation indices for each peptide for the individual patient tested.

Figure 32A:
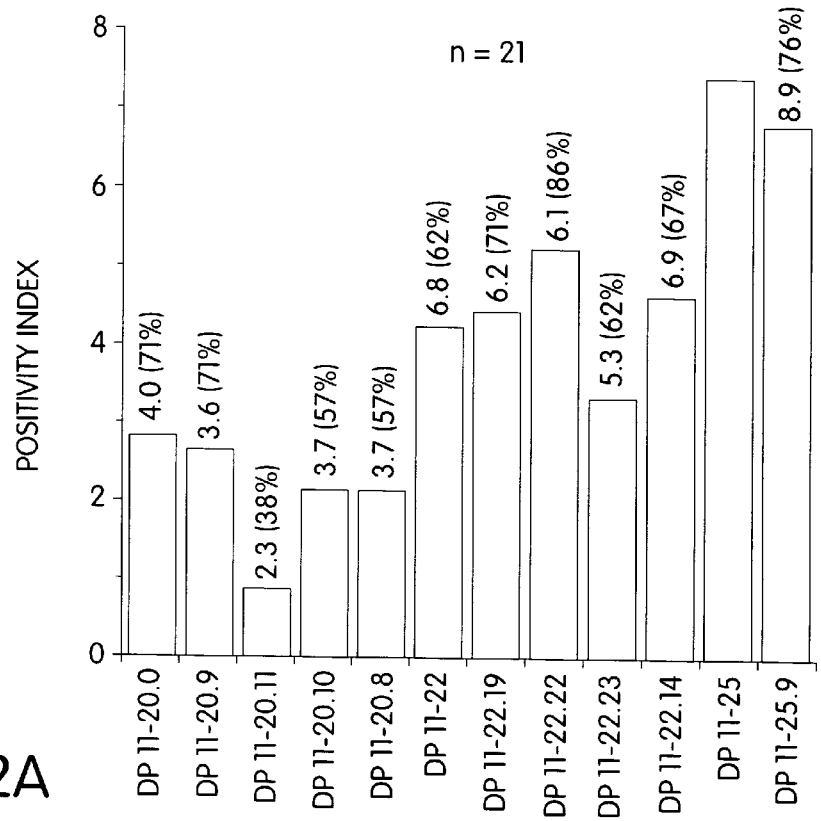
FIG. 32a and 32b are graphic representations depicting the responses of T cell lines from 21 patients (some matched) primed in vitro with mite group II allergen (Der p II) and analyzed for response to various peptides and modified peptides of the invention, the y axis indicates the positivity index for each peptide tested which is the means S.I. multiplied by the by the percent of individuals tested responding to the peptide with a mean S.I. of at least 2.
Figure 32B:
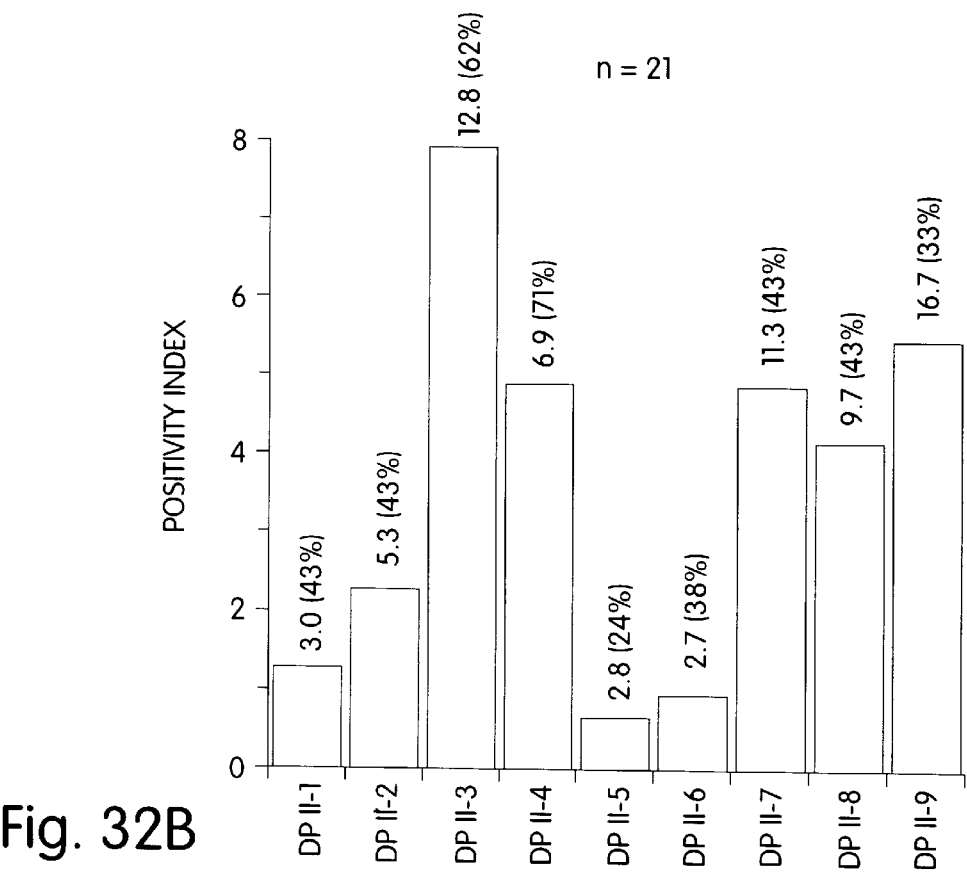

The above procedure was followed with 18 patients in the studies using peptides derived from Der p I and Der f I (FIGS. 31a–b), and 21 patients in the studies with Der p II peptides (FIGS. 32a–b). Individual patient results were used in calculating the mean S.I. for each peptide if the patient responded to the Der p I or Der p II protein at an S.I. of 2.0 or greater and the patient responded to at least one peptide derived from a house dust mite allergen at an S.I. f 2.0 or greater. A summary of positive experiments from the patients tested is shown in FIGS. 32a and 32b and FIGS. 33a and 33b. The bars represent the positivity index. Above each bar is the percent of positive responses with an S.I. of at least 2.0 to the peptide or protein in the group of patients tested. In parenthesis above each bar are the mean stimulation indices for each peptide or protein for the group of patients tested.

As shown in FIG. 31a, all eighteen T cell lines responded positively to modified peptides DP I-23.31 (SEQ ID NO: 165), DP I-23.35 (SEQ ID NO: 167), and DP I-26.6 (SEQ ID NO:168) when primed with affinity purified Der p I, and as shown in FIG. 32a, is all 21 T cell lines responded positively to modified peptides DP II-20.9 (SEQ ID NO:169), DP II-20.11 (SEQ ID NO:169), DP II-20.10 (SEQ ID NO:170), DP II-20.8 (SEQ ID NO: 171), DP II-22.19 (SEQ ID NO: 172), DP II-22.22 (SEQ ID NO: 175), DP II-22.23 (SEQ ID NO:177), DP II-22.14 (SEQ ID NO:180), and DP II-25.9 (SEQ ID NO: 183), when primed with Der p II indicating that all of the modified peptides tested contain at least one T cell epitope. The other peptides in FIGS. 31a–b and 32a–b were previously tested (see, Examples III–IX and XI) and were used in these studies as controls.

Preparation of (EBV)-transformed B Cells for Use as Antigen Presenting Cells

Autologous EBV-transformed cell lines were $\gamma$-irradiated with 25,000 Rad and used as antigen presenting cells in secondary proliferation assays and secondary bulk stimulations. These EBV-transformed cell lines were made by incubating $5 \times 10^6$ PBL with 1 ml of B-59/8 Marmoset cell line (ATCC CRL1612, American Type Culture Collection, Rockville, Md.) conditioned medium in the presence of 1 $\mu$g/ml phorbol 12-myristate 13-acetate (PMA) at 37° C. for 60 minutes in 12×75 mm polypropylene round-bottom Falcon snap cap tubes (Becton Dickinson Labware, Lincoln Park, N.J.). These cells were then diluted to $1.25 \times 10^6$ cells/ml in RPMI-1640 as described above except supplemented with 10% heat-inactivated fetal bovine serum and cultured in 200 $\mu$l aliquots in flat bottom culture plates until visible colonies were detected. They were then transferred to larger wells until the cell lines were established.

EXAMPLE XV

Direct binding assay if IgE to Modified Der p and Der f Peptides

Plasma samples from 19 mite-allergic patients (4+ skin test) and a pool of plasma from 18 additional patients were tested using the procedure outlined in Example XIII with minor differences (Costar ELISA plates were used instead of Corning, and 10 $\mu$l/ml peptides were coated onto the plates instead of 5 $\mu$l/ml. In each case, a control was run for IgE binding to uncoated plates (no peptide). No plasma samples contained IgE to any of the peptides. All samples did contain IgE to Der p I and/orDer p II. The modified peptides tested were, DP II-20.8 (SEQ ID NO: 171), DP II-20.9 (SEQ ID NO: 169), DPII-20.10 (SEQ ID NO: 170), DP II-20.11 (SEQ ID NO:169), DP I 23.31 (SEQ ID NO: 165), DP I 23.35 (SEQ ID NO:167), DP II-22.14 (SEQ ID NO: 180), DP II-22.19 (SEQ ID NO:172), DP II-22.22 (SEQ ID NO:175), DP II-22.23 (SEQ ID NO: 177), and DP II-25.9 (SEQ ID NO:183)

EXAMPLE XVI

Analysis of IgE-Producing B Lymphocytes in Atopic and Non-Atopic Individuals

The factors influencing the progression of a normal immune response to foreign antigen involving IgM to IgG to an allergic response involving IgE, are unknown, as are the properties of allergens that induce this transition. Although Burastero et al., *J. Allergy Clin. Immunol.*, 91:1075–1081 (1993) reported that the atopic subjects had significantly higher frequencies of Der p-specific T cells than did healthy subjects, both O'Heir et al., *Immunology*, 66:499–504 (1989) and Wierenga et al., *Eur. J. Immunol.*, 20:1519–1526 (1990) have cloned T cells specific for Der p I and Der p II allergens from, both atopic and non-atopic donors, supporting the current findings that both atopic and non-atopic subjects mount an antibody response to Der p. Only those clones isolated from mite-allergic subjects however, could be induced by mite allergens to provide help for IgE synthesis by autologous B lymphocytes (O'Heir et al, (supra I and Wierenga et al., (supra)) Furthermore, Parronchi et al., *Proc. Natl. Acad. Sci. USA*, 88:4538–4542 (1991) found that only allergen specific clones from atopic subjects produced IL4 and IL5 and provided help for IgE synthesis, whereas tetanus toxoid-specific clines isolated from the same subject produced IL4 and IFN-$\gamma$, and were unable to provide help for IgE synthesis. Taken together, these studies suggest that T lymphocytes of atopic subjects respond to allergens differently than those of non-atopic subjects, producing a panel of lymphokines (high IL4, low IFN-γ) that favors the production of IgE (Pene et al., *Proc. Natl. Acad. Sci. USA*, 85:6880–6884 (1988). Because IL4 enhances IgE production by directing isotype switch recombination to the Cε locus (Gascan et al. *J. Eap. Med.*, 173:747–750 (1991), such a mechanism would result in an increased frequency of IgE-producing B cell precursors, and may help to account for the differences in precursor frequency observed in the studies described below. The specific genetic, regulatory, or environmental differences that underlie the distinct T cell responses to allergen in atopic and non-atopic subjects remain to be elucidated.

The frequency of B cell precursors in atopic and non-atopic subjects committed to the production of IgE, IgM and IgG was directly compared by limiting dilution analysis of EBV transformants. Although no difference was found in the IgM or IgG-producing B cell precursor frequency, the atopic subjects had a significantly higher frequency of B lymphocytes committed to the production of IgE (0.79% of total IgG-producing cells, as compared to 0.15% for the control group; p<0.005). This difference was associated with significantly greater total plasma IgE concentration in the atopic group (1.08 µg/ml) as compared to non-atopic control subjects (0.110 µg/ml)(p<0.005), suggesting that one factor contributing to the high plasma IgE titers in atopic subjects may be the increased frequency of IgE-producing B lymphocytes. The titers of allergen-specific IgE, IgM, and IgG in the plasma of atopic and non-atopic subjects were also compared. Plasma samples from 12 atopic and 12 non-atopic subjects were assayed for levels of total IgM, IgG, and IgE using specific ELISAs (direct ELISA, competitive inhibition ELISA). Although only the atopic subjects produced IgE directed against the allergy to which they were sensitive, atopic and non-atopic subjects had comparable plasma titers of IgM and IgG specific for the major house dust-mite allergens, Der p I and Der p II, or the major ragweed allergen, Amb a I. This finding was supported by the similar frequencies of allergen-specific IgM-producing B lymphocytes in the atopic and non-atopic subjects. Thus, although all exposed individuals undergo an immune response to the allergen involving the production of specific IgM and IgG, only in atopic subjects is the response extended to include specific IgE. The evidence thus indicates that the higher frequency of IgE-producing B lymphocytes and the higher titers of total IgE characteristic of allergic subjects may be indicative of a regulatory environment that favors the production of allergen-specific IgE.

EXAMPLE XVII

Determination of the Percentage of Total House Dust Mite Group I T Cell Reactivity and Patient Coverage of the Combination of Unique Der p I and Der f Peptides Synthesis of Overlapping Peptides Der p I was divided into a set of 17 overlapping peptides. Overlapping peptides and Der p I and Der f I unique peptides (i.e. DPI-21.2, DFI-23.31, DPI-26.6) were synthesized using standard Fmoc/tBoc synthetic chemistry and purified by Reverse Phase HPLC. FIG. 33 shows the unique Der p I, and Der f I peptides and FIG. 34 shows the overlapping Der p I peptides used in these studies. The peptide names are consistent througout.

T cell responses to Group I overlapping peptides and unique peptides

Peripheral blood mononuclear cells (PBMC) were purified by Ficoll-Hypaque centrifugation of 60 ml of heparinized peripheral blood from house dust mite-allergic individuals who exhibited clinical symptoms of mite allergy and who were skin test positive for house dust mite.

Figure 35:
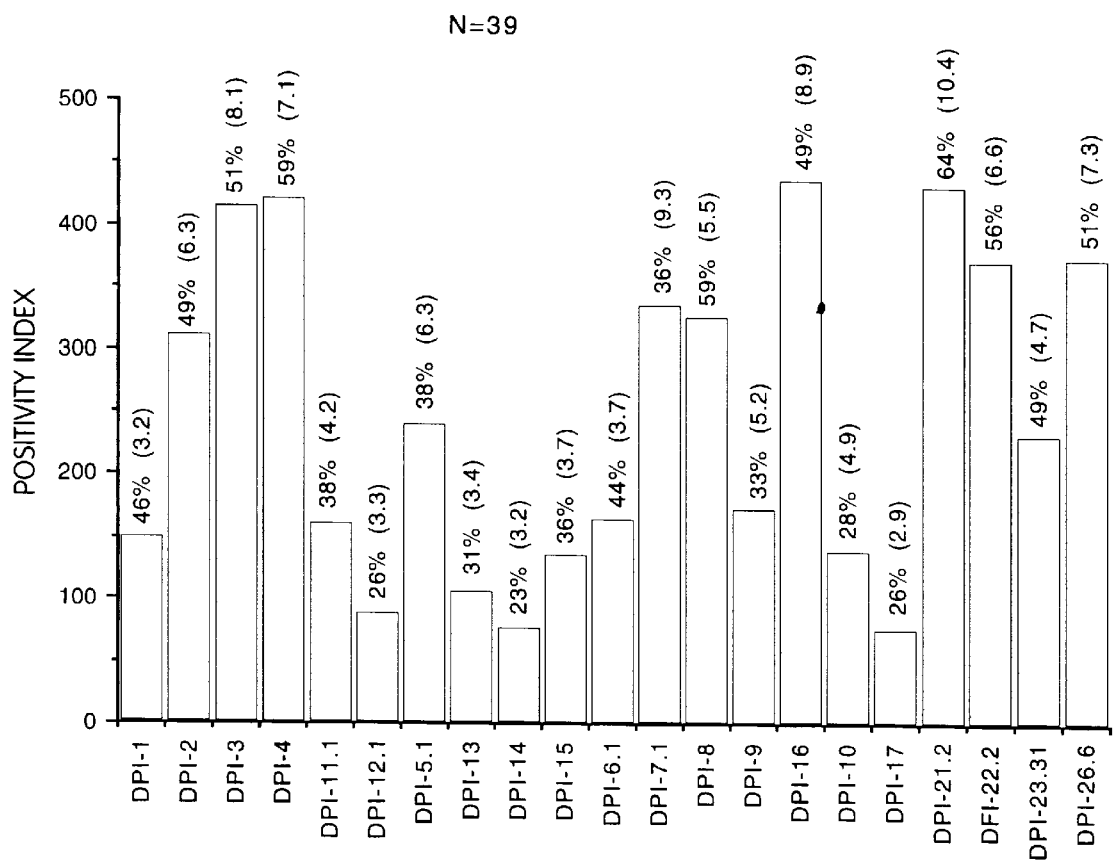
FIG. 35 is a graphic representation depicting T cell responses to the overlapping Der p I peptides shown in FIG. 2 and the Group I "unique" peptides, DPI-21.2 (SEQ. ID. NO. 28), DFI-22.2 (SEQ. ID. NO. 93), DFI-23.31(SEQ. ID. NO. 165), DFI-26.6 (SEQ. ID. NO. 168), shown in FIG. 33. The mean S.I. shown above each bar (in parenthesis) as well as the percentage of responses, the positivity index (mean S.I. multiplied by percentage of responses), is the Y axis.

$10^7$ PBMC fro each patient were cultured in 5 ml RPMI-1640 containing 5% pooled human AB serum and supplemented with glutamine, penicillin, streptomycin and HEPES buffer in the presence of 20 µg/ml purified native Der p I/ml at 37° C. for 6 days. Viable cells were then purified by Ficoll-Hypaque entriguation and cultured for 2–3 additional weeks in RPMI-1640/5% AB serum containing 5 units recombinant human IL-2/ml and 5 units recombinant human IL4/ml. The resting T cells were then tested in a secondary proliferation assay to assess T cell responses to purified native Der p I, overlapping peptides and unique peptides. For assay, $2\times10^4$ resting T cells were cultured in 200 µl of RPMI-1640/5% AB serum for 3 days at 37° C. in the presence of $2\times10^4$ autologous Epstein-Barr virus transformed B cells (20,000 Rads) or in the presence of $5\times10^4$ PBMC (3500 Rads) as antigen presenting cells with various concentrations of purified native Der p I or synthetic Der p I unique or peptide or overlapping peptides. Each well then received 1 µCi tritiated thymidine for 16 hours. The counts incorporated were collected onto glass fiber filters and processed for liquid scintillation counting. Medium alone, acting as negative control, contained no allergen or peptide. The results are shown in FIG. 35. The highest stimulation index greater than or equal to 2.0 in response to each peptide was recorded for each subject tested. The data were then analyzed by the equations described earlier in the specification.

The combination of Group I candidate peptides DPI-21.2, DFI-22.2, DPI-23.31, DPI-26.6 had a range of T cell reactivity of about 38–67& based on an analysis of 39 patients, the frequency of response at 82% represents reactivity to at least one of the candidate peptides, indicating that this combination of peptides fits the first criteria for "unique" peptides of the invention in that the combination of peptides DPI-21.2, DFI-22.2, DPI-23.31, DPI-26.6 comprise a sufficient percentage of the total T cell reactivity to Group I protein allergens from Der p and Der f in a substantial percentage of the population tested.

EXAMPLE XVIII

Determination of the Percentage of Total House Dust Mite Group II T Cell Reactivity and Patient Coverage of the Combination of Unique Der p II Candidate Peptides Synthesis of Overlapping Peptides Der p II was divided into a set of 9 overlapping peptides. Overlapping Der p II peptides and Der p II unique peptides (i.e. DPII-20.9 (SEQ. ID. NO. 169), DPII-22.14 (SEQ. ID. NO. 180), and DPII-25.15 (SEQ. ID. NO. 188)) were synthesized using standard Fmoc/tBoc synthetic chemistry and purified by Reverse Phase HPLC. FIG. 33 shows the unique Der p II peptides and FIG. 34 shows the overlapping Der p II peptides used in these studies. The peptide names are consistent throughout.

T cell responses to Group II overlapping peptides and unique candidate peptides

Secondary Der p II reactive T cell cultures derived from 30 mite-allergic patients were analyzed for reactivity to an overlapping set of Der p II peptides and Der p II candidate peptides in an in vitro T cell proliferation assay as described in Example XVII. The results are shown in FIG. 36. The highest stimulation index greater than or equal to 2.0 in response to each peptide was recorded for each subject tested. The data were then analyzed by the equations described earlier in the specification.

The combination of candidate peptides DPII-20.9 (SEQ. ID. NO. 169), DPII-22.14 (SEQ. ID. NO. 180), and DPII-25.15 (SEQ. ID. NO. 188), had a range of T cell reactivity of about 36%–51% based on an analysis of 30 patients (FIG. 36). The frequency of response to at least one of the candidate peptides was about 63%, indicating that this combination of peptides fits the first criteria for "unique" peptides of the invention, in that the combination of Der p II peptides DPII-20.9 (SEQ. ID. NO. 169), DPII-22.14 (SEQ. ID. NO. 180), and DPII-25.15 (SEQ. ID. NO. 188), comprise a sufficient percentage of the total T cell reactivity to Der p II in a substantial percentage of the population tested.

EXAMPLE XIX

Determination of pH-solubility and pH-stability Profiles of Candidate Peptides of the Invention 1. Buffer Preparation 50 mM sodium phosphate stock solutions:

Stock solution A: 0.66 g (0.05 mol) of monobasic sodium phosphate monohydrate U.S.P. and 50 mg EDTA disodium dihydrate, U.S.P. were dissolved in 100 mL of WFI. The solution was filtered through a 0.2 micron filter Stock solution B: 0.71 g (0.05 mol) of dibasic sodium phosphate U.S.P. were disolved in 100 ml WFI. The solution was filtered through a 0.2 micron filter.

2. Initial peptide dispersions

Dispersion A: 3.0 mg of each candidate peptide,DPI-21.2 (SEQ. ID. NO. 28), DFI-22.2 (SEQ. ID. NO. 93), DFI-23.31 (SEQ. ID. NO. 165), DFI-26.6 (SEQ. ID. NO. 168), DPII-20.9 (SEQ. ID. NO. 169), DPII-22.14 (SEQ. ID. NO. 180) and DPII-25.15 (SEQ. ID. NO. 188), was weighed out separately and placed in separate 1.5 mL eppendoff vials with 600 μL of stock solution A. The composition was agitated for 1 seconds to mix well.

Dispersion B: 3.0 mg of each peptide, DPI-21.2 (SEQ. ID. NO. 28), DFI-22.2 (SEQ. ID. NO. 93), DFI-23.31(SEQ. ID. NO. 165), DFI-26.6 (SEQ. ID. NO. 168), DPII-20.9 (SEQ. ID. NO. 169), DPII-22.14 (SEQ. ID. NO. 180) and DPII-25.15 (SEQ. ID. NO. 188), was weighed out separately and placed in separate 1.5 mL eppendoff vials with 600 μL of stock solution B. The mixture was agitated for 5 seconds to mix well.

Dispersions A and B were sonicated for 2 minutes for good homogeneity. A small volume was pipetted from each dispersion into a labeled eppendoff vial according to the following volume ratio:

| Vial # | Suspension A (μL) | Suspension B (μL) | Total Volume (μL) | Estimated final pH |
|---|---|---|---|---|
| 1 | 100 | 0 | 100 | 5.2 |
| 2 | 80 | 20 | 100 | 6.2 |
| 3 | 60 | 40 | 100 | 6.6 |
| 4 | 40 | 60 | 100 | 6.8 |
| 5 | 20 | 80 | 100 | 7.1 |
| 6 | 0 | 100 | 100 | 8.0 |

The resultant solutions/suspensions were stored in the dark at about 22° C.±2 for 24 hours without agitation. The solutions were filtered and filtrates were analyzed for pH and peptide concentration.

The concentration of filtered peptide solutions was determined by HPLC analysis. In this experiment, the solubility of peptide at each pH is defined as the amount of peptide remaining in solution after filtration through a membrane filter having a 0.2 micrometer pore size. The extent of degradation of peptides was estimated by calculating the percent of total degradant peak area over the total peak area.

The pH values with respect to the solubility values was plotted and are shown in FIG. 37 for each respective peptide. As shown in the solubility curve for each peptide as represented in FIG. 37, peptides DPI-21.2 (SEQ. ID. NO. 28), DFI-22.2 (SEQ. ID. NO. 93), DFI-23.31 (SEQ. ID. NO. 165), DFI-26.6 (SEQ. ID. NO. 168), DPII-20.9 (SEQ. ID. NO. 169), DPII-22.14 (SEQ. ID. NO. 180) and DPII-25.15 (SEQ. ID. NO. 188) are each soluble at greater than 3 mg/ml at a pH in the pH range of pH 6 to pH 8.

Figure 38:
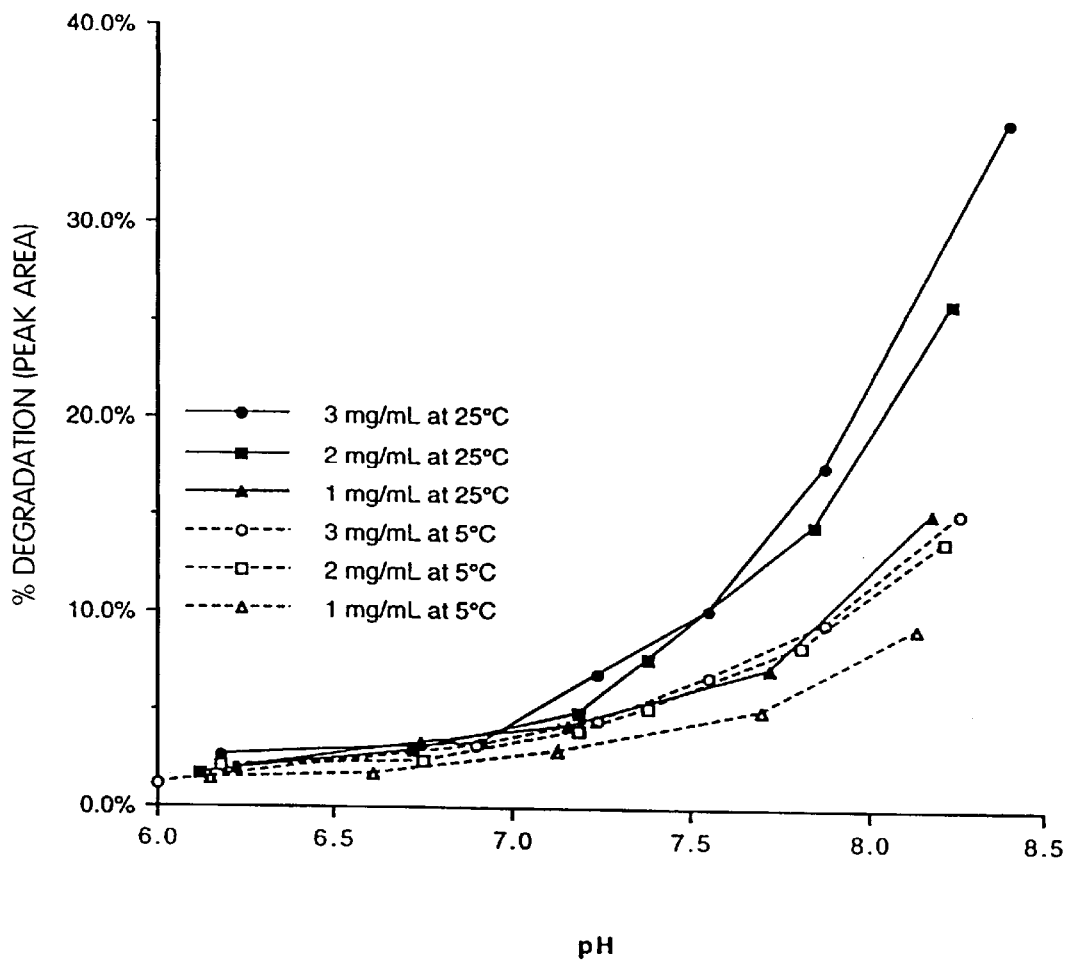
FIG. 38 is a pH-stability profile of candidate peptides DPI-21.2 (SEQ. ID. NO. 28), DFI-22.2 (SEQ. ID. NO. 93), DFI-23.31(SEQ. ID. NO. 165), DFI-26.6 (SEQ. ID. NO. 168), DPII-20.9 (SEQ. ID. NO. 169), DPII-22.14 (SEQ. ID. NO. 180) and DPII-25.15 (SEQ. ID. NO. 188) in an equal concentration combination. Degradation of peptide is calculated as % degradation (determined by peak area using HPLC analysis) of peptide observed after 24 hours at about 22° C. ±2 and about 5° C., at various theoretical concentrations of 3.0, 2.0 and 1.0 mg/ml of peptide over a pH range of 6.0 to 8.5.

The pH-stability profiles for each peptide DPI-21.2 (SEQ. ID. NO. 28), DFI-22.2 (SEQ. ID. NO. 93), DFI-23.31(SEQ. ID. NO. 165), DFI-26.6 (SEQ. ID. NO. 168), DPII-20.9 (SEQ. ID. NO. 169), DPII-22.14 (SEQ. ID. NO. 180) and DPII-25.15 (SEQ. ID. NO. 188) in equal concentration combination at 3, 2, and 1 mg/ml per peptide and prepared in duplicate as described above with one set stored at about 5° C. for 24 hours and one set stored at about 22° C.±2 for 24 hours, were calculated and tabulated as a function of the percentage of total of degradant peak area (FIG. 38). As can be seen from the data in FIG. 38, the percent degradation of peptide at each concentration was less for peptides stored at about 5° C. for 24 hours as compared to peptides stored at 22° C.±2 for 24 hours over the critical pH range of pH 6.0 to pH 8.0. However, acceptable solution stability is demonstrated for all the peptides in a common "window" within the pH range of pH 6 to pH 8 at either temperature.

Therefore, each of peptides DPI-21.2 (SEQ. ID. NO. 28), DFI-22.2 (SEQ. ID. NO. 93), DFI-23.31(SEQ. ID. NO. 165), DFI-26.6 (SEQ. ID. NO. 168), DPII-20.9 (SEQ. ID. NO. 169), DPII-22.14 (SEQ. ID. NO. 180) and DPII-25.15 (SEQ. ID. NO. 188) was determined to possess the appropriate solubility and stability required of a unique peptide of the invention.

Although the invention has been described with reference to its preferred embodiments, other embodiments can achieve the same results. Variations and modifications to the present invention will be obvious to those skilled in the art and is intended to cover in the appended claims all such modifications and equivalents that follow in the true spirit and scope of the invention.

SEQUENCE LISTING (1) GENERAL INFORMATION:

(iii) NUMBER OF SEQUENCES: 207

(2) INFORMATION FOR SEQ ID NO:1:

(i) SEQUENCE CHARACTERISTICS:
      (A) LENGTH: 834 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 1..738

(xi) SEQUENCE DESCRIPTION: SEQ ID NO:1:

```
AAA AAC CGA TTT TTG ATG AGT GCA GAA GCT TTT GAA CAC CTC AAA ACT        48
Lys Asn Arg Phe Leu Met Ser Ala Glu Ala Phe Glu His Leu Lys Thr
 1               5                  10                  15

CAA TTC GAT TTG AAT GCT GAA ACT AAC GCC TGC AGT ATC AAT GGA AAT        96
Gln Phe Asp Leu Asn Ala Glu Thr Asn Ala Cys Ser Ile Asn Gly Asn
             20                  25                  30

GCT CCA GCT GAA ATC GAT TTG CGA CAA ATG CGA ACT GTC ACT CCC ATT       144
Ala Pro Ala Glu Ile Asp Leu Arg Gln Met Arg Thr Val Thr Pro Ile
         35                  40                  45

CGT ATG CAA GGA GGC TGT GGT TCA TGT TGG GCT TTC TCT GGT GTT GCC       192
Arg Met Gln Gly Gly Cys Gly Ser Cys Trp Ala Phe Ser Gly Val Ala
     50                  55                  60

GCA ACT GAA TCA GCT TAT TTG GCT CAC CGT AAT CAA TCA TTG GAT CTT       240
Ala Thr Glu Ser Ala Tyr Leu Ala His Arg Asn Gln Ser Leu Asp Leu
 65                  70                  75                  80

GCT GAA CAA GAA TTA GTC GAT TGT GCT TCC CAA CAC GGT TGT CAT GGT       288
Ala Glu Gln Glu Leu Val Asp Cys Ala Ser Gln His Gly Cys His Gly
                 85                  90                  95

GAT ACC ATT CCA CGT GGT ATT GAA TAC ATC CAA CAT AAT GGT GTC GTC       336
Asp Thr Ile Pro Arg Gly Ile Glu Tyr Ile Gln His Asn Gly Val Val
            100                 105                 110

CAA GAA AGC TAC TAT CGA TAC GTT GCA CGA GAA CAA TCA TGC CGA CGA       384
Gln Glu Ser Tyr Tyr Arg Tyr Val Ala Arg Glu Gln Ser Cys Arg Arg
        115                 120                 125

CCA AAT GCA CAA CGT TTC GGT ATC TCA AAC TAT TGC CAA ATT TAC CCA       432
Pro Asn Ala Gln Arg Phe Gly Ile Ser Asn Tyr Cys Gln Ile Tyr Pro
    130                 135                 140

CCA AAT GCA AAC AAA ATT CGT GAA GCT TTG GCT CAA ACC CAC AGC GCT       480
Pro Asn Ala Asn Lys Ile Arg Glu Ala Leu Ala Gln Thr His Ser Ala
145                 150                 155                 160

ATT GCC GTC ATT ATT GGC ATC AAA GAT TTA GAC GCA TTC CGT CAT TAT       528
Ile Ala Val Ile Ile Gly Ile Lys Asp Leu Asp Ala Phe Arg His Tyr
                165                 170                 175

GAT GGC CGA ACA ATC ATT CAA CGC GAT AAT GGT TAC CAA CCA AAC TAT       576
Asp Gly Arg Thr Ile Ile Gln Arg Asp Asn Gly Tyr Gln Pro Asn Tyr
            180                 185                 190

CAC GCT GTC AAC ATT GTT GGT TAC AGT AAC GCA CAA GGT GTC GAT TAT       624
His Ala Val Asn Ile Val Gly Tyr Ser Asn Ala Gln Gly Val Asp Tyr
        195                 200                 205

TGG ATC GTA CGA AAC AGT TGG GAT ACC AAT TGG GGT GAT AAT GGT TAC       672
Trp Ile Val Arg Asn Ser Trp Asp Thr Asn Trp Gly Asp Asn Gly Tyr
    210                 215                 220
```

```
GGT TAT TTT GCT GCC AAC ATC GAT TTG ATG ATG ATT GAA GAA TAT CCA      720
Gly Tyr Phe Ala Ala Asn Ile Asp Leu Met Met Ile Glu Glu Tyr Pro
225                 230                 235                 240

TAT GTT GTC ATT CTC TAAACAAAAA GACAATTTCT TATATGATTG TCACTAATTT      775
Tyr Val Val Ile Leu
            245

ATTTAAAATC AAAATTTTTT AGAAAATGAA TAAATTCATT CACAAAAATT AAAAAAAA      834
```

(2) INFORMATION FOR SEQ ID NO:2:

(i) SEQUENCE CHARACTERISTICS:
        (A) LENGTH: 245 amino acids
        (B) TYPE: amino acid
        (D) TOPOLOGY: linear (ii) MOLECULE TYPE: protein (xi) SEQUENCE DESCRIPTION: SEQ ID NO:2:

```
Lys Asn Arg Phe Leu Met Ser Ala Glu Ala Phe Glu His Leu Lys Thr
 1               5                  10                  15

Gln Phe Asp Leu Asn Ala Glu Thr Asn Ala Cys Ser Ile Asn Gly Asn
            20                  25                  30

Ala Pro Ala Glu Ile Asp Leu Arg Gln Met Arg Thr Val Thr Pro Ile
        35                  40                  45

Arg Met Gln Gly Gly Cys Gly Ser Cys Trp Ala Phe Ser Gly Val Ala
 50                  55                  60

Ala Thr Glu Ser Ala Tyr Leu Ala His Arg Asn Gln Ser Leu Asp Leu
 65                  70                  75                  80

Ala Glu Gln Glu Leu Val Asp Cys Ala Ser Gln His Gly Cys His Gly
                85                  90                  95

Asp Thr Ile Pro Arg Gly Ile Glu Tyr Ile Gln His Asn Gly Val Val
            100                 105                 110

Gln Glu Ser Tyr Tyr Arg Tyr Val Ala Arg Glu Gln Ser Cys Arg Arg
        115                 120                 125

Pro Asn Ala Gln Arg Phe Gly Ile Ser Asn Tyr Cys Gln Ile Tyr Pro
    130                 135                 140

Pro Asn Ala Asn Lys Ile Arg Glu Ala Leu Ala Gln Thr His Ser Ala
145                 150                 155                 160

Ile Ala Val Ile Ile Gly Ile Lys Asp Leu Asp Ala Phe Arg His Tyr
                165                 170                 175

Asp Gly Arg Thr Ile Ile Gln Arg Asp Asn Gly Tyr Gln Pro Asn Tyr
            180                 185                 190

His Ala Val Asn Ile Val Gly Tyr Ser Asn Ala Gln Gly Val Asp Tyr
        195                 200                 205

Trp Ile Val Arg Asn Ser Trp Asp Thr Asn Trp Gly Asp Asn Gly Tyr
    210                 215                 220

Gly Tyr Phe Ala Ala Asn Ile Asp Leu Met Met Ile Glu Glu Tyr Pro
225                 230                 235                 240

Tyr Val Val Ile Leu
            245
```

(2) INFORMATION FOR SEQ ID NO:3:

(i) SEQUENCE CHARACTERISTICS:
        (A) LENGTH: 588 base pairs
        (B) TYPE: nucleic acid
        (C) STRANDEDNESS: single
        (D) TOPOLOGY: linear (ii) MOLECULE TYPE: cDNA (ix) FEATURE:
  (A) NAME/KEY: CDS
  (B) LOCATION: 69..509

(xi) SEQUENCE DESCRIPTION: SEQ ID NO:3:

```
CACAAATTCT TCTTTCTTCC TTACTACTGA TCATTAATCT GAAAACAAAA CCAAACAAAC        60

CATTCAAA ATG ATG TAC AAA ATT TTG TGT CTT TCA TTG TTG GTC GCA GCC       110
         Met Met Tyr Lys Ile Leu Cys Leu Ser Leu Leu Val Ala Ala
           1               5                  10

GTT GCT CGT GAT CAA GTC GAT GTC AAA GAT TGT GCC AAT CAT GAA ATC        158
Val Ala Arg Asp Gln Val Asp Val Lys Asp Cys Ala Asn His Glu Ile
 15              20                  25                  30

AAA AAA GTT TTG GTA CCA GGA TGC CAT GGT TCA GAA CCA TGT ATC ATT        206
Lys Lys Val Leu Val Pro Gly Cys His Gly Ser Glu Pro Cys Ile Ile
             35                  40                  45

CAT CGT GGT AAA CCA TTC CAA TTG GAA GCC GTT TTC GAA GCC AAC CAA        254
His Arg Gly Lys Pro Phe Gln Leu Glu Ala Val Phe Glu Ala Asn Gln
         50                  55                  60

AAC ACA AAA ACG GCT AAA ATT GAA ATC AAA GCC TCA ATC GAT GGT TTA        302
Asn Thr Lys Thr Ala Lys Ile Glu Ile Lys Ala Ser Ile Asp Gly Leu
     65                  70                  75

GAA GTT GAT GTT CCC GGT ATC GAT CCA AAT GCA TGC CAT TAC ATG AAA        350
Glu Val Asp Val Pro Gly Ile Asp Pro Asn Ala Cys His Tyr Met Lys
 80                  85                  90

TGC CCA TTG GTT AAA GGA CAA CAA TAT GAT ATT AAA TAT ACA TGG AAT        398
Cys Pro Leu Val Lys Gly Gln Gln Tyr Asp Ile Lys Tyr Thr Trp Asn
 95                 100                 105                 110

GTT CCG AAA ATT GCA CCA AAA TCT GAA AAT GTT GTC GTC ACT GTT AAA        446
Val Pro Lys Ile Ala Pro Lys Ser Glu Asn Val Val Val Thr Val Lys
             115                 120                 125

GTT ATG GGT GAT GAT GGT GTT TTG GCC TGT GCT ATT GCT ACT CAT GCT        494
Val Met Gly Asp Asp Gly Val Leu Ala Cys Ala Ile Ala Thr His Ala
         130                 135                 140

AAA ATC CGC GAT TAAATAAACA AAATTTATTG ATTTTGTAAT CACAAATGAT            546
Lys Ile Arg Asp
        145

TGATTTTCTT TCCAAAAAAA AAATAAATAA AATTTTGGGA AT                         588
```

(2) INFORMATION FOR SEQ ID NO:4:

(i) SEQUENCE CHARACTERISTICS:
    (A) LENGTH: 146 amino acids
    (B) TYPE: amino acid
    (D) TOPOLOGY: linear (ii) MOLECULE TYPE: protein (xi) SEQUENCE DESCRIPTION: SEQ ID NO:4:

```
Met Met Tyr Lys Ile Leu Cys Leu Ser Leu Leu Val Ala Ala Val Ala
  1               5                  10                  15

Arg Asp Gln Val Asp Val Lys Asp Cys Ala Asn His Glu Ile Lys Lys
             20                  25                  30

Val Leu Val Pro Gly Cys His Gly Ser Glu Pro Cys Ile Ile His Arg
         35                  40                  45

Gly Lys Pro Phe Gln Leu Glu Ala Val Phe Glu Ala Asn Gln Asn Thr
     50                  55                  60

Lys Thr Ala Lys Ile Glu Ile Lys Ala Ser Ile Asp Gly Leu Glu Val
 65                  70                  75                  80

Asp Val Pro Gly Ile Asp Pro Asn Ala Cys His Tyr Met Lys Cys Pro
                 85                  90                  95
```

```
Leu Val Lys Gly Gln Gln Tyr Asp Ile Lys Tyr Thr Trp Asn Val Pro
            100                 105                 110
Lys Ile Ala Pro Lys Ser Glu Asn Val Val Thr Val Lys Val Met
        115                 120                 125
Gly Asp Asp Gly Val Leu Ala Cys Ala Ile Ala Thr His Ala Lys Ile
130                 135                 140
Arg Asp
145
```

(2) INFORMATION FOR SEQ ID NO:5:

(i) SEQUENCE CHARACTERISTICS:
        (A) LENGTH: 1072 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 36..1001

(xi) SEQUENCE DESCRIPTION: SEQ ID NO:5:

```
CGTTTTCTTC CATCAAAATT AAAAATTCAT CAAAA ATG AAA TTC GTT TTG GCC        53
                                       Met Lys Phe Val Leu Ala
                                        1               5

ATT GCC TCT TTG TTG GTA TTG AGC ACT GTT TAT GCT CGT CCA GCT TCA      101
Ile Ala Ser Leu Leu Val Leu Ser Thr Val Tyr Ala Arg Pro Ala Ser
            10                  15                  20

ATC AAA ACT TTT GAA GAA TTC AAA AAA GCC TTC AAC AAA AAC TAT GCC      149
Ile Lys Thr Phe Glu Glu Phe Lys Lys Ala Phe Asn Lys Asn Tyr Ala
        25                  30                  35

ACC GTT GAA GAG GAA GAA GTT GCC CGT AAA AAC TTT TTG GAA TCA TTG      197
Thr Val Glu Glu Glu Glu Val Ala Arg Lys Asn Phe Leu Glu Ser Leu
    40                  45                  50

AAA TAT GTT GAA GCT AAC AAA GGT GCC ATC AAC CAT TTG TCC GAT TTG      245
Lys Tyr Val Glu Ala Asn Lys Gly Ala Ile Asn His Leu Ser Asp Leu
55                  60                  65                  70

TCA TTG GAT GAA TTC AAA AAC CGT TAT TTG ATG AGT GCT GAA GCT TTT      293
Ser Leu Asp Glu Phe Lys Asn Arg Tyr Leu Met Ser Ala Glu Ala Phe
                75                  80                  85

GAA CAA CTC AAA ACT CAA TTC GAT TTG AAT GCC GAA ACA AGC GCT TGC      341
Glu Gln Leu Lys Thr Gln Phe Asp Leu Asn Ala Glu Thr Ser Ala Cys
            90                  95                 100

CGT ATC AAT TCG GTT AAC GTT CCA TCG GAA TTG GAT TTA CGA TCA CTG      389
Arg Ile Asn Ser Val Asn Val Pro Ser Glu Leu Asp Leu Arg Ser Leu
        105                 110                 115

CGA ACT GTC ACT CCA ATC CGT ATG CAA GGA GGC TGT GGT TCA TGT TGG      437
Arg Thr Val Thr Pro Ile Arg Met Gln Gly Gly Cys Gly Ser Cys Trp
    120                 125                 130

GCT TTC TCT GGT GTT GCC GCA ACT GAA TCA GCT TAT TTG GCC TAC CGT      485
Ala Phe Ser Gly Val Ala Ala Thr Glu Ser Ala Tyr Leu Ala Tyr Arg
135                 140                 145                 150

AAC ACG TCT TTG GAT CTT TCT GAA CAG GAA CTC GTC GAT TGC GCA TCT      533
Asn Thr Ser Leu Asp Leu Ser Glu Gln Glu Leu Val Asp Cys Ala Ser
                155                 160                 165

CAA CAC GGA TGT CAC GGC GAT ACA ATA CCA AGA GGC ATC GAA TAC ATC      581
Gln His Gly Cys His Gly Asp Thr Ile Pro Arg Gly Ile Glu Tyr Ile
            170                 175                 180
```

```
CAA CAA AAT GGT GTC GTT GAA GAA AGA AGC TAT CCA TAC GTT GCA CGA      629
Gln Gln Asn Gly Val Val Glu Glu Arg Ser Tyr Pro Tyr Val Ala Arg
        185                 190                 195

GAA CAA CGA TGC CGA CGA CCA AAT TCG CAA CAT TAC GGT ATC TCA AAC      677
Glu Gln Arg Cys Arg Arg Pro Asn Ser Gln His Tyr Gly Ile Ser Asn
200                 205                 210

TAC TGC CAA ATT TAT CCA CCA GAT GTG AAA CAA ATC CGT GAA GCT TTG      725
Tyr Cys Gln Ile Tyr Pro Pro Asp Val Lys Gln Ile Arg Glu Ala Leu
215                 220                 225                 230

ACT CAA ACA CAC ACA GCT ATT GCC GTC ATT ATT GGC ATC AAA GAT TTG      773
Thr Gln Thr His Thr Ala Ile Ala Val Ile Ile Gly Ile Lys Asp Leu
                235                 240                 245

AGA GCT TTC CAA CAT TAT GAT GGA CGA ACA ATC ATT CAA CAT GAC AAT      821
Arg Ala Phe Gln His Tyr Asp Gly Arg Thr Ile Ile Gln His Asp Asn
        250                 255                 260

GGT TAT CAA CCA AAC TAT CAT GCC GTC AAC ATT GTC GGT TAC GGA AGT      869
Gly Tyr Gln Pro Asn Tyr His Ala Val Asn Ile Val Gly Tyr Gly Ser
            265                 270                 275

ACA CAA GGC GAC GAT TAT TGG ATC GTA CGA AAC AGT TGG GAT ACT ACC      917
Thr Gln Gly Asp Asp Tyr Trp Ile Val Arg Asn Ser Trp Asp Thr Thr
280                 285                 290

TGG GGA GAT AGC GGA TAC GGA TAT TTC CAA GCC GGA AAC AAC CTC ATG      965
Trp Gly Asp Ser Gly Tyr Gly Tyr Phe Gln Ala Gly Asn Asn Leu Met
295                 300                 305                 310

ATG ATC GAA CAA TAT CCA TAT GTT GTA ATC ATG TGAACATTTG AAATTGAATA   1018
Met Ile Glu Gln Tyr Pro Tyr Val Val Ile Met
                315                 320

TATTTATTTG TTTTCAAAAT AAAAACAACT ACTCTTGCGA GTATTTTTTA CTCG         1072

(2) INFORMATION FOR SEQ ID NO:6:

(i) SEQUENCE CHARACTERISTICS:
        (A) LENGTH: 321 amino acids
        (B) TYPE: amino acid
        (D) TOPOLOGY: linear (ii) MOLECULE TYPE: protein (xi) SEQUENCE DESCRIPTION: SEQ ID NO:6:

Met Lys Phe Val Leu Ala Ile Ala Ser Leu Leu Val Leu Ser Thr Val
1               5                   10                  15

Tyr Ala Arg Pro Ala Ser Ile Lys Thr Phe Glu Glu Phe Lys Lys Ala
                20                  25                  30

Phe Asn Lys Asn Tyr Ala Thr Val Glu Glu Glu Val Ala Arg Lys
            35                  40                  45

Asn Phe Leu Glu Ser Leu Lys Tyr Val Glu Ala Asn Lys Gly Ala Ile
    50                  55                  60

Asn His Leu Ser Asp Leu Ser Leu Asp Glu Phe Lys Asn Arg Tyr Leu
65                  70                  75                  80

Met Ser Ala Glu Ala Phe Glu Gln Leu Lys Thr Gln Phe Asp Leu Asn
                85                  90                  95

Ala Glu Thr Ser Ala Cys Arg Ile Asn Ser Val Asn Val Pro Ser Glu
            100                 105                 110

Leu Asp Leu Arg Ser Leu Arg Thr Val Thr Pro Ile Arg Met Gln Gly
        115                 120                 125

Gly Cys Gly Ser Cys Trp Ala Phe Ser Gly Val Ala Ala Thr Glu Ser
    130                 135                 140

Ala Tyr Leu Ala Tyr Arg Asn Thr Ser Leu Asp Leu Ser Glu Gln Glu
145                 150                 155                 160
```

```
Leu Val Asp Cys Ala Ser Gln His Gly Cys His Gly Asp Thr Ile Pro
                165                 170                 175

Arg Gly Ile Glu Tyr Ile Gln Gln Asn Gly Val Val Glu Glu Arg Ser
                180                 185                 190

Tyr Pro Tyr Val Ala Arg Glu Gln Arg Cys Arg Arg Pro Asn Ser Gln
            195                 200                 205

His Tyr Gly Ile Ser Asn Tyr Cys Gln Ile Tyr Pro Pro Asp Val Lys
            210                 215                 220

Gln Ile Arg Glu Ala Leu Thr Gln Thr His Thr Ala Ile Ala Val Ile
225                 230                 235                 240

Ile Gly Ile Lys Asp Leu Arg Ala Phe Gln His Tyr Asp Gly Arg Thr
                245                 250                 255

Ile Ile Gln His Asp Asn Gly Tyr Gln Pro Asn Tyr His Ala Val Asn
                260                 265                 270

Ile Val Gly Tyr Gly Ser Thr Gln Gly Asp Asp Tyr Trp Ile Val Arg
                275                 280                 285

Asn Ser Trp Asp Thr Thr Trp Gly Asp Ser Gly Tyr Gly Tyr Phe Gln
                290                 295                 300

Ala Gly Asn Asn Leu Met Met Ile Glu Gln Tyr Pro Tyr Val Val Ile
305                 310                 315                 320

Met
```

(2) INFORMATION FOR SEQ ID NO:7:

(i) SEQUENCE CHARACTERISTICS:
        (A) LENGTH: 491 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..390

(xi) SEQUENCE DESCRIPTION: SEQ ID NO:7:

```
GAT CAA GTC GAT GTT AAA GAT TGT GCC AAC AAT GAA ATC AAA AAA GTA      48
Asp Gln Val Asp Val Lys Asp Cys Ala Asn Asn Glu Ile Lys Lys Val
 1               5                  10                  15

ATG GTC GAT GGT TGC CAT GGT TCT GAT CCA TGC ATA ATC CAT CGT GGT      96
Met Val Asp Gly Cys His Gly Ser Asp Pro Cys Ile Ile His Arg Gly
            20                  25                  30

AAA CCA TTC ACT TTG GAA GCC TTA TTC GAT GCC AAC CAA AAC ACT AAA     144
Lys Pro Phe Thr Leu Glu Ala Leu Phe Asp Ala Asn Gln Asn Thr Lys
        35                  40                  45

ACC GCT AAA ACT GAA ATC AAA GCC AGC CTC GAT GGT CTT GAA ATT GAT     192
Thr Ala Lys Thr Glu Ile Lys Ala Ser Leu Asp Gly Leu Glu Ile Asp
    50                  55                  60

GTT CCC GGT ATT GAT ACC AAT GCT TGC CAT TTT ATG AAA TGT CCA TTG     240
Val Pro Gly Ile Asp Thr Asn Ala Cys His Phe Met Lys Cys Pro Leu
65                  70                  75                  80

GTT AAA GGT CAA CAA TAT GAT GCC AAA TAT ACA TGG AAT GTG CCC AAA     288
Val Lys Gly Gln Gln Tyr Asp Ala Lys Tyr Thr Trp Asn Val Pro Lys
                85                  90                  95

ATT GCA CCA AAA TCT GAA AAC GTT GTC GTT ACA GTC AAA CTT GTT GGT     336
Ile Ala Pro Lys Ser Glu Asn Val Val Val Thr Val Lys Leu Val Gly
            100                 105                 110

GAT AAT GGT GTT TTG GCT TGC GCT ATT GCT ACC CAC GCT AAA ATC CGT     384
Asp Asn Gly Val Leu Ala Cys Ala Ile Ala Thr His Ala Lys Ile Arg
        115                 120                 125
```

```
GAT TAAAAAAAAA AAATAAATAT GAAAATTTTC ACCAACATCG AACAAAATTC      437
Asp
    130

AATAACCAAA ATTTGAATCA AAAACGGAAT TCCAAGCTGA GCGCCGGTCG CTAC     491
```

(2) INFORMATION FOR SEQ ID NO:8:

(i) SEQUENCE CHARACTERISTICS:
        (A) LENGTH: 129 amino acids
        (B) TYPE: amino acid
        (D) TOPOLOGY: linear (ii) MOLECULE TYPE: protein (xi) SEQUENCE DESCRIPTION: SEQ ID NO:8:

```
Asp Gln Val Asp Val Lys Asp Cys Ala Asn Asn Glu Ile Lys Lys Val
 1               5                  10                  15

Met Val Asp Gly Cys His Gly Ser Asp Pro Cys Ile Ile His Arg Gly
            20                  25                  30

Lys Pro Phe Thr Leu Glu Ala Leu Phe Asp Ala Asn Gln Asn Thr Lys
        35                  40                  45

Thr Ala Lys Thr Glu Ile Lys Ala Ser Leu Asp Gly Leu Glu Ile Asp
    50                  55                  60

Val Pro Gly Ile Asp Thr Asn Ala Cys His Phe Met Lys Cys Pro Leu
65                  70                  75                  80

Val Lys Gly Gln Gln Tyr Asp Ala Lys Tyr Thr Trp Asn Val Pro Lys
                85                  90                  95

Ile Ala Pro Lys Ser Glu Asn Val Val Val Thr Val Lys Leu Val Gly
            100                 105                 110

Asp Asn Gly Val Leu Ala Cys Ala Ile Ala Thr His Ala Lys Ile Arg
        115                 120                 125

Asp
```

(2) INFORMATION FOR SEQ ID NO:9:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:9:

```
Thr Asn Ala Cys Ser Ile Asn Gly Asn Ala Pro Ala Glu Ile Asp Leu
 1               5                  10                  15

Arg Gln Met Arg
            20
```

(2) INFORMATION FOR SEQ ID NO:10:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:10:

Glu Ile Asp Leu Arg Gln Met Arg Thr Val Thr Pro Ile Arg Met Gln
1               5                   10                  15

Gly Gly Cys Gly Ser Cys Trp Ala Phe Ser Gly
            20                  25

(2) INFORMATION FOR SEQ ID NO:11:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:11:

Thr Val Thr Pro Ile Arg Met Gln Gly Gly Cys Gly Ser Cys Trp Ala
1               5                   10                  15

Phe Ser Gly Val Ala Ala Thr Glu Ser Ala Tyr Leu Ala
            20                  25

(2) INFORMATION FOR SEQ ID NO:12:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:12:

Val Ala Ala Thr Glu Ser Ala Tyr Leu Ala His Arg Asn Gln Ser Leu
1               5                   10                  15

Asp Leu Ala Glu Gln
            20

(2) INFORMATION FOR SEQ ID NO:13:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:13:

His Arg Asn Gln Ser Leu Asp Leu Ala Glu Gln Glu Leu Val Asp Cys
1               5                   10                  15

Ala Ser Gln His Gly Cys
            20

(2) INFORMATION FOR SEQ ID NO:14:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:14:

```
Glu Leu Val Asp Cys Ala Ser Gln His Gly Cys His Gly Asp Thr Ile
1               5                   10                  15
Pro Arg Gly Ile Glu
                20
```

(2) INFORMATION FOR SEQ ID NO:15:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:15:

```
Gly Asp Thr Ile Pro Arg Gly Ile Glu Tyr Ile Gln His Asn Gly Val
1               5                   10                  15
Val Gln Glu Ser Tyr Tyr Arg Tyr Val Ala Arg Glu
                20                  25
```

(2) INFORMATION FOR SEQ ID NO:16:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:16:

```
Glu Tyr Ile Gln His Asn Gly Val Val Gln Glu Ser Tyr Tyr Arg Tyr
1               5                   10                  15
Val Ala Arg Glu
                20
```

(2) INFORMATION FOR SEQ ID NO:17:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:17:

```
His Asn Gly Val Val Gln Glu Ser Tyr Tyr Arg Tyr Val Ala Arg Glu
1               5                   10                  15
Gln Ser Cys Arg Arg Pro Asn Ala Gln
                20                  25
```

(2) INFORMATION FOR SEQ ID NO:18:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:18:

```
Gln Ser Cys Arg Arg Pro Asn Ala Gln Arg Phe Gly Ile Ser Asn Tyr
1               5                  10                  15

Cys Gln Ile
```

(2) INFORMATION FOR SEQ ID NO:19:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:19:

```
Arg Phe Gly Ile Ser Asn Tyr Cys Gln Ile Tyr Pro Pro Asn Ala Asn
1               5                  10                  15

Lys Ile Arg Glu Ala Leu
                20
```

(2) INFORMATION FOR SEQ ID NO:20:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:20:

```
Tyr Pro Pro Asn Ala Asn Lys Ile Arg Glu Ala Leu Ala Gln Thr His
1               5                  10                  15

Ser Ala Ile Ala Val Ile Ile Gly
                20
```

(2) INFORMATION FOR SEQ ID NO:21:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:21:

```
Ala Gln Thr His Ser Ala Ile Ala Val Ile Ile Gly Ile Lys Asp Leu
1               5                  10                  15

Asp Ala Phe Arg His Tyr Asp Gly Arg Thr
                20                  25
```

(2) INFORMATION FOR SEQ ID NO:22:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:22:

```
Ile Lys Asp Leu Asp Ala Phe Arg His Tyr Asp Gly Thr Arg Ile Ile
1               5                   10                  15

Gln Arg Asp Asn Gly Tyr Gln Pro Asn Tyr
            20                  25
```

(2) INFORMATION FOR SEQ ID NO:23:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:23:

```
Ile Ile Gln Arg Asp Asn Gly Tyr Gln Pro Asn Tyr His Ala Val Asn
1               5                   10                  15

Ile Val Gly Tyr Ser Asn Ala
            20
```

(2) INFORMATION FOR SEQ ID NO:24:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:24:

```
His Ala Val Asn Ile Val Gly Tyr Ser Asn Ala Gln Gly Val Asp Tyr
1               5                   10                  15

Trp Ile Val Arg Asn Ser
            20
```

(2) INFORMATION FOR SEQ ID NO:25:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:25:

```
Gln Gly Val Asp Tyr Trp Ile Val Arg Asn Ser Trp Asp Thr Asn Trp
1               5                   10                  15

Gly Asp Asn Gly Tyr Gly Tyr Phe
            20
```

(2) INFORMATION FOR SEQ ID NO:26:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:26:

-continued

```
Gly Asp Asn Gly Tyr Gly Tyr Phe Ala Ala Asn Ile Asp Leu Met Met
1               5                   10                  15

Ile Glu Glu Tyr Pro Tyr Val Val Ile Leu
            20                  25
```

(2) INFORMATION FOR SEQ ID NO:27:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:27:

```
Thr Asn Ala Cys Ser Ile Asn Gly Asn Ala Pro Ala Glu Ile Asp Leu
1               5                   10                  15

Arg Gln Met Arg Thr Val Thr Pro Ile Arg Met Gln
            20                  25
```

(2) INFORMATION FOR SEQ ID NO:28:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:28:

```
Ser Ile Asn Gly Asn Ala Pro Ala Glu Ile Asp Leu Arg Gln Met Arg
1               5                   10                  15

Thr Val Thr Pro Ile Arg Met Gln
            20
```

(2) INFORMATION FOR SEQ ID NO:29:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:29:

```
Ala Phe Ser Gly Val Ala Ala Thr Glu Ser Ala Tyr Leu Ala His Arg
1               5                   10                  15

Asn Gln Ser Leu Asp Leu Ala Glu Gln Glu Leu Val Asp
            20                  25
```

(2) INFORMATION FOR SEQ ID NO:30:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:30:

Val Ala Ala Thr Glu Ser Ala Tyr Leu Ala His Arg Asn Gln Ser Leu
1               5                   10                  15

Asp Leu Ala Glu Gln Glu Leu Val Asp
            20                  25

(2) INFORMATION FOR SEQ ID NO:31:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:31:

Ala Phe Ser Gly Val Ala Ala Thr Glu Ser Ala Tyr Leu Ala His Arg
1               5                   10                  15

Asn Gln Ser Leu Asp Leu Ala Glu Gln
            20                  25

(2) INFORMATION FOR SEQ ID NO:32:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:32:

Val Ala Ala Thr Glu Ser Ala Tyr Leu Ala His Arg Asn Gln Ser Leu
1               5                   10                  15

Asp Leu Ala Glu Gln Glu Leu Val Asp Cys Ala Ser Gln
            20                  25

(2) INFORMATION FOR SEQ ID NO:33:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:33:

Glu Tyr Ile Gln His Asn Gly Val Val Gln Ser Tyr Tyr Arg Tyr
1               5                   10                  15

Val Ala Arg Glu Gln Cys Arg Arg Pro Asn Ala Gln
            20                  25

(2) INFORMATION FOR SEQ ID NO:34:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:34:

```
Asp Thr Ile Pro Arg Gly Ile Glu Tyr Ile Gln His Asn Gly Val Val
 1               5                  10                  15

Gln Glu Ser Tyr Tyr Arg Tyr Val Ala Arg Glu Gln Ser
                20                  25
```

(2) INFORMATION FOR SEQ ID NO:35:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:35:

```
Gln Ile Tyr Pro Pro Asn Ala Asn Lys Ile Arg Glu Ala Leu Ala Gln
 1               5                  10                  15

Thr His Ser Ala Ile Ala Val Ile Ile Gly Ile Lys Asp
                20                  25
```

(2) INFORMATION FOR SEQ ID NO:36:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:36:

```
Gln Ile Tyr Pro Pro Asn Ala Asn Lys Ile Arg Glu Ala Leu Ala Gln
 1               5                  10                  15

Thr His Ser Ala Ile Ala
                20
```

(2) INFORMATION FOR SEQ ID NO:37:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:37:

```
Ile Ile Gly Ile Lys Asp Leu Asp Ala Phe Arg His Tyr Asp Gly Arg
 1               5                  10                  15

Thr Ile Ile Gln Arg Asp Asn Gly Tyr Gln
                20                  25
```

(2) INFORMATION FOR SEQ ID NO:38:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:38:

```
Arg Asp Asn Gly Tyr Gln Phe Asn Tyr His Ala Val Asn Ile Val Gly
1               5                   10                  15

Tyr Ser Asn Ala Gln Gly Val Asp Tyr
            20                  25
```

(2) INFORMATION FOR SEQ ID NO:39:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:39:

```
Asn Ile Val Gly Tyr Ser Asn Ala Gln Gly Val Asp Tyr Trp Ile Val
1               5                   10                  15

Arg Asn Ser Trp Asp Thr Asn Trp Gly Asp Asn Gly Tyr
            20                  25
```

(2) INFORMATION FOR SEQ ID NO:40:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:40:

```
Asn Ile Val Gly Tyr Ser Asn Ala Gln Gly Val Asp Tyr Trp Ile Val
1               5                   10                  15

Arg Asn Ser Trp Asp Thr Asn
            20
```

(2) INFORMATION FOR SEQ ID NO:41:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:41:

```
Asp Gln Val Asp Val Lys Asp Cys Ala Asn His Glu Ile Lys Lys Val
1               5                   10                  15

Leu Val Pro Gly
            20
```

(2) INFORMATION FOR SEQ ID NO:42:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:42:

```
His Glu Ile Lys Lys Val Leu Val Pro Gly Cys His Gly Ser Glu Pro
1               5                   10                  15

Cys Ile Ile His Arg Gly Lys Pro Phe
                20              25
```

(2) INFORMATION FOR SEQ ID NO:43:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:43:

```
His Gly Ser Glu Pro Cys Ile Ile His Arg Gly Lys Pro Phe Gln Leu
1               5                   10                  15

Glu Ala Val Phe Glu Ala Asn Gln Asn Thr Lys Thr Ala
                20                  25
```

(2) INFORMATION FOR SEQ ID NO:44:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:44:

```
Gln Leu Glu Ala Val Phe Glu Ala Asn Gln Asn Thr Lys Thr Ala Lys
1               5                   10                  15

Ile Glu Ile Lys Ala Ser Ile Asp Gly
                20                  25
```

(2) INFORMATION FOR SEQ ID NO:45:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:45:

```
Lys Ile Glu Ile Lys Ala Ser Ile Asp Gly Leu Glu Val Asp Val Pro
1               5                   10                  15

Gly Ile Asp Pro Asn Ala Cys His Tyr Met Lys
                20                  25
```

(2) INFORMATION FOR SEQ ID NO:46:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:46:

```
Leu Glu Val Asp Val Pro Gly Ile Asp Pro Asn Ala Cys His Tyr Met
1               5                   10                  15
Lys Cys Pro Leu Val Lys Gly Gln Gln Tyr
                20                  25
```

(2) INFORMATION FOR SEQ ID NO:47:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:47:

```
Cys Pro Leu Val Lys Gly Gln Gln Tyr Asp Ile Lys Tyr Thr Trp Asn
1               5                   10                  15
Val Pro Lys Ile Ala Pro Lys Ser Glu Asn Val
                20                  25
```

(2) INFORMATION FOR SEQ ID NO:48:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:48:

```
Asp Ile Lys Tyr Thr Trp Asn Val Pro Lys Ile Ala Pro Lys Ser Glu
1               5                   10                  15
Asn Val Val Thr Val Lys Val Met Gly
                20                  25
```

(2) INFORMATION FOR SEQ ID NO:49:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:49:

```
Val Val Thr Val Lys Val Met Gly Asp Asp Gly Val Leu Ala Cys Ala
1               5                   10                  15
Ile Ala Thr His Ala Lys Ile Arg Asp
                20                  25
```

(2) INFORMATION FOR SEQ ID NO:50:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:50:

Asp Gln Val Asp Val Lys Asp Cys Ala Asn His Glu Ile Lys Lys Val
1               5                   10                  15

Leu Val Pro Gly Cys His Gly Ser Glu Pro
            20                  25

(2) INFORMATION FOR SEQ ID NO:51:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:51:

Asp Gln Val Asp Val Lys Asp Glu Ala Asn His Glu Ile Lys Lys Val
1               5                   10                  15

Leu Val Pro Gly Cys His Gly Ser Glu Pro
            20                  25

(2) INFORMATION FOR SEQ ID NO:52:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:52:

Asp Gln Val Asp Val Lys Asp Ser Ala Asn His Glu Ile Lys Lys Val
1               5                   10                  15

Leu Val Pro Gly Cys His Gly Ser Glu Pro
            20                  25

(2) INFORMATION FOR SEQ ID NO:53:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:53:

Asp Gln Val Asp Val Lys Asp Cys Ala Asn His Glu Ile Lys Lys Val
1               5                   10                  15

Leu Val Pro Gly Glu His Gly Ser Glu Pro
            20                  25

(2) INFORMATION FOR SEQ ID NO:54:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:54:

```
Asp Gln Val Asp Val Lys Asp Cys Ala Asn His Glu Ile Lys Lys Val
1               5                   10                  15

Leu Val Pro Gly Ser His Gly Ser Glu Pro
                20                  25

(2) INFORMATION FOR SEQ ID NO:55:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:55:

Asp Gln Val Asp Val Lys Asp Glu Ala Asn His Glu Ile Lys Lys Val
1               5                   10                  15

Leu Val Pro Gly Glu His Gly Ser Glu Pro
                20                  25

(2) INFORMATION FOR SEQ ID NO:56:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:56:

Asp Gln Val Asp Val Lys Asp Ser Ala Asn His Glu Ile Lys Lys Val
1               5                   10                  15

Leu Val Pro Gly Ser His Gly Ser Glu Pro
                20                  25

(2) INFORMATION FOR SEQ ID NO:57:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:57:

Asp Gln Val Asp Val Lys Asp Glu Ala Asn His Glu Ile Lys Lys Val
1               5                   10                  15

Leu Val Pro Gly
                20

(2) INFORMATION FOR SEQ ID NO:58:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:58:
```

```
Asp Gln Val Asp Val Lys Asp Ser Ala Asn His Glu Ile Lys Lys Val
1               5                   10                  15
Leu Val Pro Gly
            20
```

(2) INFORMATION FOR SEQ ID NO:59:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:59:

```
His Glu Ile Lys Lys Val Leu Val Pro Gly Cys His Gly Ser Glu Pro
1               5                   10                  15
```

(2) INFORMATION FOR SEQ ID NO:60:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:60:

```
His Glu Ile Lys Lys Val Leu Val Pro Gly Glu His Gly Ser Glu Pro
1               5                   10                  15
```

(2) INFORMATION FOR SEQ ID NO:61:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:61:

```
His Glu Ile Lys Lys Val Leu Val Pro Gly Ser His Gly Ser Glu Pro
1               5                   10                  15
```

(2) INFORMATION FOR SEQ ID NO:62:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:62:

```
Lys Pro Phe Gln Leu Glu Ala Val Phe Glu Ala Asn Gln Asn Thr Lys
1               5                   10                  15
Thr Ala Lys Ile Glu Ile Lys Ala Ser Thr Asp Gly
                20                  25
```

(2) INFORMATION FOR SEQ ID NO:63:

(i) SEQUENCE CHARACTERISTICS:
    (A) LENGTH: 28 amino acids
    (B) TYPE: amino acid
    (D) TOPOLOGY: linear (ii) MOLECULE TYPE: peptide (v) FRAGMENT TYPE: N-terminal (xi) SEQUENCE DESCRIPTION: SEQ ID NO:63:

```
Gln Leu Glu Ala Val Phe Glu Ala Asn Gln Asn Thr Lys Thr Ala Lys
1               5                  10                  15

Ile Glu Ile Lys Ala Ser Ile Asp Gly Leu Glu Val
                20                  25
```

(2) INFORMATION FOR SEQ ID NO:64:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:64:

```
Phe Glu Ala Asn Gln Asn Thr Lys Thr Ala Lys Ile Glu Ile Lys Ala
1               5                  10                  15

Ser Ile Asp Gly Leu Glu Val Asp Val Pro Gly
                20                  25
```

(2) INFORMATION FOR SEQ ID NO:65:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:65:

```
Gln Asn Thr Lys Thr Ala Lys Ile Glu Ile Lys Ala Ser Ile Asp Gly
1               5                  10                  15

Leu Glu Val Asp Val Pro Gly
                20
```

(2) INFORMATION FOR SEQ ID NO:66:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:66:

```
Pro Leu Val Lys Gly Gln Gln Tyr Asp Ile Lys Tyr Thr Trp Asn Val
1               5                  10                  15

Pro Lys Ile Ala Pro Lys Ser Glu Asn Val
                20                  25
```

(2) INFORMATION FOR SEQ ID NO:67:

(i) SEQUENCE CHARACTERISTICS:
    (A) LENGTH: 26 amino acids
    (B) TYPE: amino acid
    (D) TOPOLOGY: linear (ii) MOLECULE TYPE: peptide (v) FRAGMENT TYPE: N-terminal (xi) SEQUENCE DESCRIPTION: SEQ ID NO:67:

```
Pro Leu Val Lys Gly Gln Gln Tyr Asp Ile Lys Tyr Thr Tyr Asn Val
1               5                   10                  15
Pro Lys Ile Ala Pro Lys Ser Glu Asn Val
            20                  25
```

(2) INFORMATION FOR SEQ ID NO:68:

(i) SEQUENCE CHARACTERISTICS:
    (A) LENGTH: 13 amino acids
    (B) TYPE: amino acid
    (D) TOPOLOGY: linear (ii) MOLECULE TYPE: peptide (v) FRAGMENT TYPE: N-terminal (xi) SEQUENCE DESCRIPTION: SEQ ID NO:68:

```
Lys Ser Glu Asn Val Val Val Thr Val Lys Val Met Gly
1               5                   10
```

(2) INFORMATION FOR SEQ ID NO:69:

(i) SEQUENCE CHARACTERISTICS:
    (A) LENGTH: 23 amino acids
    (B) TYPE: amino acid
    (D) TOPOLOGY: linear (ii) MOLECULE TYPE: peptide (v) FRAGMENT TYPE: N-terminal (xi) SEQUENCE DESCRIPTION: SEQ ID NO:69:

```
Thr Val Lys Val Met Gly Asp Asp Gly Val Leu Ala Cys Ala Ile Ala
1               5                   10                  15
Thr His Ala Lys Ile Arg Asp
            20
```

(2) INFORMATION FOR SEQ ID NO:70:

(i) SEQUENCE CHARACTERISTICS:
    (A) LENGTH: 23 amino acids
    (B) TYPE: amino acid
    (D) TOPOLOGY: linear (ii) MOLECULE TYPE: peptide (v) FRAGMENT TYPE: N-terminal (xi) SEQUENCE DESCRIPTION: SEQ ID NO:70:

```
Thr Val Lys Val Met Gly Asp Asp Gly Val Leu Ala Glu Ala Ile Ala
1               5                   10                  15
Thr His Ala Lys Ile Arg Asp
            20
```

(2) INFORMATION FOR SEQ ID NO:71:

(i) SEQUENCE CHARACTERISTICS:
    (A) LENGTH: 23 amino acids
    (B) TYPE: amino acid (D) TOPOLOGY: linear (ii) MOLECULE TYPE: peptide (v) FRAGMENT TYPE: N-terminal (xi) SEQUENCE DESCRIPTION: SEQ ID NO:71:

Thr Val Lys Val Leu Gly Asp Asp Gly Val Leu Ala Ser Ala Ile Ala
1               5                   10                  15

Thr His Ala Lys Ile Arg Asp
            20

(2) INFORMATION FOR SEQ ID NO:72:

(i) SEQUENCE CHARACTERISTICS:
         (A) LENGTH: 21 amino acids
         (B) TYPE: amino acid
         (D) TOPOLOGY: linear (ii) MOLECULE TYPE: peptide (v) FRAGMENT TYPE: N-terminal (xi) SEQUENCE DESCRIPTION: SEQ ID NO:72:

Thr Ser Ala Cys Arg Ile Asn Ser Val Asn Val Pro Ser Glu Leu Asp
1               5                   10                  15

Leu Arg Ser Leu Arg
            20

(2) INFORMATION FOR SEQ ID NO:73:

(i) SEQUENCE CHARACTERISTICS:
         (A) LENGTH: 27 amino acids
         (B) TYPE: amino acid
         (D) TOPOLOGY: linear (ii) MOLECULE TYPE: peptide (v) FRAGMENT TYPE: N-terminal (xi) SEQUENCE DESCRIPTION: SEQ ID NO:73:

Glu Leu Asp Leu Arg Ser Leu Arg Thr Val Thr Pro Ile Arg Met Gln
1               5                   10                  15

Gly Gly Cys Gly Ser Cys Trp Ala Phe Ser Gly
            20                  25

(2) INFORMATION FOR SEQ ID NO:74:

(i) SEQUENCE CHARACTERISTICS:
         (A) LENGTH: 29 amino acids
         (B) TYPE: amino acid
         (D) TOPOLOGY: linear (ii) MOLECULE TYPE: peptide (v) FRAGMENT TYPE: N-terminal (xi) SEQUENCE DESCRIPTION: SEQ ID NO:74:

Thr Val Thr Pro Ile Arg Met Gln Gly Gly Cys Gly Ser Cys Trp Ala
1               5                   10                  15

Phe Ser Gly Val Ala Ala Thr Glu Ser Ala Tyr Leu Ala
            20                  25

(2) INFORMATION FOR SEQ ID NO:75:

(i) SEQUENCE CHARACTERISTICS:
         (A) LENGTH: 21 amino acids
         (B) TYPE: amino acid -continued

```
            (D) TOPOLOGY: linear (ii) MOLECULE TYPE: peptide (v) FRAGMENT TYPE: N-terminal (xi) SEQUENCE DESCRIPTION: SEQ ID NO:75:

Val Ala Ala Thr Glu Ser Ala Tyr Leu Ala Tyr Arg Asn Thr Ser Leu
1               5                  10                  15
Asp Leu Ser Glu Gln
            20

(2) INFORMATION FOR SEQ ID NO:76:

(i) SEQUENCE CHARACTERISTICS:
            (A) LENGTH: 22 amino acids
            (B) TYPE: amino acid
            (D) TOPOLOGY: linear (ii) MOLECULE TYPE: peptide (v) FRAGMENT TYPE: N-terminal (xi) SEQUENCE DESCRIPTION: SEQ ID NO:76:

Tyr Arg Asn Thr Ser Leu Asp Leu Ser Glu Gln Glu Leu Val Asp Cys
1               5                  10                  15
Ala Ser Gln His Gly Cys
            20

(2) INFORMATION FOR SEQ ID NO:77:

(i) SEQUENCE CHARACTERISTICS:
            (A) LENGTH: 21 amino acids
            (B) TYPE: amino acid
            (D) TOPOLOGY: linear (ii) MOLECULE TYPE: peptide (v) FRAGMENT TYPE: N-terminal (xi) SEQUENCE DESCRIPTION: SEQ ID NO:77:

Glu Leu Val Asp Cys Ala Ser Gln His Gly Cys His Gly Asp Thr Ile
1               5                  10                  15
Pro Arg Gly Ile Glu
            20

(2) INFORMATION FOR SEQ ID NO:78:

(i) SEQUENCE CHARACTERISTICS:
            (A) LENGTH: 28 amino acids
            (B) TYPE: amino acid
            (D) TOPOLOGY: linear (ii) MOLECULE TYPE: peptide (v) FRAGMENT TYPE: N-terminal (xi) SEQUENCE DESCRIPTION: SEQ ID NO:78:

Gly Asp Thr Ile Pro Arg Gly Ile Glu Tyr Ile Gln Gln Asn Gly Val
1               5                  10                  15
Val Glu Glu Arg Ser Tyr Pro Tyr Val Ala Arg Glu
            20                  25

(2) INFORMATION FOR SEQ ID NO:79:

(i) SEQUENCE CHARACTERISTICS:
            (A) LENGTH: 25 amino acids
            (B) TYPE: amino acid
```

(D) TOPOLOGY: linear (ii) MOLECULE TYPE: peptide (v) FRAGMENT TYPE: N-terminal (xi) SEQUENCE DESCRIPTION: SEQ ID NO:79:

Gln Asn Gly Val Val Glu Glu Arg Ser Tyr Pro Tyr Val Ala Arg Glu
1               5                  10                  15

Gln Arg Cys Arg Arg Pro Asn Ser Gln
            20                  25

(2) INFORMATION FOR SEQ ID NO:80:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:80:

Gln Arg Cys Arg Arg Pro Asn Ser Gln His Tyr Gly Ile Ser Asn Tyr
1               5                  10                  15

Cys Gln Ile (2) INFORMATION FOR SEQ ID NO:81:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:81:

His Tyr Gly Ile Ser Asn Tyr Cys Gln Ile Tyr Pro Pro Asp Val Lys
1               5                  10                  15

Gln Ile Arg Glu Ala Leu
            20

(2) INFORMATION FOR SEQ ID NO:82:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:82:

Tyr Pro Pro Asp Val Lys Gln Ile Arg Glu Ala Leu Phe Gln Thr His
1               5                  10                  15

Thr Ala Ile Ala Val Ile Ile Gly
            20

(2) INFORMATION FOR SEQ ID NO:83:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:83:

Thr Gln Thr His Thr Ala Ile Ala Val Ile Ile Gly Ile Lys Asp Leu
1               5                  10                  15

Arg Ala Phe Gln His Tyr Asp Gly Arg Thr
            20                  25

(2) INFORMATION FOR SEQ ID NO:84:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:84:

Ile Lys Asp Leu Arg Ala Phe Gln His Tyr Asp Gly Arg Thr Ile Ile
1               5                  10                  15

Gln His Asp Asn Gly Tyr Gln Pro Asn Tyr
            20                  25

(2) INFORMATION FOR SEQ ID NO:85:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:85:

Asp Gly Arg Thr Ile Ile Gln His Asp Asn Gly Tyr Gln Pro Asn
1               5                  10                  15

NFORMATION FOR SEQ ID NO:86:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:86:

Ile Ile Gln His Asp Asn Gly Tyr Gln Pro Asn Tyr His Ala Val Asn
1               5                  10                  15

Ile Val Gly Tyr Gly Ser Thr
            20

(2) INFORMATION FOR SEQ ID NO:87:

(i) SEQUENCE CHARACTERISTICS:
        (A) LENGTH: 22 amino acids
        (B) TYPE: amino acid
        (D) TOPOLOGY: linear (ii) MOLECULE TYPE: peptide

```
        (v) FRAGMENT TYPE: N-terminal (xi) SEQUENCE DESCRIPTION: SEQ ID NO:87:

His Ala Val Asn Ile Val Gly Tyr Gly Ser Thr Gln Gly Asp Asp Tyr
1               5                  10                  15

Trp Ile Val Arg Asn Ser
            20

(2) INFORMATION FOR SEQ ID NO:88:

(i) SEQUENCE CHARACTERISTICS:
             (A) LENGTH: 24 amino acids
             (B) TYPE: amino acid
             (D) TOPOLOGY: linear (ii) MOLECULE TYPE: peptide (v) FRAGMENT TYPE: N-terminal (xi) SEQUENCE DESCRIPTION: SEQ ID NO:88:

Gln Gly Asp Asp Tyr Trp Ile Val Arg Asn Ser Trp Asp Thr Thr Trp
1               5                  10                  15

Gly Asp Ser Gly Tyr Gly Tyr Phe
            20

(2) INFORMATION FOR SEQ ID NO:89:

(i) SEQUENCE CHARACTERISTICS:
             (A) LENGTH: 26 amino acids
             (B) TYPE: amino acid
             (D) TOPOLOGY: linear (ii) MOLECULE TYPE: peptide (v) FRAGMENT TYPE: N-terminal (xi) SEQUENCE DESCRIPTION: SEQ ID NO:89:

Gly Asp Ser Gly Tyr Gly Tyr Phe Gln Ala Gly Asn Asn Leu Met Met
1               5                  10                  15

Ile Glu Gln Tyr Pro Tyr Val Val Ile Met
            20                  25

(2) INFORMATION FOR SEQ ID NO:90:

(i) SEQUENCE CHARACTERISTICS:
             (A) LENGTH: 29 amino acids
             (B) TYPE: amino acid
             (D) TOPOLOGY: linear (ii) MOLECULE TYPE: peptide (v) FRAGMENT TYPE: N-terminal (xi) SEQUENCE DESCRIPTION: SEQ ID NO:90:

Thr Ser Ala Cys Arg Ile Asn Ser Val Asn Val Pro Ser Glu Leu Asp
1               5                  10                  15

Leu Arg Ser Leu Arg Thr Val Thr Pro Ile Arg Met Gln
            20                  25

(2) INFORMATION FOR SEQ ID NO:91:

(i) SEQUENCE CHARACTERISTICS:
             (A) LENGTH: 25 amino acids
             (B) TYPE: amino acid
             (D) TOPOLOGY: linear (ii) MOLECULE TYPE: peptide
```

(v) FRAGMENT TYPE: N-terminal (xi) SEQUENCE DESCRIPTION: SEQ ID NO:91:

Arg Ile Asn Ser Val Asn Val Pro Ser Glu Leu Asp Leu Arg Ser Leu
1               5                   10                  15

Arg Thr Val Thr Pro Ile Arg Met Gln
            20                  25

(2) INFORMATION FOR SEQ ID NO:92:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:92:

Ala Phe Ser Gly Val Ala Ala Thr Glu Ser Ala Tyr Leu Ala Tyr Arg
1               5                   10                  15

Asn Thr Ser Leu Asp Leu Ser Glu Gln Glu Leu Val Asp
            20                  25

(2) INFORMATION FOR SEQ ID NO:93:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:93:

Val Ala Ala Thr Glu Ser Ala Tyr Leu Ala Tyr Arg Asn Thr Ser Leu
1               5                   10                  15

Asp Leu Ser Glu Gln Glu Leu Val Asp
            20                  25

(2) INFORMATION FOR SEQ ID NO:94:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:94:

Val Ala Ala Thr Glu Ser Ala Tyr Leu Ala Tyr Arg Asn Thr Ser Leu
1               5                   10                  15

Asp Leu Ser Glu Gln Glu Leu Val Asp Cys Ala Ser Gln
            20                  25

(2) INFORMATION FOR SEQ ID NO:95:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:95:

Glu Tyr Ile Gln Gln Asn Gly Val Val Glu Glu Arg Ser Tyr Pro Tyr
1               5                   10                  15

Val Ala Arg Glu Gln Arg Cys Arg Arg Pro Asn Ser Gln
                20                  25

(2) INFORMATION FOR SEQ ID NO:96:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:96:

Asp Thr Ile Pro Arg Gly Ile Glu Tyr Ile Gln Gln Asn Gly Val Val
1               5                   10                  15

Glu Glu Arg Ser Tyr Pro Tyr Val Ala Arg Glu Gln Arg
                20                  25

(2) INFORMATION FOR SEQ ID NO:97:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:97:

Gln Ile Tyr Pro Pro Asp Val Lys Gln Ile Arg Glu Ala Leu Thr Gln
1               5                   10                  15

Thr His Thr Ala Ile Ala Val Ile Ile Gly Ile Lys Asp
                20                  25

(2) INFORMATION FOR SEQ ID NO:98:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:98:

Gln Ile Tyr Pro Pro Asp Val Lys Gln Ile Arg Glu Ala Leu Thr Gln
1               5                   10                  15

Thr His Thr Ala Ile Ala
                20

(2) INFORMATION FOR SEQ ID NO:99:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:99:

Ile Ile Gly Ile Lys Asp Leu Arg Ala Phe Gln His Tyr Asp Gly Arg
1               5                   10                  15

Thr Ile Ile Gln His Asp Asn Gly Tyr Gln
                20                  25

(2) INFORMATION FOR SEQ ID NO:100:

(i) SEQUENCE CHARACTERISTICS:
         (A) LENGTH: 25 amino acids
         (B) TYPE: amino acid
         (D) TOPOLOGY: linear (ii) MOLECULE TYPE: peptide (v) FRAGMENT TYPE: N-terminal (xi) SEQUENCE DESCRIPTION: SEQ ID NO:100:

His Asp Asn Gly Tyr Gln Pro Asn Tyr His Ala Val Asn Ile Val Gly
1               5                   10                  15

Tyr Gly Ser Thr Gln Gly Asp Asp Tyr
                20                  25

(2) INFORMATION FOR SEQ ID NO:101:

(i) SEQUENCE CHARACTERISTICS:
         (A) LENGTH: 29 amino acids
         (B) TYPE: amino acid
         (D) TOPOLOGY: linear (ii) MOLECULE TYPE: peptide (v) FRAGMENT TYPE: N-terminal (xi) SEQUENCE DESCRIPTION: SEQ ID NO:101:

Asn Ile Val Gly Tyr Gly Ser Thr Gln Gly Asp Asp Tyr Trp Ile Val
1               5                   10                  15

Arg Asn Ser Trp Asp Thr Thr Trp Gly Asp Ser Gly Tyr
                20                  25

(2) INFORMATION FOR SEQ ID NO:102:

(i) SEQUENCE CHARACTERISTICS:
         (A) LENGTH: 23 amino acids
         (B) TYPE: amino acid
         (D) TOPOLOGY: linear (ii) MOLECULE TYPE: peptide (v) FRAGMENT TYPE: N-terminal (xi) SEQUENCE DESCRIPTION: SEQ ID NO:102:

Asn Ile Val Gly Tyr Gly Ser Thr Gln Gly Asp Asp Tyr Trp Ile Val
1               5                   10                  15

Arg Asn Ser Trp Asp Thr Thr
                20

(2) INFORMATION FOR SEQ ID NO:103:

(i) SEQUENCE CHARACTERISTICS:
         (A) LENGTH: 20 amino acids
         (B) TYPE: amino acid
         (D) TOPOLOGY: linear (ii) MOLECULE TYPE: peptide (v) FRAGMENT TYPE: N-terminal (xi) SEQUENCE DESCRIPTION: SEQ ID NO:103:

Asp Gln Val Asp Val Lys Asp Cys Ala Asn Asn Glu Ile Lys Lys Val
1               5                   10                  15
Met Val Asp Gly
            20

(2) INFORMATION FOR SEQ ID NO:104:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:104:

Asn Glu Ile Lys Lys Val Met Val Asp Gly Cys His Gly Ser Asp Pro
1               5                   10                  15
Cys Ile Ile His Arg Gly Lys Pro Phe
            20                  25

(2) INFORMATION FOR SEQ ID NO:105:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:105:

His Gly Ser Asp Pro Cys Ile Ile His Arg Gly Lys Pro Phe Thr Leu
1               5                   10                  15
Glu Ala Leu Phe Asp Ala Asn Gln Asn Thr Lys Thr Ala
            20                  25

(2) INFORMATION FOR SEQ ID NO:106:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:106:

His Arg Gly Lys Pro Phe Thr Leu Glu Ala Leu Phe Asp Ala Asn Gln
1               5                   10                  15
Asn Thr Lys (2) INFORMATION FOR SEQ ID NO:107:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:107:

Thr Leu Glu Ala Leu Phe Asp Ala Asn Gln Asn Thr Lys Thr Ala Lys
1               5                   10                  15

Ile Glu Ile Lys Ala Ser Leu Asp Gly
            20                  25

(2) INFORMATION FOR SEQ ID NO:108:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:108:

Gln Asn Thr Lys Thr Ala Lys Ile Glu Ile Lys Ala Ser Leu Asp Gly
1               5                   10                  15

Leu Glu Ile Asp Val Pro Gly Ile Asp Thr
            20                  25

(2) INFORMATION FOR SEQ ID NO:109:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:109:

Lys Ile Glu Ile Lys Ala Ser Leu Asp Gly Leu Glu Ile Asp Val Pro
1               5                   10                  15

Gly Ile Asp Thr Asn Ala Cys His Phe Met Lys
            20                  25

(2) INFORMATION FOR SEQ ID NO:110:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:110:

Leu Glu Ile Asp Val Pro Gly Ile Asp Thr Asn Ala Cys His Phe Met
1               5                   10                  15

Lys Cys Pro Leu Val Lys Gly Gln Gln Tyr
            20                  25

(2) INFORMATION FOR SEQ ID NO:111:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:111:

Cys Pro Leu Val Lys Gly Gln Gln Tyr Asp Ala Lys Tyr Thr Trp Asn
1               5                   10                  15

Val Pro Lys Ile Ala Pro Lys Ser Glu Asn Val
                20                  25

(2) INFORMATION FOR SEQ ID NO:112:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:112:

Asp Ala Lys Tyr Thr Trp Asn Val Pro Lys Ile Ala Pro Lys Ser Glu
1               5                   10                  15

Asn Val Val Val Thr Val Lys Leu Val Gly
                20                  25

(2) INFORMATION FOR SEQ ID NO:113:

(i) SEQUENCE CHARACTERISTICS:
        (A) LENGTH: 35 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:113:

Pro Lys Ile Ala Pro Lys Ser Glu Asn Val Val Val Thr Val Lys Leu
1               5                   10                  15

Val Gly Asp Asn Gly Val Leu Ala Cys Ala Ile Ala Thr His Ala Lys
                20                  25                  30

Ile Arg Asp
         35

(2) INFORMATION FOR SEQ ID NO:114:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:114:

Val Val Thr Val Lys Leu Val Gly Asp Asn Gly Val Leu Ala Cys Ala
1               5                   10                  15

Ile Ala Thr His Ala Lys Ile Arg Asp
                20                  25

(2) INFORMATION FOR SEQ ID NO:115:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:115:

Lys Pro Phe Thr Leu Glu Ala Leu Phe Asp Ala Asn Gln Asn Thr Lys
1               5                   10                  15

Thr Ala Lys Ile Glu Ile Lys Ala Ser Leu Asp Gly
            20                  25

(2) INFORMATION FOR SEQ ID NO:116:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:116:

Thr Leu Glu Ala Leu Phe Asp Ala Asn Gln Asn Thr Lys Thr Ala Lys
1               5                   10                  15

Ile Glu Ile Lys Ala Ser Leu Asp Gly Leu Glu Ile
            20                  25

(2) INFORMATION FOR SEQ ID NO:117:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:117:

His Arg Asn Gln Ser Leu Asp Leu Ala Glu Gln Asp Leu Val Asp Cys
1               5                   10                  15

Ala Ser Gln His Gly Cys
            20

(2) INFORMATION FOR SEQ ID NO:118:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:118:

Asp Leu Val Asp Cys Ala Ser Gln His Gly Cys His Gly Asp Thr Ile
1               5                   10                  15

Pro Arg Gly Ile Glu
            20

(2) INFORMATION FOR SEQ ID NO:119:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:119:

His Gly Ser Glu Pro Cys Ile Ile His Arg Gly Lys Pro Phe Gln Leu
1               5                   10                  15

Glu Ala Val Phe Glu Ala Val Gln Asn Thr Lys Thr Ala
            20                  25

(2) INFORMATION FOR SEQ ID NO: 120:

(i) SEQUENCE CHARACTERISTICS:
  (A) LENGTH: 25 amino acids
  (B) TYPE: amino acid
  (D) TOPOLOGY: linear (ii) MOLECULE TYPE: peptide (v) FRAGMENT TYPE: internal (xi) SEQUENCE DESCRIPTION: SEQ ID NO: 120:

Lys Ser Ile Asn Gly Asn Ala Pro Ala Glu Ile Asp Leu Arg Gln Leu
1               5                   10                  15

Arg Thr Val Thr Pro Ile Arg Leu Gln
            20                  25

(2) INFORMATION FOR SEQ ID NO: 121:

(i) SEQUENCE CHARACTERISTICS:
  (A) LENGTH: 31 amino acids
  (B) TYPE: amino acid
  (D) TOPOLOGY: linear (ii) MOLECULE TYPE: peptide (v) FRAGMENT TYPE: internal (xi) SEQUENCE DESCRIPTION: SEQ ID NO: 121:

Lys Lys Glu Tyr Ile Gln His Asn Gly Val Val Gln Glu Ser Tyr Tyr
1               5                   10                  15

Arg Tyr Val Ala Arg Glu Gln Ser Cys Arg Arg Pro Asn Ala Gln
            20                  25                  30

(2) INFORMATION FOR SEQ ID NO: 122:

(i) SEQUENCE CHARACTERISTICS:
  (A) LENGTH: 31 amino acids
  (B) TYPE: amino acid
  (D) TOPOLOGY: linear (ii) MOLECULE TYPE: peptide (v) FRAGMENT TYPE: internal (xi) SEQUENCE DESCRIPTION: SEQ ID NO: 122:

Lys Lys Glu Tyr Ile Gln His Asn Gly Val Val Gln Glu Ser Tyr Tyr
1               5                   10                  15

Arg Tyr Val Ala Arg Glu Gln Ser Ser Arg Arg Pro Asn Ala Gln
            20                  25                  30

(2) INFORMATION FOR SEQ ID NO: 123:

(i) SEQUENCE CHARACTERISTICS:
  (A) LENGTH: 31 amino acids
  (B) TYPE: amino acid
  (D) TOPOLOGY: linear -continued (ii) MOLECULE TYPE: peptide (v) FRAGMENT TYPE: internal (xi) SEQUENCE DESCRIPTION: SEQ ID NO: 123:

Lys Lys Glu Tyr Ile Gln His Asn Gly Val Val Gln Glu Ser Tyr Tyr
1               5                   10                  15

Arg Tyr Val Ala Arg Glu Gln Ser Glu Arg Arg Pro Asn Ala Gln
            20                  25                  30

(2) INFORMATION FOR SEQ ID NO: 124:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 124:

Asp Lys Glu Tyr Ile Gln His Asn Gly Val Val Gln Glu Ser Tyr Tyr
1               5                   10                  15

Arg Tyr Val Ala Arg Glu Gln Ser Ser Arg Arg Pro Asn Ala Gln Arg
            20                  25                  30

(2) INFORMATION FOR SEQ ID NO: 125:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 125:

Asp Lys Glu Tyr Ile Gln His Asn Gly Val Val Gln Glu Ser Tyr Tyr
1               5                   10                  15

Arg Tyr Val Ala Arg Glu Gln Ser Cys Arg Arg Pro Asn Ala Gln Arg
            20                  25                  30

(2) INFORMATION FOR SEQ ID NO: 126:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 126:

Asp Glu Tyr Ile Gln His Asn Gly Val Val Gln Glu Ser Tyr Tyr Arg
1               5                   10                  15

Tyr Val Ala Arg Glu Gln Ser Cys Arg Arg Asp Asp
            20                  25

(2) INFORMATION FOR SEQ ID NO: 127:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 127:

Asp Glu Tyr Ile Gln His Asn Gly Val Val Gln Glu Ser Tyr Tyr Arg
1               5                   10                  15

Tyr Val Ala Arg Glu Gln Ser Ser Arg Arg Asp Asp
            20                  25

(2) INFORMATION FOR SEQ ID NO: 128:

(i) SEQUENCE CHARACTERISTICS:
            (A) LENGTH: 28 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 128:

Asp Glu Tyr Ile Gln His Asn Gly Val Val Gln Glu Ser Tyr Tyr Arg
1               5                   10                  15

Tyr Val Ala Arg Glu Gln Ser Cys Arg Arg Pro Asp
            20                  25

(2) INFORMATION FOR SEQ ID NO: 129:

(i) SEQUENCE CHARACTERISTICS:
            (A) LENGTH: 28 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 129:

Asp Glu Tyr Ile Gln His Asn Gly Val Val Gln Glu Ser Tyr Tyr Arg
1               5                   10                  15

Tyr Val Ala Arg Glu Gln Ser Ser Arg Arg Pro Asp
            20                  25

(2) INFORMATION FOR SEQ ID NO: 130:

(i) SEQUENCE CHARACTERISTICS:
            (A) LENGTH: 24 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 130:

Asp Glu Tyr Ile Gln His Asn Gly Val Val Gln Glu Ser Tyr Tyr Arg
1               5                   10                  15

Tyr Val Ala Arg Glu Gln Ser Glu
            20

(2) INFORMATION FOR SEQ ID NO: 131:

(i) SEQUENCE CHARACTERISTICS:
            (A) LENGTH: 15 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 131:

Arg Tyr Val Ala Arg Glu Gln Ser Cys Arg Arg Pro Asn Ala Gln
1               5                  10                  15

NFORMATION FOR SEQ ID NO: 132:

(i) SEQUENCE CHARACTERISTICS:
            (A) LENGTH: 15 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 132:

Arg Tyr Val Ala Arg Glu Gln Ser Glu Arg Arg Pro Asn Ala Gln
1               5                  10                  15

(2) INFORMATION FOR SEQ ID NO: 133:

(i) SEQUENCE CHARACTERISTICS:
            (A) LENGTH: 15 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 133:

Arg Tyr Val Ala Arg Glu Gln Ser Ser Arg Arg Pro Asn Ala Gln
1               5                  10                  15

NFORMATION FOR SEQ ID NO: 134:

(i) SEQUENCE CHARACTERISTICS:
            (A) LENGTH: 26 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 134:

Asp Glu Gly Ile Lys Asp Leu Asp Ala Phe Arg His Tyr Asp Gly Arg
1               5                  10                  15

Thr Ile Ile Gln Arg Asp Asn Gly Tyr Gln
            20                  25

(2) INFORMATION FOR SEQ ID NO: 135:

(i) SEQUENCE CHARACTERISTICS:
            (A) LENGTH: 13 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 135:

Ile Gly Ile Lys Asp Leu Asp Ala Phe Arg His Tyr Asp
1               5                  10

(2) INFORMATION FOR SEQ ID NO: 136:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 136:

Asp Ala Phe Arg His Tyr Asp Gly Arg Thr Ile Ile Gln
1               5                  10

NFORMATION FOR SEQ ID NO: 137:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 137:

Thr Ile Ile Gln Arg Asp Asn Gly Tyr Gln Pro Asn Tyr
1               5                  10

(2) INFORMATION FOR SEQ ID NO: 138:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 138:

Asp Gln Val Asp Val Lys Asp Ser Ala Asn His Glu Ile Lys Lys Val
1               5                  10                 15

Leu Val Pro Gly Ser His Gly Ser Glu Pro Lys
                20                  25

(2) INFORMATION FOR SEQ ID NO: 139:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 139:

Asp Lys Gln Leu Glu Ala Val Phe Glu Ala Asn Gln Asn Thr Lys Thr
1               5                  10                 15

Ala Lys Ile Glu Ile Lys Ala Ser Ile Asp Gly Leu Glu Val Asp
                20                  25                  30

(2) INFORMATION FOR SEQ ID NO: 140:

(i) SEQUENCE CHARACTERISTICS:
        (A) LENGTH: 31 amino acids
        (B) TYPE: amino acid (D) TOPOLOGY: linear (ii) MOLECULE TYPE: peptide (v) FRAGMENT TYPE: internal (xi) SEQUENCE DESCRIPTION: SEQ ID NO: 140:

Asp Lys Gln Leu Glu Ala Val Phe Glu Ala Asn Gln Asn Thr Lys Thr
1               5                  10                  15

Ala Lys Ile Glu Ile Lys Ala Ser Ile Asp Gly Leu Glu Val Lys
            20                  25                  30

(2) INFORMATION FOR SEQ ID NO: 141:

(i) SEQUENCE CHARACTERISTICS:
         (A) LENGTH: 25 amino acids
         (B) TYPE: amino acid
         (D) TOPOLOGY: linear (ii) MOLECULE TYPE: peptide (v) FRAGMENT TYPE: internal (xi) SEQUENCE DESCRIPTION: SEQ ID NO: 141:

Gln Leu Glu Ala Val Phe Glu Ala Asn Gln Asn Thr Lys Thr Ala Lys
1               5                  10                  15

Ile Glu Ile Lys Ala Ser Ile Asp Glu
            20                  25

(2) INFORMATION FOR SEQ ID NO: 142:

(i) SEQUENCE CHARACTERISTICS:
         (A) LENGTH: 27 amino acids
         (B) TYPE: amino acid
         (D) TOPOLOGY: linear (ii) MOLECULE TYPE: peptide (v) FRAGMENT TYPE: internal (xi) SEQUENCE DESCRIPTION: SEQ ID NO: 142:

Asp Lys Gln Leu Glu Ala Val Phe Glu Ala Asn Gln Asn Thr Lys Thr
1               5                  10                  15

Ala Lys Ile Glu Ile Lys Ala Ser Ile Asp Glu
            20                  25

(2) INFORMATION FOR SEQ ID NO: 143:

(i) SEQUENCE CHARACTERISTICS:
         (A) LENGTH: 13 amino acids
         (B) TYPE: amino acid
         (D) TOPOLOGY: linear (ii) MOLECULE TYPE: peptide (v) FRAGMENT TYPE: internal (xi) SEQUENCE DESCRIPTION: SEQ ID NO: 143:

Ala Lys Ile Glu Ile Lys Ala Ser Ile Asp Gly Leu Glu
1               5                  10

NFORMATION FOR SEQ ID NO: 144:

(i) SEQUENCE CHARACTERISTICS:
         (A) LENGTH: 28 amino acids
         (B) TYPE: amino acid
         (D) TOPOLOGY: linear (ii) MOLECULE TYPE: peptide (v) FRAGMENT TYPE: internal (xi) SEQUENCE DESCRIPTION: SEQ ID NO: 144:

Asp Lys Glu Gln Leu Glu Ala Val Phe Glu Ala Asn Gln Asn Thr Lys
1               5                  10                  15

Thr Ala Lys Ile Glu Ile Lys Ala Ser Ile Asp Glu
            20                  25

(2) INFORMATION FOR SEQ ID NO: 145:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 145:

Asp Lys Glu Gln Leu Glu Ala Val Phe Glu Ala Asn Gln Asn Thr Lys
1               5                  10                  15

Thr Ala Lys Ile Glu Ile Lys Ala Ser Ile Asp Glu Glu
            20                  25

(2) INFORMATION FOR SEQ ID NO: 146:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 146:

Leu Glu Ala Val Phe Glu Ala Asn Gln Asn Thr Lys Thr Ala Lys
1               5                  10                  15

(2) INFORMATION FOR SEQ ID NO: 147:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 147:

Leu Glu Ala Val Phe Glu Ala Asn Gln Ala Thr Lys Thr Ala Lys
1               5                  10                  15

(2) INFORMATION FOR SEQ ID NO: 148:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 148:

```
Lys Thr Val Lys Val Leu Gly Asp Asp Gly Val Leu Ala Ser Ala Ile
1               5                   10                  15
Ala Thr His Ala Lys Ile Arg Asp
            20
```

(2) INFORMATION FOR SEQ ID NO: 149:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 149:

```
Asp Thr Val Lys Val Leu Gly Asp Asp Gly Val Leu Ala Ser Ala Ile
1               5                   10                  15
Ala Thr His Ala Lys Ile Arg Asp
            20
```

(2) INFORMATION FOR SEQ ID NO: 150:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 150:

```
Met Gly His His His His His His Glu Phe
1               5                   10
```

(2) INFORMATION FOR SEQ ID NO: 151:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 151:

```
Lys Lys Glu Tyr Ile Gln His Asn Gly Val Val Gln Glu Ser Tyr Tyr
1               5                   10                  15
Arg Tyr Val Ala Arg Glu Gln Ser Cys Arg Arg Pro Asn Ala Gln
            20                  25                  30
```

(2) INFORMATION FOR SEQ ID NO: 152:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 152:

```
Lys Glu Tyr Ile Gln His Asn Gly Val Val Gln Glu Ser Tyr Tyr Arg
1               5                   10                  15
```

Tyr Val Ala Arg Glu Gln Ser Cys Arg Arg Pro Asn Ala Gln
            20                  25                  30

(2) INFORMATION FOR SEQ ID NO: 153:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 153:

Glu Tyr Ile Gln His Asn Gly Val Val Gln Glu Ser Tyr Tyr Arg Tyr
1               5                   10                  15

Val Ala Arg Glu Gln Ser Ser Arg Arg Pro Asn Ala Gln
            20                  25

(2) INFORMATION FOR SEQ ID NO: 154:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 154:

Glu Tyr Ile Gln His Asn Gly Val Val Gln Glu Ser Tyr Tyr Arg Tyr
1               5                   10                  15

Val Ala Arg Glu Gln Ser Glu Arg Arg Pro Asn Ala Gln
            20                  25

(2) INFORMATION FOR SEQ ID NO: 155:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 155:

Lys Lys Gln Leu Glu Ala Val Phe Glu Ala Asn Gln Asn Thr Lys Thr
1               5                   10                  15

Ala Lys Ile Glu Ile Lys Ala Ser Ile Asp Gly Leu Glu Val
            20                  25                  30

(2) INFORMATION FOR SEQ ID NO: 156:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 156:

Lys Gln Leu Glu Ala Val Phe Glu Ala Asn Gln Asn Thr Lys Thr Ala
1               5                   10                  15

```
Lys Ile Glu Ile Lys Ala Ser Ile Asp Gly Leu Glu Val Lys
            20                  25                  30
```

(2) INFORMATION FOR SEQ ID NO: 157:

(i) SEQUENCE CHARACTERISTICS:
        (A) LENGTH: 129 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 157:

```
Asp Gln Val Asp Val Lys Asp Cys Ala Asn Asn Glu Ile Lys Lys Val
1               5                   10                  15

Met Val Pro Gly Cys His Gly Ser Glu Pro Cys Ile Ile His Arg Gly
            20                  25                  30

Lys Pro Phe Thr Leu Glu Ala Leu Phe Asp Ala Asn Gln Asn Thr Lys
            35                  40                  45

Thr Ala Lys Ile Glu Ile Lys Ala Ser Leu Asp Gly Leu Glu Ile Asp
        50                  55                  60

Val Pro Gly Ile Asp Thr Asn Ala Cys His Phe Val Lys Cys Pro Leu
65                  70                  75                  80

Val Lys Gly Gln Gln Tyr Asp Ile Lys Tyr Thr Trp Asn Val Pro Lys
                85                  90                  95

Ile Ala Pro Lys Ser Glu Asn Val Val Thr Val Lys Leu Ile Gly
            100                 105                 110

Asp Asn Gly Val Leu Ala Cys Ala Ile Ala Thr His Ala Lys Ile Arg
        115                 120                 125

Asp
```

(2) INFORMATION FOR SEQ ID NO: 158:

(i) SEQUENCE CHARACTERISTICS:
        (A) LENGTH: 130 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 158:

```
Asp Gln Val Asp Val Lys Asp Cys Ala Asn Asn Glu Ile Lys Lys Val
1               5                   10                  15

Met Val Pro Gly Cys His Gly Ser Glu Pro Cys Ile Ile His Arg Gly
            20                  25                  30

Lys Pro Phe Thr Leu Glu Ala Leu Phe Asp Ala Asn Gln Asn Thr Lys
            35                  40                  45

Thr Ala Lys Ile Glu Ile Lys Ala Ser Leu Asp Gly Leu Glu Ile Asp
        50                  55                  60

Val Pro Gly Ile Asp Thr Asn Ala Cys His Phe Met Lys Cys Pro Leu
65                  70                  75                  80

Val Lys Gly Gln Gln Tyr Asp Ala Lys Tyr Thr Trp Asn Val Pro Lys
                85                  90                  95

Ile Ala Pro Lys Ser Glu Asn Val Val Val Thr Val Lys Leu Val Gly
            100                 105                 110

Asp Asn Gly Val Leu Ala Cys Ala Ile Ile Ala Thr His Ala Lys Ile
        115                 120                 125
```

Arg Asp
   130

(2) INFORMATION FOR SEQ ID NO: 159:

(i) SEQUENCE CHARACTERISTICS:
        (A) LENGTH: 129 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 159:

Asp Gln Val Asp Val Lys Asp Cys Ala Asn Asn Glu Ile Lys Lys Val
1               5                   10                  15

Met Val Pro Gly Cys His Gly Ser Glu Pro Cys Ile Ile His Arg Gly
            20                  25                  30

Lys Pro Phe Thr Leu Glu Ala Leu Phe Asp Ala Asn Gln Asn Thr Lys
        35                  40                  45

Thr Ala Lys Ile Glu Thr Lys Ala Ser Leu Asp Gly Leu Glu Ile Asp
    50                  55                  60

Val Pro Gly Ile Asp Thr Asn Ala Cys His Phe Met Lys Cys Pro Leu
65                  70                  75                  80

Val Lys Gly Gln Gln Tyr Asp Ala Lys Tyr Thr Trp Asn Val Pro Lys
                85                  90                  95

Ile Ala Pro Lys Ser Glu Asn Val Val Thr Val Lys Leu Val Gly
            100                 105                 110

Asp Asn Gly Val Leu Ala Cys Ala Ile Ala Thr His Ala Lys Ile Arg
        115                 120                 125

Asp (2) INFORMATION FOR SEQ ID NO: 160:

(i) SEQUENCE CHARACTERISTICS:
        (A) LENGTH: 92 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 160:

Asp Gln Val Asp Val Lys Asp Cys Ala Asn Ser Glu Ile Lys Lys Val
1               5                   10                  15

Met Val Pro Gly Cys His Gly Ser Glu Pro Cys Ile Ile His Arg Gly
            20                  25                  30

Lys Pro Phe Thr Leu Glu Ala Leu Phe Asp Ala Asn Gln Asn Thr Lys
        35                  40                  45

Thr Ala Lys Ile Glu Ile Lys Ala Ser Leu Asp Gly Leu Glu Ile Asp
    50                  55                  60

Val Pro Gly Ile Asp Thr Asn Ala Cys His Phe Met Lys Cys Pro Leu
65                  70                  75                  80

Val Lys Gly Gln Gln Tyr Asp Ile Lys Tyr Thr Trp
                85                  90

(2) INFORMATION FOR SEQ ID NO: 161:

(i) SEQUENCE CHARACTERISTICS:

(A) LENGTH: 84 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 161:

Asp Gln Val Asp Val Lys Asp Cys Ala Asn Asn Glu Ile Lys Lys Val
1               5                  10                  15

Met Val Pro Gly Cys His Gly Ser Glu Pro Cys Ile Ile His Arg Gly
             20                  25                  30

Lys Pro Phe Thr Leu Glu Ala Leu Phe Asp Ala Asn Gln Asn Thr Lys
         35                  40                  45

Thr Ala Lys Ile Glu Ile Lys Ala Ser Leu Asp Gly Leu Glu Ile Asp
    50                  55                  60

Val Pro Gly Ile Asp Thr Asn Ala Cys His Phe Met Lys Cys Pro Leu
65                  70                  75                  80

Val Lys Gly Gln (2) INFORMATION FOR SEQ ID NO: 162:

(i) SEQUENCE CHARACTERISTICS:
        (A) LENGTH: 61 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 162:

Asp Gln Val Asp Val Lys Asp Cys Ala Asn Asn Glu Ile Lys Lys Val
1               5                  10                  15

Met Val Pro Gly Cys His Gly Ser Glu Pro Cys Ile Ile His Arg Gly
             20                  25                  30

Lys Pro Phe Thr Leu Glu Ala Leu Phe Asp Ala Asn Gln Asn Thr Lys
         35                  40                  45

Ala Lys Thr Glu Ile Lys Ala Ser Leu Asp Gly Leu Glu
    50                  55                  60

(2) INFORMATION FOR SEQ ID NO:163:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:163:

Lys Lys Glu Tyr Ile Gln His Asn Gly Val Val Gln Glu Ser Tyr Tyr
1               5                  10                  15

Arg Tyr Val Ala Arg Glu Gln Ser Cys Arg Arg Pro Asn Ala Glu Arg
             20                  25                  30

(2) INFORMATION FOR SEQ ID NO:164:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:164:

Lys Lys Glu Tyr Ile Gln His Asn Gly Val Val Gln Glu Ser Tyr Tyr
1               5                   10                  15
Arg Tyr Val Ala Arg Glu Gln Ser Cys Arg Arg Pro Asn Ala Glu Lys
            20                  25                  30

(2) INFORMATION FOR SEQ ID NO:165:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:165:

Asp Glu Glu Gly Val Val Gln Glu Ser Tyr Tyr Arg Tyr Val Ala Arg
1               5                   10                  15
Glu Gln Ser Cys Arg Arg Pro Asn Ala Glu
            20                  25

(2) INFORMATION FOR SEQ ID NO:166:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:166:

Asp Lys Glu Gly Val Val Gln Glu Ser Tyr Tyr Arg Tyr Val Ala Arg
1               5                   10                  15
Glu Gln Ser Cys Arg Arg Pro Asn Ala Lys Glu
            20                  25

(2) INFORMATION FOR SEQ ID NO:167:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:167:

Asp Glu Lys Glu Gly Val Val Gln Glu Ser Tyr Tyr Arg Tyr Val Ala
1               5                   10                  15
Arg Glu Gln Ser Cys Arg Arg Pro Asn Ala Asp Lys Glu
            20                  25

(2) INFORMATION FOR SEQ ID NO:168:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:168:

```
Asp Glu Gly Ile Lys Asp Leu Asp Ala Phe Arg His Tyr Asp Gly Arg
1               5                  10                  15
Thr Ile Ile Gln Arg Asp Asn Gly Tyr Glu
            20                  25
```

(2) INFORMATION FOR SEQ ID NO:169:

(i) SEQUENCE CHARACTERISTICS:
            (A) LENGTH: 25 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:169:

```
Asp Gln Val Asp Val Lys Asp Cys Ala Asn His Glu Ile Lys Lys Val
1               5                  10                  15
Leu Val Pro Gly Cys His Gly Ser Glu
            20                  25
```

(2) INFORMATION FOR SEQ ID NO:170:

(i) SEQUENCE CHARACTERISTICS:
            (A) LENGTH: 26 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:170:

```
Asp Gln Val Asp Val Lys Asp Cys Ala Asn His Glu Ile Lys Lys Val
1               5                  10                  15
Leu Val Pro Gly Cys His Gly Ser Glu Gly
            20                  25
```

(2) INFORMATION FOR SEQ ID NO:171:

(i) SEQUENCE CHARACTERISTICS:
            (A) LENGTH: 27 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:171:

```
Asp Gln Val Asp Val Lys Asp Cys Ala Asn His Glu Ile Lys Lys Val
1               5                  10                  15
Leu Val Pro Gly Cys His Gly Ser Glu Pro Lys
            20                  25
```

(2) INFORMATION FOR SEQ ID NO:172:

(i) SEQUENCE CHARACTERISTICS:
            (A) LENGTH: 24 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:172:

Asp Lys Glu Leu Glu Ala Val Phe Glu Ala Asn Gln Asn Thr Lys Thr
1               5                  10                  15

Ala Lys Ile Glu Ile Lys Ala Asp
            20

(2) INFORMATION FOR SEQ ID NO:173:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:173:

Asp Lys Glu Leu Glu Ala Val Phe Glu Ala Asn Gln Asn Thr Lys Thr
1               5                  10                  15

Ala Lys Ile Glu Ile Lys Ala Lys
            20

(2) INFORMATION FOR SEQ ID NO:174:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:174:

Asp Lys Glu Leu Glu Ala Val Phe Glu Ala Asn Gln Asn Thr Lys Thr
1               5                  10                  15

Ala Lys Ile Glu Ile Lys Asp
            20

(2) INFORMATION FOR SEQ ID NO:175:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:175:

Asp Lys Glu Leu Glu Ala Val Phe Glu Ala Asn Gln Asn Thr Lys Thr
1               5                  10                  15

Ala Lys Ile Glu Ile Lys Lys
            20

(2) INFORMATION FOR SEQ ID NO:176:

(i) SEQUENCE CHARACTERISTICS:
        (A) LENGTH: 22 amino acids
        (B) TYPE: amino acid
        (D) TOPOLOGY: linear

```
    (ii) MOLECULE TYPE: peptide (v) FRAGMENT TYPE: internal (xi) SEQUENCE DESCRIPTION: SEQ ID NO:176:

Asp Lys Glu Leu Glu Ala Val Phe Glu Ala Asn Gln Asn Thr Lys Thr
1               5                  10                  15

Ala Lys Ile Glu Ile Lys
            20

(2) INFORMATION FOR SEQ ID NO:177:

(i) SEQUENCE CHARACTERISTICS:
         (A) LENGTH: 21 amino acids
         (B) TYPE: amino acid
         (D) TOPOLOGY: linear (ii) MOLECULE TYPE: peptide (v) FRAGMENT TYPE: internal (xi) SEQUENCE DESCRIPTION: SEQ ID NO:177:

Asp Lys Glu Leu Glu Ala Val Phe Glu Ala Asn Gln Asn Thr Lys Thr
1               5                  10                  15

Ala Lys Ile Glu Asp
            20

(2) INFORMATION FOR SEQ ID NO:178:

(i) SEQUENCE CHARACTERISTICS:
         (A) LENGTH: 21 amino acids
         (B) TYPE: amino acid
         (D) TOPOLOGY: linear (ii) MOLECULE TYPE: peptide (v) FRAGMENT TYPE: internal (xi) SEQUENCE DESCRIPTION: SEQ ID NO:178:

Asp Lys Glu Leu Glu Ala Val Phe Glu Ala Asn Gln Asn Thr Lys Thr
1               5                  10                  15

Ala Lys Ile Glu Lys
            20

(2) INFORMATION FOR SEQ ID NO:179:

(i) SEQUENCE CHARACTERISTICS:
         (A) LENGTH: 20 amino acids
         (B) TYPE: amino acid
         (D) TOPOLOGY: linear (ii) MOLECULE TYPE: peptide (v) FRAGMENT TYPE: internal (xi) SEQUENCE DESCRIPTION: SEQ ID NO:179:

Asp Lys Glu Leu Glu Ala Val Phe Glu Ala Asn Gln Asn Thr Lys Thr
1               5                  10                  15

Ala Lys Ile Glu
            20

(2) INFORMATION FOR SEQ ID NO:180:

(i) SEQUENCE CHARACTERISTICS:
         (A) LENGTH: 20 amino acids
         (B) TYPE: amino acid
         (D) TOPOLOGY: linear
```

(ii) MOLECULE TYPE: peptide (v) FRAGMENT TYPE: internal (xi) SEQUENCE DESCRIPTION: SEQ ID NO:180:

Asp Lys Glu Leu Glu Ala Val Phe Glu Ala Asn Gln Asn Thr Lys Thr
1               5                   10                  15
Ala Lys Ala Glu
            20

(2) INFORMATION FOR SEQ ID NO:181:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:181:

Thr Val Lys Val Met Gly Asp Asp Gly Val Leu Ala Cys Ala Ile Ala
1               5                   10                  15
Thr His Ala Lys Ile Arg Asp
            20

(2) INFORMATION FOR SEQ ID NO:182:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:182:

Thr Val Lys Leu Val Gly Asp Asp Gly Val Leu Ala Cys Ala Ile Ala
1               5                   10                  15
Thr His Ala Lys Ile Arg Asp
            20

(2) INFORMATION FOR SEQ ID NO:183:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:183:

Asp Lys Thr Val Lys Val Met Gly Asp Asp Gly Val Leu Ala Cys Ala
1               5                   10                  15
Ile Ala Thr His Ala Lys Ile Arg Asp Lys Glu
            20                  25

(2) INFORMATION FOR SEQ ID NO:184:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:184:

```
Asp Lys Thr Val Lys Leu Val Gly Asp Asn Gly Val Leu Ala Cys Ala
1               5                  10                  15
Ile Ala Thr His Ala Lys Ile Arg Asp Lys Glu
                20                  25
```

(2) INFORMATION FOR SEQ ID NO:185:

(i) SEQUENCE CHARACTERISTICS:
            (A) LENGTH: 16 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:185:

```
Asp Lys Thr Val Lys Leu Val Gly Asp Asp Gly Val Leu Ala Cys Ala
1               5                  10                  15
```

NFORMATION FOR SEQ ID NO:186:

(i) SEQUENCE CHARACTERISTICS:
            (A) LENGTH: 16 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:186:

```
Asp Lys Thr Val Lys Leu Val Gly Asp Asn Gly Val Leu Ala Cys Ala
1               5                  10                  15
```

(2) INFORMATION FOR SEQ ID NO:187:

(i) SEQUENCE CHARACTERISTICS:
            (A) LENGTH: 27 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:187:

```
Lys Lys Thr Val Lys Val Met Gly Asp Asp Gly Val Leu Ala Cys Ala
1               5                  10                  15
Ile Ala Thr His Ala Lys Ile Arg Asp Lys Lys
                20                  25
```

(2) INFORMATION FOR SEQ ID NO:188:

(i) SEQUENCE CHARACTERISTICS:
            (A) LENGTH: 28 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:188:

5,968,526
175
-continued
176

```
Asp Glu Glu Thr Val Lys Val Met Gly Asp Asp Gly Val Leu Ala Cys
1               5                   10                  15

Ala Ile Ala Thr His Ala Lys Ile Arg Asp Glu Glu
            20                  25
```

(2) INFORMATION FOR SEQ ID NO:189:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:189:

```
Asp Lys Glu Lys Thr Val Lys Val Met Gly Asp Asp Gly Val Leu Ala
1               5                   10                  15

Cys Ala Ile Ala Thr His Ala Lys Ile Arg Asp Lys Glu Lys
            20                  25                  30
```

(2) INFORMATION FOR SEQ ID NO:190:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:190:

```
Lys Lys Thr Val Lys Val Met Gly Asp Asp Gly Val Leu Ala Cys Ala
1               5                   10                  15

Ile Ala Thr His Ala Lys Lys Lys
            20
```

(2) INFORMATION FOR SEQ ID NO:191:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:191:

```
Asp Lys Glu Lys Thr Val Lys Val Met Gly Asp Asp Gly Val Leu Ala
1               5                   10                  15

Cys Ala Ile Ala Thr His Ala Lys Lys Lys
            20                  25
```

(2) INFORMATION FOR SEQ ID NO:192:

(i) SEQUENCE CHARACTERISTICS:
        (A) LENGTH: 549 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS (B) LOCATION: 1..543

(xi) SEQUENCE DESCRIPTION: SEQ ID NO:192:

```
ATT ATT GGC ATC AAA GAT TTA GAC GCA TTC CGT CAT TAT GAT GGC CGA        48
Ile Ile Gly Ile Lys Asp Leu Asp Ala Phe Arg His Tyr Asp Gly Arg
  1               5                  10                  15

ACA ATC ATT CAA CGC GAT AAT GGT TAC CAA ACT GTT AAA GTT CTG GGT        96
Thr Ile Ile Gln Arg Asp Asn Gly Tyr Gln Thr Val Lys Val Leu Gly
                 20                  25                  30

GAT GAT GGT GTT TTG GCC TCT GCT ATT GCT ACT CAT GCT AAA ATC CGC       144
Asp Asp Gly Val Leu Ala Ser Ala Ile Ala Thr His Ala Lys Ile Arg
             35                  40                  45

GAT GTT GCC GCA ACT GAA TCA GCT TAT TTG GCC TAC CGT AAC ACG TCT       192
Asp Val Ala Ala Thr Glu Ser Ala Tyr Leu Ala Tyr Arg Asn Thr Ser
         50                  55                  60

TTG GAT CTT TCT GAA CAG GAA CTC GTC GAT CAA TTG GAA GCC GTT TTC       240
Leu Asp Leu Ser Glu Gln Glu Leu Val Asp Gln Leu Glu Ala Val Phe
 65                  70                  75                  80

GAA GCC AAC CAA AAC ACA AAA ACC GCT AAA ATT GAA ATC AAA GCC TCA       288
Glu Ala Asn Gln Asn Thr Lys Thr Ala Lys Ile Glu Ile Lys Ala Ser
                 85                  90                  95

ATC GAT GGT TTA GAA GTT GAA TAC ATC CAA CAT AAT GGT GTC GTC CAA       336
Ile Asp Gly Leu Glu Val Glu Tyr Ile Gln His Asn Gly Val Val Gln
            100                 105                 110

GAA AGC TAC TAT CGA TAC GTT GCA CGA GAA CAA TCA TGC CGA CGA CCA       384
Glu Ser Tyr Tyr Arg Tyr Val Ala Arg Glu Gln Ser Cys Arg Arg Pro
        115                 120                 125

AAT GCA CAA GAT CAA GTC GAT GTC AAA GAT TCT GCC AAT CAT GAA ATC       432
Asn Ala Gln Asp Gln Val Asp Val Lys Asp Ser Ala Asn His Glu Ile
    130                 135                 140

AAA AAA GTT TTG GTA CCA GGA TCG CAT GGT TCA GAA CCA AGT ATC AAT       480
Lys Lys Val Leu Val Pro Gly Ser His Gly Ser Glu Pro Ser Ile Asn
145                 150                 155                 160

GGA AAT GCT CCA GCT GAA ATC GAT TTG CGA CAA ATG CGA ACT GTC ACT       528
Gly Asn Ala Pro Ala Glu Ile Asp Leu Arg Gln Met Arg Thr Val Thr
                165                 170                 175

CCC ATT CGT ATG CAA TAATGA                                            549
Pro Ile Arg Met Gln
            180
```

(2) INFORMATION FOR SEQ ID NO:193:

(i) SEQUENCE CHARACTERISTICS:
        (A) LENGTH: 181 amino acids
        (B) TYPE: amino acid
        (D) TOPOLOGY: linear (ii) MOLECULE TYPE: protein (xi) SEQUENCE DESCRIPTION: SEQ ID NO:193:

```
Ile Ile Gly Ile Lys Asp Leu Asp Ala Phe Arg His Tyr Asp Gly Arg
  1               5                  10                  15

Thr Ile Ile Gln Arg Asp Asn Gly Tyr Gln Thr Val Lys Val Leu Gly
                 20                  25                  30

Asp Asp Gly Val Leu Ala Ser Ala Ile Ala Thr His Ala Lys Ile Arg
             35                  40                  45

Asp Val Ala Ala Thr Glu Ser Ala Tyr Leu Ala Tyr Arg Asn Thr Ser
         50                  55                  60

Leu Asp Leu Ser Glu Gln Glu Leu Val Asp Gln Leu Glu Ala Val Phe
 65                  70                  75                  80
```

```
Glu Ala Asn Gln Asn Thr Lys Thr Ala Lys Ile Glu Ile Lys Ala Ser
                85                  90                  95

Ile Asp Gly Leu Glu Val Glu Tyr Ile Gln His Asn Gly Val Val Gln
            100                 105                 110

Glu Ser Tyr Tyr Arg Tyr Val Ala Arg Glu Gln Ser Cys Arg Arg Pro
        115                 120                 125

Asn Ala Gln Asp Gln Val Asp Val Lys Asp Ser Ala Asn His Glu Ile
130                 135                 140

Lys Lys Val Leu Val Pro Gly Ser His Gly Ser Glu Pro Ser Ile Asn
145                 150                 155                 160

Gly Asn Ala Pro Ala Glu Ile Asp Leu Arg Gln Met Arg Thr Val Thr
                165                 170                 175

Pro Ile Arg Met Gln
                180

(2) INFORMATION FOR SEQ ID NO:194:

(i) SEQUENCE CHARACTERISTICS:
        (A) LENGTH: 549 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..543

(xi) SEQUENCE DESCRIPTION: SEQ ID NO:194:

ACT GTT AAA GTT CTG GGT GAT GAT GGT GTT TTG GCC TCT GCT ATT GCT      48
Thr Val Lys Val Leu Gly Asp Asp Gly Val Leu Ala Ser Ala Ile Ala
 1               5                  10                  15

ACT CAT GCT AAA ATC CGC GAT GTT GCC GCA ACT GAA TCA GCT TAT TTG      96
Thr His Ala Lys Ile Arg Asp Val Ala Ala Thr Glu Ser Ala Tyr Leu
                20                  25                  30

GCC TAC CGT AAC ACG TCT TTG GAT CTT TCT GAA CAG GAA CTC GTC GAT     144
Ala Tyr Arg Asn Thr Ser Leu Asp Leu Ser Glu Gln Glu Leu Val Asp
            35                  40                  45

GAA TAC ATC CAA CAT AAT GGT GTC GTC CAA GAA AGC TAC TAT CGA TAC     192
Glu Tyr Ile Gln His Asn Gly Val Val Gln Glu Ser Tyr Tyr Arg Tyr
        50                  55                  60

GTT GCA CGA GAA CAA TCA TGC CGA CGA CCA AAT GCA CAA CAA TTG GAA     240
Val Ala Arg Glu Gln Ser Cys Arg Arg Pro Asn Ala Gln Gln Leu Glu
 65                 70                  75                  80

GCC GTT TTC GAA GCC AAC CAA AAC ACA AAA ACG GCT AAA ATT GAA ATC     288
Ala Val Phe Glu Ala Asn Gln Asn Thr Lys Thr Ala Lys Ile Glu Ile
                85                  90                  95

AAA GCC TCA ATC GAT GGT TTA GAA GTT ATT ATT GGC ATC AAA GAT TTA     336
Lys Ala Ser Ile Asp Gly Leu Glu Val Ile Ile Gly Ile Lys Asp Leu
            100                 105                 110

GAC GCA TTC CGT CAT TAT GAT GGC CGA ACA ATC ATT CAA CGC GAT AAT     384
Asp Ala Phe Arg His Tyr Asp Gly Arg Thr Ile Ile Gln Arg Asp Asn
        115                 120                 125

GGT TAC CAA AGT ATC AAT GGA AAT GCT CCA GCT GAA ATC GAT TTG CGA     432
Gly Tyr Gln Ser Ile Asn Gly Asn Ala Pro Ala Glu Ile Asp Leu Arg
130                 135                 140

CAA ATG CGA ACT GTC ACT CCC ATT CGT ATG CAA GAT CAA GTC GAT GTC     480
Gln Met Arg Thr Val Thr Pro Ile Arg Met Gln Asp Gln Val Asp Val
145                 150                 155                 160
```

```
AAA GAT TCT GCC AAT CAT GAA ATC AAA AAA GTT TTG GTA CCA GGA TCG        528
Lys Asp Ser Ala Asn His Glu Ile Lys Lys Val Leu Val Pro Gly Ser
            165                 170                 175

CAT GGT TCA GAA CCA TAATGA                                              549
His Gly Ser Glu Pro
            180
```

(2) INFORMATION FOR SEQ ID NO:195:

(i) SEQUENCE CHARACTERISTICS:
        (A) LENGTH: 181 amino acids
        (B) TYPE: amino acid
        (D) TOPOLOGY: linear (ii) MOLECULE TYPE: protein (xi) SEQUENCE DESCRIPTION: SEQ ID NO:195:

```
Thr Val Lys Val Leu Gly Asp Asp Gly Val Leu Ala Ser Ala Ile Ala
 1               5                  10                  15

Thr His Ala Lys Ile Arg Asp Val Ala Ala Thr Glu Ser Ala Tyr Leu
            20                  25                  30

Ala Tyr Arg Asn Thr Ser Leu Asp Leu Ser Glu Gln Glu Leu Val Asp
        35                  40                  45

Glu Tyr Ile Gln His Asn Gly Val Val Gln Glu Ser Tyr Tyr Arg Tyr
    50                  55                  60

Val Ala Arg Glu Gln Ser Cys Arg Arg Pro Asn Ala Gln Gln Leu Glu
65                  70                  75                  80

Ala Val Phe Glu Ala Asn Gln Asn Thr Lys Thr Ala Lys Ile Glu Ile
                85                  90                  95

Lys Ala Ser Ile Asp Gly Leu Glu Val Ile Gly Ile Lys Asp Leu
                100                 105                 110

Asp Ala Phe Arg His Tyr Asp Gly Arg Thr Ile Ile Gln Arg Asp Asn
                115                 120                 125

Gly Tyr Gln Ser Ile Asn Gly Asn Ala Pro Ala Glu Ile Asp Leu Arg
    130                 135                 140

Gln Met Arg Thr Val Thr Pro Ile Arg Met Gln Asp Gln Val Asp Val
145                 150                 155                 160

Lys Asp Ser Ala Asn His Glu Ile Lys Lys Val Leu Val Pro Gly Ser
                165                 170                 175

His Gly Ser Glu Pro
            180
```

(2) INFORMATION FOR SEQ ID NO:196:

(i) SEQUENCE CHARACTERISTICS:
        (A) LENGTH: 549 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..543

(xi) SEQUENCE DESCRIPTION: SEQ ID NO:196:

```
ACT GTT AAA GTT TTG GGT GAT GAT GGT GTT TTG GCC TCA GCT ATT GCT         48
Thr Val Lys Val Leu Gly Asp Asp Gly Val Leu Ala Ser Ala Ile Ala
 1               5                  10                  15

ACT CAT GCT AAA ATC CGC GAT AGT ATC AAT GGA AAT GCT CCA GCT GAA         96
Thr His Ala Lys Ile Arg Asp Ser Ile Asn Gly Asn Ala Pro Ala Glu
            20                  25                  30
```

```
ATC GAT TTG CGA CAA ATG CGA ACT GTC ACT CCC ATT CGT ATG CAA GAA        144
Ile Asp Leu Arg Gln Met Arg Thr Val Thr Pro Ile Arg Met Gln Glu
        35                  40                  45

TAC ATC CAA CAT AAT GGT GTC GTC CAA GAA AGC TAC TAT CGA TAC GTT        192
Tyr Ile Gln His Asn Gly Val Val Gln Glu Ser Tyr Tyr Arg Tyr Val
    50                  55                  60

GCA CGA GAA CAA TCA TGC CGA CGA CCA AAT GCA CAA ATT ATT GGC ATC        240
Ala Arg Glu Gln Ser Cys Arg Arg Pro Asn Ala Gln Ile Ile Gly Ile
65                  70                  75                  80

AAA GAT TTA GAC GCA TTC CGT CAT TAT GAT GGC CGA ACA ATC ATT CAA        288
Lys Asp Leu Asp Ala Phe Arg His Tyr Asp Gly Arg Thr Ile Ile Gln
                85                  90                  95

CGC GAT AAT GGT TAC CAA CAA TTG GAA GCC GTT TTC GAA GCC AAC CAA        336
Arg Asp Asn Gly Tyr Gln Gln Leu Glu Ala Val Phe Glu Ala Asn Gln
            100                 105                 110

AAC ACA AAA ACG GCT AAA ATT GAA ATC AAA GCC TCA ATC GAT GGT TTA        384
Asn Thr Lys Thr Ala Lys Ile Glu Ile Lys Ala Ser Ile Asp Gly Leu
        115                 120                 125

GAA GTT GAT CAA GTC GAT GTC AAA GAT TCA GCC AAT CAT GAA ATC AAA        432
Glu Val Asp Gln Val Asp Val Lys Asp Ser Ala Asn His Glu Ile Lys
    130                 135                 140

AAA GTT TTG GTA CCA GGA TCA CAT GGT TCA GAA CCA GTT GCC GCA ACT        480
Lys Val Leu Val Pro Gly Ser His Gly Ser Glu Pro Val Ala Ala Thr
145                 150                 155                 160

GAA TCA GCT TAT TTG GCC TAC CGT AAC ACG TCT TTG GAT CTT TCT GAA        528
Glu Ser Ala Tyr Leu Ala Tyr Arg Asn Thr Ser Leu Asp Leu Ser Glu
                165                 170                 175

CAG GAA CTC GTC GAT TAGTAG                                             549
Gln Glu Leu Val Asp
            180

(2) INFORMATION FOR SEQ ID NO:197:

(i) SEQUENCE CHARACTERISTICS:
        (A) LENGTH: 181 amino acids
        (B) TYPE: amino acid
        (D) TOPOLOGY: linear (ii) MOLECULE TYPE: protein (xi) SEQUENCE DESCRIPTION: SEQ ID NO:197:

Thr Val Lys Val Leu Gly Asp Asp Gly Val Leu Ala Ser Ala Ile Ala
1               5                   10                  15

Thr His Ala Lys Ile Arg Asp Ser Ile Asn Gly Asn Ala Pro Ala Glu
            20                  25                  30

Ile Asp Leu Arg Gln Met Arg Thr Val Thr Pro Ile Arg Met Gln Glu
        35                  40                  45

Tyr Ile Gln His Asn Gly Val Val Gln Glu Ser Tyr Tyr Arg Tyr Val
    50                  55                  60

Ala Arg Glu Gln Ser Cys Arg Arg Pro Asn Ala Gln Ile Ile Gly Ile
65                  70                  75                  80

Lys Asp Leu Asp Ala Phe Arg His Tyr Asp Gly Arg Thr Ile Ile Gln
                85                  90                  95

Arg Asp Asn Gly Tyr Gln Gln Leu Glu Ala Val Phe Glu Ala Asn Gln
            100                 105                 110

Asn Thr Lys Thr Ala Lys Ile Glu Ile Lys Ala Ser Ile Asp Gly Leu
        115                 120                 125

Glu Val Asp Gln Val Asp Val Lys Asp Ser Ala Asn His Glu Ile Lys
    130                 135                 140
```

```
Lys Val Leu Val Pro Gly Ser His Gly Ser Glu Pro Val Ala Ala Thr
145                 150                 155                 160

Glu Ser Ala Tyr Leu Ala Tyr Arg Asn Thr Ser Leu Asp Leu Ser Glu
            165                 170                 175

Gln Glu Leu Val Asp
        180
```

(2) INFORMATION FOR SEQ ID NO: 198:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO: 198:

```
Asp Lys Gln Leu Glu Ala Val Phe Glu Ala Asn Gln Ala Thr Lys Thr
1               5                   10                  15

Ala Lys Ile Glu Ile Lys Ala Ser Ile Asp Glu
            20                  25
```

(2) INFORMATION FOR SEQ ID NO: 199:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO: 199:

```
Asp Glu Lys Leu Glu Ala Val Phe Glu Ala Asn Gln Asn Thr Lys Thr
1               5                   10                  15

Ala Lys Ile Glu Ile Lys Ala Ser Asp
            20                  25
```

(2) INFORMATION FOR SEQ ID NO: 200:

(i) SEQUENCE CHARACTERISTICS:
        (A) LENGTH: 24 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO: 200:

```
Asp Lys Glu Leu Glu Ala Val Phe Glu Ala Asn Gln Asn Thr Lys Thr
1               5                   10                  15

Ala Lys Ile Glu Ile Lys Ala Asp
            20
```

(2) INFORMATION FOR SEQ ID NO: 201:

(i) SEQUENCE CHARACTERISTICS:
        (A) LENGTH: 24 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO: 201:

Asp Lys Glu Leu Glu Ala Val Phe Glu Ala Asn Gln Asn Thr Lys Thr
1               5                   10                  15
Ala Lys Ile Glu Ile Lys Ala Lys
            20

(2) INFORMATION FOR SEQ ID NO: 202:

(i) SEQUENCE CHARACTERISTICS:
            (A) LENGTH: 23 amino acids
            (B) TYPE: amino acid
            (C) STRANDEDNESS:
            (D) TOPOLOGY: linear (ii) MOLECULE TYPE: peptide (v) FRAGMENT TYPE: internal (xi) SEQUENCE DESCRIPTION: SEQ ID NO: 202:

Asp Lys Glu Leu Glu Ala Val Phe Glu Ala Asn Gln Asn Thr Lys Thr
1               5                   10                  15
Ala Lys Ile Glu Ile Lys Asp
            20

(2) INFORMATION FOR SEQ ID NO: 203:

(i) SEQUENCE CHARACTERISTICS:
            (A) LENGTH: 16 amino acids
            (B) TYPE: amino acid
            (C) STRANDEDNESS:
            (D) TOPOLOGY: linear (ii) MOLECULE TYPE: peptide (v) FRAGMENT TYPE: internal (xi) SEQUENCE DESCRIPTION: SEQ ID NO: 203:

Asp Lys Thr Ala Lys Ile Glu Ile Lys Ala Ser Ile Asp Gly Leu Glu
1               5                   10                  15

(2) INFORMATION FOR SEQ ID NO: 204:

(i) SEQUENCE CHARACTERISTICS:
            (A) LENGTH: 15 amino acids
            (B) TYPE: amino acid
            (C) STRANDEDNESS:
            (D) TOPOLOGY: linear (ii) MOLECULE TYPE: peptide (v) FRAGMENT TYPE: internal (xi) SEQUENCE DESCRIPTION: SEQ ID NO: 204:

Lys Thr Ala Lys Ile Glu Ile Lys Ala Ser Ile Asp Gly Leu Glu
1               5                   10                  15

(2) INFORMATION FOR SEQ ID NO: 205:

(i) SEQUENCE CHARACTERISTICS:
            (A) LENGTH: 20 amino acids
            (B) TYPE: amino acid
            (C) STRANDEDNESS:
            (D) TOPOLOGY: linear (ii) MOLECULE TYPE: peptide (v) FRAGMENT TYPE: internal (xi) SEQUENCE DESCRIPTION: SEQ ID NO: 205:

Glu Tyr Ile Gln His Asn Gly Val Val Gln Glu Ser Tyr Tyr Arg Tyr
1               5                   10                  15

Val Ala Arg Glu
            20

(2) INFORMATION FOR SEQ ID NO: 206:

(i) SEQUENCE CHARACTERISTICS:
        (A) LENGTH: 29 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO: 206:

His Gly Ser Glu Pro Cys Ile Ile His Arg Gly Lys Pro Phe Gln Leu
1               5                   10                  15

Glu Ala Val Phe Glu Ala Asn Gln Asn Thr Lys Thr Ala
            20                  25

(2) INFORMATION FOR SEQ ID NO: 207:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO: 207:

Gln Leu Glu Ala Val Phe Glu Ala Asn Gln Asn Thr Lys Thr Ala Lys
1               5                   10                  15

Ile Glu Ile Lys Ala Ser Ile Asp Gly Leu Glu Val
            20                  25

We claim:

1. A method of detecting sensitivity to house dust mite in an individual, comprising combining a blood sample obtained from the individual with at least one isolated peptide of Der p I having an amino acid sequence substantially corresponding to an amino acid sequence of a peptide selected from the group consisting of:

a) DP I-1 (SEQ ID NO: 9);
b) DP I-2 (SEQ ID NO: 10);
c) DP I-3 (SEQ ID NO: 11);
d) DP I-4 (SEQ ID NO: 12);
e) DPI-11.1 (SEQ ID NO: 13);
f) DP I-12.1 (SEQ ID NO: 14);
g) DP I-5 (SEQ ID NO: 15);
h) DP I-13 (SEQ ID NO: 17);
i) DPI-14 (SEQ ID NO: 18);
j) DPI-15 (SEQ ID NO: 19);
k) DP I-6.1 (SEQ ID NO: 20);
l) DP I-7.1 (SEQ ID NO: 21);
m) DP I-8 (SEQ ID NO: 22);
n) DP I-9 (SEQ ID NO: 23);
o) DP I-16 (SEQ ID NO: 24);
p) DP I-10 (SEQ ID NO: 25);
q) DP I-17 (SEQ ID NO: 26);
r) DP I-21.1 (SEQ ID NO: 27);
s) DP I-21.2 (SEQ ID NO: 28);
t) DP I-22.1 (SEQ ID NO: 29);
u) DP I-22.2 (SEQ ID NO: 30);
v) DP I-22.3 (SEQ ID NO: 31);
w) DP I-22.4 (SEQ ID NO: 32);
x) DP I-23.1 (SEQ ID NO: 33);
y) DP I-23.2 (SEQ ID NO: 34);
z) DP I-25.1 (SEQ ID NO: 35);
a') DP I-25.2 (SEQ ID NO: 36);
b') DP I-26,1 (SEQ ID NO: 37);
c') DP I-27.1 (SEQ ID NO: 38);
d') DP I-28.1 (SEQ ID NO: 39);

e') DP I-28.2 (SEQ ID NO: 40); and f') DP I-5.1 (SEQ ID NO: 16)

under conditions appropriate for binding of blood components with the peptide, and determining the extent to which such binding occurs as indicative of sensitivity in the individual to house dust mite.

2. A method of claim 1 wherein the extent to which binding occurs is determined by assessing T cell function, T cell proliferation or a combination thereof.

3. A method of detecting sensitivity to house dust mite in an individual, comprising combining a blood sample obtained from the individual with all or a portion of at least one isolated peptide of a protein allergen of the genus Dermatophagoides, said peptide or portion thereof comprising at least one T cell epitope of said protein allergen, said peptide having the formula $X_n$—Y—$Z_m$, wherein Y is an amino acid sequence selected from the group consisting of:

a) DF I-21.1 (SEQ ID NO:90);
b) DF I-21.2 (SEQ ID NO:91);
c) DF I-22.1 (SEQ ID NO:92);
d) DF I-22.2 (SEQ ID NO:93);
e) DF I-22.4 (SEQ ID NO:94);
f) DF I-23.1 (SEQ ID NO:95);
g) DF I-23.2 (SEQ ID NO:96);
h) DF I-25.1 (SEQ ID NO:97);
i) DF I-25.2 (SEQ ID NO:98);
j) DF I-26.1 (SEQ ID NO:99);
k) DF I-27.1 (SEQ ID NO:100);
l) DF I-28.1 (SEQ ID NO:101);
m) DF I-28.2 (SEQ ID NO:102);
n) DF I-1 (SEQ ID NO:72);
o) DP II-20 (SEQ ID NO:50);
p) DP II-20.1 (SEQ ID NO:51);
q) DP II-20.2 (SEQ ID NO:52);
r) DP II-20.3 (SEQ ID NO:53);
s) DP II-20.4 (SEQ ID NO:54);
t) DP II-20.5 (SEQ ID NO:55);
u) DP II-20.6 (SEQ ID NO:56);
v) DP II-1 (SEQ ID NO:41);
w) DP II-1.1 (SEQ ID NO:57);
x) DP II-1.2 (SEQ ID NO:58);
y) DP II-2.1 (SEQ ID NO:59);
z) DP II-2.2 (SEQ ID NO:60);
a') DP II-2.3 (SEQ ID NO:61);
b') DP II-21 (SEQ ID NO:62);
c') DP II-22 (SEQ ID NO:63);
d') DP II-26 (SEQ ID NO:64);
e') DP II-26.1 (SEQ ID NO:65);
f') DP II-23 (SEQ ID NO:66);
g') DP II-23.1 (SEQ ID NO:67);
h') DP II-24 (SEQ ID NO:68);
i') DP II-25 (SEQ ID NO:69);
j') DP II-25.1 (SEQ ID NO:70);
k') DP II-25.2 (SEQ ID NO:71);
l') DF II-1 (SEQ ID NO:103);
m') DF II-2 (SEQ ID NO:104);
n') DF II-13.1 (SEQ ID NO:105);
o') DF II-3.1 (SEQ ID NO:106);
p') DF II-4.5 (SEQ ID NO:107);
q') DF II-4.3 (SEQ ID NO:108);
r') DF II-15 (SEQ ID NO:109);
s') DF II-16 (SEQ ID NO:110);
t') DF II-17 (SEQ ID NO:111);
u') DF II-18 (SEQ ID NO:112);
v') DF II-19 (SEQ ID NO:113);
w') DF II-19.1 (SEQ ID NO:114);
x') DF II-21 (SEQ ID NO:115); and
y') DF II-22 (SEQ ID NO:116)

wherein $X_n$ are amino acid residues contiguous to the amino terminus of Y in the amino acid sequence of said protein allergen, wherein $Z_m$ are amino acid residues contiguous to the carboxy terminus of Y in the amino acid sequence of said protein allergen, wherein n is 0–30 and wherein m is 0–30 with the proviso that if n+m=0, Y is not DFI-22.2 (SEQ ID NO:93) under conditions appropriate for binding of blood components with the peptide or portion thereof, and determining the extent to which such binding occurs as indicative of sensitivity in the individual to house dust mite.

4. A method of claim 3 wherein the extent to which binding occurs is determined by assessing T cell function, T cell proliferation or a combination thereof.

5. A method of detecting sensitivity to house dust mite in an individual, comprising combining a blood sample obtained from the individual with at least one isolated modified peptide of a protein allergen of the genus Dermatophagoides comprising at least one T cell epitope of said protein allergen, said peptide selected from the group consisting of:

a) DP I-21.7 (SEQ ID NO: 120);
b) DP I-23.10 (SEQ ID NO: 121);
c) DP I-23.11 (SEQ ID NO: 124);
d) DP I-23.12 (SEQ ID NO: 125);
e) DP I-23.5 (SEQ ID NO: 126);
f) DP I-23.6 (SEQ ID NO: 127);
g) DP I-23.7 (SEQ ID NO: 128);
h) DP I-23.8 (SEQ ID NO: 129);
i) DP I-23.9 (SEQ ID NO: 130);
j) DP I-26.2 (SEQ ID NO: 134);
k) DP II-20.7 (SEQ ID NO: 138);
l) DP II-22.6 (SEQ ID NO: 139);
m) DP II-22.3 (SEQ ID NO: 140);
n) DP II-22.4 (SEQ ID NO: 141);
o) DP II-22.5 (SEQ ID NO: 142);
p) DP II-25.3 (SEQ ID NO: 148);
q) DP II-25.4 (SEQ ID NO: 149);
r) DP I-23.13 (SEQ ID NO: 122);
s) DP I-23.14 (SEQ ID NO: 123);
t) DP I-23.15 (SEQ ID NO: 131);
u) DP I-23.16 (SEQ ID NO: 132);
v) DP I-23.17 (SEQ ID NO: 133);
w) DP I-26.3 (SEQ ID NO: 135);
x) DP I-26.4 (SEQ ID NO: 136);
y) DP I-26.5 (SEQ ID NO: 137);
z) DP I-22.7 (SEQ ID NO: 143);
a') DP II-22.8 (SEQ ID NO: 144);
b') DP II-22.9 (SEQ ID NO: 145);
c') DP II-22.10 (SEQ ID NO: 146);
d') DP II-22.11 (SEQ ID NO: 147);
e') DP I-23.32 (SEQ ID NO: 163);

f') DPI-23.33 (SEQ ID NO: 164);
g') DP II-25.16 (SEQ ID NO: 189);
h') DP I-23.34 (SEQ ID NO: 166);
i') DP I-23.35 (SEQ ID NO: 167);
j') DP II-25.14 (SEQ ID NO: 187);
k') DF II-25.13 (SEQ ID NO: 186);
l') DP II-20.11 (SEQ ID NO: 169);
m') DP II-20.10 (SEQ ID NO: 170);
n') DP II-20.8 (SEQ ID NO: 171);
o') DP II-22.19 (SEQ ID NO: 172);
p') DP II-22.20 (SEQ ID NO: 173);
q') DP II-22.21 (SEQ ID NO: 174);
r') DP II-22.22 (SEQ ID NO: 175);
s') DP II-22.26 (SEQ ID NO: 176);
t') DP II-22.23 (SEQ ID NO: 177);
u') DP II-22.24 (SEQ ID NO: 178);
v') DP II-22.25 (SEQ ID NO: 179);
w') DF II-25.10 (SEQ ID NO: 184);
x') DF II-25.11 (SEQ ID NO: 182);
y') DP II-25.9 (SEQ ID NO: 183);
z') DP II-25.17 (SEQ ID NO: 190: and
a") DP II-25.18 (SEQ ID NO: 191); all as shown in FIGS. 29 and 30
under conditions appropriate for binding of blood components with the peptide, and determining the extent to which such binding occurs as indicative of sensitivity in the individual to house dust mite.

6. A method of claim 5 wherein the extent to which binding occurs is determined by assessing T cell function, T cell proliferation or a combination thereof.

7. A method of detecting sensitivity to house dust mite in an individual,. comprising combining a blood sample obtained from the individual with at least one peptide selected from the group consisting of: DPI-21.2 (SEQ ID NO. 28), DFI-22.2 (SEQ ID NO. 93), DPI-23.31 (SEQ. ID. NO. 165), DPI-26.6 (SEQ. ID. NO. 168), DPII-20.9 (SEQ. ID. NO. 169), DPII-22.14 (SEQ. ID. NO. 180) and DPII-25.15 (SEQ. ID. NO. 188).

8. The method of claim 7 wherein the extent to which binding occurs is determined by assessing T cell function, T cell proliferation, or a combination of thereof.

9. A method of detecting sensitivity to house dust mite in an individual comprising administering a diagnostic test selected from the group consisting of: radio-allergersorbent test (RAST), paper radioimmunosorbent test (PRIST), enzyme linked immunosorbent assay (ELISA), radioimmunoassays (RIA), immuno-radiometric assays (IRMA), luminescence immunoassays (LIA), histamine release assays, IgE immunoblots, immediate type hypersensitivity (ITH) and delayed type hypersensitivity (DTH), using a peptide selected from the group consisting of: DPI-21.2 (SEQ ID NO:28), DFI-22.2 (SEQ. ID. NO. 93), DPI-23.31 (SEQ. ID. NO. 165), DPI-26.6 (SEQ ID NO:168), DPII-20.9 (SEQ. ID. NO. 169), DPII-22.14 (SEQ. ID. NO. 180) and DPII-25.15 (SEQ ID NO: 188).

10. The method of claim 9 wherein said diagnostic test is a RAST test.

11. A method of detecting sensitivity to house dust mite in an individual comprising adminsitering a diagnostic test selected from the group consisting of: radio-allergersorbent test (RAST), paper radioimmunosorbent test (PRIST), enzyme linked immunosorbent assay (ELISA), radioimmunoassays (RIA), immuno-radiometric assays (IRMA), luminescence immunoassays (LIA), histamine release assays, IgE immunoblots, immediate type hypersensitivity (ITH) and delayed type hypersensitivity (DTH), using a peptide selected from the group consisting of:

a) DP I-21.1 (SEQ ID NO: 27);
b) DP I-21.2 (SEQ ID NO: 28);
c) DP I-22.1 (SEQ ID NO: 29);
d) DP I-22.2 (SEQ ID NO: 30);
e) DP I-22.3 (SEQ ID NO: 31);
f) DP I-22.4 (SEQ ID NO: 32);
g) DP I-23.1 (SEQ ID NO: 33);
h) DP I-23.2 (SEQ ID NO: 34);
i) DP I-25.1 (SEQ ID NO: 35);
j) DP I-25.2 (SEQ ID NO: 36);
k) DP I-26.1 (SEQ ID NO: 37);
l) DP I-27.1 (SEQ ID NO: 38);
m) DP I-28.1 (SEQ ID NO: 39);
n) DP I-28.2 (SEQ ID NO: 40);
o) DP I-1 (SEQ ID NO: 9);
p) DF I-1 (SEQ ID NO: 72);
q) DF I-21.1 (SEQ ID NO: 90);
r) DF I-21.2 (SEQ ID NO: 91);
s) DF I-22.1 (SEQ ID NO: 92);
t) DF I-22.2 (SEQ ID NO: 93);
u) DF I-22.4 (SEQ ID NO: 94);
v) DF I-23.1 (SEQ ID NO: 95);
w) DF I-23.2 (SEQ ID NO: 96);
x) DF I-25.1 (SEQ ID NO: 97);
y) DF I-25.2 (SEQ ID NO: 98);
z) DF I-26.1 (SEQ ID NO: 99);
a') DF I-27.1 (SEQ ID NO: 100);
b') DF I-28.1 (SEQ ID NO: 101);
c') DF I-28.2 (SEQ ID NO: 102);
d') DP II-20 (SEQ ID NO: 50);
e') DP II-20.1 (SEQ ID NO: 51);
f') DP II-20.2 (SEQ ID NO: 52);
g') DP II-20.3 (SEQ ID NO: 53);
h') DP II-20.4 (SEQ ID NO: 54);
i') DP II-20.5 (SEQ ID NO: 55);
j') DP II 20.6 (SEQ ID NO: 56);
k') DP II-1 (SEQ ID NO: 41);
l') DP II-1.1 (SEQ ID NO: 57);
m') DP II-1.2 (SEQ ID NO: 58);
n') DP II-2.1 (SEQ ID NO: 59);
o') DP II-2.2 (SEQ ID NO: 60);
p') DP II-2.3 (SEQ ID NO: 61);
q') DP 11-21 (SEQ ID NO: 62);
r') DP II-22 (SEQ ID NO: 63);
s') DP II-26 (SEQ ID NO: 64);
t') DP II-26.1 (SEQ ID NO: 65);
u') DP II-23 (SEQ ID NO: 66);
v') DP II-23.1 (SEQ ID NO: 67);
w') DP II-24 (SEQ ID NO: 68);
x') DP II-25 (SEQ ID NO: 69);
y') DP II-25.1 (SEQ ID NO: 70);
z') DP II-25.2 (SEQ ID NO: 71);
a") DF II-1 (SEQ ID NO: 103)

b") DF II-2 (SEQ ID NO: 104);
c") DF II-13.1 (SEQ ID NO: 105);
d") DF II-3.1 (SEQ ID NO: 106);
e") DF II-4.5 (SEQ ID NO: 107);
f") DF II-4.3 (SEQ ID NO: 108);
g") DF II-15 (SEQ ID NO: 109);
h") DF I-16 (SEQ ID NO: 110);
i") DF II-17 (SEQ ID NO: 111);
j") DF II-18 (SEQ ID NO: 112);
k") DF II-19 (SEQ ID NO: 113);
l") DF II-19.1 (SEQ ID NO: 114)
m") DF II-21 (SEQ ID NO: 115);
n") DF II-22 (SEQ ID NO: 116).

12. A method of detecting sensitivity to house dust mite in an individual comprising adminsitering a diagnostic test selected from the group consisting of: radio-allergersorbent test (RAST), paper radioimmunosorbent test (PRIST), enzyme linked immunosorbent assay (ELISA), radioimmunoassays (RIA), immuno-radiometric assays (IRMA), luminescence immunoassays (LIA), histamine release assays, IgE immunoblots, immediate type hypersensitivity (ITH) and delayed type hypersensitivity (DTH), using a peptide selected from the group consisting of:
  a) DP I-21.7 (SEQ ID NO: 120);
  b) DP I-23.10 (SEQ ID NO: 121);
  c) DP I-23.11 (SEQ ID NO: 124);
  d) DP I-23.12 (SEQ ID NO: 125);
  e) DP I-23.5 (SEQ ID NO: 126);
  f) DP I-23.6 (SEQ ID NO: 127);
  g) DP I-23.7 (SEQ ID NO: 128);
  h) DP I-23.8 (SEQ ID NO: 129);
  i) DP I-23.9 (SEQ ID NO: 130);
  j) DP I-26.2 (SEQ ID NO: 134);
  k) DP 11-20.7 (SEQ ID NO: 138);
  v') DP II-22.25; (SEQ ID NO: 179);
  w') DP II-22.14 (SEQ ID NO: 180);
  x') DF II-25.11 (SEQ ID NO: 182);
  y') DP II-25.9 (SEQ ID NO: 183);
  z') DF II-25.10 (SEQ ID NO: 184);
  a") DF II-25.13 (SEQ ID NO: 186);
  b") DP II-25.14 (SEQ ID NO: 187);
  c") DP II-25.15 (SEQ ID NO: 188);
  d") DP II-25.16 (SEQ ID NO: 189);
  e") DP II-25.17 (SEQ ID NO: 190);
  f") DP II-25.18 (SEQ ID NO: 191); all as shown in FIGS. 29 and 30.

13. A method of detecting sensitivity to house dust mite in an individual comprising adminsitering a diagnostic test selected from the group consisting of: radio-allergersorbent test (RAST), paper radioimmunosorbent test (PRIST), enzyme linked immunosorbent assay (ELISA), radioimmunoassays (RIA), immuno-radiometric assays (IRMA), luminescence immunoassays (LIA), histamine release assays, IgE immunoblots, immediate type hypersensitivity (ITH) and delayed type hypersensitivity (DTH), using a peptide selected from the group consisting of:
  a) DP I-21.1 (SEQ ID NO: 27);
  b) DP I-21.2 (SEQ ID NO: 28);
  c) DP I-22.1 (SEQ ID NO: 29);
  d) DP I-22.2 (SEQ ID NO: 30);
  e) DP I-22.3 (SEQ ID NO: 31);
  f) DP I-22.4 (SEQ ID NO: 32);
  g) DP I-23.1 (SEQ ID NO: 33);
  h) DP I-23.2 (SEQ ID NO: 34);
  i) DP I-25.1 (SEQ ID NO: 35);
  j) DP I-25.2 (SEQ ID NO: 36);
  k) DP I-26.1 (SEQ ID NO: 37);
  l) DP I-27.1 (SEQ ID NO: 38);
  m) DP I-28.1 (SEQ ID NO: 39);
  n) DP I-28.2 (SEQ ID NO: 40);
  o) DP I-1 (SEQ ID NO: 9);
  p) DF I-1 (SEQ ID NO: 72);
  q) DF I-21.1 (SEQ ID NO: 90);
  r) DF I-21.2 (SEQ ID NO: 91);
  l) DP II-22.6 (SEQ ID NO: 139);
  m) DP II-22.3 (SEQ ID NO: 140);
  n) DP II-22.4 (SEQ ID NO: 141);
  o) DP II-22.5 (SEQ ID NO: 142);
  p) DP II-25.3 (SEQ ID NO: 148);
  q) DP II-25.4 (SEQ ID NO: 149);
  r) DPI-23.13(SEQ ID NO: 122);
  s) DP I-23.14 (SEQ ID NO: 123);
  t) DP I-23.15 (SEQ ID NO: 131);
  u) DP I-23.16 (SEQ ID NO: 132);
  v) DP I-23.17 (SEQ ID NO: 133);
  w) DP I-26.3 (SEQ ID NO: 135);
  x) DP I-26.4 (SEQ ID NO: 136);
  y) DP I-26.5 (SEQ ID NO: 137);
  z) DP II-22.7 (SEQ ID NO: 143);
  a') DP II-22.8 (SEQ ID NO: 144);
  b') DP II-22.9 (SEQ ID NO: 145);
  c') DP II-22.10 (SEQ ID NO: 146);
  d') DP II-22.11 (SEQ ID NO: 147)
  e') DP I-23.32 (SEQ ID NO: 163);
  f') DPI-23.33 (SEQ ID NO: 164);
  g') DP I-23.31 (SEQ ID NO: 165);
  h') DP I-23.34 (SEQ ID NO: 166);
  i') DP I-23.35 (SEQ ID NO: 167);
  j') DP I-26.6 (SEQ ID NO: 168);
  k') DP II-20.9 (SEQ ID NO: 169);
  l') DP II-20.11 (SEQ ID NO: 169);
  m') DP I-20.10 (SEQ ID NO: 170);
  n') DP II-20.8 (SEQ ID NO: 171);
  o') DP II-22.19 (SEQ ID NO: 172);
  p') DP II-22.20 (SEQ ID NO: 173);
  q') DP II-22.21 (SEQ ID NO: 174);
  r') DP II-22.22 (SEQ ID NO: 175);
  s') DP II-22.26 (SEQ ID NO: 176);
  t') DP II-22.23 (SEQ ID NO: 177);
  u') DP 11-22.24 (SEQ ID NO: 178);
  s) DF I-22.1 (SEQ ID NO: 92);
  t) DF I-22.2 (SEQ ID NO: 93);
  u) DF I-22.4 (SEQ ID NO: 94);
  v) DF I-23.1 (SEQ ID NO: 95);
  w) DF I-23.2 (SEQ ID NO: 96);
  x) DF I-25.1 (SEQ ID NO: 97);

y) DF I-25.2 (SEQ ID NO: 98);
z) DF I-26.1 (SEQ ID NO: 99);
a') DF I-27.1 (SEQ ID NO: 100);
b') DF I-28.1 (SEQ ID NO: 101);
c') DF I-28.2 (SEQ ID NO: 102);
d') DP II-20 (SEQ ID NO: 50);
e') DP II-20.1 (SEQ ID NO: 51);
f') DP II-20.2 (SEQ ID NO: 52);
g') DP II-20.3 (SEQ ID NO: 53);
h') DP I-20.4 (SEQ ID NO: 54);
i') DP II-20.5 (SEQ ID NO: 55);
j') DP II 20.6 (SEQ ID NO: 56);
k') DP II-1 (SEQ ID NO: 41);
l') DP II-1.1 (SEQ ID NO: 57);
m') DP II-1.2 (SEQ ID NO: 58);
n') DP II-2.1 (SEQ ID NO: 59);
o') DP II-2.2 (SEQ ID NO: 60);
p') DP II-2.3 (SEQ ID NO: 61);
q') DP II-21 (SEQ ID NO: 62);
r') DP II-22 (SEQ ID NO: 63);
s') DP II-26 (SEQ ID NO: 64);
t') DP II-26.1 (SEQ ID NO: 65);
u') DP II-23 (SEQ ID NO: 66);
v') DP II-23.1 (SEQ ID NO: 67);
w') DP II-24 (SEQ ID NO: 68);
x') DP II-25 (SEQ ID NO: 69);
y') DP II-25.1 (SEQ ID NO: 70);
z') DP II-25.2 (SEQ ID NO: 71);
a") DF II-1 (SEQ ID NO: 103)
b") DF II-2 (SEQ ID NO: 104);
c") DF II-13.1 (SEQ ID NO: 105);
d") DF I-3.1 (SEQ ID NO: 106);
e") DF II-4.5 (SEQ ID NO: 107);
f") DF II-4.3 (SEQ ID NO: 108);
g") DF I-15 (SEQ ID NO: 109);
h") DF II-16 (SEQ ID NO: 110);
i") DF II-17 (SEQ ID NO: 111);
j") DF II-18 (SEQ ID NO: 112);
k") DF II-19 (SEQ ID NO: 113);
l") DF II-19.1 (SEQ ID NO: 114);
m") DF II-21 (SEQ ID NO: 115); and
n") DF II-22 (SEQ ID NO: 116).

* * * * *

UNITED STATES PATENT AND TRADEMARK OFFICE
CERTIFICATE OF CORRECTION

PATENT NO.   : 5,968,526
DATED        : October 19, 1999
INVENTOR(S)  : Richard D. Garman et al.

It is certified that error appears in the above-identified patent and that said Letters Patent is hereby corrected as shown below:

Column 189,
Line 64, insert a space between "DP I-14" and "(SEQ"
Line 65, insert a space between "DP I-15" and "(SEQ"

Signed and Sealed this

Twenty-third Day of July, 2002

Attest:

JAMES E. ROGAN
Attesting Officer           Director of the United States Patent and Trademark Office